US011866719B1

(12) United States Patent
Cermák et al.

(10) Patent No.: US 11,866,719 B1
(45) Date of Patent: Jan. 9, 2024

(54) HETEROLOGOUS INTEGRATION OF REGULATORY ELEMENTS TO ALTER GENE EXPRESSION IN WHEAT CELLS AND WHEAT PLANTS

(71) Applicant: INARI AGRICULTURE TECHNOLOGY, INC., Cambridge, MA (US)

(72) Inventors: Tomáš Cermák, Brookline, MA (US); Richard Bailey Flavell, Malibu, CA (US); Michael Andreas Kock, Rheinfelden (DE); Eva Konecna, Brookline, MA (US); Yajie Niu, Lexington, MA (US); Michael Lee Nuccio, Salem, NH (US); Jennifer Raji, Waltham, MA (US); Randall William Shultz, Acton, MA (US); Davide Sosso, Cambridge, MA (US); Maria Margarita D. Unson, Pawcatuck, CT (US); John P. Casey, Jr., Boston, MA (US); Jonathan Dallas George Jones, Norwich (GB)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 78 days.

(21) Appl. No.: 16/430,958

(22) Filed: Jun. 4, 2019

Related U.S. Application Data

(60) Provisional application No. 62/680,447, filed on Jun. 4, 2018.

(51) Int. Cl.
*C12N 15/82* (2006.01)

(52) U.S. Cl.
CPC ....... *C12N 15/8241* (2013.01); *C12N 15/827* (2013.01); *C12N 15/8213* (2013.01); *C12N 15/8216* (2013.01); *C12N 15/8266* (2013.01); *C12N 15/8269* (2013.01); *C12N 15/8271* (2013.01); *C12N 15/8279* (2013.01)

(58) Field of Classification Search
None
See application file for complete search history.

(56) References Cited

U.S. PATENT DOCUMENTS

| | | |
|---|---|---|
| 6,300,543 B1 | 10/2001 | Cass et al. |
| 6,453,242 B1 | 9/2002 | Eisenberg et al. |
| 6,534,261 B1 | 3/2003 | Cox, III et al. |
| 7,422,889 B2 | 9/2008 | Sauer et al. |
| 7,691,995 B2 | 4/2010 | Zamore et al. |
| 7,786,350 B2 | 8/2010 | Allen et al. |
| 7,816,581 B2 | 10/2010 | Gilbertson et al. |
| 8,030,473 B2 | 10/2011 | Carrington et al. |
| 8,314,290 B2 | 11/2012 | Allen et al. |
| 8,334,430 B2 | 12/2012 | Allen et al. |
| 8,395,023 B2 | 3/2013 | Gilbertson et al. |
| 8,404,928 B2 | 3/2013 | Allen et al. |
| 8,410,334 B2 | 4/2013 | Allen et al. |
| 8,697,359 B1 | 4/2014 | Zhang |
| 8,771,945 B1 | 7/2014 | Zhang |
| 8,795,965 B2 | 8/2014 | Zhang |
| 8,816,153 B2 | 8/2014 | Gilbertson et al. |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,946,511 B2 | 2/2015 | Allen et al. |
| 8,993,233 B2 | 3/2015 | Zhang et al. |
| 8,999,641 B2 | 4/2015 | Zhang et al. |
| 9,040,774 B2 | 5/2015 | Ivashuta et al. |
| 9,139,838 B2 | 9/2015 | Huang et al. |
| 9,192,112 B2 | 11/2015 | Allen et al. |
| 2005/0144669 A1 | 6/2005 | Reinhart et al. |
| 2009/0293148 A1 | 11/2009 | Ren et al. |
| 2013/0326645 A1 | 12/2013 | Cost et al. |
| 2015/0059010 A1 | 2/2015 | Cigan et al. |
| 2015/0082478 A1 | 3/2015 | Cigan et al. |
| 2015/0307889 A1 | 10/2015 | Petolino et al. |
| 2015/0344912 A1 | 12/2015 | Kim et al. |
| 2016/0017348 A1 | 1/2016 | Jacobsen et al. |

(Continued)

FOREIGN PATENT DOCUMENTS

| | | |
|---|---|---|
| WO | 2015/131101 A1 | 9/2015 |
| WO | 2016/007347 A1 | 1/2016 |

(Continued)

OTHER PUBLICATIONS

Sjolander Phylogenomic inference of protein molecular function: advances and challenges. Bioinformatics. Jan. 22, 2004;20(2):170-9. (Year: 2004).*
Whisstock J.C. et al. Prediction of protein function from protein sequence and structure. Q Rev Biophys. Aug. 2003;36(3):307-40. Review. (Year: 2003).*
Kano-Murakami Y. et al. A rice homeotic gene, OSH1, causes unusual phenotypes in transgenic tobacco. FEBS Lett. Nov. 22, 1993;334(3):365-8. (Year: 1993).*
An et al. Heterologous expression of IbMYB1a by different promoters exhibits different patterns of anthocyanin accumulation in tobacco. Plant Physiol. Biochem. Apr. 2015;89:1-10. Epub Feb. 7, 2015. (Year: 2015).*
Agris Binding Sites List, <<https://agris-knowledgebase.org/AtcisDB/bindingsites.html>>, retrieved Oct. 16, 2020, 13 pages.

(Continued)

*Primary Examiner* — Cynthia E Collins
(74) *Attorney, Agent, or Firm* — McKee, Voorhees & Sease, PLC

(57) ABSTRACT

The disclosure relates to precise modifications in wheat plant genomes including the heterologous integration of nucleic acid sequences that include a regulatory element at a predetermined locus. Also provided are wheat cells, wheat plants, wheat seeds, and processed wheat products comprising the modified wheat genomes.

14 Claims, 1 Drawing Sheet
Specification includes a Sequence Listing.

(56) References Cited

U.S. PATENT DOCUMENTS

| | | | |
|---|---|---|---|
| 2016/0138008 | A1 | 5/2016 | Doudna et al. |
| 2016/0194653 | A1 | 7/2016 | Cutler et al. |
| 2016/0208243 | A1 | 7/2016 | Zhang et al. |
| 2016/0264891 | A1 | 9/2016 | Ng et al. |
| 2016/0264981 | A1 | 9/2016 | Yang et al. |
| 2017/0037432 | A1 | 2/2017 | Donohoue et al. |
| 2017/0166912 | A1 | 6/2017 | Brower-Toland et al. |
| 2019/0264218 | A1 | 8/2019 | Shultz et al. |
| 2019/0352655 | A1 | 11/2019 | Niu et al. |
| 2020/0362366 | A1* | 11/2020 | Davey ............ A01H 5/10 |

FOREIGN PATENT DOCUMENTS

| | | |
|---|---|---|
| WO | 2016007948 A1 | 1/2016 |
| WO | 2016123514 A1 | 8/2016 |

OTHER PUBLICATIONS

Burstein et al., "New CRISPR-Cas Systems from Uncultivated Microbes", Nature, Feb. 9, 2017, pp. 237-241, vol. 542, No. 7640.

Cong et al., "Muliplex Genome Engineering Using CRISPR/Cas Systems", Science, Feb. 15, 2013, pp. 819-823, vol. 15, No. 339.

Fauser et al., "Both CRISPR/Cas-Based Nucleases and Nickases Can Be Used Efficiently for Genome Engineering in *Arabidoposis thaliana*", The Plant Journal, 2014, pp. 348-359, vol. 79.

Ferre-D'Amare et al., "Small Self-Cleaving Ribozymes", Cold Spring Harbour Perspectives in Biology, 2010, pp. 1-12.

Hendel et al., "Chemically Modified Guide RNAs Enhance CRISPR-Cas Genome Editing in Human Primary Cells", National Biotechnology, Sep. 2015, pp. 985-989, vol. 33, No. 9.

Kagale et al., "EAR Motif-Mediated Transcriptional Repression in Plants", Epigenetics, Feb. 2011, pp. 141-146, vol. 6, No. 2.

Komor et al., "Programmable Editing of a Target Base in Genomic DNA without Double-Stranded DNA Cleavage", Nature, Oct. 20, 2016, pp. 420-424, vol. 533, No. 7603.

Liu et al., "C2c1-sgRNA Complex Structure Reveals RNA-Guided DNA Cleavage Mechanism", Molecular Cell, Jan. 19, 2017, pp. 310-322, vol. 65.

Mahfouz et al., "TALE Nucleases and Next Generation GM Crops", GM Crops, 2011, pp. 99-103, vol. 2, No. 2.

Mahfouz et al., "De Novo-Engineered Transcription Activator-Like Effector (TALE) Hybrid Nuclease with Novel DNA Binding Specificity Creates Double-Strand Breaks", PNAS, Feb. 8, 2011, pp. 2623-2628, vol. 108, No. 6.

Ran et al., "Genome Engineering Using the CRISPR-Cas9 System", Nature Protocols, 2013, pp. 2281-2308, vol. 8, No. 11.

Shmakov et al., "Discovery and Functional Characterization of Diverse Class 2 CRISPR-Cas Systems", Molecular and Cellular Biology, Nov. 5, 2015, pp. 385-397, vol. 60, No. 3.

Ulmasov et al., "Aux/IAA Proteins Repress Expression of Reporter Genes Containing Natural and Highly Active Synthetic Auxin Response Elements", The Plant Cell, Nov. 1997, pp. 1963-1971, vol. 9.

Walker et al., "Molecular Mechanisms of Auxin Action", Plant Biology, 1998, pp. 434-439.

Xing et al., "A CRISPR/Cas9 Toolkit for Multiplex Genome Editing in Plants", BMC Plant Biology, 2014, pp. 1-12, vol. 14, No. 327.

Yang et al., "PAM-Dependent Target DNA Recognition and Cleavage by C2c1 CRISPR-Cas Endonuclease", Cell, Dec. 15, 2016, pp. 1814-1828, vol. 167.

You et al., "Design of LNA Probes that Improve Mismatch Discrimination", Nucleic Acids Research, 2006, pp. 1-11, vol. 34, No. 8.

Zetsche et al., "Cpf1 is a Single RNA-Guided Endonuclease of a Class 2 CRISPR-Cas System", Oct. 22, 2015, pp. 759-771, vol. 163.

Andersson et al., "Efficient Targeted Multiallelic Mutagenesis in Tetraploid Potato (Solanum tuberosum) by Transient CRISPR-Cas9 Expression in Protoplasts", Plant Cell Rep., 2017, pp. 117-128, vol. 36.

Bartlett et al., "Mapping Genome-Wide Transcription Factor Binding Sites Using DAP-Seq", Nat. Protoc., 2017, pp. 1659-1672, vol. 12, No. 8.

Bortesi et al., "The CRISPR/Cas9 System for Plant Genome Editing and Beyond", Biotechnology Advances, 2015, pp. 41-52, vol. 33, No. 1.

Burgess et al., "Advances in Understanding Cis Regulation of the Plant Gene with Emphasis on Comparative Genomics", Current Opinion in Plant Biology, 2015, pp. 141-147, vol. 27.

Dixon et al., "Teosinte BRANCHED1 Regulates Inflorescence Architecture and Development in Bread Wheat (*Triticum aestivum*)", The Plant Cell, Mar. 2018, pp. 563-581, vol. 30.

Dryanova et al., "Data Mining for miRNAs and Their Targets in the Triticeae", Genome, 2008, pp. 433-443, vol. 51, No. 6.

ERISdb: a Database of Plant Splice Sites downloaded from <http://lemur.amu.edu.pl/share/ERISdb/home.html> on Mar. 2, 2020.

Gordon et al., "Characterization of Triticum Aestivum Abscisic Acid Receptors and a Possible Role for These in Mediating Fusairum Head Blight Susceptibility in Wheat", PLOS One, Oct. 18, 2016, pp. 1-23.

Han et al., "Identification and Characterization of microRNAs in the Flag Leaf and Developing Seed of Wheat (*Triticum aestivum* L.)", BMC Geomics, 2014, pp. 1-14, vol. 15, No. 289.

He et al., "Improved Regulatory Element Prediction Based on Tissue-Specific Local Epigenomic Signatures", PNAS, 2017, pp. 1633-1640.

Je et al., "Signaling from Maize Organ Primordia via FASCIATED EAR3 Regulates Stem Cell Proliferation and Yield Traits", Nature Genetics, Jul. 2016, pp. 785-794, vol. 48, No. 7.

Kagale et al., "EAR Motif-Mediated Transcriptional Repression in Plants", Epigenetics, 2011, pp. 141-146, vol. 6, No. 2.

Kolmer et al., "Analysis of the Lr34/Yr18 Rust Resistance Region in Wheat Germplasm", Crop Science, Sep.-Oct. 2008, pp. 1841-1852, vol. 48.

Krattinger et al., "A Putative ABC Transporter Confers Durable Resistance to Multiple Fungal Pathogens in Wheat", Science, Mar. 6, 2009, pp. 1360-1363, vol. 323.

Li et al., "Overexpression of Wheat Gene TaMOR Improves Root System Architecture and Grain Yield in Oryza Sativa", Journal of Experimental Botany, 2016, pp. 4155-4167, vol. 67, No. 14.

Li et al., "Wheat WCBP1 Encodes a Putative Copper-Binding Protein Involved in Stripe Rust Resistance and Inhibition of Leaf Senescence", BMC Plant Biology, 2015, pp. 1-15, vol. 15, No. 239.

Liang et al., "Efficient DNA-free Genome Editing of Bread Wheat Using CRISPR/Cas9 Ribonucleoprotein Complexes", Nature Communications, Jan. 18, 2017, vol. 8, No. 14261.

Liu et al., "Genome-Wide Association Analysis of Powdery Mildew Resistance in U.S. Winter Wheat", Scientific Reports, Sep. 28, 2017, pp. 1-11, vol. 7, No. 11743.

Maruthachalam et al., "How to Make Haploid Arabidopsis Thaliana", Department of Plant Biology, found at www.openwetware.org/images/d/d3/Haploid_Arabidopsis_protocol.pdf, 7 pages.

MiRbase, <http://www.mirbase.org <http://www.mirbase.org>>, retrieved Oct. 16, 2020, 2 pages.

Mout et al., "Directed Cytosolic Delivery of CRISPR/Cas9-Ribonucleoprotein for Efficient Gene Editing", ACS Nano, 2017, pp. 2452-2458, vol. 11.

Office Action for U.S. Appl. No. 16/146,871 dated Mar. 20, 2020.

Office Action for U.S. Appl. No. 16/261,233 dated Jun. 12, 2020.

Office Action for U.S. Appl. No. 16/261,243 dated Jun. 26, 2020.

Ogbonnaya et al., "Synthetic Hexaploids: Harnessing Species of the Primary Gene Pool for Wheat Improvement", Plant Breeding Reviews, 2013, pp. 35-122, vol. 37.

Oka et al., "Genome-Wide Mapping of Transcriptional Enhancer Candidates Using DNA and Chromatin Features in Maize", Genome Biology, 2017, 24 pages, vol. 18. No. 137.

O'Malley et al., "Cistrome and Epicistrome Features Shape the Regulatory DNA Landscape", Cell, 2016, pp. 1280-1292, vol. 165.

Pearce et al., "RNA-Seq Studies Using Wheat PHYTOCHROME B and PHYTOCHROME C Mutants Reveal Shared and Specific Functions in the Regulation of Flowering and Shade-Avoidance Pathways", BMC Plant Biology, 2016, pp. 1-19, vol. 16, No. 141.

(56) References Cited

OTHER PUBLICATIONS

Pnueli et al., "The Self-Pruning Gene of Tomato Regulates Vegetative to Reproductive Switching of Sympodial Meristems and is the Ortholog of CEN and TFL1", Development, 1998, pp. 1979-1989, vol. 123, No. 11.
Ravi et al., "A Haploid Genetics Toolbox for Arabidopsis thaliana", Nature Communications, Oct. 31, 2014, pp. 1-8, vol. 5, No. 5334.
Schaeffer et al., "CRISPR/Cas9-Mediated Genome Editing and Gene Replacement in Plants: Transitioning from Lab to Field", Plant Science, 2015, pp. 130-142, vol. 240.
Soyk et al., "Bypassing Negative Epistasis on Yield in Tomato Imposed by a Domestication Gene", Cell, 2017, pp. 1142-1155, vol. 169.
Stelpflug et al., "Consistent and Heritable Alterations of DNA Methylation Are Induced by Tissue Culture in Maize", Genetics, Sep. 2014, pp. 209-218, vol. 198.
Stroud et al., "Plants Regenerated from Tissue Culture Contain Stable Epigenome Changes in Rice", eLife, 2013, pp. 1-14, vol. 2, e00354.
Svitashev et al., "Targeted Mutagenesis, Precise Gene Editing, and Site-Specific Gene Insertion in Maize using Cas9 and Guide RNA", Plant Physiology, 2015, pp. 931-945, vol. 169.
Szczesniak et al., "ERISdb: A Database of Plant Splice Sites and Splicing Signals", Plant Cell Physiol., 2013, 8 pages, vol. 54, No. 2.
Tomato Genome Consortium, "The Tomato Genome Sequence Provides Insight into Fleshy Fruit Evolution", Nature, 2012, pp. 635-641, vol. 485, No. 7400.
Ulmasov et al., "Aux/IAA Proteins Repress Expression of Reporter Genes Containing Natural and Highly Active Synthetic Auxin Response Elements", The Plant Cell, 1997, pp. 1963-1971, vol. 9.
Walker et al., "Molecular Mechanisms of Auxin Action", Current Opinion in Plant Biology, 1998, pp. 434-439, vol. 1.
Wang et al, "Simultaneous Editing of Three Homoeoalleles in Hexaploid in Hexaploid Bread Wheat Confers Heritable Resistance to Powdery Mildew", Nature Biotechnology, Sep. 2014, pp. 947-952, vol. 32, No. 9.
Wheat Urgi, <<https://wheat-urgi.versailles.inra.fr/Seq-Repository/Assemblies>>, retrieved Oct. 16, 2020, 3 pages.
Yao et al., "Closing and Characterization of MicroRNAs from Wheat (*Triticum aestivum* L.)", Genome Biology, Jun. 1, 2007, pp. R96.1-R96.13, vol. 8, No. 6, Article R96.
Zhang et al., "Novel Function of a Putative MOC1 Ortholog Associated with Spikelet No. Per Spike in Common Wheat", Scientific Reports, Jul. 22, 2015, pp. 1-13, vol. 5, No. 12211.
Zhang, et al, "Efficient and Transgene-Free Genome Editing in Wheat Through Transient Expression of CRISPR/Cas9 DNA or RNA", Nature Communication, 7:12617, Aug. 25, 2016, pp. 1-8.
Intellectual Property Office of Singapore, "Second Written Opinion" in connection with Application No. 11201906795S, Application Filing Date Jan. 29, 2018, Date of Second Written Opinion dated Apr. 22, 2021, 8 pages, 2021.
Gil-Humanes et al., "High-efficiency gene targeting in hexaploid wheat using DNA replicons and CRISPR/Cas9", The Plant Journal, vol. 89, pp. 1251-1262, 2017.
Kuzay et al., "Identification of a candidate gene for a QTL for spikelet number per spike on wheat chromosome arm 7AL by high-resolution genetic mapping", Theoretical and Applied Genetics, vol. 132, pp. 2689-2705, 2019.
Weinthal et al., "Plant Genome Editing and its Applications in Cereals", IntechOpen, DOI: 10.5772/66818, 15 pages, Dec. 14, 2016.
Richardson et al., "Enhancing homology-directed genome editing by catalytically active and inactive CRISPR-Cas9 using asymmetric donor DNA", Nature Biotechnology, vol. 34, No. 3, pp. 339-345, Mar. 2016.
United States Patent and Trademark Office in connection with U.S. Appl. No. 16/480,992, filed Jul. 25, 2019, "Final Office Action", 29 pages, dated Jan. 7, 2022.

* cited by examiner

A
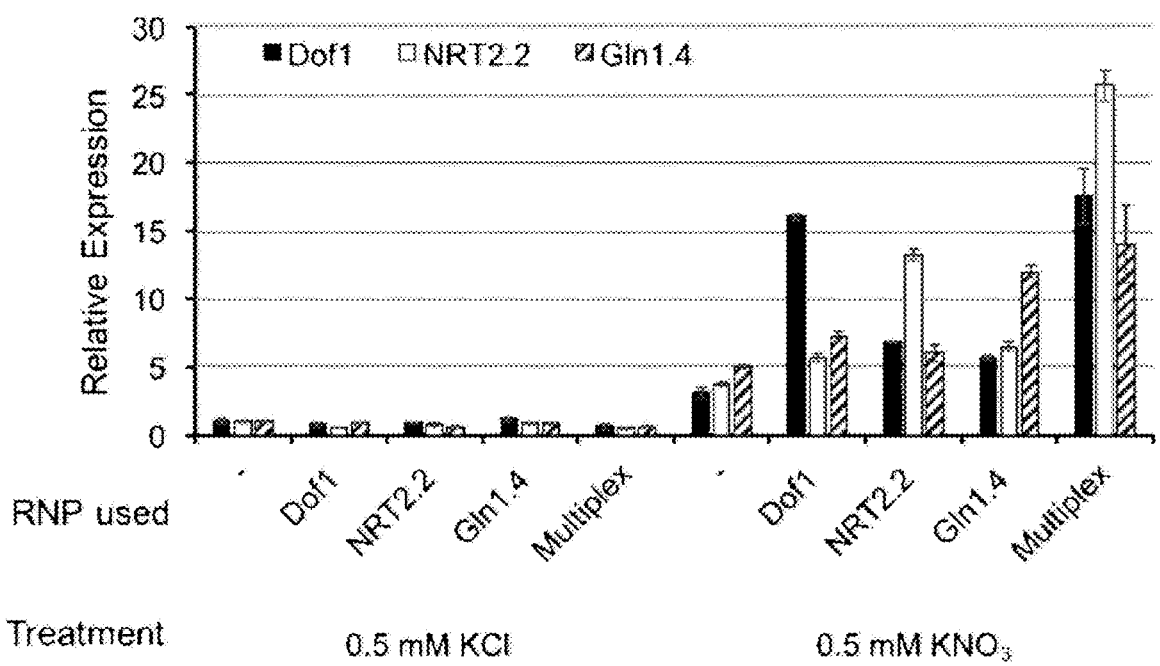
B
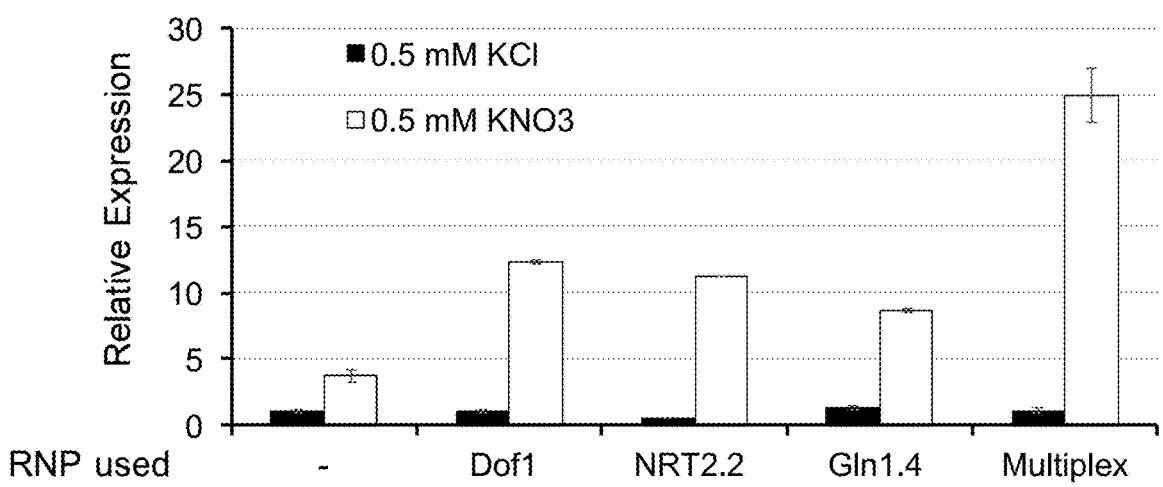
FIG. 1A,B

HETEROLOGOUS INTEGRATION OF REGULATORY ELEMENTS TO ALTER GENE EXPRESSION IN WHEAT CELLS AND WHEAT PLANTS

RELATED APPLICATIONS

This application claims the benefit of U.S. Provisional Patent Application No. 62/680,447, filed Jun. 4, 2018, which is incorporated herein by reference in its entirety.

INCORPORATION OF SEQUENCE LISTING

The sequence listing contained in the file named 10013US1_ST25.txt, which is 6106147 bytes as measured in Microsoft Windows, created on May 29, 2019 and electronically filed via EFS-Web on Jun. 4, 2019, is incorporated herein by reference in its entirety.

FIELD OF THE INVENTION

Aspects of this invention relate to plant breeding methods and compositions. Disclosed herein are novel plant cells, plants and seeds derived from such plant cells and having enhanced traits, and methods of making and using such plant cells and derived plants and seeds.

BACKGROUND

Plant breeding and engineering currently relies on Mendelian genetics or recombinant techniques.

SUMMARY

Disclosed herein are methods for providing novel wheat plant cells, protoplasts, callus, tissues, or plant parts, wheat plants, and wheat seeds having one or more altered genetic sequences. Among other features, the methods and compositions described herein enable the stacking of preferred alleles or homeoalleles without introducing unwanted genetic or epigenetic variation in the modified wheat plants or wheat plant cells. The efficiency and reliability of these precise modification methods are significantly improved relative to traditional wheat breeding, and can be used to augment traditional wheat breeding techniques or as a substitute for them.

There are two wild diploid wheats, *Triticum boeoticum* and *Triticum urartu*. *Triticum boeoticum* is the wild ancestor of domesticated einkorn, *Triticum monococcum*. Cells of the diploid wheats each contain 2 complements of 7 chromosomes, one from the mother and one from the father (2n=2x=14, where 2n is the number of chromosomes in each somatic cell, and x is the basic chromosome number). However, polyploidy is common in wheat, particularly domesticated wheats. The polyploid wheats are tetraploid (4 sets of chromosomes, 2n=4x=28, where the monoploid number x=7 and the haploid number n=14), or hexaploid (6 sets of chromosomes, 2n=6x=42, where the monoploid number x=7 and the haploid number n=21). The tetraploid wild wheats are wild emmer, *Triticum dicoccoides*, and *Triticum araraticum*. Wild emmer is the ancestor of all the domesticated tetraploid wheats, with one exception: *Triticum araraticum* is the wild ancestor of *Triticum timopheevi*. Common or bread wheat, *Triticum aestivum*, is an allohexaploid (an allopolyploid with six sets of chromosomes: two sets from each of three different diploid species that are its distant ancestors). Of the six sets of chromosomes in *Triticum aestivum*, two come from *Triticum urartu* (einkorn wheat) and two from *Aegilops speltoides*. This hybridisation created the species *Triticum turgidum* (durum wheat). The last two sets of *Triticum aestivum* chromosomes came from wild goat-grass, *Aegilops tauschii*. The somatic cells of *Triticum aestivum* are hexaploid, with six sets of chromosomes, 2n=6x=42 (where the monoploid number x=7 and the haploid number n=21); the gametes are haploid for their own species, but can be considered in a sense triploid, with three sets of chromosomes, by comparison to a probable evolutionary ancestor, einkorn wheat.

The compositions and methods disclosed herein are useful for effecting single or multiple precisely predetermined and non-random modifications in the genome of a wheat plant, including effecting one or multiple precise modifications in one or multiple copies of a given allele (homeoallele) that occurs in the wheat plant; in embodiments, one or multiple precise modifications are made in both homeoalleles of a gene in at least one of the A genome, the B genome, and the D genome of a allohexaploid wheat such as *Triticum aestivum*. In embodiments, at least one precise modification is made in a region of the wheat genome that is recalcitrant (e.g., by traditional breeding of a male wheat parent plant to a female wheat parent plant) to meiotic or mitotic recombination. In embodiments, multiple precise modifications are effected in a single step. In embodiments, single or multiple precise modifications in the wheat genome are effected without the use of DNA (for example, by means of a ribonucleoprotein including a sequence-specific nuclease and a guide RNA). In embodiments, single or multiple precise modifications in the wheat genome are effected without the use of bacterially-mediated transformation (such as by means of *Agrobacterium*). In embodiments, single or multiple precise modifications in the wheat genome are effected without the use of selection (e.g., antibiotic selection or herbicide selection). In embodiments, single or multiple precise modifications in the wheat genome are effected without the need for callus culture.

In one aspect, the invention provides a wheat plant having a modified genome that results in the wheat plant exhibiting modified architecture in comparison to an unmodified wheat plant having an reference genome, wherein the modified genome differs from the reference genome by including precisely predetermined and non-random modifications of at least two genes of interest, wherein each of the predetermined modifications is selected from the group consisting of: (a) heterologous integration of the nucleic acid sequence of a non-coding regulatory element that is encoded by at least one donor polynucleotide molecule at a predetermined locus in the 5' untranslated region upstream of the start codon of the coding sequence of a gene of interest in the reference genome; (b) heterologous integration of the nucleic acid sequence of a non-coding regulatory element that is encoded by at least one donor polynucleotide molecule at a predetermined locus downstream of the stop codon of a gene of interest in the reference genome; (c) deletion, addition, or substitution of at least one nucleotide in a regulatory element that regulates expression of a gene of interest in the reference genome; (d) deletion, addition, or substitution of at least one nucleotide in coding sequence of a gene of interest in the reference genome; and (e) a combination of any of (a), (b), (c), and (d), wherein the gene of interest is selected from the group consisting of pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, and TaSnrk2.10-4A, or is a gene encoding a protein having at least 90% identity to a sequence selected from the group consisting of the sequences identified by SEQ ID NOs:257-303, or is a genomic sequence selected from the sequences identified by SEQ ID NOs:475-521. In embodiments, the at least two genes of interest include at least one homeoallele each of two or more genes selected from the group consisting of pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, and TaSnrk2.10-4A. In some embodiments, the modified genome further differs from the reference genome by including (a) a predetermined modification in at least one homeoallele of a gene selected from TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, LR34, Lr67, Sr22, Sr33, Sr35, Sr45, Sr50, Tsn1, Yr36 (WKS1), Snn1, TaMLO-A 1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV 1SM, SOD, APX, GS2, NAM, rbcL, IVR1, and a1, or (b) a predetermined modification in a gene encoding a protein having at least 90% identity to a sequence selected from the group consisting of the sequences identified by SEQ ID NOs:304-474, or (c) a predetermined modification in a genomic sequence selected from the group consisting of the sequences identified by SEQ ID NOs:522-692.

In another aspect, the invention provides a wheat plant having a modified genome that results in the wheat plant exhibiting improved abiotic stress tolerance in comparison to an unmodified wheat plant having an reference genome, wherein the modified genome differs from the reference genome by including precisely predetermined and non-random modifications of at least two genes of interest, wherein each of the predetermined modifications is selected from the group consisting of: (a) heterologous integration of the nucleic acid sequence of a non-coding regulatory element that is encoded by at least one donor polynucleotide molecule at a predetermined locus in the 5' untranslated region upstream of the start codon of the coding sequence of a gene of interest in the reference genome; (b) heterologous integration of the nucleic acid sequence of a non-coding regulatory element that is encoded by at least one donor polynucleotide molecule at a predetermined locus downstream of the stop codon of a gene of interest in the reference genome; (c) deletion, addition, or substitution of at least one nucleotide in a regulatory element that regulates expression of a gene of interest in the reference genome; (d) deletion, addition, or substitution of at least one nucleotide in coding sequence of a gene of interest in the reference genome; and (e) a combination of any of (a), (b), (c), and (d), wherein the gene of interest is selected from the group consisting of TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, and UBA, or is a gene encoding a protein having at least 90% identity to a sequence selected from the group consisting of the sequences identified by SEQ ID NOs:304-362, or is a genomic sequence selected from the sequences identified by SEQ ID NOs:522-580. In embodiments, the at least two genes of interest include at least one homeoallele each of two or more genes selected from the group consisting of TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, and UBA. In some embodiments, the modified genome further differs from the reference genome by including (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, Fhb1, LR34, Lr67, Sr22, Sr33, Sr35, Sr45, Sr50, Tsn1, Yr36 (WKS1), Snn1, TaMLO-A1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV1SM, SOD, APX, GS2, NAM, rbcL, IVR1, and a1, or (b) a predetermined modification in a gene encoding a protein having at least 90% identity to a sequence selected from the group consisting of the sequences identified by SEQ ID NOs:257-303 and 363-474, or (c) a predetermined modification in a genomic sequence selected from the group consisting of the sequences identified by SEQ ID NOs:475-521 and 581-692.

In another aspect, the invention provides a wheat plant having a modified genome that results in the wheat plant exhibiting improved disease resistance in comparison to an unmodified wheat plant having an reference genome, wherein the modified genome differs from the reference genome by including precisely predetermined and non-random modifications of at least two genes of interest, wherein each of the predetermined modifications is selected from the group consisting of: (a) heterologous integration of the nucleic acid sequence of a non-coding regulatory element that is encoded by at least one donor polynucleotide molecule at a predetermined locus in the 5' untranslated region upstream of the start codon of the coding sequence of a gene of interest in the reference genome; (b) heterologous integration of the nucleic acid sequence of a non-coding regulatory element that is encoded by at least one donor polynucleotide molecule at a predetermined locus downstream of the stop codon of a gene of interest in the reference genome; (c) deletion, addition, or substitution of at least one nucleotide in a regulatory element that regulates expression of a gene of interest in the reference genome; (d) deletion, addition, or substitution of at least one nucleotide in coding sequence of a gene of interest in the reference genome; and (e) a combination of any of (a), (b), (c), and (d), wherein the gene of interest is selected from the group consisting of Fhb1, LR34, Lr67, Sr22, Sr33, Sr35, Sr45, Sr50, Tsn1, Yr36 (WKS1), Snn1, TaMLO-A 1, TaMLO-B1, and TaMLO-D1, or is a gene encoding a protein having at least 90% identity to a sequence selected from the group consisting of the sequences identified by SEQ ID NOs:363-398, or is a genomic sequence selected from the sequences identified by SEQ ID NOs:581-616. In embodiments, the at least two genes of interest include at least one homeoallele each of two or more genes selected from the group consisting of Fhb1, LR34, Lr67, Sr22, Sr33, Sr35, Sr45, Sr50, Tsn1, Yr36 (WKS1), Snn1, TaMLO-A1, TaMLO-B1, and TaMLO-D1. In some embodiments, the modified genome further differs from the reference genome by including (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP- A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV1SM, SOD, APX, GS2, NAM, rbcL, IVR1, and a1, or (b) a predetermined modification in a gene encoding a protein having at least 90% identity to a sequence selected from the group consisting of the sequences identified by SEQ ID NOs:257-362 and 399-474, or (c) a predetermined modification in a genomic sequence selected from the group consisting of the sequences identified by SEQ ID NOs:475-580 and 617-692.

In another aspect, the invention provides a wheat plant having a modified genome that results in the wheat plant exhibiting modified flowering time in comparison to an unmodified wheat plant having an reference genome, wherein the modified genome differs from the reference genome by including precisely predetermined and non-random modifications of at least two genes of interest, wherein each of the predetermined modifications is selected from the group consisting of: (a) heterologous integration of the nucleic acid sequence of a non-coding regulatory element that is encoded by at least one donor polynucleotide molecule at a predetermined locus in the 5' untranslated region upstream of the start codon of the coding sequence of a gene of interest in the reference genome; (b) heterologous integration of the nucleic acid sequence of a non-coding regulatory element that is encoded by at least one donor polynucleotide molecule at a predetermined locus downstream of the stop codon of a gene of interest in the reference genome; (c) deletion, addition, or substitution of at least one nucleotide in a regulatory element that regulates expression of a gene of interest in the reference genome; (d) deletion, addition, or substitution of at least one nucleotide in coding sequence of a gene of interest in the reference genome; and (e) a combination of any of (a), (b), (c), and (d), wherein the gene of interest is selected from the group consisting of FT, FKF1, PhyB, WCO1, ZenMFT-3D, MADS, TaGI1, WAP1, NFYB-A, NFYB-B, and NFYB-D, or is a gene encoding a protein having at least 90% identity to a sequence selected from the group consisting of the sequences identified by SEQ ID NOs:399-424, or is a genomic sequence selected from the sequences identified by SEQ ID NOs:617-642. In embodiments, the at least two genes of interest include at least one homeoallele each of two or more genes selected from the group consisting of FT, FKF1, PhyB, WCO1, ZenMFT-3D, MADS, TaGI1, WAP1, NFYB-A, NFYB-B, and NFYB-D. In some embodiments, the modified genome further differs from the reference genome by including (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, LR34, Lr67, Sr22, Sr33, Sr35, Sr45, Sr50, Tsn1, Yr36 (WKS1), Snn1, TaMLO-A1, TaMLO-B1, TaMLO-D1, NAC1, Skp1, TIF, WCBP1, WRKY, TaSAG6, TaSAG3, TaSAG1, FeSOD, CWINV2SM, CWINV1SM, SOD, APX, GS2, NAM, rbcL, IVR1, and a1, or (b) a predetermined modification in a gene encoding a protein having at least 90% identity to a sequence selected from the group consisting of the sequences identified by SEQ ID NOs:257-398 and 425-474, or (c) a predetermined modification in a genomic sequence selected from the group consisting of the sequences identified by SEQ ID NOs:475-616 and 643-692.

In another aspect, the invention provides a wheat plant having a modified genome that results in the wheat plant exhibiting improved photosynthesis in comparison to an unmodified wheat plant having an reference genome, wherein the modified genome differs from the reference genome by including precisely predetermined and non-random modifications of at least two genes of interest, wherein each of the predetermined modifications is selected from the group consisting of: (a) heterologous integration of the nucleic acid sequence of a non-coding regulatory element that is encoded by at least one donor polynucleotide molecule at a predetermined locus in the 5' untranslated region upstream of the start codon of the coding sequence of a gene of interest in the reference genome; (b) heterologous integration of the nucleic acid sequence of a non-coding regulatory element that is encoded by at least one donor polynucleotide molecule at a predetermined locus downstream of the stop codon of a gene of interest in the reference genome; (c) deletion, addition, or substitution of at least one nucleotide in a regulatory element that regulates expression of a gene of interest in the reference genome; (d) deletion, addition, or substitution of at least one nucleotide in coding sequence of a gene of interest in the reference genome; and (e) a combination of any of (a), (b), (c), and (d), wherein the gene of interest is selected from the group consisting of NAC1, Skp1, TIF, and WCBP1, or is a gene encoding a protein having at least 90% identity to a sequence selected from the group consisting of the sequences identified by SEQ ID NOs:425-434, or is a genomic sequence selected from the sequences identified by SEQ ID NOs:643-652. In embodiments, the at least two genes of interest include at least one homeoallele each of two or more genes selected from the group consisting of NAC1, Skp1, TIF, and WCBP1. In some embodiments, the modified genome further differs from the reference genome by including (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, LR34, Lr67, Sr22, Sr33, Sr35, Sr45, Sr50, Tsn1, Yr36 (WKS1), Snn1, TaMLO-A1, TaMLO-B1, TaMLO-D1, FT, FKF1, PhyB, WCO1, ZenMFT-3D, MADS, TaGI1, WAP1, NFYB-A, NFYB-B, NFYB-D, WRKY, TaSAG6, TaSAG3, TaSAG1, FeSOD, CWINV2SM, CWINV 1SM, SOD, APX, GS2, NAM, rbcL, IVR1, a1, or (b) a predetermined modification in a gene encoding a protein having at least 90% identity to a sequence selected from the group consisting of the sequences identified by SEQ ID NOs:257-424 and 435-474, or (c) a predetermined modification in a genomic sequence selected from the group consisting of the sequences identified by SEQ ID NOs:475-642 and 653-692.

In another aspect, the invention provides a wheat plant having a modified genome that results in the wheat plant exhibiting modified senescence in comparison to an unmodified wheat plant having an reference genome, wherein the modified genome differs from the reference genome by including precisely predetermined and non-random modifications of at least two genes of interest, wherein each of the predetermined modifications is selected from the group consisting of: (a) heterologous integration of the nucleic acid sequence of a non-coding regulatory element that is encoded by at least one donor polynucleotide molecule at a predetermined locus in the 5' untranslated region upstream of the start codon of the coding sequence of a gene of interest in the reference genome; (b) heterologous integration of the nucleic acid sequence of a non-coding regulatory element that is encoded by at least one donor polynucleotide molecule at a predetermined locus downstream of the stop codon of a gene of interest in the reference genome; (c) deletion, addition, or substitution of at least one nucleotide in a regulatory element that regulates expression of a gene of interest in the reference genome; (d) deletion, addition, or substitution of at least one nucleotide in coding sequence of a gene of interest in the reference genome; and (e) a combination of any of (a), (b), (c), and (d), wherein the gene of interest is selected from the group consisting of WRKY, TaSAG6, TaSAG3, TaSAG1, FeSOD, CWINV2SM, CWINV1SM, SOD, APX, GS2, NAM, rbcL, IVR1, and a1, or is a gene encoding a protein having at least 90% identity to a sequence selected from the group consisting of the sequences identified by SEQ ID NOs:435-474, or is a genomic sequence selected from the sequences identified by SEQ ID NOs:653-692. In embodiments, the at least two genes of interest include at least one homeoallele each of two or more genes selected from the group consisting of WRKY, TaSAG6, TaSAG3, TaSAG1, FeSOD, CWINV2SM, CWINV ISM, SOD, APX, GS2, NAM, rbcL, IVR1, and a1. In some embodiments, the modified genome further differs from the reference genome by including (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, LR34, Lr67, Sr22, Sr33, Sr35, Sr45, Sr50, Tsn1, Yr36 (WKS1), Snn1, TaMLO-A 1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, and WCBP1, or (b) a predetermined modification in a gene encoding a protein having at least 90% identity to a sequence selected from the group consisting of the sequences identified by SEQ ID NOs:257-434, or (c) a predetermined modification in a genomic sequence selected from the group consisting of the sequences identified by SEQ ID NOs:475-652.

In embodiments of the wheat plant having a modified genome, the predetermined modifications of at least two genes of interest include modifications of only non-coding sequences of the reference genome, or of only coding sequences of the reference genome, or of a combination of coding and non-coding sequences of the reference genome. In some embodiments, the modified genome comprises only changes to non-coding sequences of the reference genome, such as sequence changes that result in modified (e.g., increased or decreased) expression of at least one of the genes of interest or a change in stability or half-life of the transcript of at least one of the genes of interest. In embodiments, at least one of the predetermined modifications of at least two genes of interest results in increased expression of the gene of interest, relative to expression of the gene of interest in the reference genome. In embodiments, at least one of the predetermined modifications of at least two genes of interest results in decreased expression of the gene of interest, relative to expression of the gene of interest in the reference genome.

In embodiments of the wheat plant having a modified genome, at least one of the predetermined modifications of at least two genes of interest includes multiple predetermined modifications of a single gene of interest in the reference genome. As domesticated wheat plants are allotetraploid or allohexaploid, it is of particular interest to modify multiple homeoalleles of a given gene of interest. Thus, in embodiments, the predetermined modifications of at least two genes of interest includes a predetermined modification of multiple homeoalleles of a gene of interest. For example, in embodiments, the wheat plant is common bread wheat, *Triticum aestivum*, an allohexaploid, wherein the reference genome consists of an A genome, a B genome, and a D genome, and wherein the A genome only, the B genome only, the D genome only, or any combination of the A, B, and D genomes is homozygous for at least one of the predetermined modifications of at least two genes of interest.

The modification of the wheat genome is achieved by any suitable sequence-specific nuclease, with, if necessary, donor polynucleotide molecules such as those described in detail herein. In embodiments, the wheat plant with a modified genome is grown directly from a genome-modified wheat plant cell or tissue (e.g., an embryo, ovule, zygote, microspore, pollen, or meristem tissue) without the use of selection (e.g., by use of antibiotics or herbicides) and without culture involving callus or other cellular dedifferentiation step. The wheat plant having a modified genome therefore differs significantly from wheat plants having a genome modified by traditional breeding (i.e., crossing of a male parent wheat plant and a female parent wheat plant), where unwanted and random exchange of genomic regions as well as random mitotically or meiotically generated genetic and epigenetic changes in the genome typically occurs during the cross and are then found in the progeny plants. Thus, in embodiments of the wheat plant with a modified genome, the modified genome is more than 99.9% identical to the reference genome. In embodiments, the modified genome is devoid of random mitotically or meiotically generated genetic or epigenetic changes relative to the reference genome. In embodiments, the modified genome includes a difference of epigenetic changes in less than 0.01% of the genome relative to the reference genome. In embodiments, the modified genome includes: (a) a difference of DNA methylation in less than 0.01% of the genome, relative to the reference genome; or (b) a difference of DNA methylation in less than 0.005% of the genome, relative to the reference genome; or (c) a difference of DNA methylation in less than 0.001% of the genome, relative to the reference genome. In embodiments, the gene of interest is located on a chromosome in the wheat plant cell, and the modified genome includes: (a) a difference of DNA methylation in less than 0.01% of the portion of the genome that is contained within the chromosome containing the gene of interest, relative to the reference genome; or (b) a difference of DNA methylation in less than 0.005% of the portion of the genome that is contained within the chromosome containing the gene of interest, relative to the reference genome; or (c) a difference of DNA methylation in less than 0.001% of the portion of the genome that is contained within the chromosome containing the gene of interest, relative to the reference genome. In embodiments, the modified genome has not more unintended changes in comparison to the reference genome than $1\times10^{-8}$ mutations per base pair per replication.

The compositions and methods described in detail herein are useful to provide a wheat plant having a modified genome containing precisely predetermined and non-random modifications of one or multiple genes, in the absence of unwanted and random exchange of genomic regions as well as random mitotically or meiotically generated genetic and epigenetic changes in the genome, wherein the predetermined modification of multiple genes result in a phenotype including one or multiple desirable traits (e.g., combinations of modified plant architecture, flowering time, and disease resistance). Thus, in embodiments of the wheat plant with a modified genome, the modified genome further differs from the reference genome by including (a) a predetermined modification in at least one homeoallele of a gene selected from the group consisting of TsVP, SEC14p, ACC synthase, D-myo-inositol-3-phosphate synthase (IPS), bZIP72, PLC1, GOLS2, PIS, NF-YB, PsbA, HB2, PP2C2, CIPK16, SAPK8, ABA8ox3, ORAP1, DIS1, VPE3, RZFP34, ZFP185, DCA1, SRFP1, SQS, TPP1, SAPK6, JIOsPR10, ClpD1, MSD1, WR1, TPS1, GS, OgTT1, FKBP20, ANN1, SIK1, NHX1, MGD, DHODH1, hsp16.9, GME-2, ChI1, CYP18-2, CNX, CBL8, CDPK13, RAN2, GGP, OVP1, ZFP177, RGG1, Em1, CTB4a, GS2, COLD1, ACA6, Rab7, TOP6A1, Hsp101, AMTR1, Rubisco activase, SPX1, GME-1, MPG1, SNAC3, SDIR1, Pgk2a-P, glyoxalase II, PUB15, IMP, HBP1b, CYP2, PEX11 (Os03g0302000), CPK4, EG1, CBSX4, SIDP366, SUV3, GA2ox6, SAPK9, RbohA, CAS, RacB, ECS, VTE1, SAPK4, CDPK7, NUS1, GL1-2, Sce1, PsbR1, CYP21-4, PIP1;3, CIPK03, GRX8, MIOX, SLG, CKX3, HAP3A, CDPK9, JAR1, MFO1, LFY, ZMM4, HD3A, MADS24, BRD2, SK2(T)(SCL, FGR), SLR1, ILI5, GW2, PTR1, GA2OX3, ETR2, EXPA4, D2, D61, PDR6, ACO4, Rab6a, SERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, PP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, NPR1, LOX3, ALD1, RLCK185, LCB2A1, PhyB1, COP1, WRKY51, PLDbeta1, RAC5, CPK12, GF14e, SBP, HIR1, BWMKY1, AOS1, LOL2, GH3, GH3-8, XB3, GLP1, MAPK6, ACS2, LRR1, MPK3, SGT1, GAP1, RAC1, TPC1, GH3-2, BIANK1, CIPK14, BIDK1, MPK6, MKK4, Gns1, CCR1, MAPKY5, RACK1A, GI, phyB, Hd16, RCN1, SPL11, Spin1, PAL, PAL1, AGPS1, NRAMP3, MTP1, ATM3, YSL2, DMAS1, MRP5, SULTR3;3, AMT1;2, AMT3;1, NRT2.3b, GS1;2, ARG, NRT2.1, AMT1;1, AlaAT, ABC1, NADH-GOGAT, RBCS, NLA1, PHF1, MYB2P-1, CASTOR, INO1, sedoheptulose-1,7-bisphosphatase (SBPase), Fbpase; fructose-1,6-bisphosphatase, DET1, Os02g0465900, Hox32, BZR1, NAL1, AlaAT, NRT2.2, esp1, GW2-CHR5, Asn synthetase, AspAT, NAD(H)-dependent GOGAT 1, Gln1-3, obap1, AAP4 (amino acid permease 4), crtRB1, MRP1, DA1, DAR1, APS1, 6-phospho-fructokinase, wx1, shrunken 1, sus1, brittle endosperm bt2, sugary 1, sbe1, MADS22, RT, GAMYB, HSP90, AOS2, SPS1, NYC1, D35, PIMT1, PIMT2, TYDC, TET9, CYP703A3, D1|D2|Os07g0558500, ABA8OX1, ABA2, NCED1, ZEP1, ALDH7, CHS1, APX2, DOS, HOX33, NYC3, and APX1, or (b) a predetermined modification in a gene encoding a protein having at least 90% identity to a sequence selected from SEQ ID NOs:693-976, or (c) is a genomic sequence selected from SEQ ID NO:977-1260.

Other aspects of the invention are related to seed of the wheat plant having a modified genome, processed products made from the seed or from the wheat plant itself or from progeny seeds or progeny plants, and methods of manufacturing a wheat plant having a modified genome, methods of manufacturing seed of a wheat plant having a modified genome, and methods of manufacturing a processed wheat product made from the seed or from the wheat plant itself or from progeny seeds or progeny plants.

In another aspect, the invention provides a wheat plant cell having a modified genome in comparison to an unmodified wheat plant cell having an reference genome, wherein the modified genome differs from the reference genome by including at least one predetermined modification of a gene disclosed in Table 10, wherein the at least one predetermined modification is selected from the group consisting of: (a) heterologous integration of a nucleic acid sequence that is encoded by at least one donor polynucleotide molecule and that includes a regulatory element, at a predetermined locus between 1-1000 nucleotides or about 1-1000 nucleotides upstream of the start codon of the coding sequence of a gene of interest in the reference genome; (b) heterologous integration of a nucleic acid sequence that is encoded by at least one donor polynucleotide molecule and that includes a regulatory element at a predetermined locus within 1000 nucleotides downstream of the stop codon of a gene disclosed in Table 10; (c) deletion, addition, or substitution of at least one nucleotide in a regulatory element that regulates expression of a gene disclosed in Table 10; (d) deletion, addition, or substitution of at least one nucleotide in coding sequence of a gene disclosed in Table 10; and (e) a combination of any of (a), (b), (c), and (d); wherein the gene disclosed in Table 10 is selected from TsVP, ZmSEC14p, ACC synthase, D-myo-inositol-3-phosphate synthase (IPS), ZmbZIP72, ZmPLC1, ZmGOLS2, ZmPIS, ZmNF-YB, ZmPsbA, HB2, ZmPP2C2, ZmCIPK16, ZmSAPK8, OsABA8ox3, OsORAP1, OsDIS1, OsVPE3, OsRZFP34, ZFP185, DCA1, OsSRFP1, SQS, OsTPP1, SAPK6, JIOsPR10, OsClpD1, MSD1, OsWR1, OsTPS1, OsGS, OgTT1, OsFKBP20, OsANN1, OsSIK1, OsNHX1, OsMGD, OsDHODH1, Oshsp16.9, OsGME-2, OsChI1, OsCYP18-2, OsCNX, OsCBL8, OsCDPK13, OsRAN2, OsGGP, OVP1, ZFP177, RGG1, OsEm1, CTB4a, GS2, COLD1, OsACA6, OsRab7, OsTOP6A 1, osHsp101, OsAMTR1, Rubisco activase, OsSPX1, OsGME-1, OsMPG1, SNAC3, OsSDIR1, OsPgk2a-P, glyoxalase II, OsPUB15, OsIMP, OsHBP1b, OsCYP2, OsPEXI1 (Os03g0302000), OsCPK4, EG1, OsCBSX4, OsSIDP366, OsSUV3, GA2ox6, SAPK9, OsRbohA, OsCAS, OsRacB, OsECS, OsVTE1, SAPK4, OsCDPK7, NUS1, OsGL1-2, OsSce1, OsPsbR1, OsCYP21-4, OsPIP1;3, OsCIPK03, OsGRX8, OsMIOX, SLG, CKX3, HAP3A, CDPK9, JAR1, MFO1, LFY, ZMM4, HD3A, MADS24, BRD2, SK2(T)(SCL, FGR), SLR1, ILI5, GW2, ZmPTR1, GA2OX3, ETR2, EXPA4, D2, D61, PDR6, ACO4, Rab6a, OsSERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, ZmPP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, Zm NPR1, Zm LOX3, ALD1, RLCK185, LCB2A1, PhyB1, COP1, WRKY51, Os PLDbeta1, RAC5, OsCPK12, GF14e, Os SBP, OsHIR1, BWMKY1, AOS1, Os LOL2, GH3, GH3-8, XB3, GLP1, Os MAPK6, ACS2, OsLRR1, OsMPK3, Os SGT1, GAP1, Os RAC1, Os TPC1, GH3-2, OsBIANK1, CIPK14, OS BIDK1, OsMPK6, Os MKK4, Gns1, Os CCR1, Os MAPKY5, RACK1A, OsG1, OsphyB, Hd16, RCN1, SPL11, Spin1, PAL, PAL1, OsAGPS1, NRAMP3, OsMTP1, ATM3, OsYSL2, DMAS1, OsMRP5, OsSULTR3;3, AMT1;2, OsAMT3;1, OsNRT2.3b, GS1;2, OsARG, OsNRT2.1, AMT1;1, AlaAT, ABC1, NADH-GOGAT, RBCS, NLA1, PHF1, OsMYB2P-1, CASTOR, INO1, sedoheptulose-1,7-bisphosphatase (SBPase), Fbpase; fructose-1,6-bisphosphatase, OsDET1, Os02g0465900, OsHox32, OsBZR1, OsNAL1, AlaAT, ZmNRT2.2, esp1, ZmGW2-CHR5, Asn synthetase, AspAT, NAD(H)-dependent GOGAT 1, Gln1-3, obap1, ZmAAP4 (amino acid permease 4), crtRB1, ZmMRP1, ZmDA1, ZmDAR1, APS1, 6-phospho-fructokinase, wx1, shrunken 1, sus1, brittle endosperm bt2, sugary 1, sbe1, MADS22, RT, GAMYB, HSP90, AOS2, SPS1, NYC1, D35, PIMT1, PIMT2, TYDC, TEM, CYP703A3, D1|D2|Os07g0558500, ABA8OX1, OsABA2, NCED1, ZEP1, ALDH7, CHS1, APX2, DOS, HOX33, NYC3, and APX1, or is a gene encoding a protein having at least 90% identity to a sequence selected from SEQ ID NOs:693-976, or is a genomic sequence selected from SEQ ID NO:977-1260. In embodiments, the gene disclosed in Table 10 includes at least one homeoallele each of two or more genes selected from TsVP, ZmSEC14p, ACC synthase, D-myo-inositol-3-phosphate synthase (IPS), ZmbZIP72, ZmPLC1, ZmGOLS2, ZmPIS, ZmNF-YB, ZmPsbA, HB2, ZmPP2C2, ZmCIPK16, ZmSAPK8, OsABA8ox3, OsORAP1, OsDIS1, OsVPE3, OsRZFP34, ZFP185, DCA1, OsSRFP1, SQS, OsTPP1, SAPK6, JIOsPR10, OsClpD1, MSD1, OsWR1, OsTPS1, OsGS, OgTT1, OsFKBP20, OsANN1, OsSIK1, OsNHX1, OsMGD, OsDHODH1, Oshsp16.9, OsGME-2, OsChI1, OsCYP18-2, OsCNX, OsCBL8, OsCDPK13, OsRAN2, OsGGP, OVP1, ZFP177, RGG1, OsEm1, CTB4a, GS2, COLD1, OsACA6, OsRab7, OsTOP6A 1, osHsp101, OsAMTR1, Rubisco activase, OsSPX1, OsGME-1, OsMPG1, SNAC3, OsSDIR1, OsPgk2a-P, glyoxalase II, OsPUB15, OsIMP, OsHBP1b, OsCYP2, OsPEXI1 (Os03g0302000), OsCPK4, EG1, OsCBSX4, OsSIDP366, OsSUV3, GA2ox6, SAPK9, OsRbohA, OsCAS, OsRacB, OsECS, OsVTE1, SAPK4, OsCDPK7, NUS1, OsGL1-2, OsSce1, OsPsbR1, OsCYP21-4, OsPIP1;3, OsCIPK03, OsGRX8, OsMIOX, SLG, CKX3, HAP3A, CDPK9, JAR1, MFO1, LFY, ZMM4, HD3A, MADS24, BRD2, SK2(T)(SCL, FGR), SLR1, ILI5, GW2, ZmPTR1, GA2OX3, ETR2, EXPA4, D2, D61, PDR6, ACO4, Rab6a, OsSERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, ZmPP2AAI1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, Zm NPR1, Zm LOX3, ALD1, RLCK185, LCB2A1, PhyB1, COP1, WRKY51, Os PLDbeta1, RAC5, OsCPK12, GF14e, Os SBP, OsHIR1, BWMKY1, AOS1, Os LOL2, GH3, GH3-8, XB3, GLP1, Os MAPK6, ACS2, OsLRR1, OsMPK3, Os SGT1, GAP1, Os RAC1, Os TPC1, GH3-2, OsBIANK1, CIPK14, OS BIDK1, OsMPK6, Os MKK4, Gns1, Os CCR1, Os MAPKY5, RACK1A, OsG1, OsphyB, Hd16, RCN1, SPL11, Spin1, PAL, PAL1, OsAGPS1, NRAMP3, OsMTP1, ATM3, OsYSL2, DMAS1, OsMRP5, OsSULTR3;3, AMT1;2, OsAMT3;1, OsNRT2.3b, GS1;2, OsARG, OsNRT2.1, AMT1;1, AlaAT, ABC1, NADH-GOGAT, RBCS, NLA1, PHF1, OsMYB2P-1, CASTOR, INO1, sedoheptulose-1,7-bisphosphatase (SBPase), Fbpase; fructose-1,6-bisphosphatase, OsDET1, Os02g0465900, OsHox32, OsBZR1, OsNAL1, AlaAT, ZmNRT2.2, esp1, ZmGW2-CHR5, Asn synthetase, AspAT, NAD(H)-dependent GOGAT 1, Gln1-3, obap1, ZmAAP4 (amino acid permease 4), crtRB1, ZmMRP1, ZmDA1, ZmDAR1, APS1, 6-phospho-fructokinase, wx1, shrunken 1, sus1, brittle endosperm bt2, sugary 1, sbe1, MADS22, RT, GAMYB, HSP90, AOS2, SPS1, NYC1, D35, PIMT1, PIMT2, TYDC, TET9, CYP703A3, D1|D2|Os07g0558500, ABA8OX1, OsABA2, NCED1, ZEP1, ALDH7, CHS1, APX2, DOS, HOX33, NYC3, and APX1. In some embodiments, the modified genome further differs from the reference genome by including (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, Lr34, Lr67, Sr22, Sr33, Sr35, Sr45, Sr50, Tsn1, Yr36 (WKS1), Snn1, TaMLO-A1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV1SM, SOD, APX, GS2, NAM, rbcL, IVR1, and a1 as disclosed in Table 9, or (b) a predetermined modification in a gene encoding a protein having at least 90% identity to a sequence selected from SEQ ID NOs:257-474 as disclosed in Table 9, or (c) a predetermined modification in a gene selected from the genomic sequences identified as SEQ ID NOs:475-692 as disclosed in Table 9.

In a related aspect, the invention provides a method of changing expression of a sequence of interest in a genome, such as a wheat genome, including integrating a sequence encoded by a donor polynucleotide, such as a double-stranded or single-stranded polynucleotides including DNA, RNA, or a combination of DNA and RNA, at the site of at least one double-strand break (DSB) in a genome, which can be the genome of a eukaryotic nucleus (e.g., the nuclear genome of a plant cell) or a genome of an organelle (e.g., a mitochondrion or a plastid in a plant cell). Effector molecules for site-specific introduction of a DSB into a genome include various endonucleases (e.g., RNA-guided nucleases such as a type II Cas nuclease, a Cas9, a type V Cas nuclease, a Cpf1, a CasY, a CasX, a C2c1, or a C2c3) and guide RNAs that direct cleavage by an RNA-guided nuclease. Embodiments include those where the DSB is introduced into a genome by a ribonucleoprotein complex containing both a site-specific nuclease (e.g., Cas9, Cpf1, CasX, CasY, C2c1, C2c3) and at least one guide RNA, or by a site-specific nuclease in combination with at least one guide RNA; in some of these embodiments no plasmid or other expression vector is utilized to provide the nuclease, the guide RNA, or the polynucleotide. These effector molecules are delivered to the cell or organelle wherein the DSB is to be introduced by the use of one or more suitable composition or treatment, such as at least one chemical, enzymatic, or physical agent, or application of heat or cold, ultrasonication, centrifugation, electroporation, particle bombardment, and bacterially mediated transformation. It is generally desirable that the DSB is induced at high efficiency. One measure of efficiency is the percentage or fraction of the population of cells that have been treated with a DSB-inducing agent and in which the DSB is successfully introduced at the correct site in the genome. The efficiency of genome editing is assessed by any suitable method such as a heteroduplex cleavage assay or by sequencing, as described elsewhere in this disclosure. In various embodiments, the DSB is introduced at a comparatively high efficiency, e.g., at about 20, about 30, about 40, about 50, about 60, about 70, or about 80 percent efficiency, or at greater than 80, 85, 90, or 95 percent efficiency. In embodiments, the DSB is introduced upstream of, downstream of, or within the sequence of interest, which is coding, non-coding, or a combination of coding and non-coding sequence. In embodiments, a sequence encoded by the polynucleotide (such as a double-stranded DNA, a single-stranded DNA, a single-stranded DNA/RNA hybrid, or a double-stranded DNA/RNA hybrid), when integrated into the site of the DSB in the genome, is then functionally or operably linked to the sequence of interest, e.g., linked in a manner that modifies the transcription or the translation of the sequence of interest or that modifies the stability of a transcript including that of the sequence of interest. Embodiments include those where two or more DSBs are introduced into a genome, and wherein a sequence encoded by a polynucleotide (such as a double-stranded DNA, a single-stranded DNA, a single-stranded DNA/RNA hybrid, or a double-stranded DNA/RNA hybrid) that is integrated into each DSB is the same or different for each of the DSBs. In embodiments, at least two DSBs are introduced into a genome by one or more nucleases in such a way that genomic sequence (coding, non-coding, or a combination of coding and non-coding sequence) is deleted between the DSBs (leaving a deletion with blunt ends, overhangs or a combination of a blunt end and an overhang), and a sequence encoded by a polynucleotide (such as a double-stranded DNA, a single-stranded DNA, a single-stranded DNA/RNA hybrid, or a double-stranded DNA/RNA hybrid) molecule is integrated between the DSBs (i.e., at the location of the deleted genomic sequence). The method is particularly useful for integrating into the site of a DSB a heterologous nucleotide sequence that provides a useful function or use. For example, the method is useful for integrating or introducing into the genome a heterologous sequence that stops or knocks out expression of a sequence of interest (such as a gene encoding a protein), or a heterologous sequence that is a unique identifier nucleotide sequence, or a heterologous sequence that is (or that encodes) a sequence recognizable by a specific binding agent or that binds to a specific molecule, or a heterologous sequence that stabilizes or destabilizes a transcript containing it. Embodiments include use of the method to integrate or introduce into a genome the sequence of a non-coding regulatory element, such as a promoter or promoter-like element (e.g., sequence of an auxin-binding or hormone-binding or transcription-factor-binding element, or sequence of or encoding an aptamer or riboswitch), or a sequence-specific binding or cleavage site sequence (e.g., sequence of or encoding an endonuclease cleavage site, a small RNA recognition site, a recombinase site, a splice site, or a transposon recognition site). In embodiments, the method is used to delete or otherwise modify to make non-functional an endogenous functional sequence, such as a hormone- or transcription-factor-binding element, or a small RNA or recombinase or transposon recognition site. In embodiments, additional molecules are used to effect a desired expression result or a desired genomic change. For example, the method is used to integrate heterologous recombinase recognition site sequences at two DSBs in a genome, and the appropriate recombinase molecule is employed to excise genomic sequence located between the recombinase recognition sites. In another example, the method is used to integrate a polynucleotide-encoded heterologous small RNA recognition site sequence at a DSB in a sequence of interest in a genome, wherein when the small RNA is present (e.g., expressed endogenously or transiently or transgenically), the small RNA binds to and cleaves the transcript of the sequence of interest that contains the integrated small RNA recognition site. In another example, the method is used to integrate in the genome of a wheat plant or plant cell a donor polynucleotide-encoded promoter or promoter-like element that is responsive to a specific molecule (e.g., an auxin, a hormone, a drug, an herbicide, or a polypeptide), wherein a specific level of expression of the sequence of interest is obtained by providing the corresponding specific molecule to the plant or plant cell; in a non-limiting example, an auxin-binding element is integrated into the promoter region of a protein-coding sequence in the genome of a plant or plant cell, whereby the expression of the protein is upregulated when the corresponding auxin is exogenously provided to the plant or plant cell (e.g., by adding the auxin to the medium of the plant cell or by spraying the auxin onto the plant). Another aspect of the invention is a wheat cell including in its genome a heterologous DNA sequence, wherein the heterologous sequence includes (a) nucleotide sequence of a polynucleotide integrated by the method at the site of a DSB in the genome, and (b) genomic nucleotide sequence adjacent to the site of the DSB; related aspects include a plant containing such a cell including in its genome a heterologous DNA sequence, progeny seed or plants (including hybrid progeny seed or plants) of the plant, and processed or commodity products derived from the plant or from progeny seed or plants. In another aspect, the invention provides a heterologous nucleotide sequence including (a) nucleotide sequence of a polynucleotide (such as a double-stranded DNA, a single-stranded DNA, a single-stranded DNA/RNA hybrid, or a double-stranded DNA/RNA hybrid) molecule integrated by the method at the site of a DSB in a genome, and (b) genomic nucleotide sequence adjacent to the site of the DSB; related aspects include larger polynucleotides such as a plasmid, vector, or chromosome including the heterologous nucleotide sequence, as well as a polymerase primer for amplification of the heterologous nucleotide sequence.

In another aspect, the invention provides a composition including a wheat plant cell and a donor polynucleotide molecule (such as a double-stranded DNA, a single-stranded DNA, a single-stranded DNA/RNA hybrid, or a double-stranded DNA/RNA hybrid) that is capable of being integrated at (or having its sequence integrated at) a double-strand break in genomic sequence in the wheat plant cell. In various embodiments, the wheat plant cell is an isolated plant cell or plant protoplast, or is in a wheat plant, a zygotic or somatic embryo, seed, plant part, or plant tissue. In embodiments the wheat plant cell is capable of division or differentiation. In embodiments the plant cell is haploid, diploid, or polyploid. In embodiments, the wheat plant cell includes a double-strand break (DSB) in its genome, at which DSB site the donor polynucleotide molecule is integrated using methods disclosed herein. In embodiments, at least one DSB is induced in the wheat plant cell's genome by including in the composition a DSB-inducing agent, for example, various endonucleases (e.g., RNA-guided nucleases such as a type II Cas nuclease, a Cas9, a type V Cas nuclease, a Cpf1, a CasY, a CasX, a C2c1, or a C2c3) and guide RNAs that direct cleavage by an RNA-guided nuclease; sequence encoded by the donor polynucleotide molecule is integrated into the DSB thus induced using methods disclosed herein. Specific embodiments include compositions including a wheat plant cell, at least one donor polynucleotide molecule, and at least one ribonucleoprotein complex containing both a site-specific nuclease (e.g., Cas9, Cpf1, CasX, CasY, C2c1, C2c3) and at least one guide RNA; in some of these embodiments, the composition contains no plasmid or other transcribable expression vector for providing the nuclease, the guide RNA, or the donor polynucleotide. In embodiments of the composition, the donor polynucleotide molecule is double-stranded DNA or RNA or a combination of DNA and RNA, and is blunt-ended, or contains one or more terminal overhangs, or contains chemical modifications such as phosphorothioate bonds or a detectable label. In other embodiments, the donor polynucleotide molecule is a single-stranded polynucleotide composed of DNA or RNA or a combination of DNA or RNA, and can further be chemically modified or labelled. In various embodiments of the composition, the donor polynucleotide molecule includes a nucleotide sequence that provides a useful function when integrated into the site of the DSB. For example, in various non-limiting embodiments the donor polynucleotide molecule includes: sequence that is recognizable by a specific binding agent or that binds to a specific molecule or encodes an RNA molecule or an amino acid sequence that binds to a specific molecule, or sequence that is responsive to a specific change in the physical environment or encodes an RNA molecule or an amino acid sequence that is responsive to a specific change in the physical environment, or heterologous sequence, or sequence that serves stop transcription or translation at the site of the DSB, or sequence having secondary structure (e.g., double-stranded stems or stem-loops) or than encodes a transcript having secondary structure (e.g., double-stranded RNA that is cleavable by a Dicer-type ribonuclease). In particular embodiments, the modifications to the wheat cell or plant will affect the activity or expression of one or more genes or proteins listed in Table 9, and in some embodiments two or more of those genes or proteins. In particular embodiments, the modifications to the wheat cell or plant will affect the activity or expression of one or more genes or proteins listed in Table 10, and in some embodiments two or more of those genes or proteins. In particular embodiments, the modifications to the wheat cell or plant will affect the activity or expression of one or more genes or proteins listed in Table 9 and of one or more genes or proteins listed in Table 10. In related embodiments, the activity or expression of one or more genes or proteins listed in Table 9 will be altered by the introduction or creation of one or more of the regulatory sequences listed in Table 8. In related embodiments, the activity or expression of one or more genes or proteins listed in Table 10 will be altered by the introduction or creation of one or more of the regulatory sequences listed in Table 8.

In another aspect, the invention provides a reaction mixture including: (a) a wheat plant cell having at least one double-strand break (DSB) at a locus in its genome; and (b) a donor polynucleotide molecule (such as a double-stranded DNA, a single-stranded DNA, a single-stranded DNA/RNA hybrid, or a double-stranded DNA/RNA hybrid) capable of being integrated into (or having its sequence integrated at) the DSB (preferably by non-homologous end-joining (NHEJ)), wherein the donor polynucleotide molecule has a length of between about 18 to about 300 base-pairs or about 18 to about 300 base-pairs (or nucleotides, if single-stranded), or between about 30 to about 100 base-pairs or about 30 to about 100 base-pairs (or nucleotides, if single-stranded); wherein the donor polynucleotide molecule includes a sequence which, if integrated at the DSB, forms a heterologous insertion (wherein the sequence of the donor polynucleotide molecule is heterologous with respect to the genomic sequence flanking the insertion site or DSB). In embodiments of the reaction mixture, the wheat plant cell is an isolated plant cell or plant protoplast. In various embodiments, the wheat plant cell is an isolated plant cell or plant protoplast, or is in a wheat plant, a zygotic or somatic embryo, seed, plant part, or plant tissue. In embodiments the wheat plant cell is capable of division or differentiation. In embodiments the wheat plant cell is haploid, diploid, or polyploid. In embodiments of the reaction mixture, the donor polynucleotide molecule includes a nucleotide sequence that provides a useful function or use when integrated into the site of the DSB. For example, in various non-limiting embodiments the donor polynucleotide molecule includes: sequence that is recognizable by a specific binding agent or that binds to a specific molecule or encodes an RNA molecule or an amino acid sequence that binds to a specific molecule, or sequence that is responsive to a specific change in the physical environment or encodes an RNA molecule or an amino acid sequence that is responsive to a specific change in the physical environment, or heterologous sequence, or sequence that serves to stop transcription or translation at the site of the DSB, or sequence having secondary structure (e.g., double-stranded stems or stem-loops) or than encodes a transcript having secondary structure (e.g., double-stranded RNA that is cleavable by a Dicer-type ribonuclease).

In another aspect, the invention provides a donor polynucleotide molecule for disrupting gene expression, wherein the donor polynucleotide molecule is double-stranded and includes at least 18 contiguous base-pairs and encoding at least one stop codon in each possible reading frame on each strand, or is single-stranded and includes at least 11 contiguous nucleotides; and wherein the donor polynucleotide molecule encodes at least one stop codon in each possible reading frame on each strand. In embodiments, the donor polynucleotide molecule is a double-stranded DNA (dsDNA) or a double-stranded DNA/RNA hybrid molecule including at least 18 contiguous base-pairs and encoding at least one stop codon in each possible reading frame on either strand. In embodiments, the donor polynucleotide molecule is a single-stranded DNA or a single-stranded DNA/RNA hybrid molecule including at least 11 contiguous nucleotides and encoding at least one stop codon in each possible reading frame on the strand. Such a donor polynucleotide molecule is especially useful in methods disclosed herein, wherein, when a sequence encoded by the donor polynucleotide molecule is integrated or inserted into a genome at the site of a DSB in a sequence of interest (such as a protein-coding gene), the sequence of the heterologously inserted donor polynucleotide molecule serves to stop translation of the transcript containing the sequence of interest and the heterologously inserted donor polynucleotide molecule sequence. Embodiments of the donor polynucleotide molecule include those wherein the donor polynucleotide molecule includes one or more chemical modifications or labels, e.g., at least one phosphorothioate modification.

In another aspect, the invention provides a method of identifying the locus of at least one double-stranded break (DSB) in genomic DNA in a wheat cell including the genomic DNA, wherein the method includes the steps of: (a)

contacting the genomic DNA having a DSB with a donor polynucleotide molecule (such as a double-stranded DNA, a single-stranded DNA, a single-stranded DNA/RNA hybrid, or a double-stranded DNA/RNA hybrid), wherein the donor polynucleotide molecule is capable of being integrated (or having its sequence integrated) at the DSB (preferably by non-homologous end-joining (NHEJ)) and has a length of between about 18 to about 300 base-pairs or about 18 to about 300 base-pairs (or nucleotides, if single-stranded), or between about 30 to about 100 base-pairs or about 30 to about 100 base-pairs (or nucleotides, if single-stranded); wherein a sequence encoded by the donor polynucleotide molecule, if integrated at the DSB, forms a heterologous insertion; and (b) using at least part of the sequence of the donor polynucleotide molecule as a target for PCR primers to allow amplification of DNA in the locus of the DSB. In a related aspect, the invention provides a method of identifying the locus of double-stranded breaks (DSBs) in genomic DNA in a pool of wheat cells (such as wheat cells or protoplasts), wherein the pool of wheat cells includes cells having genomic DNA with a sequence encoded by a donor polynucleotide molecule inserted at the locus of the double-stranded breaks; wherein the donor polynucleotide molecule is capable of being integrated (or having its sequence integrated) at the DSB and has a length of between about 18 to about 300 base-pairs or about 18 to about 300 base-pairs (or nucleotides, if single-stranded), or between about 30 to about 100 base-pairs or about 30 to about 100 base-pairs (or nucleotides, if single-stranded); wherein a sequence encoded by the donor polynucleotide molecule, if integrated at the DSB, forms a heterologous insertion; and wherein the sequence of the donor polynucleotide molecule is used as a target for PCR primers to allow amplification of DNA in the region of the double-stranded breaks. In embodiments, the pool of wheat cells is a population of wheat cells or wheat protoplasts, wherein at least some of the wheat cells contain multiple or different DSBs in the genome, each of which can be introduced into the genome by a different guide RNA.

In another aspect, the invention provides a method of identifying the nucleotide sequence of a locus in a wheat genome that is associated with a phenotype, the method including the steps of: (a) providing to a population of wheat cells having the genome: (i) multiple different guide RNAs (gRNAs) to induce multiple different double strand breaks (DSBs) in the genome, wherein each DSB is produced by an RNA-guided nuclease guided to a locus on the genome by one of the gRNAs, and (ii) polynucleotide (such as double-stranded DNA, single-stranded DNA, single-stranded DNA/RNA hybrid, and double-stranded DNA/RNA hybrid) donor molecules having a defined nucleotide sequence, wherein the donor polynucleotide molecules are capable of being integrated (or having their sequence integrated) into the DSBs by non-homologous end-joining (NHEJ); whereby when at least a sequence encoded by some of the donor polynucleotide molecules are inserted into at least some of the DSBs, a genetically heterogeneous population of cells is produced; (b) selecting from the genetically heterogeneous population of wheat cells a subset of wheat cells that exhibit a phenotype of interest; (c) using a pool of PCR primers that bind to at least part of the nucleotide sequence of the donor polynucleotide molecules to amplify from the subset of wheat cells DNA from the locus of a DSB into which one of the donor polynucleotide molecules has been inserted; and (d) sequencing the amplified DNA to identify the locus associated with the phenotype of interest. In embodiments of the method, the gRNA is provided as a polynucleotide, or as a ribonucleoprotein including the gRNA and the RNA-guided nuclease. Related aspects include the wheat cells produced by the method and pluralities, arrays, and genetically heterogeneous populations of such wheat cells, as well as the subset of wheat cells in which the locus associated with the phenotype has been identified, and wheat callus, wheat seedlings, wheat plantlets, and wheat plants and their seeds, grown or regenerated from such wheat cells.

In another aspect, the invention provides a method of modifying a wheat cell by effecting the precise integration into one or more predetermined loci in the wheat genome of a heterologous sequence encoded by at least one donor polynucleotide molecule, wherein the method comprises contacting the wheat cell with one or more sequence-specific nucleases and one or more guide RNA molecules and one or more donor polynucleotide molecules. In embodiments, the sequence of at least two different donor polynucleotide molecules is each heterologously integrated at a different predetermined locus in the wheat genome. In embodiments, the sequence encoded by at least one donor polynucleotide molecule is a heterologous non-coding regulatory sequence that when integrated in the wheat genome results in a change of expression (e.g., increased or decreased expression) of one or more genes of interest; in embodiments, such a change in expression of one or more genes of interest results in a detectable phenotype in the wheat cell, or in a desirable trait in a wheat plant grown from the wheat cell, in comparison to a control wheat plant lacking the heterologously integrated sequence. In embodiments, precise integration of a heterologous non-coding regulatory sequence in the upstream or downstream region of a gene of interest in the wheat genome results in an increase in expression of the gene of interest that is at least a 10%, 15%, 20%, 25%, 30%, 35%, 40%, 50%, 60%, 70%, 80%, 90%, 95%, or 100% or greater increase, e.g., at least a 2-fold, 5-fold, 10-fold, 20-fold, 30-fold, 40-fold, 50-fold, or 100-fold increase, or even greater than 100-fold increase, in comparison to the expression of the gene of interest in the absence of the precisely integrated heterologous non-coding regulatory sequence. In embodiments, expression of the gene of interest is increased between 10-100%; between 2-fold and 5-fold; between 2 and 10-fold; between 10-fold and 50-fold; between 10-fold and a 100-fold; between 100-fold and 1000-fold; between 1000-fold and 5,000-fold; between 5,000-fold and 10,000 fold, in comparison to the expression of the gene of interest in the absence of the precisely integrated heterologous non-coding regulatory sequence. In embodiments, expression of the gene of interest is increased about 10-100%; about 2-fold to 5-fold; about 2 to 10-fold; about 10-fold to 50-fold; about 10-fold to a 100-fold; about 100-fold to 1000-fold; about 1000-fold to 5,000-fold; or about 5,000-fold to 10,000 fold, in comparison to the expression of the gene of interest in the absence of the precisely integrated heterologous non-coding regulatory sequence. In embodiments, precise integration of a heterologous non-coding regulatory sequence in the upstream or downstream region of a gene of interest in the wheat genome results in a decrease in expression of the gene of interest that is at least a 5%, 10%, 15%, 20%, 25%, 30%, 35%, 40%, 50%, 60%, 70%, 80%, 90%, 95%, or 100% decrease, in comparison to the expression of the gene of interest in the absence of the precisely integrated heterologous non-coding regulatory sequence. In embodiments, expression of the gene of interest is decreased between 10-100%, or between 5-20%, or between 5-50%, or between 10-25%, or between 40-80%, in comparison to the expression of the gene of interest in the absence of the precisely integrated heterologous non-coding regulatory sequence. In embodiments, expression of the gene of interest is decreased about 10-100%, or about 5-20%, or about 5-50%, or about 10-25%, or about 40-80%, in comparison to the expression of the gene of interest in the absence of the precisely integrated heterologous non-coding regulatory sequence. In embodiments, at least one of the donor polynucleotide molecules lacks sequence homology to the genome sequences adjacent to the site of integration. In embodiments, at least one of the donor polynucleotide molecules used in the method is a single-stranded DNA molecule, a single-stranded RNA molecule, a single-stranded DNA-RNA hybrid molecule, or a duplex RNA-DNA molecule. In embodiments, the heterologously inserted sequence encoded by a donor polynucleotide molecule is between 3 and 100 nucleotides in length, between 3 and 400 nucleotides in length, between 5 and 120 nucleotides in length, between 5 and 200 nucleotides in length, between 10 and 350 nucleotides in length, between 18 and 350 nucleotides in length, between 18 and 200 nucleotides in length, between 10 and 150 nucleotides in length, or between 11 and 100 nucleotides in length. In embodiments, the heterologously inserted sequence encoded by a donor polynucleotide molecule is about 3 and 100 nucleotides in length, about 3 and 400 nucleotides in length, about 5 and 120 nucleotides in length, about 5 and 200 nucleotides in length, about 10 and 350 nucleotides in length, about 18 and 350 nucleotides in length, about 18 and 200 nucleotides in length, about 10 and 150 nucleotides in length, or about 11 and 100 nucleotides in length. In embodiments, the heterologous insertion of non-coding regulatory sequence is accompanied by predetermined deletions of one or more nucleotides. In embodiments, wherein the modified wheat cell of the method is a meristematic cell, embryonic cell, or germline cell. In embodiments, the methods described in this paragraph, when practiced repeatedly or on a pool of wheat cells, result in an efficiency of at least 1%, e.g., at least 2%, 5%, 7%, 10%, 15%, 20%, 25%, 30%, 35% or more, wherein said efficiency is determined, e.g., by dividing the number of successfully targeted cells by the total number of cells targeted. In embodiments, the method of modifying a wheat cell further includes obtaining a wheat plant or growing a wheat plant from the modified wheat cell, and producing and harvesting seed from the wheat plant, or breeding the wheat plant. In embodiments In embodiments of the wheat genome modification methods described above, the donor polynucleotide molecule is tethered to an RNP including a sequence-specific nuclease and a guide RNA, or to a crRNA, by a covalent bond, a non-covalent bond, or a combination of covalent and non-covalent bonds. In a related embodiment, the invention provides a composition for modifying a genome that includes a donor polynucleotide molecule tethered to an RNP including a sequence-specific nuclease and a guide RNA, or to a crRNA, by a covalent bond, a non-covalent bond, or a combination of covalent and non-covalent bonds.

In embodiments of the wheat genome modification methods described above, the loss of epigenetic marks after modifying occurs in less than 0.1%, 0.08%, 0.05%, 0.02%, or 0.01% of the genome. In yet another embodiment of the precise modification methods described above, the genome of the modified wheat plant or wheat cell is more than 99%, e.g., more than 99.5% or more than 99.9% identical to the genome of the unmodified wheat plant or wheat cell.

Aspects of the invention also provide modified wheat plants or wheat cells that include at least two precisely predetermined and non-random modifications in its genome, wherein the modifications are determined relative to a unmodified wheat plant or wheat cell having a reference genome, and wherein the modified wheat plant or wheat cell is devoid of mitotically or meiotically generated genetic or epigenetic changes relative to the unmodified wheat plant or wheat cell. In certain embodiments, these modified wheat plants or wheat cells are obtained by the methods described in detail herein, e.g., using procedures similar to those described in detail in the working Examples. In certain embodiments, the genome of the modified wheat plants or wheat cells is at least 95%, at least 96%, at least 97%, at least 98%, at least 99%, at least 99.5%, at least 99.9%, or at least 99.99% identical to the reference genome, taking all genetic or epigenetic changes into account.

In some embodiments, the invention provides a method of manufacturing a processed wheat product, comprising: (a) modifying a wheat cell according to a method described herein; (b) growing a modified wheat plant from the modified wheat cell, and (c) processing the modified wheat plant or its seed into a processed product, thereby manufacturing a processed wheat product. In embodiments, the processed wheat product is selected from the group consisting of intact wheat grains, wheat berries, cracked wheat, parched wheat, malt, grits, groats, semolina, middlings, flakes, flour, meal, bran, germ, endosperm, starch, gluten, protein, oil, chaff, fibre, and straw, or some other commodity wheat product. The invention also provides a method of manufacturing a harvested wheat product, comprising (a) modifying a wheat cell according to a method described herein, (b) growing a modified wheat plant from the modified wheat cell, and (c) harvesting a product of the modified wheat plant, thereby manufacturing a harvested wheat product. In embodiments, the harvested wheat product is selected from the group consisting of leaves, seeds, stems or stalks, hay, fodder, silage, stover, straw, or pollen. In further related embodiments, the processed wheat products and harvested wheat products are packaged.

BRIEF DESCRIPTION OF THE DRAWINGS

FIG. 1A,B depicts results of experiments described in detail in Example 15. Panel A illustrates mean relative gene expression of Dof1 (solid black bars), NRT2.2 (solid white bars), and Gln1.4 (diagonally hatched bars) genes, normalized to tubulin expression. Null controls are indicated by the "-" symbol. Panel B illustrates mean relative gene expression of the unmodified, endogenous AMT3, normalized to tubulin expression, in the presence of KCl (solid black bars) or $KNO_3$ (solid white bars), in cells where the Dof1, NRT2.2, and Gln1.4 genes were individually modified, or where all three genes were modified ("Multiplex"). Null controls are indicated by the "-" symbol.

DETAILED DESCRIPTION OF THE INVENTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art. Where a term is provided in the singular, the inventors also contemplate aspects of the invention described by the plural of that term.

By "polynucleotide" is meant a nucleic acid molecule containing multiple nucleotides and refers to "oligonucleotides" (defined here as a polynucleotide molecule of between 2-25 nucleotides in length) and polynucleotides of 26 or more nucleotides. Polynucleotides are generally described as single- or double-stranded. Where a polynucleotide contains double-stranded regions formed by intra- or intermolecular hybridization, the length of each double-stranded region is conveniently described in terms of the number of base pairs. Aspects of this invention include the use of polynucleotides or compositions containing polynucleotides; embodiments include one or more oligonucleotides or polynucleotides or a mixture of both, including single- or double-stranded RNA or single- or double-stranded DNA or single- or double-stranded DNA/RNA hybrids or chemically modified analogues or a mixture thereof. In various embodiments, a polynucleotide (such as a single-stranded DNA/RNA hybrid or a double-stranded DNA/RNA hybrid) includes a combination of ribonucleotides and deoxyribonucleotides (e.g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides), or includes non-canonical nucleotides such as inosine, thiouridine, or pseudouridine. In embodiments, the polynucleotide includes chemically modified nucleotides (see, e.g., Verma and Eckstein (1998) Annu. Rev. Biochem., 67:99-134); for example, the naturally occurring phosphodiester backbone of an oligonucleotide or polynucleotide can be partially or completely modified with phosphorothioate, phosphorodithioate, or methylphosphonate internucleotide linkage modifications; modified nucleoside bases or modified sugars can be used in oligonucleotide or polynucleotide synthesis; and oligonucleotides or polynucleotides can be labelled with a fluorescent moiety (e.g., fluorescein or rhodamine or a fluorescence resonance energy transfer or FRET pair of chromophore labels) or other label (e.g., biotin or an isotope). Modified nucleic acids, particularly modified RNAs, are disclosed in U.S. Pat. No. 9,464,124, incorporated by reference in its entirety herein. For some polynucleotides (especially relatively short polynucleotides, e.g., oligonucleotides of 2-25 nucleotides or base-pairs, or polynucleotides of about 25 to about 300 nucleotides or base-pairs), use of modified nucleic acids, such as locked nucleic acids ("LNAs"), is useful to modify physical characteristics such as increased melting temperature ($T_m$) of a polynucleotide duplex incorporating DNA or RNA molecules that contain one or more LNAs; see, e.g., You et al. (2006) *Nucleic Acids Res.*, 34:1-11 (e60), doi:10.1093/nar/gkl175.

Reagents, compositions, and methods for genome editing: CRISPR technology for editing the genes of eukaryotes is disclosed in U.S. Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in U.S. Patent Application Publication 2016/0208243 A1. Other CRISPR nucleases useful for editing genomes include C2c1 and C2c3 (see Shmakov et al. (2015) *Mol. Cell,* 60:385-397) and CasX and CasY (see Burstein et al. (2016) *Nature*, doi:10.1038/nature21059). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in in U.S. Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246).

CRISPR (Clustered Regularly Interspaced Short Palindromic Repeats)/Cas (CRISPR-associated) systems, or CRISPR systems, are adaptive defense systems originally discovered in bacteria and archaea. CRISPR systems use RNA-guided nucleases termed CRISPR-associated or "Cas" endonucleases (e.g., Cas9 or Cpf1) to cleave foreign DNA. In a typical CRISPR/Cas system, a Cas endonuclease is directed to a target nucleotide sequence (e.g., a site in the genome that is to be sequence-edited) by sequence-specific, non-coding "guide RNAs" that target single- or double-stranded DNA sequences. In microbial hosts, CRISPR loci encode both Cas endonucleases and "CRISPR arrays" of the non-coding RNA elements that determine the specificity of the CRISPR-mediated nucleic acid cleavage.

Three classes (I-III) of CRISPR systems have been identified across a wide range of bacterial hosts. The well characterized class II CRISPR systems use a single Cas endonuclease (rather than multiple Cas proteins). One class II CRISPR system includes a type II Cas endonuclease such as Cas9, a CRISPR RNA ("crRNA"), and a trans-activating crRNA ("tracrRNA"). The crRNA contains a "guide RNA", typically a 20-nucleotide RNA sequence that corresponds to (i.e., is identical or nearly identical to, or alternatively is complementary or nearly complementary to) a 20-nucleotide target DNA sequence. The crRNA also contains a region that binds to the tracrRNA to form a partially double-stranded structure which is cleaved by RNase III, resulting in a crRNA/tracrRNA hybrid. The crRNA/tracrRNA hybrid then directs the Cas9 endonuclease to recognize and cleave the target DNA sequence.

The target DNA sequence must generally be adjacent to a "protospacer adjacent motif" ("PAM") that is specific for a given Cas endonuclease; however, PAM sequences are short and relatively non-specific, appearing throughout a given genome. CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). Some endonucleases, e.g., Cas9 endonucleases, are associated with G-rich PAM sites, e.g., 5'-NGG, and perform blunt-end cleaving of the target DNA at a location 3 nucleotides upstream from (5' from) the PAM site.

Another class II CRISPR system includes the type V endonuclease Cpf1, which is a smaller endonuclease than is Cas9; examples include AsCpf1 (from *Acidaminococcus* sp.) and LbCpf1 (from *Lachnospiraceae* sp.). Cpf1-associated CRISPR arrays are processed into mature crRNAs without the requirement of a tracrRNA; in other words, a Cpf1 system requires only the Cpf1 nuclease and a crRNA to cleave the target DNA sequence. Cpf1 endonucleases, are associated with T-rich PAM sites, e.g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e.g., Zetsche et al. (2015) *Cell*, 163:759-771. Other CRISPR nucleases useful in methods and compositions of the invention include C2c1 and C2c3 (see Shmakov et al. (2015)*Mol. Cell*, 60:385-397). Like other CRISPR nucleases, C2c1 from *Alicyclobacillus acidoterrestris* (AacC2c1; amino acid sequence with accession ID TOD7A2, deposited on-line at www[dot]ncbi[dot]nlm [dot]nih[dot]gov/protein/1076761101) requires a guide RNA and PAM recognition site; C2c1 cleavage results in a staggered seven-nucleotide DSB in the target DNA (see Yang et al. (2016) *Cell*, 167:1814-1828.e12) and is reported to have high mismatch sensitivity, thus reducing off-target effects (see Liu et al. (2016) *Mol. Cell*, available on line at dx[dot]doi[dot]org/10[dot]1016/j[dot]molcel[dot]2016[dot] 11.040). Yet other CRISPR nucleases include nucleases identified from the genomes of uncultivated microbes, such as CasX and CasY (e.g., a CRISPR-associated protein CasY from an uncultured Parcubacteria group bacterium, amino acid sequence with accession ID APG80656, deposited on-line at www[dot]ncbi[dot]nlm[dot]nih[dot]gov/protein/ APG80656.1]); see Burstein et al. (2016) *Nature*, doi: 10.1038/nature21059.

For the purposes of gene editing, CRISPR arrays can be designed to contain one or multiple guide RNA sequences corresponding to a desired target DNA sequence; see, for example, Cong et al. (2013) *Science*. 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell*, 163:759-771. In practice, guide RNA sequences are generally designed to have a length of between 17-24 nucleotides (frequently 19, 20, or 21 nucleotides) or 17-24 nucleotides and exact complementarity (i.e., perfect base-pairing) to the targeted gene or nucleic acid sequence; guide RNAs having less than 100% complementarity to the target sequence can be used (e.g., a gRNA with a length of 20 nucleotides and between 1-4 mismatches or 1-4 mismatches to the target sequence) but can increase the potential for off-target effects. The design of effective guide RNAs for use in plant genome editing is disclosed in U.S. Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.* 14:327-340. Chemically modified sgRNAs have been demonstrated to be effective in genome editing; see, for example, Hendel et al. (2015) *Nature Biotechnol.,* 985-991.

CRISPR-type genome editing has value in various aspects of agriculture research and development. CRISPR elements, i.e., CRISPR endonucleases and CRISPR single-guide RNAs, are useful in effecting genome editing without remnants of the CRISPR elements or selective genetic markers occurring in progeny. Alternatively, genome-inserted CRISPR elements are useful in plant lines adapted for multiplex genetic screening and breeding. For instance, a plant species can be created to express one or more of a CRISPR endonuclease such as a Cas9- or a Cpf1-type endonuclease or combinations with unique PAM recognition sites. Cpf1 endonuclease and corresponding guide RNAs and PAM sites are disclosed in U.S. Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for trait introgression. Multiple endonucleases can be provided in expression cassettes with the appropriate promoters to allow multiple genome editing in a spatially or temporally separated fashion in either in chromosome DNA or episome DNA.

Whereas wild-type Cas9 generates double-strand breaks (DSBs) at specific DNA sequences targeted by a gRNA, a number of CRISPR endonucleases having modified functionalities are available, for example: (1) a "nickase" version of Cas9 generates only a single-strand break; (2) a catalytically inactive Cas9 ("dCas9") does not cut the target DNA but interferes with transcription; (3) dCas9 on its own or fused to a repressor peptide can repress gene expression; (4) dCas9 fused to an activator peptide can activate or increase gene expression; (5) dCas9 fused to FokI nuclease ("dCas9-FokI") can be used to generate DSBs at target sequences homologous to two gRNAs; and (6) dCas9 fused to histone-modifying enzymes (e.g., histone acetyltransferases, histone methyltransferases, histone deacetylases, and histone demethylases) can be used to alter the epigenome in a site-specific manner, for example, by changing the methylation or acetylation status at a particular locus. See, e.g., the numerous CRISPR/Cas9 plasmids disclosed in and publicly available from the Addgene repository (Addgene, 75 Sidney St., Suite 550A, Cambridge, MA 02139; addgene[dot]org/ crispr/). A "double nickase" Cas9 that introduces two separate double-strand breaks, each directed by a separate guide RNA, is described as achieving more accurate genome editing by Ran et al. (2013) *Cell,* 154:1380-1389.

In some embodiments, the methods of genome modification described herein provide a means for avoiding unwanted epigenetic changes (such as a change in DNA methylation) that can arise from tissue culturing modified plant cells; see, e.g., Stroud et al. (2013) *eLife* 2013; 2:e00354. In embodiments using the methods described herein, in the absence of tissue culture, epigenetic changes (e.g, a loss of DNA methylation) occurs in less than 0.01% of the genome. This contrasts with results obtained with monocot (rice) plants where tissue culture methods resulted in losses of DNA methylation that occurred, as determined by bisulfite sequencing, at 1344 places that are on average 334 base pairs long, which is equivalent to a loss of DNA methylation over an average of 0.1% of the genome; see, e.g., Stroud et al. (2013) *eLife* 2013; 2:e00354; doi:10.7554/ eLife.00354. In other words, the loss of epigenetic marks using the genome modification techniques described herein without tissue culture is about 10 times lower than the loss observed when the usual plant tissue culture techniques (e.g., use of callus culture) are employed. In embodiments of the modified wheat plants and wheat cells described herein, the modified wheat plants and wheat cells does not have significant losses of DNA methylation compared to the unmodified wheat plant or cell with the reference genome; in other words, the methylation pattern of the genome of the modified wheat plant or cell is not greatly different from the methylation pattern of the reference genome of the unmodified wheat plant or cell. In embodiments, the difference between the methylation pattern of the genome of the modified wheat plant cell or plant and the methylation pattern of the reference genome of the unmodified wheat plant cell or plant is less than 0.1%, or less than 0.05%, or less than 0.02%, or less than 0.01%, or less than 0.005%, or less than 0.001% of the genome.

CRISPR technology for editing the genes of eukaryotes is disclosed in U.S. Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in U.S. Patent Application Publication 2016/0208243 A1. Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in in U.S. Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety.

In some embodiments, one or more vectors driving expression of one or more polynucleotides encoding elements of a genome-editing system (e.g., encoding a guide RNA or a nuclease) are introduced into a plant cell or a plant protoplast, whereby these elements, when expressed, result in alteration of a target nucleotide sequence. In embodiments, a vector comprises a regulatory element such as a promoter operably linked to one or more polynucleotides encoding elements of a genome-editing system. In such embodiments, expression of these polynucleotides can be controlled by selection of the appropriate promoter, particularly promoters functional in a plant cell; useful promoters include constitutive, conditional, inducible, and temporally or spatially specific promoters (e.g., a tissue specific promoter, a developmentally regulated promoter, or a cell cycle regulated promoter). In embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amare and Scott (2014) *Cold Spring Harbor Perspectives Biol.*, 2:a003574). In embodiments, the promoter is a pol II promoter operably linked to a nucleotide sequence encoding one or more guide RNAs. In embodiments, the promoter operably linked to one or more polynucleotides encoding elements of a genome-editing system is a constitutive promoter that drives DNA expression in plant cells; in embodiments, the promoter drives DNA expression in the nucleus or in an organelle such as a chloroplast or mitochondrion. Examples of constitutive promoters include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and a opaline synthase (NOS) and octapine synthase (OCS) promoter from *Agrobacterium tumefaciens*. In embodiments, the promoter operably linked to one or more polynucleotides encoding elements of a genome-editing system is a promoter from figwort mosaic virus (FMV), a RUBISCO promoter, or a pyruvate phosphate dikinase (PDK) promoter, which is active in the chloroplasts of mesophyll cells. Other contemplated promoters include cell-specific or tissue-specific or developmentally regulated promoters, for example, a promoter that limits the expression of the nucleic acid modification system to germline or reproductive cells (e.g., promoters of genes encoding DNA ligases, recombinases, replicases, or other genes specifically expressed in germline or reproductive cells); in such embodiments, the nuclease-mediated genetic modification (e.g., chromosomal or episomal double-stranded DNA cleavage) is limited only those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

In some embodiments, elements of a genome-editing system (e.g., an RNA-guided nuclease and a guide RNA) are operably linked to separate regulatory elements for expression (e.g., promoters, enhancers, introns, or terminators) on separate vectors. In other embodiments, two or more elements of a genome-editing system expressed from the same or different promoters are combined in a single vector, optionally with one or more additional vectors providing any additional necessary elements of a genome-editing system not included in the first vector. For example, multiple guide RNAs can be expressed from one vector, with the appropriate RNA-guided nuclease expressed from a second vector. In another example, one or more vectors for the expression of one or more guide RNAs (e.g., crRNAs or sgRNAs) are delivered to a cell (e.g., a plant cell or a plant protoplast) that expresses the appropriate RNA-guided nuclease, or to a cell that otherwise contains the nuclease, such as by way of prior administration thereto of a vector for in vivo expression of the nuclease.

Genome-editing system elements that are combined in a single vector may be arranged in any suitable orientation, such as one element located 5 with respect to ("upstream" of) or 3' with respect to ("downstream" of) a second element. The coding sequence of one element may be located on the same or opposite strand of the coding sequence of a second element, and oriented in the same or opposite direction. In embodiments, the endonuclease and the nucleic acid-targeting guide RNA may be operably linked to and expressed from the same promoter. In embodiments, a single promoter drives expression of a transcript encoding an endonuclease and the guide RNA, embedded within one or more intron sequences (e.g., each in a different intron, two or more in at least one intron, or all in a single intron), which can be plant-derived; such use of introns is especially contemplated when the expression vector is being transformed or transfected into a monocot plant cell or a monocot plant protoplast.

Expression vectors provided herein may contain a DNA segment near the 3' end of an expression cassette that acts as a signal to terminate transcription and directs polyadenylation of the resultant mRNA. Such a 3' element is commonly referred to as a "3'-untranslated region" or "3'-UTR" or a "polyadenylation signal". Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in U.S. Patent Application Publication 2002/0192813 A1, incorporated herein by reference.

In certain embodiments, a vector or an expression cassette includes additional components, e.g., a polynucleotide encoding a drug resistance or herbicide gene or a polynucleotide encoding a detectable marker such as green fluorescent protein (GFP) or beta-glucuronidase (gus) to allow convenient screening or selection of cells expressing the vector. In embodiments, the vector or expression cassette includes additional elements for improving delivery to a plant cell or plant protoplast or for directing or modifying expression of one or more genome-editing system elements, for example, fusing a sequence encoding a cell-penetrating peptide, localization signal, transit, or targeting peptide to the RNA-guided nuclease, or adding a nucleotide sequence to stabilize a guide RNA; such fusion proteins (and the polypeptides encoding such fusion proteins) or combination polypeptides, as well as expression cassettes and vectors for their expression in a cell, are specifically claimed. In embodiments, an RNA-guided nuclease (e.g., Cas9, Cpf1, CasY, CasX, C2c1, or C2c3) is fused to a localization signal, transit, or targeting peptide, e.g., a nuclear localization signal (NLS), a chloroplast transit peptide (CTP), or a mitochondrial targeting peptide (MTP); in a vector or an expression cassette, the nucleotide sequence encoding any of these can be located either 5' and/or 3' to the DNA encoding the nuclease. For example, a plant-codon-optimized Cas9 (pco-Cas9) from *Streptococcus pyogenes* and *S. thermophilus* containing nuclear localization signals and codon-optimized for expression in maize is disclosed in PCT/US2015/018104 (published as WO/2015/131101 and claiming priority to U.S. Provisional Patent Application 61/945,700), incorporated herein by reference. In another example, a chloroplast-targeting RNA is appended to the 5' end of an mRNA encoding an endonuclease to drive the accumulation of the mRNA in chloroplasts; see Gomez, et al. (2010) *Plant Signal Behav.,* 5: 1517-1519. In an embodiment, a Cas9 from *Streptococcus pyogenes* is fused to a nuclear localization signal (NLS), such as the NLS from SV40. In an embodiment, a Cas9 from *Streptococcus pyogenes* is fused to a cell-penetrating peptide (CPP), such as octa-arginine or nona-arginine or a homoarginine 12-mer oligopeptide, or a CPP disclosed in the database of cell-penetrating peptides CPPsite 2.0, publicly available at crdd[dot]osdd[dot]net/raghava/cppsite/. In an example, a Cas9 from *Streptococcus pyogenes* (which normally carries a net positive charge) is modified at the N-terminus with a negatively charged glutamate peptide "tag" and at the C-terminus with a nuclear localization signal (NLS); when mixed with cationic arginine gold nanoparticles (ArgNPs), self-assembled nanoassemblies were formed which were shown to provide good editing efficiency in human cells; see Mout et al. (2017) *ACS Nano*, doi:10.1021/acsnano.6b07600. In an embodiment, a Cas9 from *Streptococcus pyogenes* is fused to a chloroplast transit peptide (CTP) sequence. In embodiments, a CTP sequence is obtained from any nuclear gene that encodes a protein that targets a chloroplast, and the isolated or synthesized CTP DNA is appended to the 5' end of the DNA that encodes a nuclease targeted for use in a chloroplast. Chloroplast transit peptides and their use are described in U.S. Pat. Nos. 5,188,642, 5,728,925, and 8,420,888, all of which are incorporated herein by reference in their entirety. Specifically, the CTP nucleotide sequences provided with the sequence identifier (SEQ ID) numbers 12-15 and 17-22 of U.S. Pat. No. 8,420,888 are incorporated herein by reference. In an embodiment, a Cas9 from *Streptococcus pyo-genes* is fused to a mitochondrial targeting peptide (MTP), such as a plant MTP sequence; see, e.g., Jores et al. (2016) *Nature Communications,* 7:12036-12051.

Plasmids designed for use in plants and encoding CRISPR genome editing elements (CRISPR nucleases and guide RNAs) are publicly available from plasmid repositories such as Addgene (Cambridge, Massachusetts; also see "addgene [dot]com") or can be designed using publicly disclosed sequences, e.g., sequences of CRISPR nucleases. In embodiments, such plasmids are used to co-express both CRISPR nuclease mRNA and guide RNA(s); in other embodiments, CRISPR endonuclease mRNA and guide RNA are encoded on separate plasmids. In embodiments, the plasmids are *Agrobacterium* TI plasmids. Materials and methods for preparing expression cassettes and vectors for CRISPR endonuclease and guide RNA for stably integrated and/or transient plant transformation are disclosed in PCT/US2015/018104 (published as WO/2015/131101 and claiming priority to U.S. Provisional Patent Application 61/945,700), U.S. Patent Application Publication 2015/0082478 A1, and PCT/US2015/038767 (published as WO/2016/007347 and claiming priority to U.S. Provisional Patent Application 62/023,246), all of which are incorporated herein by reference in their entirety. In embodiments, such expression cassettes are isolated linear fragments, or are part of a larger construct that includes bacterial replication elements and selectable markers; such embodiments are useful, e.g., for particle bombardment or nanoparticle delivery or protoplast transformation. In embodiments, the expression cassette is adjacent to or located between T-DNA borders or contained within a binary vector, e.g., for *Agrobacterium*-mediated transformation. In embodiments, a plasmid encoding a CRISPR nuclease is delivered to cell (such as a plant cell or a plant protoplast) for stable integration of the CRISPR nuclease into the genome of cell, or alternatively for transient expression of the CRISPR nuclease. In embodiments, plasmids encoding a CRISPR nuclease are delivered to a plant cell or a plant protoplast to achieve stable or transient expression of the CRISPR nuclease, and one or multiple guide RNAs (such as a library of individual guide RNAs or multiple pooled guide RNAs) or plasmids encoding the guide RNAs are delivered to the plant cell or plant protoplast individually or in combinations, thus providing libraries or arrays of plant cells or plant protoplasts (or of plant callus or whole plants derived therefrom), in which a variety of genome edits are provided by the different guide RNAs. A pool or arrayed collection of diverse modified plant cells comprising subsets of precise modifications (e.g., a collection of plant cells or plants where some plants are homozygous and some are heterozygous for one, two, three or more precise modifications) can be compared to determine the function of modified sequences (e.g., mutated or deleted sequences or genes) or the function of sequences being inserted. In other words, the methods and tools described herein can be used to perform "reverse genetics."

In certain embodiments where the genome-editing system is a CRISPR system, expression of the guide RNA is driven by a plant U6 spliceosomal RNA promoter, which can be native to the genome of the plant cell or from a different species, e.g., a U6 promoter from maize, tomato, or soybean such as those disclosed in PCT/US2015/018104 (published as WO 2015/131101 and claiming priority to U.S. Provisional Patent Application 61/945,700), incorporated herein by reference, or a homologue thereof; such a promoter is operably linked to DNA encoding the guide RNA for directing an endonuclease, followed by a suitable 3' element such as a U6 poly-T terminator. In another embodiment, an expression cassette for expressing guide RNAs in plants is used, wherein the promoter is a plant U3, 7SL (signal recognition particle RNA), U2, or U5 promoter, or chimerics thereof, e.g., as described in PCT/US2015/018104 (published as WO 2015/131101 and claiming priority to U.S. Provisional Patent Application 61/945,700), incorporated herein by reference. When multiple or different guide RNA sequences are used, a single expression construct may be used to correspondingly direct the genome editing activity to the multiple or different target sequences in a cell, such a plant cell or a plant protoplast. In various embodiments, a single vector includes 1, 2, 3, 4, 5, 6, 7, 8, 9, 10, about 15, about 20, or more guide RNA sequences; in other embodiments, 1, 2, 3, 4, 5, 6, 7, 8, 9, 10, about 15, about 20, or more guide RNA sequences are provided on multiple vectors, which can be delivered to one or multiple plant cells or plant protoplasts (e.g., delivered to an array of plant cells or plant protoplasts, or to a pooled population of plant cells or plant protoplasts).

In embodiments, one or more guide RNAs and the corresponding RNA-guided nuclease are delivered together or simultaneously. In other embodiments, one or more guide RNAs and the corresponding RNA-guided nuclease are delivered separately; these can be delivered in separate, discrete steps and using the same or different delivery techniques. In an example, an RNA-guided nuclease is delivered to a cell (such as a plant cell or plant protoplast) by particle bombardment, on carbon nanotubes, or by *Agrobacterium*-mediated transformation, and one or more guide RNAs is delivered to the cell in a separate step using the same or different delivery technique. In embodiments, an RNA-guided nuclease encoded by a DNA molecule or an mRNA is delivered to a cell with enough time prior to delivery of the guide RNA to permit expression of the nuclease in the cell; for example, an RNA-guided nuclease encoded by a DNA molecule or an mRNA is delivered to a plant cell or plant protoplast between 1-12 hours (e.g., about 1, 2, 3, 4, 5, 6, 7, 8, 9, 10, 11, or 12 hours) or about 1-12 hours, between about 1-6 hours or about 1-6 hours, or between about 2-6 hours or about 2-6 hours prior to the delivery of the guide RNA to the plant cell or plant protoplast. In embodiments, whether the RNA-guided nuclease is delivered simultaneously with or separately from an initial dose of guide RNA, succeeding "booster" doses of guide RNA are delivered subsequent to the delivery of the initial dose; for example, a second "booster" dose of guide RNA is delivered to a plant cell or plant protoplast between 1-12 hours (e.g., about 1, 2, 3, 4, 5, 6, 7, 8, 9, 10, 11, or 12 hours) or about 1-12 hours, between about 1-6 hours or about 1-6 hours, or between about 2-6 hours or about 2-6 hours subsequent to the delivery of the initial dose of guide RNA to the plant cell or plant protoplast. Similarly, in some embodiments, multiple deliveries of an RNA-guided nuclease or of a DNA molecule or an mRNA encoding an RNA-guided nuclease are used to increase efficiency of the genome modification.

In embodiments, the desired genome modification involves non-homologous recombination, in this case non-homologous end-joining of genomic sequence across one or more introduced double-strand breaks (DSBs); generally, such embodiments do not require a template sequence encoded by a donor polynucleotide molecule having homology "arms" (regions of homologous or complimentary sequence to genomic sequence flanking the site of the DSB). In various embodiments described herein, donor polynucleotides encoding sequences for targeted insertion at double-stranded breaks are single-stranded polynucleotides comprising RNA or DNA or both types of nucleotides; or the donor polynucleotides are at least partially double-stranded and comprise RNA, DNA or both types of nucleotides. Other modified nucleotides may also be used.

In other embodiments, the desired genome modification involves homologous recombination, wherein one or more double-stranded DNA breaks (DSBs) in the target nucleotide sequence is generated by the RNA-guided nuclease and guide RNA(s), followed by repair of the break(s) using a homologous recombination mechanism ("homology-directed repair"). In such embodiments, a template sequence encoded by a donor polynucleotide molecule and including the desired nucleotide sequence to be inserted or "knocked-in" at the DSB generally includes homology "arms" (regions of homologous or complimentary sequence to genomic sequence flanking the site of the DSB). In embodiments, a template sequence encoded by a donor polynucleotide molecule that encodes a nucleotide change over a region of less than about 50 nucleotides is conveniently provided in the form of single-stranded DNA; larger donor templates (e.g., more than about 100 nucleotides) are often conveniently provided as double-stranded DNA donor polynucleotides.

In certain embodiments directed to the precise integration of a heterologous sequence by homologous recombination, a template sequence encoded by a donor polynucleotide molecule has a core nucleotide sequence that differs from the target nucleotide sequence (e.g., the endogenous genomic sequence of a gene of interest) by at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, or more nucleotides. This core sequence is flanked by "homology arms" or regions of high sequence identity with the targeted nucleotide sequence; in embodiments, the regions of high identity include at least 10, at least 15, at least 20, at least 25, at least 30, at least 40, at least 50, at least 100, at least 150, at least 200, at least 300, at least 400, at least 500, at least 600, at least 750, or at least 1000 nucleotides on each side of the core sequence. In embodiments where the donor polynucleotide molecule is in the form of a single-stranded DNA, the core sequence is flanked by homology arms including at least 10, at least 20, at least 30, at least 40, at least 50, at least 60, at least 70, at least 80, or at least 100 nucleotides on each side of the core sequence. In embodiments where the donor polynucleotide molecule is in the form of a double-stranded DNA, the core sequence is flanked by homology arms including at least 10, at least 15, at least 20, at least 25, at least 30, at least 40, at least 50, at least 100, at least 150, at least 200, at least 300, at least 400, at least 500, at least 600, at least 750, or at least 1000 nucleotides on each side of the core sequence. In an embodiment, two separate double-strand breaks are introduced into the cell's target nucleotide sequence with a "double nickase" Cas9 (see Ran et al. (2013) *Cell*, 154:1380-1389), together with or followed by delivery of the donor polynucleotide molecule.

Delivery methods and delivery agents: Aspects of the invention involve various treatments employed to deliver to a plant cell or protoplast a guide RNA (gRNA), such as a crRNA or sgRNA (or a polynucleotide encoding such), and/or a donor polynucleotide molecule encoding a sequence for precise insertion at a predetermined double-strand break in a genome. In embodiments, one or more treatments are employed to deliver the gRNA into a plant cell or plant protoplast, e.g., through barriers such as a cell wall or a plasma membrane or nuclear envelope or other lipid bilayer.

Unless otherwise stated, the various compositions and methods described herein for delivering guide RNAs and nucleases to a plant cell or protoplast are also generally useful for delivering donor polynucleotides to the cell. The delivery of donor polynucleotides can be simultaneous with, or separate from (generally after) delivery of the nuclease and guide RNA to the cell. For example, a donor polynucleotide can be transiently introduced into a plant cell or plant protoplast, optionally with the nuclease and/or gRNA; in certain embodiments, the donor template is provided to the plant cell or plant protoplast in a quantity that is sufficient to achieve the desired insertion of the donor polynucleotide sequence but donor polynucleotides do not persist in the plant cell or plant protoplast after a given period of time (e.g., after one or more cell division cycles).

In certain embodiments, a gRNA or donor polynucleotide, in addition to other agents involved in precise genomic modifications, can be delivered to a plant cell or protoplast by directly contacting the plant cell or protoplast with a composition comprising the gRNA(s) or donor polynucleotide(s). For example, a gRNA-containing composition in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant cell (or plant part or tissue containing the plant cell) or plant protoplast (e.g., through abrasion or puncture or otherwise disruption of the cell wall or cell membrane, by spraying or dipping or soaking or otherwise directly contacting, or by microinjection). In certain embodiments, a plant cell (or plant part or tissue containing the plant cell) or plant protoplast is soaked in a liquid gRNA-containing composition, whereby the gRNA is delivered to the plant cell or plant protoplast. In embodiments, the gRNA-containing composition is delivered using negative or positive pressure, for example, using vacuum infiltration or application of hydrodynamic or fluid pressure. In embodiments, the gRNA-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the gRNA-containing composition to a plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In embodiments, the gRNA-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the gRNA; see, e.g., Broothaerts et al. (2005) *Nature*, 433:629-633. Any of these techniques or a combination thereof are alternatively employed on the plant part or tissue or intact plant (or seed) from which a plant cell or plant protoplast is optionally subsequently obtained or isolated; in embodiments, the gRNA-containing composition is delivered in a separate step after the plant cell or plant protoplast has been obtained or isolated.

In embodiments, a treatment employed in delivery of a gRNA to a plant cell or plant protoplast is carried out under a specific thermal regime, which can involve one or more appropriate temperatures, e.g., chilling or cold stress (exposure to temperatures below that at which normal plant growth occurs), or heating or heat stress (exposure to temperatures above that at which normal plant growth occurs), or treating at a combination of different temperatures. In embodiments, a specific thermal regime is carried out on the plant cell or plant protoplast, or on a plant or plant part from which a plant cell or plant protoplast is subsequently obtained or isolated, in one or more steps separate from the gRNA delivery. In embodiments, following delivery of a gRNA or other editing reagents, a plant cell or plant protoplast is treated to an incubation step of between 10 minutes to about 4 hours or 10 minutes to about 4 hours at an elevated temperature, e.g., about 30, about 35, about 37, or about 40 degrees Celsius, that is above room temperature (which is typically around 24 to 26 degrees Celsius), followed by an extended (12 hours to several days) incubation at room temperature.

In embodiments, a whole plant or plant part or seed, or an isolated plant cell or plant protoplast, or the plant or plant part from which a plant cell or plant protoplast is obtained or isolated, is treated with one or more delivery agents which can include at least one chemical, enzymatic, or physical agent, or a combination thereof. In embodiments, a gRNA-containing composition further includes one or more one chemical, enzymatic, or physical agent for delivery. In embodiments that further include the step of providing an RNA-guided nuclease or a polynucleotide that encodes the RNA-guided nuclease, a gRNA-containing composition including the RNA-guided nuclease or polynucleotide that encodes the RNA-guided nuclease further includes one or more one chemical, enzymatic, or physical agent for delivery. Treatment with the chemical, enzymatic or physical agent can be carried out simultaneously with the gRNA delivery, with the RNA-guided nuclease delivery, or in one or more separate steps that precede or follow the gRNA delivery or the RNA-guided nuclease delivery. In embodiments, a chemical, enzymatic, or physical agent, or a combination of these, is associated or complexed with the polynucleotide composition, with the gRNA or polynucleotide that encodes or is processed to the gRNA, or with the RNA-guided nuclease or polynucleotide that encodes the RNA-guided nuclease; examples of such associations or complexes include those involving non-covalent interactions (e.g., ionic or electrostatic interactions, hydrophobic or hydrophilic interactions, formation of liposomes, micelles, or other heterogeneous composition) and covalent interactions (e.g., peptide bonds, bonds formed using cross-linking agents). In non-limiting examples, a gRNA or polynucleotide that encodes or is processed to the gRNA is provided as a liposomal complex with a cationic lipid; a gRNA or polynucleotide that encodes or is processed to the gRNA is provided as a complex with a carbon nanotube; and an RNA-guided nuclease is provided as a fusion protein between the nuclease and a cell-penetrating peptide. Examples of agents useful for delivering a gRNA or polynucleotide that encodes or is processed to the gRNA or a nuclease or polynucleotide that encodes the nuclease include the various cationic liposomes and polymer nanoparticles reviewed by Zhang et al. (2007) *J. Controlled Release*, 123:1-10, and the cross-linked multilamellar liposomes described in U.S. Patent Application Publication 2014/0356414 A1, incorporated by reference in its entirety herein.

In embodiments, the chemical agent is at least one selected from the group consisting of:

(a) solvents (e.g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e.g., perfluorodecalin, perfluoromethyldecalin);

(c) glycols or polyols (e.g., propylene glycol, polyethylene glycol);

(d) surfactants, including cationic surfactants, anionic surfactants, non-ionic surfactants, and amphiphilic surfactants, e.g., alkyl or aryl sulfates, phosphates, sulfonates, or carboxylates; primary, secondary, or tertiary amines; quaternary ammonium salts; sultaines; betaines; cationic lipids; phospholipids; tallowamine; bile acids such as cholic acid; long chain alcohols; organosilicone surfactants including nonionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e.g., cellulase, pectolyase, maceroenzyme, pectinase), including cell-penetrating or pore-forming peptides (e.g., (BO100)2K8, Genscript; poly-lysine, poly-arginine, or poly-homoarginine peptides; gamma zein, see U.S. Patent Application publication 2011/0247100, incorporated herein by reference in its entirety; transcription activator of human immunodeficiency virus type 1 ("HIV-1 Tat") and other Tat proteins, see. e.g., www[dot]lifetein[dot]com/Cell_Penetrating_Peptides[dot]html and Järver (2012) *Mol. Therapy-Nucleic Acids*, 1:e27,1-17); octa-arginine or nona-arginine; poly-homoarginine (see Unnamalai et al. (2004) *FEBS Letters*, 566:307-310); see also the database of cell-penetrating peptides CPPsite 2.0 publicly available at crdd[dot]osdd[dot]net/raghava/cppsite/

(h) RNase inhibitors;

(i) cationic branched or linear polymers such as chitosan, poly-lysine, DEAE-dextran, polyvinylpyrrolidone ("PVP"), or polyethylenimine ("PEI", e.g., PEI, branched, MW 25,000, CAS #9002-98-6; PEI, linear, MW 5000, CAS #9002-98-6; PEI linear, MW 2500, CAS #9002-98-6);

(j) dendrimers (see, e.g., U.S. Patent Application Publication 2011/0093982, incorporated herein by reference in its entirety);

(k) counter-ions, amines or polyamines (e.g., spermine, spermidine, putrescine), osmolytes, buffers, and salts (e.g., calcium phosphate, ammonium phosphate);

(l) polynucleotides (e.g., non-specific double-stranded DNA, salmon sperm DNA);

(m) transfection agents (e.g., Lipofectin®, Lipofectamine®, and Oligofectamine®, and Invivofectamine® (all from Thermo Fisher Scientific, Waltham, MA), PepFect (see Ezzat et al. (2011) *Nucleic Acids Res.*, 39:5284-5298), TransIt® transfection reagents (Minis Bio, LLC, Madison, WI), and poly-lysine, poly-homoarginine, and poly-arginine molecules including octo-arginine and nono-arginine as described in Lu et al. (2010) *J. Agric. Food Chem.*, 58:2288-2294);

(n) antibiotics, including non-specific DNA double-strand-break-inducing agents (e.g., phleomycin, bleomycin, talisomycin); and (o) antioxidants (e.g., glutathione, dithiothreitol, ascorbate).

In embodiments, the chemical agent is provided simultaneously with the gRNA (or polynucleotide encoding the gRNA or that is processed to the gRNA), for example, the polynucleotide composition including the gRNA further includes one or more chemical agent. In embodiments, the gRNA or polynucleotide encoding the gRNA or that is processed to the gRNA is covalently or non-covalently linked or complexed with one or more chemical agent; for example, the gRNA or polynucleotide encoding the gRNA or that is processed to the gRNA can be covalently linked to a peptide or protein (e.g., a cell-penetrating peptide or a pore-forming peptide) or non-covalently complexed with cationic lipids, polycations (e.g., polyamines), or cationic polymers (e.g., PEI). In embodiments, the gRNA or polynucleotide encoding the gRNA or that is processed to the gRNA is complexed with one or more chemical agents to form, e.g., a solution, liposome, micelle, emulsion, reverse emulsion, suspension, colloid, or gel.

In embodiments, the physical agent is at least one selected from the group consisting of particles or nanoparticles (e.g., particles or nanoparticles made of materials such as carbon, silicon, silicon carbide, gold, tungsten, polymers, or ceramics) in various size ranges and shapes, magnetic particles or nanoparticles (e.g., silenceMag Magnetotransfection™ agent, OZ Biosciences, San Diego, CA), abrasive or scarifying agents, needles or microneedles, matrices, and grids. In embodiments, particulates and nanoparticulates are useful in delivery of the polynucleotide composition or the nuclease or both. Useful particulates and nanoparticles include those made of metals (e.g., gold, silver, tungsten, iron, cerium), ceramics (e.g., aluminum oxide, silicon carbide, silicon nitride, tungsten carbide), polymers (e.g., polystyrene, polydiacetylene, and poly(3,4-ethylenedioxythiophene) hydrate), semiconductors (e.g., quantum dots), silicon (e.g., silicon carbide), carbon (e.g., graphite, graphene, graphene oxide, or carbon nanosheets, nanocomplexes, or nanotubes), and composites (e.g., polyvinylcarbazole/graphene, polystyrene/graphene, platinum/graphene, palladium/graphene nanocomposites). In embodiments, such particulates and nanoparticulates are further covalently or non-covalently functionalized, or further include modifiers or cross-linked materials such as polymers (e.g., linear or branched polyethylenimine, poly-lysine), polynucleotides (e.g., DNA or RNA), polysaccharides, lipids, polyglycols (e.g., polyethylene glycol, thiolated polyethylene glycol), polypeptides or proteins, and detectable labels (e.g., a fluorophore, an antigen, an antibody, or a quantum dot). In various embodiments, such particulates and nanoparticles are neutral, or carry a positive charge, or carry a negative charge. Embodiments of compositions including particulates include those formulated, e.g., as liquids, colloids, dispersions, suspensions, aerosols, gels, and solids. Embodiments include nanoparticles affixed to a surface or support, e.g., an array of carbon nanotubes vertically aligned on a silicon or copper wafer substrate. Embodiments include polynucleotide compositions including particulates (e.g., gold or tungsten or magnetic particles) delivered by a Biolistic-type technique or with magnetic force. The size of the particles used in Biolistics is generally in the "microparticle" range, for example, gold microcarriers in the 0.6, 1.0, and 1.6 micrometer size ranges (see, e.g., instruction manual for the Helios® Gene Gun System, Bio-Rad, Hercules, CA; Randolph-Anderson et al. (2015) "Sub-micron gold particles are superior to larger particles for efficient Biolistic® transformation of organelles and some cell types", Bio-Rad US/EG Bulletin 2015), but successful Biolistics delivery using larger (40 nanometer) nanoparticles has been reported in cultured animal cells; see O'Brian and Lummis (2011) *BMC Biotechnol.*, 11:66-71. Other embodiments of useful particulates are nanoparticles, which are generally in the nanometer (nm) size range or less than 1 micrometer, e.g., with a diameter of less than about 1 nm, less than about 3 nm, less than about 5 nm, less than about 10 nm, less than about 20 nm, less than about 40 nm, less than about 60 nm, less than about 80 nm, and less than about 100 nm. Specific, non-limiting embodiments of nanoparticles commercially available (all from Sigma-Aldrich Corp., St. Louis, MO) include gold nanoparticles with diameters of 5, 10, or 15 nm; silver nanoparticles with particle sizes of 10, 20, 40, 60, or 100 nm; palladium "nanopowder" of less than 25 nm particle size; single-, double-, and multi-walled carbon nanotubes, e.g., with diameters of 0.7-1.1, 1.3-2.3, 0.7-0.9, or 0.7-1.3 nm, or with nanotube bundle dimensions of 2-10 nm by 1-5 micrometers, 6-9 nm by 5 micrometers, 7-15 nm by 0.5-10 micrometers, 7-12 nm by 0.5-10 micrometers, 110-170 nm by 5-9 micrometers, 6-13 nm by 2.5-20 micrometers. Embodiments include polynucleotide compositions including materials such as gold, silicon, cerium, or carbon, e.g., gold or gold-coated nanoparticles, silicon carbide whiskers, carborundum, porous silica nanoparticles, gelatin/silica nanoparticles, nanoceria or cerium oxide nanoparticles (CNPs), carbon nanotubes (CNTs) such as single-, double-, or multi-walled carbon nanotubes and their chemically functionalized versions (e.g., carbon nanotubes functionalized with amide, amino, carboxylic acid, sulfonic acid, or polyethylene glycol moeities), and graphene or graphene oxide or graphene complexes; see, for example, Wong et al. (2016) *Nano Lett.*, 16:1161-1172; Giraldo et al. (2014) *Nature Materials*, 13:400-409; Shen et al. (2012) *Theranostics*, 2:283-294; Kim et al. (2011) *Bioconjugate Chem.*, 22:2558-2567; Wang et al. (2010) *J. Am. Chem. Soc. Comm.*, 132: 9274-9276; Zhao et al. (2016) *Nanoscale Res. Lett.*, 11:195-203; and Choi et al. (2016) *J. Controlled Release*, 235:222-235. See also, for example, the various types of particles and nanoparticles, their preparation, and methods for their use, e.g., in delivering polynucleotides and polypeptides to cells, disclosed in U.S. Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety.

In embodiments wherein the gRNA (or polynucleotide encoding the gRNA) is provided in a composition that further includes an RNA-guided nuclease (or a polynucleotide that encodes the RNA-guided nuclease), or wherein the method further includes the step of providing an RNA-guided nuclease or a polynucleotide that encodes the RNA-guided nuclease, one or more one chemical, enzymatic, or physical agent can similarly be employed. In embodiments, the RNA-guided nuclease (or polynucleotide encoding the RNA-guided nuclease) is provided separately, e.g., in a separate composition including the RNA-guided nuclease or polynucleotide encoding the RNA-guided nuclease. Such compositions can include other chemical or physical agents (e.g., solvents, surfactants, proteins or enzymes, transfection agents, particulates or nanoparticulates), such as those described above as useful in the polynucleotide composition used to provide the gRNA. For example, porous silica nanoparticles are useful for delivering a DNA recombinase into monocot cells; see, e.g., Martin-Ortigosa et al. (2015) *Plant Physiol.*, 164:537-547. In an embodiment, the polynucleotide composition includes a gRNA and Cas9 nuclease, and further includes a surfactant and a cell-penetrating peptide. In an embodiment, the polynucleotide composition includes a plasmid that encodes both an RNA-guided nuclease and at least on gRNA, and further includes a surfactant and carbon nanotubes. In an embodiment, the polynucleotide composition includes multiple gRNAs and an mRNA encoding the RNA-guided nuclease, and further includes gold particles, and the polynucleotide composition is delivered to a plant cell or plant protoplast by Biolistics.

In related embodiments, one or more one chemical, enzymatic, or physical agent can be used in one or more steps separate from (preceding or following) that in which the gRNA is provided. In an embodiment, the plant or plant part from which a plant cell or plant protoplast is obtained or isolated is treated with one or more one chemical, enzymatic, or physical agent in the process of obtaining or isolating the plant cell or plant protoplast. In embodiments, the plant or plant part is treated with an abrasive, a caustic agent, a surfactant such as Silwet L-77 or a cationic lipid, or an enzyme such as cellulase.

In embodiments, a gRNA is delivered to plant cells or plant protoplasts prepared or obtained from a plant, plant part, or plant tissue that has been treated with the polynucleotide compositions (and optionally the nuclease). In embodiments, one or more one chemical, enzymatic, or physical agent, separately or in combination with the polynucleotide composition, is provided/applied at a location in the plant or plant part other than the plant location, part, or tissue from which the plant cell or plant protoplast is obtained or isolated. In embodiments, the polynucleotide composition is applied to adjacent or distal cells or tissues and is transported (e.g., through the vascular system or by cell-to-cell movement) to the meristem from which plant cells or plant protoplasts are subsequently isolated. In embodiments, a gRNA-containing composition is applied by soaking a seed or seed fragment or zygotic or somatic embryo in the gRNA-containing composition, whereby the gRNA is delivered to the seed or seed fragment or zygotic or somatic embryo from which plant cells or plant protoplasts are subsequently isolated. In embodiments, a flower bud or shoot tip is contacted with a gRNA-containing composition, whereby the gRNA is delivered to cells in the flower bud or shoot tip from which plant cells or plant protoplasts are subsequently isolated. In embodiments, a gRNA-containing composition is applied to the surface of a plant or of a part of a plant (e.g., a leaf surface), whereby the gRNA is delivered to tissues of the plant from which plant cells or plant protoplasts are subsequently isolated. In embodiments a whole plant or plant tissue is subjected to particle- or nanoparticle-mediated delivery (e.g., Biolistics or carbon nanotube or nanoparticle delivery) of a gRNA-containing composition, whereby the gRNA is delivered to cells or tissues from which plant cells or plant protoplasts are subsequently isolated.

Methods of modulating expression of a sequence of interest in a genome: In one aspect, the invention provides a method of changing expression of a sequence of interest in a genome, including integrating a sequence encoded by a donor polynucleotide molecule (such as a double-stranded DNA, a single-stranded DNA, a single-stranded DNA/RNA hybrid, or a double-stranded DNA/RNA hybrid) at the site of at least one double-strand break (DSB) in a genome. The method permits site-specific integration of heterologous sequence at the site of at least one DSB, and thus at one or more locations in a genome, such as a genome of a plant cell. In embodiments, the genome is that of a nucleus, mitochondrion, or plastid in a plant cell.

The term "heterologous" describes a nucleic acid sequence that is positioned out of its naturally occurring or native context; the term also describes two adjacent nucleic acid sequences that do not naturally occur together (but are not necessarily from different species). The term "heterologous" is also used to refer to a given sequence in relationship to another—e.g., the sequence of a donor polynucleotide molecule is heterologous to the sequence of the genomic locus wherein the polynucleotide is integrated. For example, a ubiquitin promoter sequence can be used to drive expression of a gene (for example, luciferase) other than the ubiquitin gene natively driven by the promoter; in this case the ubiquitin promoter is "heterologous" to the luciferase gene (and vice versa), and the ubiquitin promoter and luciferase gene are in a heterologous arrangement relative to each other. In another example, a transcription factor binding site sequence that natively occurs only in the A genome of bread wheat is "heterologously" integrated into the B genome of bread wheat; this integration of a cis-genic sequence is also termed heterologous, and the resulting combined sequences of the A genome transcription factor binding site sequence and B genome sequence are a heterologous arrangement. By "integration of heterologous sequence" is also meant integration or insertion of one or more nucleotides, resulting in a sequence (including the inserted nucleotide(s) as well as at least some adjacent nucleotides of the genomic sequence flanking the site of insertion at the DSB) that is itself heterologous, i.e., would not otherwise or does not normally occur at the site of insertion.

The at least one DSB is introduced into the genome by any suitable technique; in embodiments one or more DSBs is introduced into the genome in a site- or sequence-specific manner, for example, by use of at least one of the group of DSB-inducing agents consisting of: (a) a nuclease capable of effecting site-specific alteration of a target nucleotide sequence, selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease; (b) a polynucleotide encoding one or more nucleases capable of effecting site-specific alteration (such as introduction of a DSB) of a target nucleotide sequence; and (c) a guide RNA (gRNA) for an RNA-guided nuclease, or a DNA encoding a gRNA for an RNA-guided nuclease. In embodiments, one or more DSBs is introduced into the genome by use of both a guide RNA (gRNA) and the corresponding RNA-guided nuclease. In an example, one or more DSBs is introduced into the genome by use of a ribonucleoprotein (RNP) that includes both a gRNA (e.g., a single-guide RNA or sgRNA that includes both a crRNA and a tracrRNA) and a Cas9. It is generally desirable that the sequence encoded by the donor polynucleotide molecule is integrated at the site of the DSB at high efficiency. One measure of efficiency is the percentage or fraction of the population of cells that have been treated with a DSB-inducing agent and donor polynucleotide molecule, and in which a sequence encoded by the donor polynucleotide molecule is successfully introduced at the DSB correctly located in the genome. The efficiency of genome editing including integration of a sequence encoded by a donor polynucleotide molecule at a DSB in the genome is assessed by any suitable method such as a heteroduplex cleavage assay or by sequencing, as described elsewhere in this disclosure. In various embodiments, the DSB is induced in the correct location in the genome at a comparatively high efficiency, e.g., at about 10, about 15, about 20, about 30, about 40, about 50, about 60, about 70, or about 80 percent efficiency, or at greater than 80, 85, 90, or 95 percent efficiency (measured as the percentage of the total population of cells in which the DSB is induced at the correct location in the genome). In various embodiments, a sequence encoded by the donor polynucleotide molecule is integrated at the site of the DSB at a comparatively high efficiency, e.g., at about 10, about 15, about 20, about 30, about 40, about 50, about 60, about 70, or about 80 percent efficiency, or at greater than 80, 85, 90, or 95 percent efficiency (measured as the percentage of the total population of cells in which the polynucleotide molecule is integrated at the site of the DSB in the correct location in the genome).

Apart from the CRISPR-type nucleases, other nucleases capable of effecting site-specific alteration of a target nucleotide sequence include zinc-finger nucleases (ZFNs), transcription activator-like effector nucleases (TAL-effector nucleases or TALENs), Argonaute proteins, and a meganuclease or engineered meganuclease. Zinc finger nucleases (ZFNs) are engineered proteins comprising a zinc finger DNA-binding domain fused to a nucleic acid cleavage domain, e.g., a nuclease. The zinc finger binding domains provide specificity and can be engineered to specifically recognize any desired target DNA sequence. For a review of the construction and use of ZFNs in plants and other organisms, see, e.g., Umov et al. (2010) *Nature Rev. Genet.*, 11:636-646. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotides bases outside their target triplet. Typically, the engineered zinc finger DNA binding domain has a novel binding specificity, compared to a naturally-occurring zinc finger protein. Modification methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) are well known and described in the literature. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described; see, e.g., Guo et al. (2010) *J. Mol. Biol.* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. For a description of the use of TALENs in plants, see Mahfouz et al. (2011) *Proc. Natl. Acad. Sci. USA,* 108:2623-2628 and Mahfouz (2011) *GM Crops,* 2:99-103.

Argonauts are proteins that can function as sequence-specific endonucleases by binding a polynucleotide (e.g., a single-stranded DNA or single-stranded RNA) that includes sequence complementary to a target nucleotide sequence) that guides the Argonaut to the target nucleotide sequence and effects site-specific alteration of the target nucleotide sequence; see, e.g., U.S. Patent Application Publication 2015/0089681, incorporated herein by reference in its entirety.

Another method of effecting targeted changes to a genome is the use of triple-forming peptide nucleic acids (PNAs) designed to bind site-specifically to genomic DNA via strand invasion and the formation of PNA/DNA/PNA triplexes (via both Watson-Crick and Hoogsteen binding) with a displaced DNA strand. PNAs consist of a charge neutral peptide-like backbone and nucleobases. The nucleobases hybridize to DNA with high affinity. The triplexes then recruit the cell's endogenous DNA repair systems to initiate site-specific modification of the genome. The desired sequence modification is provided by single-stranded 'donor DNAs' which are co-delivered as templates for repair. See, e.g., Bahal R et al (2016) *Nature Communications*, Oct. 26, 2016.

In related embodiments, zinc finger nucleases, TALENs, and Argonautes are used in conjunction with other functional domains. For example, the nuclease activity of these nucleic acid modification systems can be altered so that the enzyme binds to but does not cleave the DNA. Examples of functional domains include transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes; inhibitor of histone modifying enzymes, histone methyltransferases, histone demethylases, histone kinases, histone phosphatases, histone ribosylases, histone deribosylases, histone ubiquitinases, histone deubiquitinases, histone biotinases and histone tail proteases. Non-limiting examples of functional domains include a transcriptional activation domain, a transcription repression domain, and an SHH1, SUVH2, or SUVH9 polypeptide capable of reducing expression of a target nucleotide sequence via epigenetic modification; see, e.g., U.S. Patent Application Publication 2016/0017348, incorporated herein by reference in its entirety. Genomic DNA may also be modified via base editing using a fusion between a catalytically inactive Cas9 (dCas9) is fused to a cytidine deaminase which convert cytosine (C) to uridine (U), thereby effecting a C to T substitution; see Komor et al. (2016) *Nature,* 533:420-424.

In embodiments, the guide RNA (gRNA) has a sequence of between 16-24 nucleotides in length (e.g., 16, 17, 18, 19, 20, 21, 22, 23, or 24 nucleotides in length) or 16-24 nucleotides in length. Specific embodiments include gRNAs of 19, 20, or 21 nucleotides in length and having 100% complementarity to the target nucleotide sequence. In many embodiments the gRNA has exact complementarity (i.e., perfect base-pairing) to the target nucleotide sequence; in certain other embodiments the gRNA has less than 100% complementarity to the target nucleotide sequence. The design of effective gRNAs for use in plant genome editing is disclosed in U.S. Patent Application Publication 2015/0082478 A1, the entire specification of which is incorporated herein by reference. In embodiments where multiple gRNAs are employed, the multiple gRNAs can be delivered separately (as separate RNA molecules or encoded by separate DNA molecules) or in combination, e.g., as an RNA molecule containing multiple gRNA sequences, or as a DNA molecule encoding an RNA molecule containing multiple gRNA sequences; see, for example, U.S. Patent Application Publication 2016/0264981 A1, the entire specification of which is incorporated herein by reference, which discloses RNA molecules including multiple RNA sequences (such as gRNA sequences) separated by tRNA cleavage sequences. In other embodiments, a DNA molecule encodes multiple gRNAs which are separated by other types of cleavable transcript, for example, small RNA (e.g., miRNA, siRNA, or ta-siRNA) recognition sites which can be cleaved by the corresponding small RNA, or dsRNA-forming regions which can be cleaved by a Dicer-type ribonuclease, or sequences which are recognized by RNA nucleases such as Cys4 ribonuclease from *Pseudomonas aeruginosa*; see, e.g., U.S. Pat. No. 7,816,581, the entire specification of which is incorporated herein by reference, which discloses in FIG. 27 and elsewhere in the specification pol II promoter-driven DNA constructs encoding RNA transcripts that are released by cleavage. Efficient Cas9-mediated gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). In other embodiments, self-cleaving ribozyme sequences can be used to separate multiple gRNA sequences within a transcript.

Thus, in certain embodiments wherein the nuclease is a Cas9-type nuclease, the gRNA can be provided as a polynucleotide composition including: (a) a CRISPR RNA (crRNA) that includes the gRNA together with a separate tracrRNA, or (b) at least one polynucleotide that encodes a crRNA and a tracrRNA (on a single polynucleotide or on separate polynucleotides), or (c) at least one polynucleotide that is processed into one or more crRNAs and a tracrRNA. In other embodiments wherein the nuclease is a Cas9-type nuclease, the gRNA can be provided as a polynucleotide composition including a CRISPR RNA (crRNA) that includes the gRNA, and the required tracrRNA is provided in a separate composition or in a separate step, or is otherwise provided to the cell (for example, to a plant cell or plant protoplast that stably or transiently expresses the tracrRNA from a polynucleotide encoding the tracrRNA). In other embodiments wherein the nuclease is a Cas9-type nuclease, the gRNA can be provided as a polynucleotide composition comprising: (a) a single guide RNA (sgRNA) that includes the gRNA, or (b) a polynucleotide that encodes a sgRNA, or (c) a polynucleotide that is processed into a sgRNA. Cpf1-mediated gene editing does not require a tracrRNA; thus, in embodiments wherein the nuclease is a Cpf1-type nuclease, the gRNA is provided as a polynucleotide composition comprising (a) a CRISPR RNA (crRNA) that includes the gRNA, or (b) a polynucleotide that encodes a crRNA, or (c) a polynucleotide that is processed into a crRNA. In embodiments, the gRNA-containing composition optionally includes an RNA-guided nuclease, or a polynucleotide that encodes the RNA-guided nuclease. In other embodiments, an RNA-guided nuclease or a polynucleotide that encodes the RNA-guided nuclease is provided in a separate step. In some embodiments of the method, a gRNA is provided to a cell (e.g., a plant cell or plant protoplast) that includes an RNA-guided nuclease or a polynucleotide that encodes an RNA-guided nuclease, e.g., an RNA-guided nuclease selected from the group consisting of an RNA-guided DNA endonuclease, a type II Cas nuclease, a Cas9, a type V Cas nuclease, a Cpf1, a CasY, a CasX, a C2c1, a C2c3, an engineered RNA-guided nuclease, and a codon-optimized RNA-guided nuclease; in an example, the cell (e.g., a plant cell or plant protoplast) stably or transiently expresses the RNA-guided nuclease. In embodiments, the polynucleotide that encodes the RNA-guided nuclease is, for example, DNA that encodes the RNA-guided nuclease and is stably integrated in the genome of a plant cell or plant protoplast, DNA or RNA that encodes the RNA-guided nuclease and is transiently present in or introduced into a plant cell or plant protoplast; such DNA or RNA can be introduced, e.g., by using a vector such as a plasmid or viral vector or as an mRNA, or as vector-less DNA or RNA introduced directly into a plant cell or plant protoplast.

In embodiments that further include the step of providing to a cell (e.g., a plant cell or plant protoplast) an RNA-guided nuclease or a polynucleotide that encodes the RNA-guided nuclease, the RNA-guided nuclease is provided simultaneously with the gRNA-containing composition, or in a separate step that precedes or follows the step of providing the gRNA-containing composition. In embodiments, the gRNA-containing composition further includes an RNA-guided nuclease or a polynucleotide that encodes the RNA-guided nuclease. In other embodiments, there is provided a separate composition that includes an RNA-guided nuclease or a polynucleotide that encodes the RNA-guided nuclease. In embodiments, the RNA-guided nuclease is provided as a ribonucleoprotein (RNP) complex, e.g., a preassembled RNP that includes the RNA-guided nuclease complexed with a polynucleotide including the gRNA or encoding a gRNA, or a preassembled RNP that includes a polynucleotide that encodes the RNA-guided nuclease (and optionally encodes the gRNA, or is provided with a separate polynucleotide including the gRNA or encoding a gRNA), complexed with a protein. In embodiments, the RNA-guided nuclease is a fusion protein, i.e., wherein the RNA-guided nuclease (e.g., Cas9, Cpf1, CasY, CasX, C2c1, or C2c3) is covalently bound through a peptide bond to a cell-penetrating peptide, a nuclear localization signal peptide, a chloroplast transit peptide, or a mitochondrial targeting peptide; such fusion proteins are conveniently encoded in a single nucleotide sequence, optionally including codons for linking amino acids. In embodiments, the RNA-guided nuclease or a polynucleotide that encodes the RNA-guided nuclease is provided as a complex with a cell-penetrating peptide or other transfecting agent. In embodiments, the RNA-guided nuclease or a polynucleotide that encodes the RNA-guided nuclease is complexed with, or covalently or non-covalently bound to, a further element, e.g., a carrier molecule, an antibody, an antigen, a viral movement protein, a polymer, a detectable label (e.g., a moiety detectable by fluorescence, radioactivity, or enzymatic or immunochemical reaction), a quantum dot, or a particulate or nanoparticulate. In embodiments, the RNA-guided nuclease or a polynucleotide that encodes the RNA-guided nuclease is provided in a solution, or is provided in a liposome, micelle, emulsion, reverse emulsion, suspension, or other mixed-phase composition.

An RNA-guided nuclease can be provided to a cell (e.g., a plant cell or plant protoplast) by any suitable technique. In embodiments, the RNA-guided nuclease is provided by directly contacting a plant cell or plant protoplast with the RNA-guided nuclease or the polynucleotide that encodes the RNA-guided nuclease. In embodiments, the RNA-guided nuclease is provided by transporting the RNA-guided nuclease or a polynucleotide that encodes the RNA-guided nuclease into a plant cell or plant protoplast using a chemical, enzymatic, or physical agent as provided in detail in the paragraphs following the heading "Delivery Methods and Delivery Agents". In embodiments, the RNA-guided nuclease is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of a plant cell or plant protoplast with a polynucleotide encoding the RNA-guided nuclease; see, e.g., Broothaerts et al. (2005) *Nature*, 433:629-633. In an embodiment, the RNA-guided nuclease is provided by transcription in a plant cell or plant protoplast of a DNA that encodes the RNA-guided nuclease and is stably integrated in the genome of the plant cell or plant protoplast or that is provided to the plant cell or plant protoplast in the form of a plasmid or expression vector (e.g., a viral vector) that encodes the RNA-guided nuclease (and optionally encodes one or more gRNAs, crRNAs, or sgRNAs, or is optionally provided with a Ieparate plasmid or vector that encodes one or more gRNAs, crRNAs, or sgRNAs). In embodiments, the RNA-guided nuclease is provided to the plant cell or plant protoplast as a polynucleotide that encodes the RNA-guided nuclease, e.g., in the form of an mRNA encoding the nuclease.

Where a polynucleotide is concerned (e.g., a crRNA that includes the gRNA together with a separate tracrRNA, or a crRNA and a tracrRNA encoded on a single polynucleotide or on separate polynucleotides, or at least one polynucleotide that is processed into one or more crRNAs and a tracrRNA, or a sgRNA that includes the gRNA, or a polynucleotide that encodes a sgRNA, or a polynucleotide that is processed into a sgRNA, or a polynucleotide that encodes the RNA-guided nuclease), embodiments of the polynucleotide include: (a) double-stranded RNA; (b) single-stranded RNA; (c) chemically modified RNA; (d) double-stranded DNA; (e) single-stranded DNA; (f) chemically modified DNA; or (g) a combination of (a)-(f). Where expression of a polynucleotide is involved (e.g., expression of a crRNA from a DNA encoding the crRNA, or expression and translation of a RNA-guided nuclease from a DNA encoding the nuclease), in some embodiments it is sufficient that expression be transient, i.e., not necessarily permanent or stable in the cell. Certain embodiments of the polynucleotide further include additional nucleotide sequences that provide useful functionality; non-limiting examples of such additional nucleotide sequences include an aptamer or riboswitch sequence, nucleotide sequence that provides secondary structure such as stem-loops or that provides a sequence-specific site for an enzyme (e.g., a sequence-specific recombinase or endonuclease site), T-DNA (e.g., DNA sequence encoding a gRNA, crRNA, tracrRNA, or sgRNA is enclosed between left and right T-DNA borders from *Agrobacterium* spp. or from other bacteria that infect or induce tumours in plants), a DNA nuclear-targeting sequence, a regulatory sequence such as a promoter sequence, and a transcript-stabilizing sequence. Certain embodiments of the polynucleotide include those wherein the polynucleotide is complexed with, or covalently or non-covalently bound to, a non-nucleic acid element, e.g., a carrier molecule, an antibody, an antigen, a viral movement protein, a cell-penetrating or pore-forming peptide, a polymer, a detectable label, a quantum dot, or a particulate or nanoparticulate.

In embodiments, the at least one DSB is introduced into the genome by at least one treatment selected from the group consisting of: (a) bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection with a DSB-inducing agent; (b) Biolistics or particle bombardment with a DSB-inducing agent; (c) treatment with at least one chemical, enzymatic, or physical agent as provided in detail in the paragraphs following the heading "Delivery Methods and Delivery Agents"; and (d) application of heat or cold, ultrasonication, centrifugation, positive or negative pressure, cell wall or membrane disruption or deformation, or electroporation. It is generally desirable that introduction of the at least one DSB into the genome (i.e., the "editing" of the genome) is achieved with sufficient efficiency and accuracy to ensure practical utility. One measure of efficiency is the percentage or fraction of the population of cells that have been treated with a DSB-inducing agent and in which the DSB is successfully introduced at the correct site in the genome. The efficiency of genome editing is assessed by any suitable method such as a heteroduplex cleavage assay or by sequencing, as described elsewhere in this disclosure. Accuracy is indicated by the absence of, or minimal occurrence of, off-target introduction of a DSB (i.e., at other than the intended site in the genome).

The location where the at least one DSB is inserted varies according to the desired result, for example whether the intention is to simply disrupt expression of the sequence of interest, or to add functionality (such as placing expression of the sequence of interest under inducible control). Thus, the location of the DSB is not necessarily within or directly adjacent to the sequence of interest. In embodiments, the at least one DSB in a genome is located: (a) within the sequence of interest, (b) upstream of (i.e., 5' to) the sequence of interest, or (c) downstream of (i.e., 3' to) the sequence of interest. In embodiments, a sequence encoded by the donor polynucleotide molecule (such as a double-stranded DNA, a single-stranded DNA, a single-stranded DNA/RNA hybrid, or a double-stranded DNA/RNA hybrid), when integrated into the genome, is functionally or operably linked (e.g., linked in a manner that modifies the transcription or the translation of the sequence of interest or that modifies the stability of a transcript including that of the sequence of interest) to the sequence of interest. In embodiments, a sequence encoded by the donor polynucleotide molecule is integrated at a location 5' to and operably linked to the sequence of interest, wherein the integration location is selected to provide a specifically modulated (upregulated or downregulated) level of expression of the sequence of interest. For example, a sequence encoded by the donor polynucleotide molecule is integrated at a specific location in the promoter region of a protein-encoding gene that results in a desired expression level of the protein; in an embodiment, the appropriate location is determined empirically by integrating a sequence encoded by the donor polynucleotide molecule at about 50, about 100, about 150, about 200, about 250, about 300, about 350, about 400, about 450, and about 500 nucleotides 5' to (upstream of) the start codon of the coding sequence, and observing the relative expression levels of the protein for each integration location.

In embodiments, the donor polynucleotide sequence of interest includes coding (protein-coding) sequence, non-coding (non-protein-coding) sequence, or a combination of coding and non-coding sequence. Embodiments include a plant nuclear sequence, a plant plastid sequence, a plant mitochondrial sequence, a sequence of a symbiont, pest, or pathogen of a plant, and combinations thereof. Embodiments include exons, introns, regulatory sequences including promoters, other 5' elements and 3' elements, and genomic loci encoding non-coding RNAs including long non-coding RNAs (lncRNAs), microRNAs (miRNAs), and trans-acting siRNAs (ta-siRNAs). In embodiments, multiple sequences are altered, for example, by delivery of multiple gRNAs to the plant cell or plant protoplast; the multiple sequences can be part of the same gene (e.g., different locations in a single coding region or in different exons or introns of a protein-coding gene) or different genes. In embodiments, the sequence of an endogenous genomic locus is altered to delete, add, or modify a functional non-coding sequence; in non-limiting examples, such functional non-coding sequences include, e.g., a miRNA, siRNA, or ta-siRNA recognition or cleavage site, a splice site, a recombinase recognition site, a transcription factor binding site, or a transcriptional or translational enhancer or repressor sequence.

In embodiments, the invention provides a method of changing expression of a sequence of interest in a genome, including integrating a sequence encoded by a donor polynucleotide molecule (such as a double-stranded DNA, a single-stranded DNA, a single-stranded DNA/RNA hybrid, or a double-stranded DNA/RNA hybrid) at the site of two or more DSBs in a genome. In embodiments, the sequence of the donor polynucleotide molecule that is integrated into each of the two or more DSBs is (a) identical, or (b) different, for each of the DSBs. In embodiments, the change in expression of a sequence of interest in genome is manifested as the expression of an altered or edited sequence of interest; in non-limiting examples, the method is used to integrate sequence-specific recombinase recognition site sequences at two DSBs in a genome, whereby, in the presence of the corresponding site-specific DNA recombinase, the genomic sequence flanked on either side by the integrated recombinase recognition sites is excised from the genome (or in some instances is inverted); such an approach is useful, e.g., for deletion of larger lengths of genomic sequence, for example, deletion of all or part of an exon or of one or more protein domains. In other embodiments, at least two DSBs are introduced into a genome by one or more nucleases in such a way that genomic sequence is deleted between the DSBs (leaving a deletion with blunt ends, overhangs or a combination of a blunt end and an overhang), and a sequence encoded by at least one donor polynucleotide molecule is integrated between the DSBs (i.e., a sequence encoded by at least one individual donor polynucleotide molecule is integrated at the location of the deleted genomic sequence), wherein the genomic sequence that is deleted is coding sequence, non-coding sequence, or a combination of coding and non-coding sequence; such embodiments provide the advantage of not requiring a specific PAM site at or very near the location of a region wherein a nucleotide sequence change is desired. In an embodiment, at least two DSBs are introduced into a genome by one or more nucleases in such a way that genomic sequence is deleted between the DSBs (leaving a deletion with blunt ends, overhangs or a combination of a blunt end and an overhang), and at least one sequence encoded by a donor polynucleotide molecule is integrated between the DSBs (i.e., at least one individual sequence encoded by a donor polynucleotide molecule is integrated at the location of the deleted genomic sequence). In an embodiment, two DSBs are introduced into a genome, resulting in excision or deletion of genomic sequence between the sites of the two DSBs, and a sequence encoded by a donor polynucleotide molecule integrated into the genome at the location of the deleted genomic sequence (that is, a sequence encoded by an individual donor polynucleotide molecule is integrated between the two DSBs). Generally, the donor polynucleotide molecule with the sequence to be integrated into the genome is selected in terms of the presence or absence of terminal overhangs to match the type of DSBs introduced. In an embodiment, two blunt-ended DSBs are introduced into a genome, resulting in excision or deletion of genomic sequence between the sites of the two blunt-ended DSBs, and a sequence encoded by a blunt-ended double-stranded DNA or blunt-ended double-stranded DNA/RNA hybrid or a single-stranded DNA or a single-stranded DNA/RNA hybrid donor molecule is integrated into the genome between the two blunt-ended DSBs. In another embodiment, two DSBs are introduced into a genome, wherein the first DSB is blunt-ended and the second DSB has an overhang, resulting in deletion of genomic sequence between the two DSBs, and a sequence encoded by a double-stranded DNA or double-stranded DNA/RNA hybrid donor molecule that is blunt-ended at one terminus and that has an overhang on the other terminus (or, alternatively, a single-stranded DNA or a single-stranded DNA/RNA hybrid molecule) is integrated into the genome between the two DSBs; in an alternative embodiment, two DSBs are introduced into a genome, wherein both DSBs have overhangs but of different overhang lengths (different number of unpaired nucleotides), resulting in deletion of genomic sequence between the two DSBs, and a sequence encoded by a double-stranded DNA or double-stranded DNA/RNA hybrid donor molecule that has overhangs at each terminus, wherein the overhangs are of unequal lengths (or, alternatively, a single-stranded DNA or a single-stranded DNA/RNA hybrid donor molecule), is integrated into the genome between the two DSBs; embodiments with such DSB asymmetry (i.e., a combination of DSBs having a blunt end and an overhang, or a combination of DSBs having overhangs of unequal lengths) provide the opportunity for controlling directionality or orientation of the inserted polynucleotide, e.g., by selecting a double-stranded DNA or double-stranded DNA/RNA hybrid donor molecule having one blunt end and one terminus with unpaired nucleotides, such that the polynucleotide is integrated preferably in one orientations. In another embodiment, two DSBs, each having an overhang, are introduced into a genome, resulting in excision or deletion of genomic sequence between the sites of the two DSBs, and a sequence encoded by a double-stranded DNA or double-stranded DNA/RNA hybrid donor molecule that has an overhang at each terminus (or, alternatively, a single-stranded DNA or a single-stranded DNA/RNA hybrid donor molecule) is integrated into the genome between the two DSBs. The length of genomic sequence that is deleted between two DSBs and the length of a sequence encoded by the donor polynucleotide molecule that is integrated in place of the deleted genomic sequence can be, but need not be equal. In embodiments, the distance between any two DSBs (or the length of the genomic sequence that is to be deleted) is at least 10, at least 15, at least 20, at least 25, at least 30, at least 40, at least 50, at least 60, at least 70, at least 80, or at least 100 nucleotides; in other embodiments the distance between any two DSBs (or the length of the genomic sequence that is to be deleted) is at least 100, at least 150, at least 200, at least 300, at least 400, at least 500, at least 600, at least 750, or at least 1000 nucleotides. In embodiments where more than two DSBs are introduced into genomic sequence, it is possible to effect different deletions of genomic sequence (for example, where three DSBs are introduced, genomic sequence can be deleted between the first and second DSBs, between the first and third DSBs, and between the second and third DSBs). In some embodiments, a sequence encoded by more than one donor polynucleotide molecule (e.g., multiple copies of a sequence encoded by a donor polynucleotide molecule having a given sequence, or multiple sequences encoded by donor polynucleotide molecules with two or more different sequences) is integrated into the genome. For example, different sequences encoded by individual donor polynucleotide molecules can be individually integrated at a single locus where genomic sequence has been deleted between two DSBs, or at multiple locations where genomic sequence has been deleted (e.g., where more than two DSBs have been introduced into the genome). In embodiments, at least one exon is replaced by integrating a sequence encoded by at least one polynucleotide molecule where genomic sequence is deleted between DSBs that were introduced by at least one sequence-specific nuclease into intronic sequence flanking the at least one exon; an advantage of this approach over an otherwise similar method (i.e., differing by having the DSBs introduced into coding sequence instead of intronic sequence) is the avoidance of inaccuracies (nucleotide changes, deletions, or additions at the nuclease cleavage sites) in the resulting exon sequence or messenger RNA.

In embodiments, the methods described herein are used to delete or replace genomic sequence, which can be a relatively large sequence (e.g., all or part of at least one exon or of a protein domain) resulting in the equivalent of an alternatively spliced transcript. Additional related aspects include compositions and reaction mixtures including a plant cell or a plant protoplast and at least two guide RNAs, wherein each guide RNA is designed to effect a DSB in intronic sequence flanking at least one exon; such compositions and reaction mixtures optionally include at least one sequence-specific nuclease capable of being guided by at least one of the guide RNAs to effect a DSB in genomic sequence, and optionally include a donor polynucleotide molecule that is capable of being integrated (or having its sequence integrated) into the genome at the location of at least one DSB or at the location of genomic sequence that is deleted between the DSBs.

Donor polynucleotide molecules: Embodiments of the donor polynucleotide molecule having a sequence that is heterologously integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor polynucleotide molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor polynucleotide molecule that is integrated (or that has a sequence that is integrated) at the site of at least one double-strand break (DSB) in a genome is double-stranded and blunt-ended; in other embodiments the donor polynucleotide molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor polynucleotide molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor polynucleotide molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor polynucleotide molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cpf1 nuclease effects an off-set DSB with 5-nucleotide overhangs in the genomic sequence, the donor polynucleotide molecule that is to be integrated (or that has a sequence that is to be integrated) at the site of the DSB is double-stranded and has 5 unpaired nucleotides at one or both termini). Generally, one or both termini of the donor polynucleotide molecule contain no regions of sequence homology (identity or complementarity) to genomic regions flanking the DSB; that is to say, one or both termini of the donor polynucleotide molecule contain no regions of sequence that is sufficiently complementary to permit hybridization to genomic regions immediately adjacent to the location of the DSB. In embodiments, the donor polynucleotide molecule contains no homology to the locus of the DSB, that is to say, the donor polynucleotide molecule contains no nucleotide sequence that is sufficiently complementary to permit hybridization to genomic regions immediately adjacent to the location of the DSB. In an embodiment, the donor polynucleotide molecule that is integrated at the site of at least one double-strand break (DSB) includes between 2-20 nucleotides or 2-20 nucleotides in one (if single-stranded) or in both strands (if double-stranded), e.g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). In embodiments, the donor polynucleotide molecule is at least partially double-stranded and includes 2-20 base-pairs, e.g., 2, 3, 4, 5, 6, 7, 8, 9, 10, 11, 12, 13, 14, 15, 16, 17, 18, 19, or 20 base-pairs; in embodiments, the donor polynucleotide molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor polynucleotide molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. Non-limiting examples of such relatively small donor polynucleotide molecules of 20 or fewer base-pairs (if double-stranded) or 20 or fewer nucleotides (if single-stranded) include donor polynucleotide molecules that have at least one strand including a transcription factor recognition site sequence (e.g., such as the sequences of transcription factor recognition sites provided in the working Examples), or that have at least one strand including a small RNA recognition site, or that have at least one strand including a recombinase recognition site. In an embodiment, the donor polynucleotide molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor polynucleotide molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor polynucleotide molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded) or about 2 to about 320 base-pairs if double-stranded (or nucleotides if single-stranded), or between about 2 to about 500 base-pairs if double-stranded (or nucleotides if single-stranded) or about 2 to about 500 base-pairs (or nucleotides if single-stranded), or between about 5 to about 500 base-pairs if double-stranded (or nucleotides if single-stranded) or about 5 to about 500 base-pairs (or nucleotides if single-stranded), or between about 5 to about 300 base-pairs if double-stranded (or nucleotides if single-stranded) or about 5 to about 300 base-pairs (or nucleotides if single-stranded), or between about 11 to about 300 base-pairs if double-stranded (or nucleotides if single-stranded) or about 11 to about 300 base-pairs (or nucleotides if single-stranded), or about 18 to about 300 base-pairs if double-stranded (or nucleotides if single-stranded), or between about 30 to about 100 base-pairs if double-stranded (or nucleotides if single-stranded) or about 30 to about 100 base-pairs (or nucleotides if single-stranded). In embodiments, the donor polynucleotide molecule includes chemically modified nucleotides (see, e.g., the various modifications of internucleotide linkages, bases, and sugars described in Verma and Eckstein (1998) *Annu. Rev. Biochem.*, 67:99-134); in embodiments, the naturally occurring phosphodiester backbone of the donor polynucleotide molecule is partially or completely modified with phosphorothioate, phosphorodithioate, or methylphosphonate internucleotide linkage modifications, or the donor polynucleotide molecule includes modified nucleoside bases or modified sugars, or the donor polynucleotide molecule is labelled with a fluorescent moiety (e.g., fluorescein or rhodamine or a fluorescent nucleoside analogue) or other detectable label (e.g., biotin or an isotope). In an embodiment, the donor polynucleotide molecule is double-stranded and perfectly base-paired through all or most of its length, with the possible exception of any unpaired nucleotides at either terminus or both termini. In another embodiment, the donor polynucleotide molecule is double-stranded and includes one or more non-terminal mismatches or non-terminal unpaired nucleotides within the otherwise double-stranded duplex. In another embodiment, the donor polynucleotide molecule contains secondary structure that provides stability or acts as an aptamer. Other related embodiments include double-stranded DNA/RNA hybrid molecules, single-stranded DNA/RNA hybrid donor molecules, and single-stranded DNA donor molecules (including single-stranded, chemically modified DNA donor molecules), which in analogous procedures are integrated (or have a sequence that is integrated) at the site of a double-strand break.

In embodiments of the method, the donor polynucleotide molecule (such as a double-stranded DNA, a single-stranded DNA, a single-stranded DNA/RNA hybrid, or a double-stranded DNA/RNA hybrid) that is integrated at the site of at least one double-strand break (DSB) in a genome includes nucleotide sequence(s) on one or on both strands that provide a desired functionality when the polynucleotide is integrated into the genome. In various non-limiting embodiments of the method, the sequence encoded by a donor polynucleotide that is inserted at the site of at least one double-strand break (DSB) in a genome includes at least one sequence selected from the group consisting of:

(a) DNA encoding at least one stop codon, or at least one stop codon on each strand, or at least one stop codon within each reading frame on each strand;
(b) DNA encoding heterologous primer sequence (e.g., a sequence of about 18 to about 22 contiguous nucleotides, or of at least 18 contiguous nucleotides, that can be used to initiate DNA polymerase activity at the site of the DSB);
(c) DNA encoding a unique identifier sequence (e.g., a sequence that when inserted at the DSB creates a heterologous sequence that can be used to identify the presence of the insertion);
(d) DNA encoding a transcript-stabilizing sequence;
(e) DNA encoding a transcript-destabilizing sequence;
(f) a DNA aptamer or DNA encoding an RNA aptamer or amino acid aptamer; and
(g) DNA that includes or encodes a sequence recognizable by a specific binding agent.

In an embodiment, the sequence encoded by the donor polynucleotide molecule (such as a double-stranded DNA, a single-stranded DNA, a single-stranded DNA/RNA hybrid, or a double-stranded DNA/RNA hybrid) that is integrated at the site of at least one double-strand break (DSB) in a genome includes DNA encoding at least one stop codon, or at least one stop codon on each strand, or at least one stop codon within each reading frame on each strand. Such sequence encoded by a donor polynucleotide molecule, when integrated at a DSB in a genome can be useful for disrupting the expression of a sequence of interest, such as a protein-coding gene. An example of such a donor polynucleotide molecule is a double-stranded DNA, a single-stranded DNA, a single-stranded DNA/RNA hybrid, or a double-stranded DNA/RNA hybrid donor molecule, of at least 18 contiguous base-pairs if double-stranded or at least 11 contiguous nucleotides if single-stranded, and encoding at least one stop codon in each possible reading frame on either strand. Another example of such a donor polynucleotide molecule is a double-stranded DNA or double-stranded DNA/RNA hybrid donor molecule wherein each strand includes at least 18 and fewer than 200 contiguous base-pairs, wherein the number of base-pairs is not divisible by 3, and wherein each strand encodes at least one stop codon in each possible reading frame in the 5' to 3' direction. Another example of such a donor polynucleotide molecule is a single-stranded DNA or single-stranded DNA/RNA hybrid donor molecule wherein each strand includes at least 11 and fewer than about 300 contiguous nucleotides, wherein the number of base-pairs is not divisible by 3, and wherein the donor polynucleotide molecule encodes at least one stop codon in each possible reading frame in the 5' to 3' direction.

In an embodiment, the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes DNA encoding heterologous primer sequence (e.g., a sequence of about 18 to about 22 contiguous nucleotides, or of at least 18, at least 20, or at least 22 contiguous nucleotides that can be used to initiate DNA polymerase activity at the site of the DSB). Heterologous primer sequence can further include nucleotides of the genomic sequence directly flanking the site of the DSB.

In an embodiment, the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes nucleotides encoding a unique identifier sequence (e.g., a sequence that when inserted at the DSB creates a heterologous sequence that can be used to identify the presence of the insertion)

In an embodiment, the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes nucleotides encoding a transcript-stabilizing sequence. In an example, sequence of a double-stranded or single-stranded DNA or a DNA/RNA hybrid donor molecule encoding a 5' terminal RNA-stabilizing stem-loop (see, e.g., Suay (2005) *Nucleic Acids Rev.*, 33:4754-4761) is integrated at a DSB located 5' to the sequence for which improved transcript stability is desired. In another embodiment, the donor polynucleotide molecule that is integrated (or that has a sequence that is integrated) at the site of at least one double-strand break (DSB) in a genome includes nucleotides encoding a transcript-destabilizing sequence such as the SAUR destabilizing sequences described in detail in U.S. Patent Application Publication 2007/0011761, incorporated herein by reference.

In an embodiment, the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes a DNA aptamer or DNA encoding an RNA aptamer or amino acid aptamer. Nucleic acid (DNA or RNA) aptamers are single- or double-stranded nucleotides that bind specifically to molecules or ligands which include small molecules (e.g., secondary metabolites such as alkaloids, terpenes, flavonoids, and other small molecules, as well as larger molecules such as polyketides and non-ribosomal proteins), proteins, other nucleic acid molecules, and inorganic compounds. Introducing an aptamer at a specific location in the genome is useful, e.g., for adding binding specificity to an enzyme or for placing expression of a transcript or activity of an encoded protein under ligand-specific control. In an example, the donor polynucleotide molecule encodes a poly-histidine "tag" which is integrated at a DSB downstream of a protein or protein subunit, enabling the protein expressed from the resulting transcript to be purified by affinity to nickel, e.g., on nickel resins; in an embodiments, the donor polynucleotide molecule encodes a 6×-His tag, a 10×-His tag, or a 10×-His tag including one or more stop codons following the histidine-encoding codons, where the last is particularly useful when integrated downstream of a protein or protein subunit lacking a stop codon (see, e.g., parts[dot]igem[dot] org/Part:BBa_K844000). In embodiments, the donor polynucleotide molecule encodes a riboswitch, wherein the riboswitch includes both an aptamer which changes its conformation in the presence or absence of a specific ligand, and an expression-controlling region that turns expression on or off, depending on the conformation of the aptamer. See, for example, the regulatory RNA molecules containing ligand-specific aptamers described in U.S. Patent Application Publication 2013/0102651 and the various riboswitches described in U.S. Patent Application Publication 2005/0053951, both of which publications are incorporated herein by reference.

In an embodiment, the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes nucleotides that include or encode a sequence recognizable by (i.e., binds to) a specific binding agent. Non-limiting embodiments of specific binding agents include nucleic acids, peptides or proteins, non-peptide/non-nucleic acid ligands, inorganic molecules, and combinations thereof; specific binding agents also include macromolecular assemblages such as lipid bilayers, cell components or organelles, and even intact cells or organisms. In embodiments, the specific binding agent is an aptamer or riboswitch, or alternatively is recognized by an aptamer or a riboswitch. In an embodiment, the invention provides a method of changing expression of a sequence of interest in a genome, comprising integrating a polynucleotide molecule at the site of a DSB in a genome, wherein the donor polynucleotide molecule includes a sequence recognizable by a specific binding agent, wherein the integrated sequence encoded by the donor polynucleotide molecule is functionally or operably linked to a sequence of interest, and wherein contacting the integrated sequence encoded by the donor polynucleotide molecule with the specific binding agent results in a change of expression of the sequence of interest; in embodiments, sequences encoded by different donor polynucleotide molecules are integrated at multiple DSBs in a genome.

In an embodiment, the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes nucleotides that include or encode a sequence recognizable by (i.e., binds to) a specific binding agent, wherein:

(a) the sequence recognizable by a specific binding agent includes an auxin response element (AuxRE) sequence, the specific binding agent is an auxin, and the change of expression is upregulation; see, e.g., Walker and Estelle (1998) *Curr. Opinion Plant Biol.*, 1:434-439;

(b) the sequence recognizable by a specific binding agent includes at least one D1-4 sequence (CCTCGTGTCTC, SEQ ID NO:328; see Ulmasov et al. (1997) *Plant Cell*, 9:1963-1971), the specific binding agent is an auxin, and the change of expression is upregulation;

(c) the sequence recognizable by a specific binding agent includes at least one DR5 sequence (CCTTTTGTCTC, SEQ ID NO:329; see Ulmasov et al. (1997) *Plant Cell*, 9:1963-1971), the specific binding agent is an auxin, and the change of expression is upregulation;

(d) the sequence recognizable by a specific binding agent includes at least one m5-DR5 sequence (CCTTTTGTCNC, wherein N is A, C, or G, SEQ ID NO:330; see Ulmasov et al. (1997) *Plant Cell*, 9:1963-1971), the specific binding agent is an auxin, and the change of expression is upregulation;

(e) the sequence recognizable by a specific binding agent includes at least one P3 sequence (TGTCTC, SEQ ID NO:331), the specific binding agent is an auxin, and the change of expression is upregulation;

(f) the sequence recognizable by a specific binding agent includes a small RNA recognition site sequence, the specific binding agent is the corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein), and the change of expression is downregulation (non-limiting examples are given below, under the heading "Small RNAs");

(g) the sequence recognizable by a specific binding agent includes a microRNA (miRNA) recognition site sequence, the specific binding agent is the corresponding mature miRNA, and the change of expression is downregulation (non-limiting examples are given below, under the heading "Small RNAs");

(h) the sequence recognizable by a specific binding agent includes a microRNA (miRNA) recognition sequence for an engineered miRNA, the specific binding agent is the corresponding engineered mature miRNA, and the change of expression is downregulation;

(i) the sequence recognizable by a specific binding agent includes a transposon recognition sequence, the specific binding agent is the corresponding transposon, and the change of expression is upregulation or downregulation;

(j) the sequence recognizable by a specific binding agent includes an ethylene-responsive element binding-factor-associated amphiphilic repression (EAR) motif (LxLxL, SEQ ID NO:332 or DLNxxP, SEQ ID NO:333) sequence (see, e.g., Ragale and Rozwadowski (2011) *Epigenetics*, 6:141-146), the specific binding agent is ERF (ethylene-responsive element binding factor) or co-repressor (e.g., TOPLESS (TPL)), and the change of expression is downregulation;

(k) the sequence recognizable by a specific binding agent includes a splice site sequence (e.g., a donor site, a branching site, or an acceptor site; see, for example, the splice sites and splicing signals publicly available at the ERIS database, lemur[dot]amu[dot]edu[dot]pl/share/ERISdb/home.html), the specific binding agent is a spliceosome, and the change of expression is expression of an alternatively spliced transcript (in some cases, this can include deletion of a relatively large genomic sequence, such as deletion of all or part of an exon or of a protein domain);

(l) the sequence recognizable by a specific binding agent includes a recombinase recognition site sequence that is recognized by a site-specific recombinase, the specific binding agent is the corresponding site-specific recombinase, and the change of expression is upregulation or downregulation or expression of a transcript having an altered sequence (for example, expression of a transcript that has had a region of DNA excised by the recombinase) (non-limiting examples are given below, under the heading "Recombinases and Recombinase Recognition Sites");

(m) the sequence recognizable by a specific binding agent includes sequence encoding an RNA or amino acid aptamer or an RNA riboswitch, the specific binding agent is the corresponding ligand, and the change in expression is upregulation or downregulation;

(n) the sequence recognizable by a specific binding agent is a hormone responsive element (e.g., a nuclear receptor, or a hormone-binding domain thereof), the specific binding agent is a hormone, and the change in expression is upregulation or downregulation; or (o) the sequence recognizable by a specific binding agent is a transcription factor binding sequence, the specific binding agent is the corresponding transcription factor, and the change in expression is upregulation or downregulation (non-limiting examples are given below, under the heading "Transcription Factors").

In embodiments, the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes a nucleotide sequence that encodes an RNA molecule or an amino acid sequence that is recognizable by a specific binding agent. In embodiments, the donor polynucleotide molecule includes a nucleotide sequence that binds specifically to a ligand or that encodes an RNA molecule or an amino acid sequence that binds specifically to a ligand. In embodiments, the donor polynucleotide molecule encodes at least one stop codon on each strand, or encodes at least one stop codon within each reading frame on each strand.

In embodiments, the donor polynucleotide molecule (such as a double-stranded DNA, a single-stranded DNA, a single-stranded DNA/RNA hybrid, or a double-stranded DNA/RNA hybrid) includes at least partially self-complementary sequence, such that the donor polynucleotide molecule encodes a transcript that is capable of forming at least partially double-stranded RNA. In embodiments, the at least partially double-stranded RNA is capable of forming secondary structure containing at least one stem-loop (i.e., a substantially or perfectly double-stranded RNA "stem" region and a single-stranded RNA "loop" connecting opposite strands of the dsRNA stem. In embodiments, the at least partially double-stranded RNA is cleavable by a Dicer or other ribonuclease. In embodiments, the at least partially double-stranded RNA includes an aptamer or a riboswitch; see, e.g., the RNA aptamers described in U.S. Patent Application Publication 2013/0102651, which is incorporated herein by reference.

In embodiments, the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes or encodes a nucleotide sequence that is responsive to a specific change in the physical environment (e.g., a change in light intensity or quality, a change in temperature, a change in pressure, a change in osmotic concentration, a change in day length, or addition or removal of a ligand or specific binding agent), wherein exposing the integrated polynucleotide sequence to the specific change in the physical environment results in a change of expression of the sequence of interest. In embodiments, the donor polynucleotide molecule includes a nucleotide sequence encoding an RNA molecule or an amino acid sequence that is responsive to a specific change in the physical environment. In a non-limiting example, the donor polynucleotide molecule encodes an amino acid sequence that is responsive to light, oxygen, redox status, or voltage, such as a Light-Oxygen-Voltage (LOV) domain (see, e.g., Peter et al. (2010) *Nature Communications*, doi:10.1038/ncomms1121) or a PAS domain (see, e.g., Taylor and Zhulin (1999)*Microbiol. Mol. Biol. Reviews*, 63:479-506), proteins containing such domains, or sub-domains or motifs thereof (see, e.g., the photochemically active 36-residue N-terminal truncation of the VVD protein described by Zoltowski et al. (2007) *Science*, 316:1054-1057). In a non-limiting embodiment, integration of a LOV domain at the site of a DSB within or adjacent to a protein-coding region is used to create a heterologous fusion protein that can be photo-activated.

Small RNAs: In an embodiment, the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes DNA that includes or encodes a small RNA recognition site sequence that is recognized by a corresponding mature small RNA. Small RNAs include siRNAs, microRNAs (miRNAs), trans-acting siRNAs (ta-siRNAs) as described in U.S. Pat. No. 8,030,473, and phased small RNAs (phased sRNAs) as described in U.S. Pat. No. 8,404,928. All mature small RNAs are single-stranded RNA molecules, generally between about 18 to about 26 nucleotides in length or about 18 to about 26 nucleotides in length, which are produced from longer, completely or substantially double-stranded RNA (dsRNA) precursors. For example, siRNAs are generally processed from perfectly or near-perfectly double-stranded RNA precursors, whereas both miRNAs and phased sRNAs are processed from larger precursors that contain at least some mismatched (non-base-paired) nucleotides and often substantial secondary structure such as loops and bulges in the otherwise largely double-stranded RNA precursor. Precursor molecules include naturally occurring precursors, which are often expressed in a specific (e.g., cell- or tissue-specific, temporally specific, developmentally specific, or inducible) expression pattern. Precursor molecules also include engineered precursor molecules, designed to produce small RNAs (e.g., artificial or engineered siRNAs or miRNAs) that target specific sequences; see, e.g., U.S. Pat. Nos. 7,691,995 and 7,786,350, which are incorporated herein by reference in their entirety. Thus, in embodiments, the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes DNA that includes or encodes a small RNA precursor sequence designed to be processed in vivo to at least one corresponding mature small RNA. In embodiments, the donor polynucleotide molecule that is integrated (or that has a sequence that is integrated) at the site of at least one double-strand break (DSB) in a genome includes DNA that includes or encodes an engineered small RNA precursor sequence that is based on a naturally occurring "scaffold" precursor sequence but wherein the nucleotides of the encoded mature small RNA are designed to target a specific gene of interest that is different from the gene targeted by the natively encoded small RNA; in embodiments, the "scaffold" precursor sequence is one identified from the genome of a plant or a pest or pathogen of a plant; see, e.g., U.S. Pat. No. 8,410,334, which discloses transgenic expression of engineered invertebrate miRNA precursors in a plant, and which is incorporated herein by reference in its entirety.

Regardless of the pathway that generates the mature small RNA, the mechanism of action is generally similar; the mature small RNA binds in a sequence-specific manner to a small RNA recognition site located on an RNA molecule (such as a transcript or messenger RNA), and the resulting duplex is cleaved by a ribonuclease. The integration of a recognition site for a small RNA at the site of a DSB results in cleavage of the transcript including the integrated recognition site when and where the mature small RNA is expressed and available to bind to the recognition site. For example, a recognition site sequence for a mature siRNA or miRNA that is endogenously expressed only in male reproductive tissue of a plant can be integrated into a DSB, whereby a transcript containing the recognition site sequence is cleaved only where the mature siRNA or miRNA is expressed (i.e., in male reproductive tissue); this is useful, e.g., to prevent expression of a protein in male reproductive tissue such as pollen, and can be used in applications such as to induce male sterility in a plant or to prevent pollen development or shedding. Similarly, a recognition site sequence for a mature siRNA or miRNA that is endogenously expressed only in the roots of a plant can be integrated into a DSB, whereby a transcript containing the recognition site sequence is cleaved only in roots; this is useful, e.g., to prevent expression of a protein in roots. Non-limiting examples of useful small RNAs include: miRNAs having tissue-specific expression patterns disclosed in U.S. Pat. No. 8,334,430, miRNAs having temporally specific expression patterns disclosed in U.S. Pat. No. 8,314,290, miRNAs with stress-responsive expression patterns disclosed in U.S. Pat. No. 8,237,017, siRNAs having tissue-specific expression patterns disclosed in U.S. Pat. No. 9,139,838, and various miRNA recognition site sequences and the corresponding miRNAs disclosed in U.S. Patent Application Publication 2009/0293148. All of the patent publications referenced in this paragraph are incorporated herein by reference in their entirety. In embodiments, multiple edits in a genome are employed to obtain a desired phenotype or trait in plant. In an embodiment, one or more edits (addition, deletion, or substitution of one or more nucleotides) of an endogenous nucleotide sequence is made to provide a general phenotype; addition of at least one small RNA recognition site by insertion of the recognition site sequence at a DSB that is functionally linked to the edited endogenous nucleotide sequence achieves more specific control of expression of the edited endogenous nucleotide sequence. In an example that can be carried out in maize, an endogenous plant 5-enolpyruvylshikimate-3-phosphate synthase (EPSPS) is edited to provide a glyphosate-resistant EPSPS; for example, suitable changes include the amino acid substitutions Threonine-102-Isoleucine (T102I) and Proline-106-Serine (P106S) in the maize EPSPS sequence identified by Genbank accession number X63374 (see, for example U.S. Pat. No. 6,762,344, incorporated herein by reference). In another example, an endogenous plant acetolactate synthase (ALS) is edited to increase resistance of the enzyme to various herbicides (e.g., sulfonylurea, imidazolinone, tirazolopyrimidine, pyrimidinylthiobenzoate, sulfonylaminocarbonyltriazolinone); for example, suitable changes include the amino acid substitutions G115, A116, P191, A199, K250, M345, D370, V565, W568, and F572 to the *Nicotiana tabacum* ALS enzyme as described in U.S. Pat. No. 5,605,011, which is incorporated herein by reference. The edited herbicide-tolerant enzyme, combined with integration of at least one small RNA recognition site for a small RNA (e.g., an siRNA or a miRNA) expressed only in a specific tissue (for example, miRNAs specifically expressed in male reproductive tissue or female reproductive tissue, e.g., the miRNAs disclosed in Table 6 of U.S. Pat. No. 8,334,430 or the siRNAs disclosed in U.S. Pat. No. 9,139,838, both incorporated herein by reference) at a DSB functionally linked to (e.g., in the 3' untranslated region of) the edited herbicide-tolerant enzyme results in expression of the edited herbicide-tolerant enzyme being restricted to tissues other than those in which the small RNA is endogenously expressed, and those tissues in which the small RNA is expressed will not be resistant to herbicide application; this approach is useful, e.g., to provide male-sterile or female-sterile plants.

In other embodiments, the sequence of an endogenous genomic locus encoding one or more small RNAs (e.g., miRNAs, siRNAs, ta-siRNAs) is altered in order to express a small RNA having a sequence that is different from that of the endogenous small RNA and is designed to target a new sequence of interest (e.g., a sequence of a plant pest, plant pathogen, symbiont of a plant, or symbiont of a plant pest or pathogen). For example, the sequence of an endogenous or native genomic locus encoding a miRNA precursor can be altered in the mature miRNA and the miR* sequences, while maintaining the secondary structure in the resulting altered miRNA precursor sequence to permit normal processing of the transcript to a mature miRNA with a different sequence from the original, native mature miRNA sequence; see, for example, U.S. Pat. Nos. 7,786,350 and 8,395,023, both of which are incorporated by reference in their entirety herein, and which teach methods of designing engineered miRNAs. In embodiments, the sequence of an endogenous genomic locus encoding one or more small RNAs (e.g., miRNAs, siRNAs, ta-siRNAs) is altered in order to express one or more small RNA cleavage blockers (see, e.g., U.S. Pat. No. 9,040,774, which is incorporated by reference in its entirety herein). In embodiments, the sequence of an endogenous genomic locus is altered to encode a small RNA decoy (e.g., U.S. Pat. No. 8,946,511, which is incorporated by reference in its entirety herein). In embodiments, the sequence of an endogenous genomic locus that natively contains a small RNA (e.g., miRNA, siRNA, or ta-siRNA) recognition or cleavage site is altered to delete or otherwise mutate the recognition or cleavage site and thus decouple the genomic locus from small RNA regulation.

Recombinases and Recombinase Recognition Sites: In an embodiment, the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes DNA that includes or encodes a recombinase recognition site sequence that is recognized by a site-specific recombinase, the specific binding agent is the corresponding site-specific recombinase, and the change of expression is upregulation or downregulation or expression of a transcript having an altered sequence (for example, expression of a transcript that has had a region of DNA excised by the recombinase). The term "recombinase recognition site sequence" refers to the DNA sequences (usually a pair of sequences) that are recognized by a site-specific (i.e., sequence-specific) recombinase in a process that allows the excision (or, in some cases, inversion or translocation) of the DNA located between the sequence-specific recombination sites. For instance, Cre recombinase recognizes either loxP recombination sites or lox511 recombination sites which are heterospecific, which means that loxP and lox511 do not recombine together (see, e.g., Odell et al. (1994) *Plant Physiol.*, 106:447-458); FLP recombinase recognizes frt recombination sites (see, e.g., Lyznik et al. (1996) *Nucleic Acids Res.*, 24:3784-3789); R recombinase recognizes Rs recombination sites (see, e.g., Onounchi et al. (1991) *Nucleic Acids Res.*, 19:6373-6378); Dre recombinase recognizes rox sites (see, e.g., U.S. Pat. No. 7,422,889, incorporated herein by reference); and Gin recombinase recognizes gix sites (see, e.g., Maeser et al. (1991) *Mol. Gen. Genet.*, 230:170-176). In a non-limiting example, a pair of polynucleotides encoding loxP recombinase recognition site sequences encoded by a pair of donor polynucleotide molecules are integrated at two separate DSBs; in the presence of the corresponding site-specific DNA recombinase Cre, the genomic sequence flanked on either side by the integrated loxP recognition sites is excised from the genome (for loxP sequences that are integrated in the same orientation relative to each other within the genome) or is inverted (for loxP sites that are integrated in an inverted orientation relative to each other within the genome) or is translocated (for loxP sites that are integrated on separate DNA molecules); such an approach is useful, e.g., for deletion or replacement of larger lengths of genomic sequence, for example, deletion or replacement of one or more protein domains. In embodiments, the recombinase recognition site sequences that are integrated at two separate DSBs are heterospecific, i.e., will not recombine together; for example, Cre recombinase recognizes either loxP recombination sites or lox511 recombination sites which are heterospecific relative to each other, which means that a loxP site and a lox511 site will not recombine together but only with another recombination site of its own type.

Integration of recombinase recognition sites is useful in plant breeding; in an embodiment, the method is used to provide a first parent plant having recombinase recognition site sequences heterologously integrated at two separate DSBs; crossing this first parent plant to a second parent plant that expresses the corresponding recombinase results in progeny plants in which the genomic sequence flanked on either side by the heterologously integrated recognition sites is excised from (or in some cases, inverted in) the genome. This approach is useful, e.g., for deletion of relatively large regions of DNA from a genome, for example, for excising DNA encoding a selectable or screenable marker that was introduced using transgenic techniques. Examples of heterologous arrangements or integration patterns of recombinase recognition sites and methods for their use, particularly in plant breeding, are disclosed in U.S. Pat. No. 8,816,153 (see, for example, the Figures and working examples), the entire specification of which is incorporated herein by reference.

Transcription Factors: In an embodiment, the sequence encoded by the donor polynucleotide molecule (such as a double-stranded DNA, a single-stranded DNA, a single-stranded DNA/RNA hybrid, or a double-stranded DNA/RNA hybrid) that is integrated (or that has a sequence that is integrated) at the site of at least one double-strand break (DSB) in a genome includes a transcription factor binding sequence, the specific binding agent is the corresponding transcription factor (or more specifically, the DNA-binding domain of the corresponding transcription factor), and the change in expression is upregulation or downregulation (depending on the type of transcription factor involved). In an embodiment, the transcription factor is an activating transcription factor or activator, and the change in expression is upregulation or increased expression increased expression (e.g., increased expression of at least 10%, 15%, 20%, 25%, 30%, 35%, 40%, 50%, 60%, 70%, 80%, 90%, 95%, 100% or greater, e.g., at least a 2-fold, 5-fold, 10-fold, 20-fold, 30-fold, 40-fold, 50-fold change, 100-fold or even 1000-fold change or greater) of a sequence of interest to which the transcription factor binding sequence, when integrated at a DSB in the genome, is operably linked. In some embodiments, expression is increased between 10-100%; between 2-fold and 5-fold; between 2 and 10-fold; between 10-fold and 50-fold; between 10-fold and a 100-fold; between 100-fold and 1000-fold; between 1000-fold and 5,000-fold; between 5,000-fold and 10,000 fold. In some embodiments, expression is increased about 10-100%; about 2-fold to 5-fold; about 2 to 10-fold; about 10-fold to 50-fold; about 10-fold to a 100-fold; about 100-fold to 1000-fold; about 1000-fold to 5,000-fold; or about 5,000-fold and 10,000 fold. In some embodiments, a targeted insertion may decrease expression by at least 1%, 5%, 10%, 15%, 20%, 25%, 30%, 35%, 40%, 50%, 60%, 70%, 80%, 90%, 95%, 99% or more. In another embodiment, the transcription factor is a repressing transcription factor or repressor, and the change in expression is downregulation or decreased expression (e.g., decreased expression by at least 1%, 5%, 10%, 15%, 20%, 25%, 30%, 35%, 40%, 50%, 60%, 70%, 80%, 90%, 95%, 99% or more) of a sequence of interest to which the transcription factor binding sequence, when integrated at a DSB in the genome, is operably linked. Embodiments of transcription factors include hormone receptors, e.g., nuclear receptors, which include both a hormone-binding domain and a DNA-binding domain; in embodiments, the donor polynucleotide molecule that is integrated (or that has a sequence that is integrated) at the site of at least one double-strand break (DSB) in a genome includes or encodes a hormone-binding domain of a nuclear receptor or a DNA-binding domain of a nuclear receptor. Various non-limiting examples of transcription factor binding sequences and transcription factors are provided in the working Examples. In embodiments, the sequence recognizable by a specific binding agent is a transcription factor binding sequence selected from those publicly disclosed at arabidopsis[dot]med[dot]ohio-state[dot]edu/AtcisDB/binding-sites[dot]html and neomorph[dot]salk[dot]edu/dap_web/pages/index[dot]php.

To summarize, the methods described herein permit sequences encoded by donor polynucleotides to be inserted, in a non-multiplexed or multiplexed manner, into a plant cell genome for the purpose of modulating gene expression in a number of distinct ways. Gene expression can be modulated up or down, for example, by tuning expression through the insertion of enhancer elements and transcription start sequences (e.g., nitrate response elements and auxin binding elements). Conditional transcription factor binding sites can be added or modified to allow additional control. Similarly, transcript stabilizing and/or destabilizing sequences can be inserted using the methods herein. Via the targeted insertion of stop codons, RNAi cleavage sites, or sites for recombinases, the methods described herein allow the transcription of particular sequences to be selectively turned off (likewise, the targeted removal of such sequences can be used to turn gene transcription on).

The plant genome modification methods disclosed herein also enable transcription rates to be adjusted by the modification (optimization or de-optimization) of core promoter sequences (e.g., TATAA boxes). Proximal control elements (e.g., GC boxes; CAAT boxes) can likewise be modified. Enhancer or repressor motifs can be inserted or modified. Three-dimensional structural barriers in DNA that inhibit RNA polymerase can be created or removed via the targeted insertion of sequences, or by the modification of existing sequences. Where intron mediated enhancement is known to affect transcript rate, the relevant rate-affecting sequences can be optimized or de-optimized (by insertion of additional sequences or modification of existing sequences) to further enhance or diminish transcription. Through the insertion or modification of sequences using the modification methods described herein (including multiplexed modification methods), mRNA stability and processing can be modulated (thereby modulating gene expression). For example, mRNA stabilizing or destabilizing motifs can be inserted, removed or modified; mRNA splicing donor/acceptor sites can be inserted, removed or modified and, in some instance, create the possibility of increased control over alternate splicing. Similarly, miRNA binding sites can be added, removed or modified using the methods described herein. Epigenetic regulation of transcription can also be adjusted according to the methods described herein (e.g., by increasing or decreasing the degree of methylation of DNA, or the degree of methylation or acetylation of histones). Epigenetic regulation using the tools and methods described herein can be combined with other methods for modifying genetic sequences described herein, for the purpose of modifying a trait of a plant cell or plant, or for creating populations of modified cells and cells from which desired phenotypes can be selected.

The plant genome modification methods described herein can also be used to modulate translation efficiency by, e.g., modifying codon usage towards or away from a particular plant cell's bias. Similarly, through the use of the modification methods described herein, KOZAK sequences can be optimized or deoptimized, mRNA folding and structures affecting initation of translation can be altered, and upstream reading frames can be created or destroyed. Through alteration of coding sequences using the targeted genome modification methods described herein, the abundance and/or activity of translated proteins can be adjusted. For example, the amino acid sequences in active sites or functional sites of proteins can be modified to increase or decrease the activity of the protein as desired; in addition, or alternatively, protein stabilizing or destabilizing motifs can be added or modified. All of the gene expression and activity modification schemes described herein can be utilized in various combinations to fine-tune gene expression and activity. Using the multiplexed modification methods described herein, a plurality of specific precise modifications can be achieved in a plant cell without intervening selection or sequencing steps.

Modified wheat cells comprising specifically targeted and modified genomes: Another aspect of the invention includes the modified wheat cell, provided by the methods disclosed herein. In an embodiment, a wheat cell thus provided includes in its genome a heterologous DNA sequence that includes: (a) nucleotide sequence of a polynucleotide (such as a double-stranded DNA, a single-stranded DNA, a single-stranded DNA/RNA hybrid, or a double-stranded DNA/RNA hybrid) molecule integrated at the site of a DSB in a genome; and (b) genomic nucleotide sequence adjacent to the site of the DSB. In embodiments, the methods disclosed herein for integrating a sequence encoded by a donor polynucleotide molecule into the site of a DSB are applied to a wheat cell (e.g., a wheat cell or protoplast isolated from a whole wheat plant or wheat plant part or wheat plant tissue, or an isolated wheat cell or protoplast in suspension or plate culture); in other embodiments, the methods are applied to non-isolated wheat cells in situ or in planta, such as a wheat cell located in an intact or growing wheat plant or in a wheat plant part or wheat tissue. The methods disclosed herein for integrating a sequence encoded by a donor polynucleotide molecule into the site of a DSB are also useful in introducing heterologous sequence at the site of a DSB induced in the genome of other photosynthetic eukaryotes (e.g., green algae, red algae, diatoms, brown algae, and dinoflagellates). In embodiments, the wheat cell or protoplast is capable of division and further differentiation. In embodiments, the wheat cell or protoplast is obtained or isolated from a wheat plant or part of a wheat plant selected from the group consisting of a wheat tissue, a whole wheat plant, an intact nodal bud, a shoot apex or shoot apical meristem, a root apex or root apical meristem, lateral meristem, intercalary meristem, a seedling (e.g., a germinating seed or small seedling or a larger seedling with one or more true leaves), a whole seed (e.g., an intact seed, or a seed with part or all of its seed coat removed or treated to make permeable), a halved seed or other seed fragment, a zygotic or somatic embryo (e.g., a mature dissected zygotic embryo, a developing zygotic or somatic embryo, a dry or rehydrated or freshly excised zygotic embryo), pollen, microspores, epidermis, flower, and callus.

In some embodiments, the method includes the additional step of growing or regenerating a wheat plant from a wheat cell containing the heterologous DNA sequence of the donor polynucleotide molecule integrated at the site of a DSB and genomic nucleotide sequence adjacent to the site of the DSB, wherein the wheat plant includes at least some cells that contain the heterologous DNA sequence of the donor polynucleotide molecule integrated at the site of a DSB and genomic nucleotide sequence adjacent to the site of the DSB. In embodiments, callus is produced from the wheat cell, and wheat plantlets and plants produced from such callus. In other embodiments, whole seedlings or plants are grown directly from the wheat cell without a callus stage. Thus, additional related aspects are directed to whole seedlings and plants grown or regenerated from the wheat cell or protoplast containing sequence encoded by a donor polynucleotide molecule (such as a double-stranded DNA, a single-stranded DNA, a single-stranded DNA/RNA hybrid, or a double-stranded DNA/RNA hybrid) heterologously integrated at the site of a DSB, as well as the seeds of such wheat plants; embodiments include whole seedlings and plants grown or regenerated from the wheat cell or protoplast containing sequence encoded by a donor polynucleotide molecule heterologously integrated at the site of two or more DSBs, as well as the seeds of such wheat plants. In embodiments, the grown or regenerated wheat plant exhibits a phenotype associated with the sequence encoded by a donor polynucleotide molecule heterologously integrated at the site of a DSB. In embodiments, the grown or regenerated wheat plant includes in its genome two or more genetic modifications that in combination provide at least one phenotype of interest, wherein at least one of the two or more genetic modifications includes the sequence encoded by a donor polynucleotide molecule heterologously integrated at the site of a DSB in the genome, or wherein the two or more genetic modifications include sequence encoded by at least one donor polynucleotide heterologously integrated at two or more DSBs in the genome, or wherein the two or more genetic modifications include sequences encoded by multiple polynucleotides donor molecules heterologously integrated at different DSBs in the genome. In embodiments, a heterogeneous population of wheat cells or protoplasts, at least some of which include sequence encoded by at least one donor polynucleotide molecule heterologously integrated at the site of a DSB, is provided by the method; related aspects include a wheat plant having a phenotype of interest associated with sequence encoded by the donor polynucleotide molecule heterologously integrated at the site of a DSB, provided by either regeneration of a wheat plant having the phenotype of interest from a wheat cell or protoplast selected from the heterogeneous population of wheat cells or protoplasts, or by selection of a wheat plant having the phenotype of interest from a heterogeneous population of wheat plants grown or regenerated from the population of wheat cells or protoplasts. Examples of phenotypes of interest include (but are not limited to) herbicide resistance; improved tolerance of abiotic stress (e.g., tolerance of temperature extremes, drought, or salt) or biotic stress (e.g., resistance to bacterial or fungal pathogens); improved utilization of nutrients or water; synthesis of new or modified amounts of lipids, carbohydrates, proteins or other chemicals, including medicinal compounds; improved flavour or appearance; improved photosynthesis; improved storage characteristics (e.g., resistance to bruising, browning, or softening); increased yield; altered morphology (e.g., floral architecture or colour, plant height, branching, root structure); and changes in flowering time. In an embodiment, a heterogeneous population of wheat cells or protoplasts (or seedlings or plants grown or regenerated therefrom) is exposed to conditions permitting expression of the phenotype of interest; e.g., selection for herbicide resistance can include exposing the population of wheat cells or protoplasts (or seedlings or plants) to an amount of herbicide or other substance that inhibits growth or is toxic, allowing identification and selection of those resistant wheat cells or protoplasts (or seedlings or plants) that survive treatment. In certain embodiments, a proxy measurement can be taken of an aspect of a modified wheat plant or cell, where the measurement is indicative of a desired phenotype or trait. For example, the modification of one or more precise sequences in a genome may provide a measurable change in a molecule (e.g., a detectable change in the structure of a molecule, or a change in the amount of the molecule that is detected, or the presence or absence of a molecule) that can be used as a biomarker for a presence of a desired phenotype or trait. The proper insertion of an enhancer for increasing expression of an enzyme, for example, may be determined by detecting lower levels of the enyzme's substrate.

In some embodiments, modified wheat plants are produced from wheat cells modified according to the methods described herein without a tissue culturing step. In certain embodiments, the modified wheat cell or wheat plant does not have significant losses of methylation compared to a unmodified wheat cell or plant having an unmodified or reference genome. For example, the genome of the modified wheat plant lacks significant losses of methylation in one or more promoter regions relative to the genome of the unmodified wheat cell or plant. Similarly, in certain embodiments, an modified wheat plant or cell obtained using the methods described herein lacks significant losses of methylation in protein coding regions relative to the unmodified wheat plant or cell.

Also contemplated are new heterogeneous populations, arrays, or libraries of wheat cells and plants created by the introduction of precise modifications at one more locations in the genome. Plant compositions of the invention include succeeding generations of progeny wheat plants or progeny seeds of modified wheat plants that are grown or regenerated from wheat cells or plant protoplasts modified according to the methods herein, as well as parts of those wheat plants, or products (e.g., seeds or other edible plant parts, cleaned or processed grains or seeds, edible oils, flours or starches, proteins, and other processed products) made from the modified wheat plants or their seeds. Embodiments include wheat plants grown or regenerated from the modified wheat cells or protoplasts, wherein the plants contain cells or tissues that do not have the one or more precise modifications effected by the methods described herein, e.g., chimeric wheat plants in which some but not all cells or tissues contain the one or more precise modifications. Additional related aspects include (a) a progeny or hybrid wheat plant provided by crossing a first wheat parent plant grown or regenerated from a modified wheat cell or protoplast that has one or more precise modifications effected by the methods described herein, with a second wheat parent plant, wherein the resulting progeny or hybrid plant contains the one or more precise modifications effected by the methods described herein, and (b) a progeny or hybrid plant provided by crossing a first parent wheat plant grown or regenerated from a modified wheat cell or plant protoplast that has one or more precise modifications effected by the methods described herein, with a second wheat parent plant grown or regenerated from a different modified wheat cell or plant protoplast that has one or more precise modifications effected by the methods described herein, wherein the hybrid plant contains the precise modifications of both parent wheat plants; also contemplated is seed produced by the hybrid plant. Also envisioned as related aspects are progeny seed and progeny plants, including hybrid seed and hybrid plants, having the modified wheat plant as a parent or ancestor. In embodiments, the modified wheat cell (or the wheat plant, progeny wheat seed, progeny wheat plant grown therefrom) is haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", a protocol publicly available at www[dot]openwetware[dot]org/images/d/d3/Haploid_Arabidopsis_protocol[dot]pdf; Ravi et al. (2014) *Nature Communications*, 5:5334, doi: 10.1038/ncomms6334). Examples of haploid cells include but are not limited to plant cells obtained from haploid plants and plant cells obtained from reproductive tissues, e.g., from flowers, developing flowers or flower buds, ovaries, ovules, megaspores, anthers, pollen, and microspores. In embodiments where the modified wheat cell is haploid, the method can further include the step of chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell containing heterologous DNA sequence (i.e. sequence of the donor polynucleotide molecule integrated at the site of a DSB in the genome and genomic nucleotide sequence adjacent to the site of the DSB) to produce a doubled haploid wheat cell or protoplast that is homozygous for the precise modification(s); yet other embodiments include regeneration of a doubled haploid wheat plant from the doubled haploid wheat cell or protoplast, wherein the regenerated doubled haploid wheat plant is homozygous for the precise modification(s). Thus, embodiments include a haploid wheat cell or protoplast having at least one precise genomic modification including heterologous sequence that includes sequence encoded by a donor polynucleotide molecule integrated at the site of a DSB and genomic nucleotide sequence adjacent to the site of the DSB, as well as a doubled haploid wheat cell or protoplast or a doubled haploid wheat plant that is homozygous for the at least one precise genomic modification (e.g., homozygous for the heterologously integrated sequence). Another aspect of the invention is related to a wheat plant having at least one parent plant that is a doubled haploid wheat plant provided by the method. Production of doubled haploid wheat plants by these methods provides homozygosity in one generation, instead of requiring several generations of self-crossing to obtain homozygous plants; this may be particularly advantageous for producing hybrid wheat plants that are offspring of at least one doubled-haploid wheat plant.

Wheat plants and cells that may be modified according to the methods described herein are of any wheat or related species of interest, but especially *Triticum* species (including hybrid *Triticum* species) and *Aegilops* species. In embodiments, the wheat plant or cell is common or bread wheat (*Triticum aestivum*), spelt (*Triticum spelta*), emmer (*Triticum dicoccum*), einkorn (*Triticum monococcum*), durum wheat (*Triticum durum*), or synthetic hexaploid wheat.

In another aspect, the invention provides a heterologous nucleotide sequence including: (a) nucleotide sequence encoded by a donor polynucleotide molecule integrated by the methods disclosed herein at the site of a DSB in a wheat genome, and (b) wheat genomic nucleotide sequence adjacent to the site of the DSB. Related aspects include a plasmid, vector, or chromosome including such a heterologous nucleotide sequence, as well as polymerase primers for amplification (e.g., PCR amplification) of such a heterologous nucleotide sequence.

Compositions and reaction mixtures: In one aspect, the invention provides a composition including: (a) a wheat cell; and (b) a donor polynucleotide molecule (such as a double-stranded DNA, a single-stranded DNA, a single-stranded DNA/RNA hybrid, or a double-stranded DNA/RNA hybrid) that is capable of being integrated (or having its sequence integrated) (preferably by non-homologous end-joining (NHEJ)) at one or more double-strand breaks in a genome in the cell. In many embodiments of the composition, the wheat cell is an isolated wheat cell or protoplast, or a cell in a wheat plant, wheat plant part, wheat plant tissue, or wheat callus.

In various embodiments of the composition, the wheat cell is a cell or protoplast isolated from an intact wheat plant or a wheat plant part or wheat plant tissue (e.g., a wheat cell or protoplast cultured in liquid medium or on solid medium), or a cell located in wheat callus, an intact wheat plant, seed, or seedling, or in a wheat plant part or tissue. In embodiments, the wheat cell is a cell capable of division and/or differentiation, including a wheat cell capable of being regenerated into callus or grown directly into a plant. In embodiments, the wheat cell is diploid, polyploid, or haploid (or can be induced to become haploid).

In embodiments, the composition includes a wheat cell that includes at least one double-strand break (DSB) in its genome. Alternatively, the composition includes a wheat cell in which at least one DSB will be induced in its genome, for example, by providing at least one DSB-inducing agent to the wheat cell, e.g., either together with the donor polynucleotide molecule (such as a double-stranded DNA, a single-stranded DNA, a single-stranded DNA/RNA hybrid, or a double-stranded DNA/RNA hybrid) or separately. Thus, the composition optionally further includes at least one DSB-inducing agent. In embodiments, the composition optionally further includes at least one chemical, enzymatic, or physical delivery agent, or a combination thereof; such delivery agents and methods for their use are described in detail in the paragraphs following the heading "Delivery Methods and Delivery Agents". In embodiments, the DSB-inducing agent is at least one of the group consisting of:

(a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease;

(b) a polynucleotide encoding one or more nucleases capable of effecting site-specific alteration (such as introduction of a DSB) of a target nucleotide sequence; and (c) a guide RNA (gRNA) for an RNA-guided nuclease, or a DNA encoding a gRNA for an RNA-guided nuclease.

In embodiments, the composition includes (a) a wheat cell; (b) a donor polynucleotide molecule (such as a double-stranded DNA, a single-stranded DNA, a single-stranded DNA/RNA hybrid, or a double-stranded DNA/RNA hybrid), capable of being integrated (or having its sequence integrated) at a DSB; (c) a Cas9, a Cpf1, a CasY, a CasX, a C2c1, or a C2c3 nuclease; and (d) at least one guide RNA. In an embodiment, the composition includes (a) a wheat cell; (b) a donor polynucleotide molecule (such as a double-stranded DNA, a single-stranded DNA, a single-stranded DNA/RNA hybrid, or a double-stranded DNA/RNA hybrid), capable of being integrated (or having its sequence integrated) at a DSB; (c) at least one ribonucleoprotein including a CRISPR nuclease and a guide RNA.

In embodiments of the composition, the donor polynucleotide molecule is double-stranded and blunt-ended, or is double-stranded and has an overhang or "sticky end" consisting of unpaired nucleotides (e.g., 1, 2, 3, 4, 5, or 6 unpaired nucleotides) at one terminus or both termini; in other embodiments, the donor polynucleotide molecule is a single-stranded DNA or a single-stranded DNA/RNA hybrid. In an embodiment, the donor polynucleotide molecule is a double-stranded DNA or DNA/RNA hybrid molecule that is blunt-ended or that has an overhang at one terminus or both termini, and that has about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor polynucleotide molecule is a double-stranded DNA, a single-stranded DNA, a single-stranded DNA/RNA hybrid, or a double-stranded DNA/RNA hybrid, and includes single strands of at least 11, at least 18, at least 20, at least 30, at least 40, at least 60, at least 80, at least 100, at least 120, at least 140, at least 160, at least 180, at least 200, at least 240, at least 280, or at least 320 nucleotides. In embodiments, the donor polynucleotide molecule includes chemically modified nucleotides; in embodiments, the naturally occurring phosphodiester backbone of the polynucleotide molecule is partially or completely modified with phosphorothioate, phosphorodithioate, or methylphosphonate internucleotide linkage modifications, or the donor polynucleotide molecule includes modified nucleoside bases or modified sugars, or the donor polynucleotide molecule is labelled with a fluorescent moiety or other detectable label. In an embodiment, the donor polynucleotide molecule is double-stranded and perfectly base-paired through all or most of its length, with the possible exception of any unpaired nucleotides at either terminus or both termini. In another embodiment, the donor polynucleotide molecule is double-stranded and includes one or more non-terminal mismatches or non-terminal unpaired nucleotides within the otherwise double-stranded duplex. Other related embodiments include single- or double-stranded DNA/RNA hybrid donor molecules. Additional description of the donor polynucleotide molecule is found above in the paragraphs following the heading "Donor polynucleotide molecules".

In embodiments of the composition, the donor polynucleotide molecule includes:

(a) a nucleotide sequence that is recognizable by a specific binding agent;
(b) a nucleotide sequence encoding an RNA molecule or an amino acid sequence that is recognizable by a specific binding agent;
(c) a nucleotide sequence that encodes an RNA molecule or an amino acid sequence that binds specifically to a ligand;
(d) a nucleotide sequence that is responsive to a specific change in the physical environment; or
(e) a nucleotide sequence encoding an RNA molecule or an amino acid sequence that is responsive to a specific change in the physical environment;
(f) a nucleotide sequence encoding at least one stop codon on each strand;
(g) a nucleotide sequence encoding at least one stop codon within each reading frame on each strand; or
(h) at least partially self-complementary sequence, such that the polynucleotide molecule encodes a transcript that is capable of forming at least partially double-stranded RNA; or
(i) a combination of any of (a)-(h).

In another aspect, the invention provides a reaction mixture including: (a) a wheat cell having a double-strand break (DSB) at least one locus in its genome; and (b) a donor polynucleotide molecule (such as a double-stranded DNA, a single-stranded DNA, a single-stranded DNA/RNA hybrid, or a double-stranded DNA/RNA hybrid) capable of being integrated or inserted (or having its sequence integrated or inserted) at the DSB (preferably by non-homologous end-joining (NHEJ)), with a length of between about 18 to about 300 base-pairs (or nucleotides, if single-stranded) or about 18 to about 300 base-pairs (or nucleotides, if single-stranded), or between about 30 to about 100 base-pairs (or nucleotides, if single-stranded) or about 30 to about 100 base-pairs (or nucleotides, if single-stranded); wherein sequence encoded by the donor polynucleotide molecule, if integrated at the DSB, forms a heterologous insertion (that is to say, resulting in a concatenated nucleotide sequence that is a combination of the sequence of the polynucleotide molecule and at least some of the genomic sequence adjacent to the site of DSB, wherein the concatenated sequence is heterologous, i.e., would not otherwise or does not normally occur at the site of insertion). In embodiments, the product of the reaction mixture includes a wheat cell in which sequence encoded by the donor polynucleotide molecule has been integrated at the site of the DSB.

In many embodiments of the reaction mixture, the wheat cell is an isolated wheat cell or protoplast, or is a wheat cell in a wheat plant, wheat plant part, wheat tissue, or wheat callus. In various embodiments of the reaction mixture, the wheat cell is a wheat cell or protoplast isolated from an intact wheat plant or wheat plant part or wheat plant tissue (e.g., a wheat cell or protoplast cultured in liquid medium or on solid medium), or a wheat cell located in wheat callus, an intact wheat plant, seed, or seedling, or in a wheat plant part or tissue. In many embodiments, the wheat cell is capable of division and/or differentiation, including a wheat cell capable of being regenerated into callus or grown directly into a wheat plant. In embodiments, the wheat cell is diploid, polyploid, or haploid (or can be induced to become haploid).

In embodiments, the reaction mixture includes a wheat cell or protoplast that includes at least one double-strand break (DSB) in its genome. Alternatively, the reaction mixture includes a wheat cell or protoplast in which at least one DSB will be induced in its genome, for example, by providing at least one DSB-inducing agent to the plant cell, e.g., either together with a donor polynucleotide molecule (such as a double-stranded DNA, a single-stranded DNA, a single-stranded DNA/RNA hybrid, or a double-stranded DNA/RNA hybrid) capable of being integrated or inserted (or having its sequence integrated or inserted) at the DSB, or separately. Thus, the reaction mixture optionally further includes at least one DSB-inducing agent. In embodiments, the reaction mixture optionally further includes at least one chemical, enzymatic, or physical delivery agent, or a combination thereof; such delivery agents and methods for their use are described in detail in the paragraphs following the heading "Delivery Methods and Delivery Agents". In embodiments, the DSB-inducing agent is at least one of the group consisting of:
- (a) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), an Argonaute, and a meganuclease or engineered meganuclease;
- (b) a polynucleotide encoding one or more nucleases capable of effecting site-specific alteration (such as introduction of a DSB) of a target nucleotide sequence; and
- (c) a guide RNA (gRNA) for an RNA-guided nuclease, or a DNA encoding a gRNA for an RNA-guided nuclease.

In embodiments, the reaction mixture includes (a) a wheat cell; (b) a donor polynucleotide molecule (such as a double-stranded DNA, a single-stranded DNA, a single-stranded DNA/RNA hybrid, or a double-stranded DNA/RNA hybrid) capable of being integrated or inserted (or having its sequence integrated or inserted) at the DSB; (c) a Cas9, a Cpf1, a CasY, a CasX, a C2c1, or a C2c3 nuclease; and (d) at least one guide RNA. In an embodiment, the reaction mixture includes (a) a wheat cell or protoplast; (b) a donor polynucleotide molecule (such as a double-stranded DNA, a single-stranded DNA, a single-stranded DNA/RNA hybrid, or a double-stranded DNA/RNA hybrid) capable of being integrated or inserted (or having its sequence integrated or inserted) at the DSB; (c) at least one ribonucleoprotein including a CRISPR nuclease and a guide RNA. In an embodiment, the reaction mixture includes (a) a wheat cell or protoplast; (b) a donor polynucleotide molecule (such as a double-stranded DNA, a single-stranded DNA, a single-stranded DNA/RNA hybrid, or a double-stranded DNA/RNA hybrid) capable of being integrated or inserted (or having its sequence integrated or inserted) at the DSB; (c) at least one ribonucleoprotein including Cas9 and an sgRNA.

In embodiments of the reaction mixture, the donor polynucleotide molecule (such as a double-stranded DNA, a single-stranded DNA, a single-stranded DNA/RNA hybrid, or a double-stranded DNA/RNA hybrid) includes:
- (a) a nucleotide sequence that is recognizable by a specific binding agent;
- (b) a nucleotide sequence encoding an RNA molecule or an amino acid sequence that is recognizable by a specific binding agent;
- (c) a nucleotide sequence that encodes an RNA molecule or an amino acid sequence that binds specifically to a ligand;
- (d) a nucleotide sequence that is responsive to a specific change in the physical environment; or
- (e) a nucleotide sequence encoding an RNA molecule or an amino acid sequence that is responsive to a specific change in the physical environment;
- (f) a nucleotide sequence encoding at least one stop codon on each strand;
- (g) a nucleotide sequence encoding at least one stop codon within each reading frame on each strand; or
- (h) at least partially self-complementary sequence, such that the polynucleotide molecule encodes a transcript that is capable of forming at least partially double-stranded RNA; or
- (i) a combination of any of (a)-(h).

Additional description relating to these various embodiments of nucleotide sequences included in the donor polynucleotide molecule is found in the section headed "Methods of changing expression of a sequence of interest in a genome".

Polynucleotides for disrupting gene expression: In another aspect, the invention provides a polynucleotide (such as a double-stranded DNA, a single-stranded DNA, a single-stranded DNA/RNA hybrid, or a double-stranded DNA/RNA hybrid) molecule for disrupting gene expression in a wheat genome, including double-stranded polynucleotides containing at least 18 base-pairs and encoding at least one stop codon in each possible reading frame on each strand and single-stranded polynucleotides containing at least 11 contiguous nucleotides and encoding at least one stop codon in each possible reading frame on the strand. Such a stop-codon-containing polynucleotide, when integrated or inserted at the site of a DSB in a wheat genome, disrupts or hinders translation of an encoded amino acid sequence. In embodiments, the polynucleotide is a double-stranded DNA or double-stranded DNA/RNA hybrid molecule including at least 18 contiguous base-pairs and encoding at least one stop codon in each possible reading frame on either strand; in embodiments, the polynucleotide is a double-stranded DNA or double-stranded DNA/RNA hybrid molecule that is blunt-ended; in other embodiments, the polynucleotide is a double-stranded DNA or double-stranded DNA/RNA hybrid molecule that has one or more overhangs or unpaired nucleotides at one or both termini. In embodiments, the polynucleotide is double-stranded and includes between about 18 to about 300 nucleotides on each strand or about 18 to about 300 nucleotides on each strand. In embodiments, the polynucleotide is a single-stranded DNA or a single-stranded DNA/RNA hybrid molecule including at least 11 contiguous nucleotides and encoding at least one stop codon in each possible reading frame on the strand. In embodiments, the polynucleotide is single-stranded and includes between 11 and about 300 contiguous nucleotides in the strand or about 11 to about 300 contiguous nucleotides in the strand.

In embodiments, the polynucleotide for disrupting gene expression in a wheat genome further includes a nucleotide sequence that provides a useful function when integrated into the site of a DSB in a genome. For example, in various non-limiting embodiments the polynucleotide further includes: sequence that is recognizable by a specific binding agent or that binds to a specific molecule or encodes an RNA molecule or an amino acid sequence that binds to a specific molecule, or sequence that is responsive to a specific change in the physical environment or encodes an RNA molecule or an amino acid sequence that is responsive to a specific change in the physical environment, or heterologous sequence, or sequence that serves to stop transcription at the site of the DSB, or sequence having secondary structure (e.g., double-stranded stems or stem-loops) or than encodes a transcript having secondary structure (e.g., double-stranded RNA that is cleavable by a Dicer-type ribonuclease).

In an embodiment, the polynucleotide for disrupting gene expression in a wheat genome is a double-stranded DNA or a double-stranded DNA/RNA hybrid molecule, wherein each strand of the polynucleotide includes at least 18 and fewer than 200 contiguous base-pairs, wherein the number of base-pairs is not divisible by 3, and wherein each strand encodes at least one stop codon in each possible reading frame in the 5' to 3' direction. In an embodiment, the polynucleotide is a double-stranded DNA or a double-stranded DNA/RNA hybrid molecule, wherein the polynucleotide includes at least one phosphorothioate modification.

Related aspects include larger polynucleotides such as a plasmid, vector, or chromosome including the polynucleotide for disrupting gene expression in a wheat genome, as well as polymerase primers for amplification of the polynucleotide for disrupting gene expression in a wheat genome.

Methods of identifying the locus of a double-stranded break: In another aspect, the invention provides a method of identifying the locus of at least one double-stranded break (DSB) in wheat genomic DNA, the method including: (a) contacting the genomic DNA having a DSB with a donor polynucleotide molecule (such as a double-stranded DNA, a single-stranded DNA, a single-stranded DNA/RNA hybrid, or a double-stranded DNA/RNA hybrid) molecule, wherein the donor polynucleotide molecule is capable of being integrated (or having its sequence integrated) at the DSB and has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded) or about 2 to about 320 base-pairs if double-stranded (or nucleotides if single-stranded), between about 2 to about 500 base-pairs if double-stranded (or nucleotides if single-stranded) or about 2 to about 500 base-pairs if double-stranded (or nucleotides if single-stranded), or between about 5 to about 500 base-pairs if double-stranded (or nucleotides if single-stranded) or about 5 to about 500 base-pairs if double-stranded (or nucleotides if single-stranded), or between about 5 to about 300 base-pairs if double-stranded (or nucleotides if single-stranded) or about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or about 3 to about 120 base-pairs if double-stranded (or nucleotides if single-stranded), or about 5 to about 200 base-pairs if double-stranded (or nucleotides if single-stranded), or between about 30 to about 100 base-pairs if double-stranded (or nucleotides if single-stranded) or about 30 to about 100 base-pairs if double-stranded (or nucleotides if single-stranded); wherein sequence encoded by the donor polynucleotide molecule, if integrated at the DSB, forms a heterologous insertion; and (b) using at least part of the sequence encoded by the polynucleotide molecule as a target for PCR primers to allow amplification of DNA in the locus of the double-stranded break. In embodiments, the wheat genomic DNA is that of a nucleus, mitochondrion, or plastid. In embodiments, the DSB locus is identified by amplification using primers specific for DNA sequence encoded by the polynucleotide molecule alone; in other embodiments, the DSB locus is identified by amplification using primers specific for a combination of DNA sequence encoded by the donor polynucleotide molecule and genomic DNA sequence flanking the DSB. Such identification using a heterologously integrated DNA sequence (i.e., that encoded by the donor polynucleotide molecule) is useful, e.g., to distinguish a wheat cell containing sequence encoded by the donor polynucleotide molecule integrated at the DSB from a wheat cell that does not. Identification of an edited wheat genome from a non-edited wheat genome is important for various purposes, e.g., for commercial or regulatory tracking of cells or biological material such as wheat plants or seeds containing an edited genome.

In a related aspect, the invention provides a method of identifying the locus of double-stranded breaks (DSBs) in wheat genomic DNA in a pool of wheat cells or protoplasts, wherein the pool of wheat cells includes wheat cells having genomic DNA with sequence encoded by a donor polynucleotide molecule (such as a double-stranded DNA, a single-stranded DNA, a single-stranded DNA/RNA hybrid, or a double-stranded DNA/RNA hybrid) inserted at the locus of the double-stranded breaks; wherein the donor polynucleotide molecule is capable of being integrated (or having its sequence integrated) at the DSB and has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded) or about 2 to about 320 base-pairs if double-stranded (or nucleotides if single-stranded), or between about 2 to about 500 base-pairs if double-stranded (or nucleotides if single-stranded) or about 2 to about 500 base-pairs if double-stranded (or nucleotides if single-stranded), or between about 5 to about 500 base-pairs if double-stranded (or nucleotides if single-stranded) or about 5 to about 500 base-pairs if double-stranded (or nucleotides if single-stranded), or between about 5 to about 300 base-pairs if double-stranded (or nucleotides if single-stranded) or about 5 to about 300 base-pairs if double-stranded (or nucleotides if single-stranded), or between about 11 to about 300 base-pairs if double-stranded (or nucleotides if single-stranded) or about 11 to about 300 base-pairs if double-stranded (or nucleotides if single-stranded), or about 18 to about 300 base-pairs if double-stranded (or nucleotides if single-stranded), or about 3 to about 120 base-pairs if double-stranded (or nucleotides if single-stranded), or about 5 to about 200 base-pairs if double-stranded (or nucleotides if single-stranded), or between about 30 to about 100 base-pairs if double-stranded (or nucleotides if single-stranded) about 30 to about 100 base-pairs if double-stranded (or nucleotides if single-stranded); wherein sequence encoded by the donor polynucleotide molecule, if integrated at the DSB, forms a heterologous insertion; wherein the sequence encoded by the polynucleotide molecule is used as a target for PCR primers to allow amplification of DNA in the region of the double-stranded breaks. In embodiments, the wheat genomic DNA is that of a nucleus, mitochondrion, or plastid. In embodiments, the pool of wheat cells is a population of wheat cells or protoplasts, wherein the population of wheat cells or protoplasts include multiple different DSBs (e.g., induced by different guide RNAs) in the genome. In embodiments, each DSB locus is identified by amplification using primers specific for DNA sequence encoded by the polynucleotide molecule alone; in other embodiments, each DSB locus is identified by amplification using primers specific for a combination of DNA sequence encoded by the polynucleotide molecule and genomic DNA sequence flanking the DSB. Such identification using a heterologously integrated DNA sequence (i.e., sequence encoded by the polynucleotide molecule) is useful, e.g., to identify a wheat cell containing sequence encoded by the polynucleotide molecule integrated at a DSB from a wheat cell that does not.

In embodiments, the pool of wheat cells is a pool of isolated wheat cells or protoplasts in liquid or suspension culture, or cultured in or on semi-solid or solid media. In embodiments, the pool of wheat cells is a pool of wheat cells or plant encapsulated in a polymer or other encapsulating material, enclosed in a vesicle or liposome, or embedded in or attached to a matrix or other solid support (e.g., beads or microbeads, membranes, or solid surfaces). In embodiments, the pool of wheat cells is a pool of wheat cells or protoplasts encapsulated in a polysaccharide (e.g., pectin, agarose). In embodiments, the pool of wheat cells is a pool of wheat cells located in an intact wheat plant, wheat plant part, or wheat plant tissue, and the cells are optionally isolated from the intact wheat plant, wheat plant part, or wheat plant tissue in a step following the integration of a donor polynucleotide sequence at a DSB.

In embodiments, the donor polynucleotide molecule that is integrated (or has sequence that is integrated) at the DSB is double-stranded and blunt-ended; in other embodiments the donor polynucleotide molecule is double-stranded and has an overhang or "sticky end" consisting of unpaired nucleotides (e.g., 1, 2, 3, 4, 5, or 6 unpaired nucleotides) at one terminus or both termini. In an embodiment, the donor polynucleotide molecule that is integrated (or has sequence that is integrated) at the DSB is a double-stranded DNA or double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor polynucleotide molecule includes single strands of at least 11, at least 18, at least 20, at least 30, at least 40, at least 60, at least 80, at least 100, at least 120, at least 140, at least 160, at least 180, at least 200, at least 240, at least 280, or at least 320 nucleotides. In embodiments, the donor polynucleotide molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor polynucleotide molecule has a length of at least 2, at least 3, at least 4, at least 5, at least 6, at least 7, at least 8, at least 9, at least 10, or at least 11 base-pairs if double-stranded (or nucleotides if single-stranded), or about 2 to about 320 base-pairs if double-stranded (or nucleotides if single-stranded), or about 2 to about 500 base-pairs if double-stranded (or nucleotides if single-stranded), or about 5 to about 500 base-pairs if double-stranded (or nucleotides if single-stranded), or about 5 to about 300 base-pairs if double-stranded (or nucleotides if single-stranded), or about 11 to about 300 base-pairs if double-stranded (or nucleotides if single-stranded), or about 18 to about 300 base-pairs if double-stranded (or nucleotides if single-stranded), or about 30 to about 100 base-pairs if double-stranded (or nucleotides if single-stranded). In embodiments, the donor polynucleotide molecule includes chemically modified nucleotides; in embodiments, the naturally occurring phosphodiester backbone of the donor polynucleotide molecule is partially or completely modified with phosphorothioate, phosphorodithioate, or methylphosphonate internucleotide linkage modifications, or the donor polynucleotide molecule includes modified nucleoside bases or modified sugars, or the donor polynucleotide molecule is labelled with a fluorescent moiety or other detectable label. In an embodiment, the donor polynucleotide molecule is double-stranded and is perfectly base-paired through all or most of its length, with the possible exception of any unpaired nucleotides at either terminus or both termini. In another embodiment, the donor polynucleotide molecule is double-stranded and includes one or more non-terminal mismatches or non-terminal unpaired nucleotides within the otherwise double-stranded duplex. In related embodiments, the donor polynucleotide molecule that is integrated at the DSB is a single-stranded DNA or a single-stranded DNA/RNA hybrid. Additional description of the donor polynucleotide molecule is found above in the paragraphs following the heading "Donor polynucleotide molecules".

In embodiments, the donor polynucleotide molecule (such as a double-stranded DNA, a single-stranded DNA, a single-stranded DNA/RNA hybrid, or a double-stranded DNA/RNA hybrid) that is integrated at the DSB includes a nucleotide sequence that, if integrated (or has sequence that is integrated) at the DSB, forms a heterologous insertion that is not normally found in the wheat genome. In embodiments, sequence encoded by the polynucleotide molecule that is integrated at the DSB includes a nucleotide sequence that does not normally occur in the wheat genome containing the DSB; this can be established by sequencing of the wheat genome, or by hybridization experiments. In certain embodiments, sequence encoded by the polynucleotide molecule, when integrated at the DSB, not only permits identification of the locus of the DSB, but also imparts a functional trait to the wheat cell, or to a wheat plant including the wheat cell; in non-limiting examples, sequence encoded by the donor polynucleotide molecule that is integrated at the DSB includes at least one of the nucleotide sequences selected from the group consisting of:

(a) DNA encoding at least one stop codon, or at least one stop codon on each strand, or at least one stop codon within each reading frame on each strand;
(b) DNA encoding heterologous primer sequence (e.g., a sequence of about 18 to about 22 contiguous nucleotides, or of at least 18, at least 20, or at least 22 contiguous nucleotides that can be used to initiate DNA polymerase activity at the site of the DSB);
(c) DNA encoding a unique identifier sequence (e.g., a sequence that when inserted at the DSB creates a heterologous sequence that can be used to identify the presence of the insertion);
(d) DNA encoding a transcript-stabilizing sequence;
(e) DNA encoding a transcript-destabilizing sequence;
(f) a DNA aptamer or DNA encoding an RNA aptamer or amino acid aptamer; and
(g) DNA that includes or encodes a sequence recognizable by a specific binding agent.

Methods of identifying the nucleotide sequence of a locus in a wheat genome that is associated with a phenotge: In another aspect, the invention provides a method of identifying the nucleotide sequence of a locus in a wheat genome that is associated with a phenotype, the method including the steps of:

(a) providing to a population of wheat cells (such as plant cells or plant protoplasts) having the wheat genome:
  (i) multiple different guide RNAs (gRNAs) to induce multiple different double strand breaks (DSBs) in the wheat genome, wherein each DSB is produced by an RNA-guided nuclease guided to a locus on the wheat genome by one of the gRNAs, and (ii) donor polynucleotide molecule (such as a double-stranded DNA, a single-stranded DNA, a single-stranded DNA/RNA hybrid, or a double-stranded DNA/RNA hybrid)s having a defined nucleotide sequence, wherein the polynucleotide molecules are capable of being integrated (or have sequence that is integrated) into the DSBs by non-homologous end-joining (NHEJ);

whereby when sequence encoded by at least some of the polynucleotide molecules are inserted into at least some of the DSBs, a genetically heterogeneous population of wheat cells is produced;

(b) selecting from the genetically heterogeneous population of wheat cells a subset of wheat cells that exhibit a phenotype of interest;

(c) using a pool of PCR primers that bind to sequence encoded by the polynucleotide molecules to amplify from the subset of wheat cells DNA from the locus of a DSB into which sequence encoded by one of the polynucleotide molecules has been inserted; and (d) sequencing the amplified DNA to identify the locus associated with the phenotype of interest.

In embodiments, the genetically heterogeneous population of wheat cells undergoes one or more doubling cycles; for example, the population of wheat cells is provided with growth conditions that should normally result in cell division, and at least some of the wheat cells undergo one or more doublings. In embodiments, the genetically heterogeneous population of wheat cells is subjected to conditions permitting expression of the phenotype of interest. In embodiments, the wheat cells are provided in a single pool or population (e.g., in a single container); in other embodiments, the wheat cells are provided in an arrayed format (e.g., in microwell plates or in droplets in a microfluidics device or attached individually to particles or beads).

In embodiments, the RNA-guided nuclease or a polynucleotide that encodes the RNA-guided nuclease is exogenously provided to the population of wheat cells. In embodiments, each gRNA is provided as a polynucleotide composition including: (a) a CRISPR RNA (crRNA) that includes the gRNA, or a polynucleotide that encodes a crRNA, or a polynucleotide that is processed into a crRNA; or (b) a single guide RNA (sgRNA) that includes the gRNA, or a polynucleotide that encodes a sgRNA, or a polynucleotide that is processed into a sgRNA In embodiments, the multiple guide RNAs are provided as ribonucleoproteins (e.g., Cas9 nuclease molecules complexed with different gRNAs to form different RNPs). In embodiments, each gRNA is provided as a ribonucleoprotein (RNP) including the RNA-guided nuclease and an sgRNA. In embodiments, multiple guide RNAs are provided, as well as a single donor polynucleotide molecule having a sequence to be integrated at the resulting DSBs; in other embodiments, multiple guide RNAs are provided, as well as different donor polynucleotide molecules having a sequence to be integrated at the resulting multiple DSBs.

EMBODIMENTS

Various embodiments of the wheat plants, wheat plant parts, wheat plant seeds, wheat plant cells, processed products, and methods provided herein are included in the following non-limiting list of numbered embodiments.

1. A wheat plant having a modified genome that results in the wheat plant exhibiting modified architecture in comparison to an unmodified wheat plant having an reference genome, wherein the modified genome differs from the reference genome by including predetermined modifications of at least two genes of interest, wherein each of the predetermined modifications is selected from the group consisting of:

(a) heterologous integration of a nucleic acid sequence that is encoded by at least one donor polynucleotide molecule and that comprises a regulatory element having a nucleotide sequence selected from the group consisting of SEQ ID NOs:66-256 at a predetermined locus 1-1000 nucleotides upstream of the start codon of the coding sequence of a gene of interest in the reference genome;

(b) heterologous integration of a nucleic acid sequence that is encoded by at least one donor polynucleotide molecule and that comprises a regulatory element having a nucleotide sequence selected from the group consisting of SEQ ID NOs:66-256 at a predetermined locus within 1000 nucleotides downstream of the stop codon of a gene of interest in the reference genome;

(c) deletion, addition, or substitution of at least one nucleotide in a regulatory element that regulates expression of a gene of interest in the reference genome;

(d) deletion, addition, or substitution of at least one nucleotide in coding sequence of a gene of interest in the reference genome; and (e) a combination of any of (a), (b), (c), and (d), wherein the gene of interest is selected from the group consisting of pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, and TaSnrk2.10-4A, or is a gene encoding a protein having at least 90% identity to a sequence selected from the group consisting of the sequences identified by SEQ ID NOs:257-303.

2. The wheat plant of embodiment 1, wherein the at least two genes of interest comprise at least one homeoallele each of two or more genes selected from the group consisting of pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, and TaSnrk2.10-4A.

3. The wheat plant of embodiment 1, wherein the modified genome further differs from the reference genome by comprising (a) a predetermined modification in at least one homeoallele of a gene selected from TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, LR34, Lr67, Sr22, Sr33, Sr35, Sr45, Sr50, Tsn1, Yr36 (WKS1), Snn1, TaMLO-A1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV1SM, SOD, APX, GS2, NAM, rbcL, IVR1, and a1, or (b) a predetermined modification in a gene encoding a protein having at least 90% identity to a sequence selected from the group consisting of the sequences identified by SEQ ID NOs:304-474.

4. A wheat plant having a modified genome that results in the wheat plant exhibiting improved abiotic stress tolerance in comparison to an unmodified wheat plant having an reference genome, wherein the modified genome differs from the reference genome by comprising predetermined modifications of at least two genes of interest, wherein each of the predetermined modifications is selected from the group consisting of:
(a) heterologous integration of a nucleic acid sequence that is encoded by at least one donor polynucleotide molecule and that comprises a regulatory element having a nucleotide sequence selected from the group consisting of SEQ ID NOs:66-256 at a predetermined locus 1-1000 nucleotides upstream of the start codon of the coding sequence of a gene of interest in the reference genome;
(b) heterologous integration of a nucleic acid sequence that is encoded by at least one donor polynucleotide molecule and that comprises a regulatory element that has a nucleotide sequence selected from SEQ ID NOs: 66-256 at a predetermined locus within 1000 nucleotides downstream of the stop codon of a gene of interest in the reference genome;
(c) deletion, addition, or substitution of at least one nucleotide in a regulatory element that regulates expression of a gene of interest in the reference genome;
(d) deletion, addition, or substitution of at least one nucleotide in coding sequence of a gene of interest in the reference genome; and
(e) a combination of any of (a), (b), (c), and (d);
wherein the gene of interest is selected from the group consisting of TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, and UBA, or is a gene encoding a protein having at least 90% identity to a sequence selected from the group consisting of the sequences identified by SEQ ID NOs:304-362.

5. The wheat plant of embodiment 4, wherein the at least two genes of interest comprise at least one homeoallele each of two or more genes selected from the group consisting of TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, and UBA.

6. The wheat plant of embodiment 4, wherein the modified genome further differs from the reference genome by comprising (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, Fhb1, LR34, Lr67, Sr22, Sr33, Sr35, Sr45, Sr50, Tsn1, Yr36 (WKS1), Snn1, TaMLO-A1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV1SM, SOD, APX, GS2, NAM, rbcL, IVR1, and a1, or (b) a predetermined modification in a gene encoding a protein having at least 90% identity to a sequence selected from the group consisting of the sequences identified by SEQ ID NOs:257-303 and 363-474.

7. A wheat plant having a modified genome that results in the wheat plant exhibiting improved disease resistance in comparison to an unmodified wheat plant having an reference genome, wherein the modified genome differs from the reference genome by comprising predetermined modifications of at least two genes of interest, wherein each of the predetermined modifications is selected from the group consisting of:
(a) heterologous integration of a nucleic acid sequence that is encoded by at least one donor polynucleotide molecule and that comprises a regulatory element having a nucleotide sequence selected from the group consisting of SEQ ID NOs:66-256 at a predetermined locus 1-1000 nucleotides upstream of the start codon of the coding sequence of a gene of interest in the reference genome;
(b) heterologous integration of a nucleic acid sequence that is encoded by at least one donor polynucleotide molecule and that comprises a regulatory element that has a nucleotide sequence selected from SEQ ID NOs: 66-256 at a predetermined locus within 1000 nucleotides downstream of the stop codon of a gene of interest in the reference genome;
(c) deletion, addition, or substitution of at least one nucleotide in a regulatory element that regulates expression of a gene of interest in the reference genome;
(d) deletion, addition, or substitution of at least one nucleotide in coding sequence of a gene of interest in the reference genome; and
(e) a combination of any of (a), (b), (c), and (d);
wherein the gene of interest is selected from the group consisting of Fhb1, LR34, Lr67, Sr22, Sr33, Sr35, Sr45, Sr50, Tsn1, Yr36 (WKS1), Snn1, TaMLO-A1, TaMLO-B1, and TaMLO-D1, or is a gene encoding a protein having at least 90% identity to a sequence selected from the group consisting of the sequences identified by SEQ ID NOs:363-398.

8. The wheat plant of embodiment 7, wherein the at least two genes of interest comprise at least one homeoallele each of two or more genes selected from the group consisting of Fhb1, LR34, Lr67, Sr22, Sr33, Sr35, Sr45, Sr50, Tsn1, Yr36 (WKS1), Snn1, TaMLO-A1, TaMLO-B1, and TaMLO-D1.

9. The wheat plant of embodiment 7, wherein the modified genome further differs from the reference genome by comprising (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV1SM, SOD, APX, GS2, NAM, rbcL, IVR1, and a1, or (b) a predetermined modification in a gene encoding a protein having at least 90% identity to a sequence selected from the group consisting of the sequences identified by SEQ ID NOs:257-362 and 399-474.

10. A wheat plant having a modified genome that results in the wheat plant exhibiting modified flowering time in comparison to an unmodified wheat plant having an reference genome, wherein the modified genome differs from the reference genome by comprising predetermined modifications of at least two genes of interest, wherein each of the predetermined modifications is selected from the group consisting of:

(a) heterologous integration of a nucleic acid sequence that is encoded by at least one donor polynucleotide molecule and that comprises a regulatory element having a nucleotide sequence selected from the group consisting of SEQ ID NOs:66-256 at a predetermined locus 1-1000 nucleotides upstream of the start codon of the coding sequence of a gene of interest in the reference genome;

(b) heterologous integration of a nucleic acid sequence that is encoded by at least one donor polynucleotide molecule and that comprises a regulatory element that has a nucleotide sequence selected from SEQ ID NOs: 66-256 at a predetermined locus within 1000 nucleotides downstream of the stop codon of a gene of interest in the reference genome;

(c) deletion, addition, or substitution of at least one nucleotide in a regulatory element that regulates expression of a gene of interest in the reference genome;

(d) deletion, addition, or substitution of at least one nucleotide in coding sequence of a gene of interest in the reference genome; and (e) a combination of any of (a), (b), (c), and (d);

wherein the gene of interest is selected from the group consisting of FT, FKF1, PhyB, WCO1, ZenMFT-3D, MADS, TaGI1, WAP1, NFYB-A, NFYB-B, and NFYB-D, or is a gene encoding a protein having at least 90% identity to a sequence selected from the group consisting of the sequences identified by SEQ ID NOs:399-424.

11. The wheat plant of embodiment 10, wherein the at least two genes of interest comprise at least one homeoallele each of two or more genes selected from the group consisting of FT, FKF1, PhyB, WCO1, ZenMFT-3D, MADS, TaGI1, WAP1, NFYB-A, NFYB-B, and NFYB-D.

12. The wheat plant of embodiment 10, wherein the modified genome further differs from the reference genome by comprising (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, LR34, Lr67, Sr22, Sr33, Sr35, Sr45, Sr50, Tsn1, Yr36 (WKS1), Snn1, TaMLO-A 1, TaMLO-B1, TaMLO-D1, NAC1, Skp1, TIF, WCBP1, WRKY, TaSAG6, TaSAG3, TaSAG1, FeSOD, CWINV2SM, CWINV 1SM, SOD, APX, GS2, NAM, rbcL, IVR1, and a1, or (b) a predetermined modification in a gene encoding a protein having at least 90% identity to a sequence selected from the group consisting of the sequences identified by SEQ ID NOs:257-398 and 425-474.

13. A wheat plant having a modified genome that results in the wheat plant exhibiting improved photosynthesis in comparison to an unmodified wheat plant having an reference genome, wherein the modified genome differs from the reference genome by comprising predetermined modifications of at least two genes of interest, wherein each of the predetermined modifications is selected from the group consisting of:

(a) heterologous integration of a nucleic acid sequence that is encoded by at least one donor polynucleotide molecule and that comprises a regulatory element having a nucleotide sequence selected from the group consisting of SEQ ID NOs:66-256 at a predetermined locus 1-1000 nucleotides upstream of the start codon of the coding sequence of a gene of interest in the reference genome;

(b) heterologous integration of a nucleic acid sequence that is encoded by at least one donor polynucleotide molecule and that comprises a regulatory element that has a nucleotide sequence selected from SEQ ID NOs: 66-256 at a predetermined locus within 1000 nucleotides downstream of the stop codon of a gene of interest in the reference genome;

(c) deletion, addition, or substitution of at least one nucleotide in a regulatory element that regulates expression of a gene of interest in the reference genome;

(d) deletion, addition, or substitution of at least one nucleotide in coding sequence of a gene of interest in the reference genome; and (e) a combination of any of (a), (b), (c), and (d);

wherein the gene of interest is selected from the group consisting of NAC1, Skp1, TIF, and WCBP1, or is a gene encoding a protein having at least 90% identity to a sequence selected from the group consisting of the sequences identified by SEQ ID NOs:425-434.

14. The wheat plant of embodiment 13, wherein the at least two genes of interest comprise at least one homeoallele each of two or more genes selected from the group consisting of NAC1, Skp1, TIF, and WCBP1.

15. The wheat plant of embodiment 13, wherein the modified genome further differs from the reference genome by comprising (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, LR34, Lr67, Sr22, Sr33, Sr35, Sr45, Sr50, Tsn1, Yr36 (WKS1), Snn1, TaMLO-A 1, TaMLO-B1, TaMLO-D1, FT, FKF1, PhyB, WCO1, ZenMFT-3D, MADS, TaGI1, WAP1, NFYB-A, NFYB-B, NFYB-D, WRKY, TaSAG6, TaSAG3, TaSAG1, FeSOD, CWINV2SM, CWINV1SM, SOD, APX, GS2, NAM, rbcL, IVR1, al, or (b) a predetermined modification in a gene encoding a protein having at least 90% identity to a sequence selected from the group consisting of the sequences identified by SEQ ID NOs:257-424 and 435-474.

16. A wheat plant having a modified genome that results in the wheat plant exhibiting modified senescence in comparison to an unmodified wheat plant having an reference genome, wherein the modified genome differs from the reference genome by comprising predetermined modifications of at least two genes of interest, wherein each of the predetermined modifications is selected from the group consisting of:

(a) heterologous integration of a nucleic acid sequence that is encoded by at least one donor polynucleotide molecule and that comprises a regulatory element having a nucleotide sequence selected from the group consisting of SEQ ID NOs:66-256 at a predetermined locus 1-1000 nucleotides upstream of the start codon of the coding sequence of a gene of interest in the reference genome;

(b) heterologous integration of a nucleic acid sequence that is encoded by at least one donor polynucleotide molecule and that comprises a regulatory element that has a nucleotide sequence selected from SEQ ID NOs: 66-256 at a predetermined locus within 1000 nucleotides downstream of the stop codon of a gene of interest in the reference genome;

(c) deletion, addition, or substitution of at least one nucleotide in a regulatory element that regulates expression of a gene of interest in the reference genome;

(d) deletion, addition, or substitution of at least one nucleotide in coding sequence of a gene of interest in the reference genome; and (e) a combination of any of (a), (b), (c), and (d);

wherein the gene of interest is selected from the group consisting of WRKY, TaSAG6, TaSAG3, TaSAG1, FeSOD, CWINV2SM, CWINV1SM, SOD, APX, GS2, NAM, rbcL, IVR1, and a1, or is a gene encoding a protein having at least 90% identity to a sequence selected from the group consisting of the sequences identified by SEQ ID NOs:435-474.

17. The wheat plant of embodiment 16, wherein the at least two genes of interest comprise at least one homeoallele each of two or more genes selected from the group consisting of WRKY, TaSAG6, TaSAG3, TaSAG1, FeSOD, CWINV2SM, CWINV 1SM, SOD, APX, GS2, NAM, rbcL, IVR1, and al.

18. The wheat plant of embodiment 16, wherein the modified genome further differs from the reference genome by comprising (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, LR34, Lr67, Sr22, Sr33, Sr35, Sr45, Sr50, Tsn1, Yr36 (WKS1), Snn1, TaMLO-A 1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, and WCBP1, or (b) a predetermined modification in a gene encoding a protein having at least 90% identity to a sequence selected from the group consisting of the sequences identified by SEQ ID NOs:257-434.

19. The wheat plant of any one of embodiments 1-18, wherein the predetermined modifications of at least two genes of interest comprise modifications of only non-coding sequences of the reference genome, or of only coding sequences of the reference genome, or of a combination of coding and non-coding sequences of the reference genome.

20. The wheat plant of any one of embodiments 1-18, wherein at least one of the predetermined modifications of at least two genes of interest results in increased expression of the gene of interest, relative to expression of the gene of interest in the reference genome.

21. The wheat plant of any one of embodiments 1-18, wherein at least one of the predetermined modifications of at least two genes of interest results in decreased expression of the gene of interest, relative to expression of the gene of interest in the reference genome.

22. The wheat plant of any one of embodiments 1-18, wherein at least one of the predetermined modifications of at least two genes of interest comprises multiple predetermined modifications of a single gene of interest in the reference genome.

23. The wheat plant of any one of embodiments 1-18, wherein the predetermined modifications of at least two genes of interest comprises a predetermined modification of multiple homeoalleles of a gene of interest.

24. The wheat plant of any one of embodiments 1-18, wherein the wheat plant is a *Triticum* sp. or an *Aegilops* sp.

25. The wheat plant of any one of embodiments 1-18, wherein the wheat plant is common or bread wheat (*Triticum aestivum*), spelt (*Triticum spelta*), emmer (*Triticum dicoccum*), einkorn (*Triticum monococcum*), durum wheat (*Triticum durum*), or synthetic hexaploid wheat.

26. The wheat plant of any one of embodiments 1-18, wherein the wheat plant is an allotetraploid, wherein the reference genome consists of an A genome and a B genome, and wherein at least one of the predetermined modifications of at least two genes of interest comprises: (a) a predetermined modification of both homeoalleles of the gene of interest in the A genome, (b) a predetermined modification of both homeoalleles of the gene of interest in the B genome, or (c) a predetermined modification of at least two homeoalleles of the gene of interest in the A genome and the B genome.

27. The wheat plant of any one of embodiments 1-18, wherein the wheat plant is an allohexaploid, wherein the reference genome consists of an A genome, a B genome, and a D genome, and wherein at least one of the predetermined modifications of at least two genes of interest comprises: a) a predetermined modification of both homeoalleles of the gene of interest in the A genome, (b) a predetermined modification of both homeoalleles of the gene of interest in the B genome, (c) a predetermined modification of both homeoalleles of the gene of interest in the D genome, or (d) a predetermined modification of at least two homeoalleles of the gene of interest in any combination of the A genome, the B genome, and the D genome.

28. The wheat plant of any one of embodiments 1-18, wherein the wheat plant is an allotetraploid, wherein the reference genome consists of an A genome and a B genome, and wherein the A genome only, the B genome only, or both the A and B genomes is heterozygous for at least one of the predetermined modifications of at least two genes of interest.

29. The wheat plant of any one of embodiments 1-18, wherein the wheat plant is an allotetraploid, wherein the reference genome consists of an A genome and a B genome, and wherein the A genome only, the B genome only, or both the A and B genomes is homozygous for at least one of the predetermined modifications of at least two genes of interest.

30. The wheat plant of any one of embodiments 1-18, wherein the wheat plant is an allohexaploid, wherein the reference genome consists of an A genome, a B genome, and a D genome, and wherein the A genome only, the B genome only, the D genome only, or any combination of the A, B, and D genomes is heterozygous for at least one of the predetermined modifications of at least two genes of interest.

31. The wheat plant of any one of embodiments 1-18, wherein the wheat plant is an allohexaploid, wherein the reference genome consists of an A genome, a B genome, and a D genome, and wherein the A genome only, the B genome only, the D genome only, or any combination of the A, B, and D genomes is homozygous for at least one of the predetermined modifications of at least two genes of interest.

32. The wheat plant of any one of embodiments 1-18, wherein the heterologous integration of a nucleic acid sequence is by an HDR mechanism.

33. The wheat plant of any one of embodiments 1-18, wherein the heterologous integration of a nucleic acid sequence is by an NHEJ mechanism.

34. The wheat plant of any one of embodiments 1-18, wherein the donor polynucleotide molecule comprises ribonucleotides, deoxyribonucleotides, dideoxyribonucleotides, non-canonical nucleotides, and chemically modified nucleotides.

35. The wheat plant of any one of embodiments 1-18, wherein the donor polynucleotide molecule is selected from the group consisting of a blunt-ended double-stranded DNA, a double-stranded DNA with at least one unpaired nucleotide at one terminus or at both termini, a single-stranded DNA, a blunt-ended double-stranded DNA/RNA hybrid, and a double-stranded DNA/RNA hybrid with at least one unpaired nucleotide at one terminus or at both termini.

36. The wheat plant of any one of embodiments 1-18, wherein the donor polynucleotide molecule lacks homology to the genome sequences adjacent to the integration site.

37. The wheat plant of any one of embodiments 1-18, wherein deletion of at least one nucleotide occurs at a double-strand break in the reference genome or between multiple double-strand breaks in the reference genome.

38. The wheat plant of any one of embodiments 1-18, wherein the modified genome is more than 99.9% identical to the reference genome.

39. The wheat plant of any one of embodiments 1-18, wherein the modified genome is devoid of mitotically or meiotically generated genetic or epigenetic changes relative to the reference genome.

40. The wheat plant of any one of embodiments 1-18, wherein the modified genome comprises a difference of epigenetic changes in less than 0.01% of the genome relative to the reference genome.

41. The wheat plant of any one of embodiments 1-18, wherein the modified genome comprises:
 (a) a difference of DNA methylation in less than 0.01% of the genome, relative to the reference genome; or
 (b) a difference of DNA methylation in less than 0.005% of the genome, relative to the reference genome; or
 (c) a difference of DNA methylation in less than 0.001% of the genome, relative to the reference genome.

42. The wheat plant of any one of embodiments 1-18, wherein the gene of interest is located on a chromosome in the wheat plant cell, and wherein the modified genome comprises:
 (a) a difference of DNA methylation in less than 0.01% of the portion of the genome that is contained within the chromosome containing the gene of interest, relative to the reference genome; or
 (b) a difference of DNA methylation in less than 0.005% of the portion of the genome that is contained within the chromosome containing the gene of interest, relative to the reference genome; or
 (c) a difference of DNA methylation in less than 0.001% of the portion of the genome that is contained within the chromosome containing the gene of interest, relative to the reference genome.

43. The wheat plant of any one of embodiments 1-18, wherein the modified genome has not more unintended changes in comparison to the reference genome than $1 \times 10^{-8}$ mutations per bp per replication.

44. The wheat plant of any one of embodiments 1-18, wherein the modified genome further differs from the reference genome by comprising (a) a predetermined modification in at least one homeoallele of a gene selected from the group consisting of TsVP, SEC14p, ACC synthase, D-myo-inositol-3-phosphate synthase (IPS), bZIP72, PLC1, GOLS2, PIS, NF-YB, PsbA, HB2, PP2C2, CIPK16, SAPK8, ABA8ox3, ORAP1, DIS1, VPE3, RZFP34, ZFP185, DCA1, SRFP1, SQS, TPP1, SAPK6, JIOsPR10, ClpD1, MSD1, WR1, TPS1, GS, OgTT1, FKBP20, ANN1, SIK1, NHX1, MGD, DHODH1, hsp16.9, GME-2, ChI1, CYP18-2, CNX, CBL8, CDPK13, RAN2, GGP, OVP1, ZFP177, RGG1, Em1, CTB4a, GS2, COLD1, ACA6, Rab7, TOP6A1, Hsp101, AMTR1, Rubisco activase, SPX1, GME-1, MPG1, SNAC3, SDIR1, Pgk2a-P, glyoxalase II, PUB15, IMP, HBP1b, CYP2, PEX11 (Os03g0302000), CPK4, EG1, CBSX4, SIDP366, SUV3, GA2ox6, SAPK9, RbohA, CAS, RacB, ECS, VTE1, SAPK4, CDPK7, NUS1, GL1-2, Sce1, PsbR1, CYP21-4, PIP1;3, CIPK03, GRX8, MIOX, SLG, CKX3, HAP3A, CDPK9, JAR1, MFO1, LFY, ZMM4, HD3A, MADS24, BRD2, SK2(T)(SCL, FGR), SLR1, ILI5, GW2, PTR1, GA2OX3, ETR2, EXPA4, D2, D61, PDR6, ACO4, Rab6a, SERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, PP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, NPR1, LOX3, ALD1, RLCK185, LCB2A1, PhyB1, COP1, WRKY51, PLDbeta1, RAC5, CPK12, GF14e, SBP, HIR1, BWMKY1, AOS1, LOL2, GH3, GH3-8, XB3, GLP1, MAPK6, ACS2, LRR1, MPK3, SGT1, GAP1, RAC1, TPC1, GH3-2, BIANK1, CIPK14, BIDK1, MPK6, MKK4, Gns1, CCR1, MAPKY5, RACK1A, GI, phyB, Hd16, RCN1, SPL11, Spin1, PAL, PAL1, AGPS1, NRAMP3, MTP1, ATM3, YSL2, DMAS1, MRP5, SULTR3;3, AMT1;2, AMT3;1, NRT2.3b, GS1;2, ARG, NRT2.1, AMT1;1, AlaAT, ABC1, NADH-GOGAT, RBCS, NLA1, PHF1, MYB2P-1, CASTOR, INO1, sedoheptulose-1,7-bisphosphatase (SBPase), Fbpase; fructose-1,6-bisphosphatase, DET1, Os02g0465900, Hox32, BZR1, NAL1, AlaAT, NRT2.2, esp1, GW2-CHR5, Asn synthetase, AspAT, NAD(H)-dependent GOGAT 1, Gln1-3, obap1, AAP4 (amino acid permease 4), crtRB1, MRP1, DA1, DAR1, APS1, 6-phospho-fructokinase, wx1, shrunken 1, sus1, brittle endosperm bt2, sugary 1, sbe1, MADS22, RT, GAMYB, HSP90, AOS2, SPS1, NYC1, D35, PIMT1, PIMT2, TYDC, TET9, CYP703A3, D1|D2|Os07g0558500, ABA8OX1, ABA2, NCED1, ZEP1, ALDH7, CHS1, APX2, DOS, HOX33, NYC3, and APX1, or (b) a predetermined modification in a gene encoding a protein having at least 90% identity to a sequence selected from SEQ ID NOs:693-976, or (c) is a genomic sequence selected from SEQ ID NO:977-1260.

45. Seed of the wheat plant of any one of embodiments 1-18.

46. A progeny wheat plant of the wheat plant of any one of embodiments 1-18.

47. A processed product made from the seed of embodiment 45.

48. A processed product made from the wheat plant of any one of embodiments 1-18.

49. A processed product made from the progeny wheat plant of embodiment 46.

50. A method of manufacturing a processed wheat product, comprising the steps of: (a) growing a wheat plant of any one of embodiments 1-18 and 46; and (b) processing the wheat plant into a processed wheat product, thereby manufacturing a processed wheat product.

51. The method of embodiment 50, wherein the processed wheat product is selected from the group consisting of intact wheat grains, wheat berries, cracked wheat, parched wheat, malt, grits, groats, semolina, middlings, flakes, flour, meal, bran, germ, endosperm, starch, gluten, protein, oil, chaff, fibre, and straw.

52. A wheat plant cell having a modified genome in comparison to an unmodified wheat plant cell having an reference genome, wherein the modified genome differs from the reference genome by comprising at least one predetermined modification of a gene disclosed in Table 10, wherein the at least one predetermined modification is selected from the group consisting of:
  (a) heterologous integration of a nucleic acid sequence that is encoded by at least one donor polynucleotide molecule and that comprises a regulatory element, at a predetermined locus 1-1000 nucleotides upstream of the start codon of the coding sequence of a gene of interest in the reference genome;
  (b) heterologous integration of a nucleic acid sequence that is encoded by at least one donor polynucleotide molecule and that comprises a regulatory element at a predetermined locus within 1000 nucleotides downstream of the stop codon of a gene disclosed in Table 10;
  (c) deletion, addition, or substitution of at least one nucleotide in a regulatory element that regulates expression of a gene disclosed in Table 10;
  (d) deletion, addition, or substitution of at least one nucleotide in coding sequence of a gene disclosed in Table 10; and
  (e) a combination of any of (a), (b), (c), and (d);
    wherein the gene disclosed in Table 10 is selected from TsVP, ZmSEC14p, ACC synthase, D-myo-inositol-3-phosphate synthase (IPS), ZmbZIP72, ZmPLC1, ZmGOLS2, ZmPIS, ZmNF-YB, ZmPsbA, HB2, ZmPP2C2, ZmCIPK16, ZmSAPK8, OsABA8ox3, OsORAP1, OsDIS1, OsVPE3, OsRZFP34, ZFP185, DCA1, OsSRFP1, SQS, OsTPP1, SAPK6, JIOsPR10, OsClpD1, MSD1, OsWR1, OsTPS1, OsGS, OgTT1, OsFKBP20, OsANN1, OsSIK1, OsNHX1, OsMGD, OsDHODH1, Oshsp16.9, OsGME-2, OsChI1, OsCYP18-2, OsCNX, OsCBL8, OsCDPK13, OsRAN2, OsGGP, OVP1, ZFP177, RGG1, OsEm1, CTB4a, GS2, COLD1, OsACA6, OsRab7, OsTOP6A1, osHsp101, OsAMTR1, Rubisco activase, OsSPX1, OsGME-1, OsMPG1, SNAC3, OsSDIR1, OsPgk2a-P, glyoxalase II, OsPUB15, OsIMP, OsHBP1b, OsCYP2, OsPEXI1 (Os03g0302000), OsCPK4, EG1, OsCBSX4, OsSIDP366, OsSUV3, GA2ox6, SAPK9, OsRbohA, OsCAS, OsRacB, OsECS, OsVTE1, SAPK4, OsCDPK7, NUS1, OsGL1-2, OsSce1, OsPsbR1, OsCYP21-4, OsPIP1;3, OsCIPK03, OsGRX8, OsMIOX, SLG, CKX3, HAP3A, CDPK9, JAR1, MFO1, LFY, ZMM4, HD3A, MADS24, BRD2, SK2(T)(SCL, FGR), SLR1, ILI5, GW2, ZmPTR1, GA2OX3, ETR2, EXPA4, D2, D61, PDR6, ACO4, Rab6a, OsSERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, ZmPP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, Zm NPR1, Zm LOX3, ALD1, RLCK185, LCB2A1, PhyB1, COP1, WRKY51, Os PLDbeta1, RAC5, OsCPK12, GF14e, Os SBP, OsHIR1, BWMKY1, AOS1, Os LOL2, GH3, GH3-8, XB3, GLP1, Os MAPK6, ACS2, OsLRR1, OsMPK3, Os SGT1, GAP1, Os RAC1, Os TPC1, GH3-2, OsBIANK1, CIPK14, OS BIDK1, OsMPK6, Os MKK4, Gns1, Os CCR1, Os MAPKY5, RACK1A, OsG1, OsphyB, Hd16, RCN1, SPL 11, Spin1, PAL, PAL1, OsAGPS1, NRAMP3, OsMTP1, ATM3, OsYSL2, DMAS1, OsMRP5, OsSULTR3;3, AMT1;2, OsAMT3;1, OsNRT2.3b, GS1;2, OsARG, OsNRT2.1, AMT1;1, AlaAT, ABC1, NADH-GOGAT, RBCS, NLA1, PHF1, OsMYB2P-1, CASTOR, INO1, sedoheptulose-1,7-bisphosphatase (SBPase), Fbpase; fructose-1,6-bisphosphatase, OsDET1, Os02g0465900, OsHox32, OsBZR1, OsNAL1, AlaAT, ZmNRT2.2, esp1, ZmGW2-CHR5, Asn synthetase, AspAT, NAD(H)-dependent GOGAT 1, Gln1-3, obap1, ZmAAP4 (amino acid permease 4), crtRB1, ZmMRP1, ZmDA1, ZmDAR1, APS1, 6-phospho-fructokinase, wx1, shrunken 1, sus1, brittle endosperm bt2, sugary 1, sbe1, MADS22, RT, GAMYB, HSP90, AOS2, SPS1, NYC1, D35, PIMT1, PIMT2, TYDC, TET9, CYP703A3, D1|D2|Os07g0558500, ABA8OX1, OsABA2, NCED1, ZEP1, ALDH7, CHS1, APX2, DOS, HOX33, NYC3, and APX1, or is a gene encoding a protein having at least 90% identity to a sequence selected from SEQ ID NOs:693-976, or is a genomic sequence selected from SEQ ID NO:977-1260.

53. The wheat plant cell of embodiment 52, wherein the gene disclosed in Table 10 comprises at least one homeoallele each of two or more genes selected from TsVP, ZmSEC14p, ACC synthase, D-myo-inositol-3-phosphate synthase (IPS), ZmbZIP72, ZmPLC1, ZmGOLS2, ZmPIS, ZmNF-YB, ZmPsbA, HB2, ZmPP2C2, ZmCIPK16, ZmSAPK8, OsABA8ox3, OsORAP1, OsDIS1, OsVPE3, OsRZFP34, ZFP185, DCA1, OsSRFP1, SQS, OsTPP1, SAPK6, JIOsPR10, OsClpD1, MSD1, OsWR1, OsTPS1, OsGS, OgTT1, OsFKBP20, OsANN1, OsSIK1, OsNHX1, OsMGD, OsDHODH1, Oshsp16.9, OsGME-2, OsChI1, OsCYP18-2, OsCNX, OsCBL8, OsCDPK13, OsRAN2, OsGGP, OVP1, ZFP177, RGG1, OsEm1, CTB4a, GS2, COLD1, OsACA6, OsRab7, OsTOP6A 1, osHsp101, OsAMTR1, Rubisco activase, OsSPX1, OsGME-1, OsMPG1, SNAC3, OsSDIR1, OsPgk2a-P, glyoxalase II, OsPUB15, OsIMP, OsHBP1b, OsCYP2, OsPEXI1 (Os03g0302000), OsCPK4, EG1, OsCBSX4, OsSIDP366, OsSUV3, GA2ox6, SAPK9, OsRbohA, OsCAS, OsRacB, OsECS, OsVTE1, SAPK4, OsCDPK7, NUS1, OsGL1-2, OsSce1, OsPsbR1, OsCYP21-4, OsPIP1;3, OsCIPK03, OsGRX8, OsMIOX, SLG, CKX3, HAP3A, CDPK9, JAR1, MFO1, LFY, ZMM4, HD3A, MADS24, BRD2, SK2(T)(SCL, FGR), SLR1, ILI5, GW2, ZmPTR1, GA2OX3, ETR2, EXPA4, D2, D61, PDR6, ACO4, Rab6a, OsSERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, ZmPP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, Zm NPR1, Zm LOX3, ALD1, RLCK185, LCB2A1, PhyB1, COP1, WRKY51, Os PLD-beta1, RAC5, OsCPK12, GF14e, Os SBP, OsHIR1, BWMKY1, AOS1, Os LOL2, GH3, GH3-8, XB3, GLP1, Os MAPK6, ACS2, OsLRR1, OsMPK3, Os SGT1, GAP1, Os RAC1, Os TPC1, GH3-2, OsBIANK1, CIPK14, OS BIDK1, OsMPK6, Os MKK4, Gns1, Os CCR1, Os MAPKY5, RACK1A, OsG1, OsphyB, Hd16, RCN1, SPL11, Spin1, PAL, PAL1, OsAGPS1, NRAMP3, OsMTP1, ATM3, OsYSL2, DMAS1, OsMRP5, OsSULTR3;3, AMT1;2, OsAMT3;1, OsNRT2.3b, GS1;2, OsARG, OsNRT2.1, AMT1;1, AlaAT, ABC1, NADH-GOGAT, RBCS, NLA1, PHF1, OsMYB2P-1, CASTOR, INO1, sedoheptulose-1,7-bisphosphatase (SBPase), Fbpase; fructose-1,6-bisphosphatase, OsDET1, Os02g0465900, OsHox32, OsBZR1, OsNAL1, AlaAT, ZmNRT2.2, esp1, ZmGW2-CHR5, Asn synthetase, AspAT, NAD(H)-dependent GOGAT 1, Gln1-3, obap1, ZmAAP4 (amino acid permease 4), crtRB1, ZmMRP1, ZmDA1, ZmDAR1, APS1, 6-phospho-fructokinase, wx1, shrunken 1, sus1, brittle endosperm bt2, sugary 1, sbe1, MADS22, RT, GAMYB, HSP90, AOS2, SPS1, NYC1, D35, PIMT1, PIMT2, TYDC, TET9, CYP703A3, D1|D2|Os07g0558500, ABA8OX1, OsABA2, NCED1, ZEP1, ALDH7, CHS1, APX2, DOS, HOX33, NYC3, and APX1.

54. The wheat plant cell of embodiment 52 or embodiment 53, wherein the modified genome further differs from the reference genome by comprising (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, Lr34, Lr67, Sr22, Sr33, Sr35, Sr45, Sr50, Tsn1, Yr36 (WKS1), Snn1, TaMLO-A1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV 1SM, SOD, APX, GS2, NAM, rbcL, IVR1, and al as disclosed in Table 9, or (b) a predetermined modification in a gene encoding a protein having at least 90% identity to a sequence selected from SEQ ID NOs:257-474 as disclosed in Table 9, or (c) a predetermined modification in a gene selected from the genomic sequences identified as SEQ ID NOs:475-692 as disclosed in Table 9.

55. The wheat plant cell of any one of embodiments 52-54, wherein the at least one predetermined modification of a gene disclosed in Table 10 comprises a modification of only non-coding sequence of the reference genome, or of only coding sequence of the reference genome, or of a combination of coding and non-coding sequences of the reference genome.

56. The wheat plant cell of any one of embodiments 52-54, wherein the at least one predetermined modification of gene disclosed in Table 10 results in increased expression of the gene, relative to expression of the gene in the reference genome.

57. The wheat plant cell of any one of embodiments 52-54, wherein the at least one predetermined modification of a gene disclosed in Table 10 results in decreased expression of the gene, relative to expression of the gene in the reference genome.

58. The wheat plant cell of any one of embodiments 52-54, wherein the at least one predetermined modification of a gene disclosed in Table 10 comprises multiple predetermined modifications of a single gene disclosed in Table 10 in the reference genome.

59. The wheat plant cell of any one of embodiments 52-54, wherein the at least one predetermined modification of a gene disclosed in Table 10 comprises predetermined modifications of multiple genes disclosed in Table 10 in the reference genome.

60. The wheat plant cell of any one of embodiments 52-54, wherein the at least one predetermined modification of a gene disclosed in Table 10 comprises a predetermined modification of multiple homeoalleles of a gene disclosed in Table 10.

61. The wheat plant cell of any one of embodiments 52-54, wherein the wheat plant cell is a cell of a *Triticum* sp. or an *Aegilops* sp.

62. The wheat plant cell of any one of embodiments 52-54, wherein the wheat plant cell is a cell of common or bread wheat (*Triticum aestivum*), spelt (*Triticum spelta*), emmer (*Triticum dicoccum*), einkorn (*Triticum monococcum*), durum wheat (*Triticum durum*), or synthetic hexaploid wheat.

63. The wheat plant cell of any one of embodiments 52-54, wherein the wheat plant cell with the modified genome is an isolated wheat cell or protoplast, or is a cell in a wheat plant or in a part or tissue of a wheat plant, or is a cell in a wheat meristem, zygotic or somatic embryo, microspore, pollen, ovule, or seed.

64. The wheat plant cell of any one of embodiments 52-54, wherein the wheat plant cell is diploid.

65. The wheat plant cell of any one of embodiments 52-54, wherein the wheat plant cell is haploid.

66. The wheat plant cell of any one of embodiments 52-54, wherein the wheat plant cell is a doubled haploid.

67. The wheat plant cell of any one of embodiments 52-54, wherein the wheat plant cell with the modified genome is (a) a cell of an allotetraploid wheat plant, wherein the reference genome consists of an A genome and a B genome, at least one of which is modified in the wheat plant cell with the modified genome; or (b) is a cell of an allohexaploid wheat plant, wherein the reference genome consists of an A genome, a B genome, and a D genome, at least one of which is modified in the wheat plant cell with the modified genome.

68. The wheat plant cell of any one of embodiments 52-54, wherein the wheat plant cell is a cell of an allotetraploid wheat plant, wherein the reference genome consists of an A genome and a B genome, and wherein the at least one predetermined modification of a gene disclosed in Table 10 comprises (a) a predetermined modification of both homeoalleles of the gene in the A genome, (b) a predetermined modification of both homeoalleles of the gene in the B genome, or (c) a predetermined modification of at least two homeoalleles of the gene in the A genome and the B genome.

69. The wheat plant cell of any one of embodiments 52-54, wherein the wheat plant cell is a cell of an allohexaploid wheat plant, wherein the reference genome consists of an A genome, a B genome, and a D genome, and wherein the at least one predetermined modification of a gene disclosed in Table 10 comprises a) a predetermined modification of both homeoalleles of the gene in the A genome, (b) a predetermined modification of both homeoalleles of the gene in the B genome, (c) a predetermined modification of both homeoalleles of the gene in the D genome, or (d) a predetermined modification of at least two homeoalleles of the gene in any combination of the A genome, the B genome, and the D genome.

70. The wheat plant cell of any one of embodiments 52-54, wherein the wheat plant cell is a cell of an allotetraploid wheat plant, wherein the reference genome consists of an A genome and a B genome, and wherein the A genome only, the B genome only, or both the A and B genomes is heterozygous for the at least one predetermined modification of a gene disclosed in Table 10.

71. The wheat plant cell of any one of embodiments 52-54, wherein the wheat plant cell is a cell of an allotetraploid wheat plant, wherein the reference genome consists of an A genome and a B genome, and wherein the A genome only, the B genome only, or both the A and B genomes is homozygous for the at least one predetermined modification of a gene disclosed in Table 10.

72. The wheat plant cell of any one of embodiments 52-54, wherein the wheat plant cell is a cell of an allohexaploid wheat plant, wherein the reference genome consists of an A genome, a B genome, and a D genome, and wherein the A genome only, the B genome only, the D genome only, or any combination of the A, B, and D genomes is heterozygous for the at least one predetermined modification of a gene disclosed in Table 10.

73. The wheat plant cell of any one of embodiments 52-54, wherein the wheat plant cell is a cell of an allohexaploid wheat plant, wherein the reference genome consists of an A genome, a B genome, and a D genome, and wherein the A genome only, the B genome only, the D genome only, or any combination of the A, B, and D genomes is homozygous for the at least one predetermined modification of a gene disclosed in Table 10.

74. The wheat plant cell of any one of embodiments 52-54, wherein the heterologous integration of a nucleic acid sequence is by an HDR mechanism.

75. The wheat plant cell of any one of embodiments 52-54, wherein the heterologous integration of a nucleic acid sequence is by an NHEJ mechanism.

76. The wheat plant cell of any one of embodiments 52-54, wherein the donor polynucleotide molecule comprises ribonucleotides, deoxyribonucleotides, dideoxyribonucleotides, non-canonical nucleotides, and chemically modified nucleotides.

77. The wheat plant cell of any one of embodiments 52-54, wherein the donor polynucleotide molecule is selected from the group consisting of a blunt-ended double-stranded DNA, a double-stranded DNA with at least one unpaired nucleotide at one terminus or at both termini, a single-stranded DNA, a blunt-ended double-stranded DNA/RNA hybrid, and a double-stranded DNA/RNA hybrid with at least one unpaired nucleotide at one terminus or at both termini.

78. The wheat plant cell of any one of embodiments 52-54, wherein the donor polynucleotide molecule lacks homology to the genome sequences adjacent to the integration site.

79. The wheat plant cell of any one of embodiments 52-54, wherein deletion of at least one nucleotide occurs at a double-strand break in the reference genome or between multiple double-strand breaks in the reference genome.

80. A wheat plant comprising, or grown or regenerated from, the wheat plant cell of any one of embodiments 52-54.

81. Seed of the wheat plant of embodiment 80.

82. A progeny wheat plant of the wheat plant of embodiment 80.

83. The wheat plant of embodiment 80, wherein the modified genome is associated with a trait selected from the group consisting of improved abiotic stress tolerance, modified architecture, improved biotic stress tolerance, improved nutrient use efficiency, improved photosynthesis, modified resource partitioning, modified flowering time, and modified senescence.

84. A processed product made from the wheat plant of embodiment 80.

85. A processed product made from the seed of embodiment 81.

86. A processed product made from the progeny wheat plant of embodiment 82 or from its seed.

87. A method of manufacturing a processed wheat product, comprising the steps of: (a) growing a wheat plant of embodiment 80; and (b) processing the wheat plant into a processed wheat product, thereby manufacturing a processed wheat product.

88. The method of embodiment 87, wherein the processed wheat product is selected from the group consisting of intact wheat grains, wheat berries, cracked wheat, parched wheat, malt, grits, groats, semolina, middlings, flakes, flour, meal, bran, germ, endosperm, starch, gluten, protein, oil, chaff, fibre, and straw.

89. A method of harvesting a wheat seed from a wheat plant having a modified genome, comprising:
   (A) providing a wheat plant cell having a modified genome in comparison to an unmodified wheat cell having an reference genome;
   (B) growing from the wheat plant cell a wheat plant having the modified genome, to a stage where the wheat plant produces harvestable wheat seed; and
   (C) harvesting the wheat seed;
wherein the modified genome differs from the reference genome by comprising:
   (a) predetermined modifications of at least two genes of interest identified in Table 9, wherein each of the at least two genes of interest identified in Table 9 is selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, LR34, Lr67, Sr22, Sr33, Sr35, Sr45, Sr50, Tsn1, Yr36 (WKS1), Snn1, TaMLO-A1, TaMLO-B1, TaMLO-D1, FT, FKF1, PhyB, WCO1, ZenMFT-3D, MADS, TaGl1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV1SM, SOD, APX, GS2, NAM, rbcL, IVR1, and al as disclosed in Table 9, or is a gene encoding a protein having at least 90% identity to a sequence selected from SEQ ID NOs:257-474 as disclosed in Table 9, or is a gene having a genomic sequence selected from SEQ ID NOs:475-521 as disclosed in Table 9; and wherein each predetermined modification is selected from the group consisting of:
      (i) heterologous integration of the nucleic acid sequence of a non-coding regulator element that is encoded by at least one donor polynucleotide molecule at a predetermined locus 1-1000 nucleotides upstream of the start codon of the coding sequence of a gene of interest in the reference genome;
      (ii) heterologous integration of the nucleic acid sequence of a non-coding regulator element that is encoded by at least one donor polynucleotide molecule at a predetermined locus within 1000 nucleotides of the stop codon of a gene of interest in the reference genome;
(iii) deletion, addition, or substitution of at least one nucleotide in a regulatory element that regulates expression of a gene of interest in the reference genome;
(iv) deletion, addition, or substitution of at least one nucleotide in coding sequence of a gene of interest in the reference genome; and
(v) a combination of any of (i), (ii), (iii), and (iv); or
(b) a predetermined modification of at least one gene of interest identified in Table 10, wherein the at least one gene of interest identified in Table 10 is selected from TsVP, ZmSEC14p, ACC synthase, D-myo-inositol-3-phosphate synthase (IPS), ZmbZIP72, ZmPLC1, ZmGOLS2, ZmPIS, ZmNF-YB, ZmPsbA, HB2, ZmPP2C2, ZmCIPK16, ZmSAPK8, OsABA8ox3, OsORAP1, OsDIS1, OsVPE3, OsRZFP34, ZFP185, DCA1, OsSRFP1, SQS, OsTPP1, SAPK6, JIOsPR10, OsClpD1, MSD1, OsWR1, OsTPS1, OsGS, OgTT1, OsFKBP20, OsANN1, OsSIK1, OsNHX1, OsMGD, OsDHODH1, Oshsp16.9, OsGME-2, OsChl1, OsCYP18-2, OsCNX, OsCBL8, OsCDPK13, OsRAN2, OsGGP, OVP1, ZFP177, RGG1, OsEm1, CTB4a, GS2, COLD1, OsACA6, OsRab7, OsTOP6A1, osHsp101, OsAMTR1, Rubisco activase, OsSPX1, OsGME-1, OsMPG1, SNAC3, OsSDIR1, OsPgk2a-P, glyoxalase II, OsPUB15, OsIMP, OsHBP1b, OsCYP2, OsPEXI1 (Os03g0302000), OsCPK4, EG1, OsCBSX4, OsSIDP366, OsSUV3, GA2ox6, SAPK9, OsRbohA, OsCAS, OsRacB, OsECS, OsVTE1, SAPK4, OsCDPK7, NUS1, OsGL1-2, OsSce1, OsPsbR1, OsCYP21-4, OsPIP1;3, OsCIPK03, OsGRX8, OsMIOX, SLG, CKX3, HAP3A, CDPK9, JAR1, MFO1, LFY, ZMM4, HD3A, MADS24, BRD2, SK2(T)(SCL, FGR), SLR1, ILI5, GW2, ZmPTR1, GA2OX3, ETR2, EXPA4, D2, D61, PDR6, ACO4, Rab6a, OsSERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, ZmPP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, Zm NPR1, Zm LOX3, ALD1, RLCK185, LCB2A1, PhyB1, COP1, WRKY51, Os PLDbeta1, RAC5, OsCPK12, GF14e, Os SBP, OsHIR1, BWMKY1, AOS1, Os LOL2, GH3, GH3-8, XB3, GLP1, Os MAPK6, ACS2, OsLRR1, OsMPK3, Os SGT1, GAP1, Os RAC1, Os TPC1, GH3-2, OsBIANK1, CIPK14, OS BIDK1, OsMPK6, Os MKK4, Gns1, Os CCR1, Os MAPKY5, RACK1A, OsG1, OsphyB, Hd16, RCN1, SPL11, Spin1, PAL, PAL1, OsAGPS1, NRAMP3, OsMTP1, ATM3, OsYSL2, DMAS1, OsMRP5, OsSULTR3;3, AMT1;2, OsAMT3;1, OsNRT2.3b, GS1;2, OsARG, OsNRT2.1, AMT1;1, AlaAT, ABC1, NADH-GOGAT, RBCS, NLA1, PHF1, OsMYB2P-1, CASTOR, INO1, sedoheptulose-1,7-bisphosphatase (SBPase), Fbpase; fructose-1,6-bisphosphatase, OsDET1, Os02g0465900, OsHox32, OsBZR1, OsNAL1, AlaAT, ZmNRT2.2, esp1, ZmGW2-CHR5, Asn synthetase, AspAT, NAD(H)-dependent GOGAT 1, Gln1-3, obap1, ZmAAP4 (amino acid permease 4), crtRB1, ZmMRP1, ZmDA1, ZmDAR1, APS1, 6-phospho-fructokinase, wx1, shrunken 1, sus1, brittle endosperm bt2, sugary 1, sbe1, MADS22, RT, GAMYB, HSP90, AOS2, SPS1, NYC1, D35, PIMT1, PIMT2, TYDC, TET9, CYP703A3, D1|D2|Os07g0558500, ABA8OX1, OsABA2, NCED1, ZEP1, ALDH7, CHS1, APX2, DOS, HOX33, NYC3, and APX1 as disclosed in Table 10, or is a gene encoding a protein having at least 90% identity to a sequence selected from SEQ ID NOs:693-976 as disclosed in Table 10, or is a gene with a genomic sequence selected from SEQ ID NO:977-1260 as disclosed in Table 10; and wherein each predetermined modification is selected from the group consisting of:
(i) heterologous integration of the nucleic acid sequence of a non-coding regulator element that is encoded by at least one donor polynucleotide molecule at a predetermined locus 1-1000 nucleotides upstream of the start codon of the coding sequence of a gene of interest in the reference genome;
(ii) heterologous integration of the nucleic acid sequence of a non-coding regulator element that is encoded by at least one donor polynucleotide molecule at a predetermined locus within 1000 nucleotides of the stop codon of a gene of interest in the reference genome;
(iii) deletion, addition, or substitution of at least one nucleotide in a regulatory element that regulates expression of a gene of interest in the reference genome;
(iv) deletion, addition, or substitution of at least one nucleotide in coding sequence of a gene of interest in the reference genome; and
(v) a combination of any of (i), (ii), (iii), and (iv); or
(c) both (a) and (b).

90. The method of embodiment 89, wherein the modified genome is more than 99.9% identical to the reference genome.

91. The method of embodiment 89, wherein the modified genome is devoid of mitotically or meiotically generated genetic or epigenetic changes relative to the reference genome.

92. The method of embodiment 89, wherein the modified genome comprises a difference of epigenetic changes in less than 0.01% of the genome relative to the reference genome.

93. The method of embodiment 89 wherein the modified genome comprises:
(a) a difference of DNA methylation in less than 0.01% of the genome, relative to the reference genome; or
(b) a difference of DNA methylation in less than 0.005% of the genome, relative to the reference genome; or
(c) a difference of DNA methylation in less than 0.001% of the genome, relative to the reference genome.

94. The method of embodiment 89, wherein the gene of interest is located on a chromosome in the wheat plant cell, and wherein the modified genome comprises:
(a) a difference of DNA methylation in less than 0.01% of the portion of the genome that is contained within the chromosome containing the gene of interest, relative to the reference genome; or
(b) a difference of DNA methylation in less than 0.005% of the portion of the genome that is contained within the chromosome containing the gene of interest, relative to the reference genome; or
(c) a difference of DNA methylation in less than 0.001% of the portion of the genome that is contained within the chromosome containing the gene of interest, relative to the reference genome.

95. The method of embodiment 89, wherein the modified genome has not more unintended changes in comparison to the reference genome than $1 \times 10^{-8}$ mutations per bp per replication.

96. The method of embodiment 89, wherein the wheat plant cell is a cell of an allotetraploid wheat plant, wherein the reference genome consists of an A genome and a B genome, and wherein the A genome only, the B genome only, or both the A and B genomes is heterozygous for at least one of the predetermined modifications of at least two genes of interest identified in Table 9.

97. The method of embodiment 89, wherein the wheat plant cell is a cell of an allotetraploid wheat plant, wherein the reference genome consists of an A genome and a B genome, and wherein the A genome only, the B genome only, or both the A and B genomes is homozygous for at least one of the predetermined modifications of at least two genes of interest identified in Table 9.

98. The method of embodiment 89, wherein the wheat plant cell is a cell of an allotetraploid wheat plant, wherein the reference genome consists of an A genome and a B genome, and wherein the A genome only, the B genome only, or both the A and B genomes is heterozygous for the predetermined modification of at least one gene of interest identified in Table 10.

99. The method of embodiment 89, wherein the wheat plant cell is a cell of an allotetraploid wheat plant, wherein the reference genome consists of an A genome and a B genome, and wherein the A genome only, the B genome only, or both the A and B genomes is homozygous for the predetermined modification of at least one gene of interest identified in Table 10.

100. The method of embodiment 89, wherein the wheat plant cell is a cell of an allohexaploid wheat plant, wherein the reference genome consists of an A genome, a B genome, and a D genome, and wherein the A genome only, the B genome only, the D genome only, or any combination of the A, B, and D genomes is heterozygous for at least one of the predetermined modifications of at least two genes of interest identified in Table 9.

101. The method of embodiment 89, wherein the wheat plant cell is a cell of an allohexaploid wheat plant, wherein the reference genome consists of an A genome, a B genome, and a D genome, and wherein the A genome only, the B genome only, the D genome only, or any combination of the A, B, and D genomes is homozygous for at least one of the predetermined modifications of at least two genes of interest identified in Table 9.

102. The method of embodiment 89, wherein the wheat plant cell is a cell of an allohexaploid wheat plant, wherein the reference genome consists of an A genome, a B genome, and a D genome, and wherein the A genome only, the B genome only, the D genome only, or any combination of the A, B, and D genomes is heterozygous for the predetermined modification of at least one gene of interest identified in Table 10.

103. The method of embodiment 89, wherein the wheat plant cell is a cell of an allohexaploid wheat plant, wherein the reference genome consists of an A genome, a B genome, and a D genome, and wherein the A genome only, the B genome only, the D genome only, or any combination of the A, B, and D genomes is homozygous for the predetermined modification of at least one gene of interest identified in Table 10.

EXAMPLES

Example 1

This example illustrates techniques for preparing a plant cell or plant protoplast useful in compositions and methods of the invention, for example, in providing a reaction mixture including a plant cell having a double-strand break (DSB) at least one locus in its genome. More specifically this non-limiting example describes techniques for preparing isolated, viable plant protoplasts from monocot plants.

The following mesophyll protoplast preparation protocol (modified from one publicly available at molbio[dot]mgh[dot]harvard.edu/sheenweb/protocols_reg[dot]html) is generally suitable for use with monocot plants such as maize (*Zea mays*), rice (*Oryza sativa*), and common wheat (*Triticum aestivum*):

Prepare an enzyme solution containing 0.6 molar mannitol, 10 millimolar MES pH 5.7, 1.5% cellulase R10, and 0.3% macerozyme R10. Heat the enzyme solution at 50-55 degrees Celsius for 10 minutes to inactivate proteases and accelerate enzyme solution and cool it to room temperature before adding 1 millimolar $CaCl_2$, 5 millimolar P-mercaptoethanol, and 0.1% bovine serum albumin. Pass the enzyme solution through a 0.45 micrometer filter. Prepare a washing solution containing 0.6 molar mannitol, 4 millimolar MES pH 5.7, and 20 millimolar KCl.

Obtain second leaves of the monocot plant (e.g., maize, rice, or wheat) and cut out the middle 6-8 centimeters. Stack ten leaf sections and cut into 0.5 millimeter-wide strips without bruising the leaves. Submerge the leaf strips completely in the enzyme solution in a petri dish, cover with aluminum foil, and apply vacuum for 30 minutes to infiltrate the leaf tissue. Transfer the dish to a platform shaker and incubate for an additional 2.5 hours' digestion with gentle shaking (40 rpm). After digestion, carefully transfer the enzyme solution (now containing protoplasts) using a serological pipette through a 35 micrometer nylon mesh into a round-bottom tube; rinse the petri with 5 milliliters of washing solution and filter this through the mesh as well. Centrifuge the protoplast suspension at 1200 rpm, 2 minutes in a swing-bucket centrifuge. Aspirate off as much of the supernatant as possible without touching the pellet; gently wash the pellet once with 20 milliliters washing buffer and remove the supernatant carefully. Gently resuspend the pellet by swirling in a small volume of washing solution, then resuspend in 10-20 milliliters of washing buffer. Place the tube upright on ice for 30 minutes-4 hours (no longer). After resting on ice, remove the supernatant by aspiration and resuspend the pellet with 2-5 milliliters of washing buffer. Measure the concentration of protoplasts using a hemocytometer and adjust the concentration to $2 \times 10^5$ protoplasts/milliliter with washing buffer.

Example 2

This example illustrates culture conditions effective in improving viability of plant cells or plant protoplasts. More specifically, this non-limiting example describes media and culture conditions for improving viability of isolated plant protoplasts.

Table 1 provides the compositions of different liquid basal media suitable for culturing plant cells or plant protoplasts; final pH of all media was adjusted to 5.8 if necessary.

TABLE 1

| Component | Concentration (mg/L unless otherwise noted) | | | | |
|---|---|---|---|---|---|
| | SH | 8p | PIM | P2 | YPIM B- |
| Casamino acids | | 250 | | | |
| Coconut water | | 20000 | | | |
| Ascorbic acid | | 2 | | | |

TABLE 1-continued

| Component | Concentration (mg/L unless otherwise noted) | | | | |
|---|---|---|---|---|---|
| | SH | 8p | PIM | P2 | YPIM B- |
| biotin | | 0.01 | 0.01 | | |
| Cholicalciferol (Vitamin D-3) | | 0.01 | | | |
| choline chloride | | 1 | | | |
| Citric acid | | 40 | | | |
| Cyanocobalamin (Vitamin B-12) | | 0.02 | | | |
| D-calcium pantothenate | | 1 | 1 | | |
| D-Cellobiose | | 250 | | | |
| D-Fructose | | 250 | | | |
| D-Mannose | | 250 | | | |
| D-Ribose | | 250 | | | |
| D-Sorbitol | | 250 | | | |
| D-Xylose | | 250 | | | |
| folic acid | | 0.4 | 0.2 | | |
| Fumaric acid | | 40 | | | |
| L-Malic acid | | 40 | | | |
| L-Rhamnose | | 250 | | | |
| p-Aminobenzoic acid | | 0.02 | | | |
| Retinol (Vitamin A) | | 0.01 | | | |
| Riboflavin | | 0.2 | | | |
| Sodium pyruvate | | 20 | | | |
| 2,4-D | 0.5 | 0.2 | 1 | 5 | 1 |
| 6-benzylaminopurine (BAP) | | | | | 1 |
| Indole-3-butyric acid (IBA) | | | | 2.5 | |
| Kinetin | 0.1 | | | | |
| Naphthaleneacetic acid (NAA) | | 1 | | | |
| parachlorophenoxyacetate (pCPA) | | 2 | | | |
| Thidiazuron | | | 0.022 | | |
| Zeatin | | 0.5 | | | |
| AlCl3 | | | 0.03 | | |
| Bromocresol purple | | | 8 | | |
| CaCl$_2$•2H$_2$O | 200 | 600 | 440 | 200 | 440 |
| CoCl$_2$•6H$_2$O | 0.1 | 0.025 | | 0.1 | |
| CuSO$_4$•5H$_2$O | 0.2 | 0.025 | 0.03 | 0.2 | 0.03 |
| D-Glucose | | 68400 | 40000 | | 40000 |
| D-Mannitol | 52000 | 250 | 60000 | 52000 | 60000 |
| FeSO$_4$•7H$_2$O | 15 | 27.8 | 15 | 15 | 15 |
| H$_3$BO$_3$ | 5 | 3 | 1 | 5 | 1 |
| KCl | | 300 | | | |
| KH$_2$PO$_4$ | | 170 | 170 | | 170 |
| KI | 1 | 0.75 | 0.01 | 1 | 0.01 |
| KNO$_3$ | 2500 | 1900 | 505 | 2500 | 505 |
| MES pH 5.8 (mM) | | | 3.586 | 25 | 25 |
| MgSO$_4$•7H$_2$O | 400 | 300 | 370 | 400 | 370 |
| MnSO$_4$•H$_2$O | 10 | 10 | 0.1 | 10 | 0.1 |
| Na$_2$EDTA | 20 | 37.3 | 20 | 20 | 20 |
| Na$_2$MoO$_4$•2H$_2$O | 0.1 | 0.25 | | 0.1 | |
| NH$_4$H$_2$PO$_4$ | 300 | | | 300 | |
| NH$_4$NO$_3$ | | 600 | 160 | | 160 |
| NiCl$_2$•6H$_2$O | | | 0.03 | | |
| Sucrose | 30000 | 2500 | | 30000 | |
| ZnSO$_4$•7H$_2$O | 1 | 2 | 1 | 1 | 1 |
| Tween-80 (microliter/L) | | | 10 | | 10 |
| Inositol | 1000 | 100 | 100 | 1000 | 100 |
| Nicotinamide | | 1 | | | |
| Nicotinic acid | 5 | | 1 | 5 | 1 |
| Pyridoxine•HCl | 0.5 | 1 | 1 | 0.5 | 1 |
| Thiamine•HCl | 5 | 1 | 1 | 5 | 1 |

\* Sources for basal media:
SH - Schenk and Hildebrandt, Can. J. Bot. 50:199 (1971).
8p - Kao and Michayluk, Planta 126: 105 (1975).
P2 - SH but with hormones from Potrykus et al., Mol. Gen. Genet. 156:347 (1977).
PIM - Chupeau et al., The Plant Cell 25:2444 (2013).

Example 3

This example illustrates culture conditions effective in improving viability of plant cells or plant protoplasts. More specifically, this example describes non-limiting methods for encapsulating isolated plant protoplasts.

In embodiments, protoplasts are encapsulated in alginate or pectin, allowing the protoplasts to remain intact longer than in an equivalent liquid medium. In order to encapsulate protoplasts, a liquid medium ("calcium base") is prepared that is in all other respects identical to the final desired recipe with the exception that the calcium (usually CaCl2·2H2O) is increased to 80 millimolar. A second medium ("encapsulation base") is prepared that has no added calcium but contains 10 g/L of the encapsulation agent, e.g., by making a 20 g/L solution of the encapsulation agent and adjusting its pH with KOH or NaOH until it is about 5.8, making a 2× solution of the final medium (with no calcium), then combining these two solutions in a 1:1 ratio. Encapsulation agents include alginate (e.g., alginic acid from brown algae, catalogue number A0682, Sigma-Aldrich, St. Louis, MO) and pectin (e.g., pectin from citrus peel, catalogue number P9136, Sigma-Aldrich, St. Louis, MO; various pectins including non-amidated low-methoxyl pectin, catalogue number 1120-50 from Modernist Pantry, Portsmouth, NH). The solutions, including the encapsulation base solution, are filter-sterilized through a series of filters, with the final filter being a 0.2-micrometer filter. Protoplasts are pelleted by gentle centrifugation and resuspended in the encapsulation base; the resulting suspension is added dropwise to the calcium base, upon which the protoplasts are immediately encapsulated in solid beads.

Example 4

This example illustrates culture conditions effective in improving viability of plant cells or plant protoplasts. More specifically, this non-limiting example describes observations of effects on protoplast viability obtained by adding non-conventionally high levels of divalent cations to culture media.

Typical plant cell or plant protoplast media contain between about 2 to about 4 millimolar calcium cations and between about 1-1.5 millimolar magnesium cations. In the course of experiments varying and adding components to media, it was discovered that the addition of non-conventionally high levels of divalent cations had a surprisingly beneficial effect on plant cell or plant protoplast viability. Beneficial effects on plant protoplast viability begin to be seen when the culture medium contains about 30 millimolar calcium cations (e.g., as calcium chloride) or about 30 millimolar magnesium cations (e.g., as magnesium chloride). Even higher levels of plant protoplast viability were observed with increasing concentrations of calcium or magnesium cations, i.e., at about 40 millimolar or about 50 millimolar calcium or magnesium cations. The result of several titration experiments indicated that greatest improvement in protoplast viability was seen using media containing between about 50 to about 100 millimolar calcium cations or 50 to about 100 millimolar magnesium cations; no negative effects on protoplast viability or physical appearance was observed at these high cation levels. This was observed in multiple experiments using protoplasts obtained from several plant species including maize (multiple germplasms, e.g., B73, A188, B104, HiIIA, HiIIB, BMS), rice, wheat, soy, kale, and strawberry; improved protoplast viability was observed in both encapsulated protoplasts and non-encapsulated protoplasts. Addition of potassium chloride at the same levels had no effect on protoplast viability. It is possible that inclusion of slightly lower (but still non-conventionally high) levels of divalent cations (e.g., about 10 millimolar, about 15 millimolar, about 20 millimolar, or about 25 millimolar calcium cations or magnesium cations) in media is beneficial for plant cells or plant protoplasts of additional plant species.

In additional experiments, separate suspensions of maize B73, winter wheat, soy, and strawberry protoplasts ($2\times10^5$ cells per milliliter) were prepared in YPIM B-liquid medium containing calcium chloride at 0, 50, or 100 millimolar. One-half milliliter aliquots of the suspensions were dispensed into a 24-well microtiter plate. Viability at day 8 of culture was judged by visualization under a light microscope. At this point, the viability of the maize protoplasts in the 0, 50, and 100 millimolar calcium conditions was 10%, 30%, and 80%, respectively. There were no large differences observed at this time point for protoplasts of the other species. Viability at day 13 was judged by Evans blue staining and visualization under a light microscope. At this point, the viability of the maize protoplasts in the 0, 50, and 100 millimolar calcium conditions was 0%, 0%, and 10%, respectively; viability of the soybean protoplasts in the 0, 50, and 100 millimolar calcium conditions was 0%, 50%, and 50%, respectively; and viability of the maize protoplasts in the 0 and 50 millimolar calcium conditions was 0% and 50%, respectively (viability was not measured for the 100 millimolar condition). These results demonstrate that culture conditions including calcium cations at 50 or 100 millimolar improved viability of both monocot and dicot protoplasts over a culture time of ~13 days.

Example 5

This example illustrates a method of delivery of an effector molecule to a plant cell or plant protoplast to effect a genetic change, in this case introduction of a double-strand break in the genome. More specifically, this non-limiting example describes a method of delivering a guide RNA (gRNA) in the form of a ribonucleoprotein (RNP) to isolated plant protoplasts.

The following delivery protocol (modified from one publicly available at molbio[dot]mgh[dot]harvard.edu/sheen-web/protocols_reg[dot]html) is generally suitable for use with monocot plants such as maize (*Zea mays*), rice (*Oryza sativa*), and wheat (*Triticum aestivum* and other *Triticum* spp.):

Prepare a polyethylene glycol (PEG) solution containing 40% PEG 4000, 0.2 molar mannitol, and 0.1 molar $CaCl_2$. Prepare an incubation solution containing 170 milligram/liter $KH_2PO_4$, 440 milligram/liter $CaCl_2 \cdot 2H_2O$, 505 milligram/liter $KNO_3$, 160 milligram/liter $NH_4NO_3$, 370 milligram/liter $MgSO_4 \cdot 7H_2O$, 0.01 milligram/liter KI, 1 milligram/liter $H_3BO_3$, 0.1 milligram/liter $MnSO_4 \cdot 4H_2O$, 1 milligram/liter $ZnSO_4 \cdot 7H_2O$, 0.03 milligram/liter $CuSO_4 \cdot 5H_2O$, 1 milligram/liter nicotinic acid, 1 milligram/liter thiamine HCl, 1 milligram/liter pyridoxine HCl, 0.2 milligram/liter folic acid, 0.01 milligram/liter biotin, 1 milligram/liter D-Ca-pantothenate, 100 milligram/liter myo-inositol, 40 grams/liter glucose, 60 grams/liter mannitol, 700 milligram/liter MES, 10 microliter/liter Tween 80, 1 milligram/liter 2,4-D, and 1 milligram/liter 6-benzylaminopurine (BAP); adjust pH to 5.6.

Prepare a crRNA:tracrRNA or guide RNA (gRNA) complex by mixing equal amounts of CRISPR crRNA and tracrRNA (obtainable e.g., as custom-synthesized Alt-RT™ CRISPR crRNA and tracrRNA oligonucleotides from Integrated DNA Technologies, Coralville, IA): mix 6 microliters of 100 micromolar crRNA and 6 microliters of 100 micromolar tracrRNA, heat at 95 degrees Celsius for 5 minutes, and then cool the crRNA:tracrRNA complex to room temperature. To the cooled gRNA solution, add 10 micrograms Cas9 nuclease (Aldevron, Fargo, ND) and incubate 5 minutes at room temperature to allow the ribonucleoprotein (RNP) complex to form. Add the RNP solution to 100 microliters of monocot protoplasts (prepared as described in Example 1) in a microfuge tube; add 5 micrograms salmon sperm DNA (VWR Cat. No.: 95037-160) and an equal volume of the PEG solution. Mix gently by tapping. After 5 minutes, dilute with 880 microliters of washing buffer and mix gently by inverting the tube. Centrifuge 1 minute at 1200 rpm and then remove the supernatant. Resuspend the protoplasts in 1 milliliter incubation solution, transfer the protoplasts to a multi-well plate, and seal the plate with Parafilm M® film (Bemis, Oshkosh, WI). Plates are typically incubated about 30 minutes to about 1 hour at 37 degrees Celsius and then further incubated 24-72 hours at room temperature (about 25-26 degrees Celsius). The efficiency of genome editing is assessed by any suitable method such as heteroduplex cleavage assay or by sequencing, as described elsewhere in this disclosure. A similar protocol is used for preparing RNPs made with other CRISPR nucleases.

The following delivery protocol (modified from one described by Niu and Sheen (2012) *Methods Mol. Biol.,* 876:195-206, doi: 10.1007/978-1-61779-809-2_16) is generally suitable for use with dicot plants such as *Arabidopsis thaliana* and brassicas such as kale (*Brassica oleracea*):

Prepare a polyethylene glycol (PEG) solution containing 40% PEG 4000, 0.2 molar mannitol, and 0.1 molar $CaCl_2$. Prepare an incubation solution containing 170 milligram/liter $KH_2PO_4$, 440 milligram/liter $CaCl_2 \cdot 2H_2O$, 505 milligram/liter $KNO_3$, 160 milligram/liter $NH_4NO_3$, 370 milligram/liter $MgSO_4 \cdot 7H_2O$, 0.01 milligram/liter KI, 1 milligram/liter $H_3BO_3$, 0.1 milligram/liter $MnSO_4 \cdot 4H_2O$, 1 milligram/liter $ZnSO_4 \cdot 7H_2O$, 0.03 milligram/liter $CuSO_4 \cdot 5H_2O$, 1 milligram/liter nicotinic acid, 1 milligram/liter thiamine HCl, 1 milligram/liter pyridoxine HCl, 0.2 milligram/liter folic acid, 0.01 milligram/liter biotin, 1 milligram/liter D-Ca-pantothenate, 100 milligram/liter myo-inositol, 40 grams/liter glucose, 60 grams/liter mannitol, 700 milligram/liter MES, 10 microliter/liter Tween 80, 1 milligram/liter 2,4-D, and 1 milligram/liter 6-benzylaminopurine (BAP); adjust pH to 5.6.

Prepare a crRNA:tracrRNA or guide RNA (gRNA) complex by mixing equal amounts of CRISPR crRNA and tracrRNA (obtainable e.g., as custom-synthesized Alt-RT™ CRISPR crRNA and tracrRNA oligonucleotides from Integrated DNA Technologies, Coralville, IA): mix 6 microliters of 100 micromolar crRNA and 6 microliters of 100 micromolar tracrRNA, heat at 95 degrees Celsius for 5 minutes, and then cool the crRNA:tracrRNA complex to room temperature. To the cooled gRNA solution, add 10 micrograms Cas9 nuclease (Aldevron, Fargo, ND) and incubate 5 minutes at room temperature to allow the ribonucleoprotein (RNP) complex to form. Add the RNP solution to 100 microliters of dicot protoplasts (prepared as described in Example 1) in a microfuge tube; add 5 micrograms salmon sperm DNA (VWR Cat. No.: 95037-160) and an equal volume of the PEG solution. Mix gently by tapping. After 5 minutes, dilute with 880 microliters of washing buffer and mix gently by inverting the tube. Centrifuge 1 minute at 1200 rpm and then remove the supernatant. Resuspend the protoplasts in 1 milliliter incubation solution and transfer to a multi-well plate. In most instances, the multi-well plate is heated for at least 10 minutes to between 30 to about 42 degrees Celsius, or to about 37 degrees Celsius, before an extended incubation at room temperature. For example, the protoplasts are incubated at a temperature of between about 30 to about 45 degrees Celsius for a period of time, e.g., for 10, 20, 30, 40, 45, 50, 60 minutes or for even longer periods (generally for incubation at only moderate heat, such as 30, 32, or 35 degrees Celsius), e. g., 2, 3, 4, 5, 6, 8, 10, 12, 18, 24, 30, 36, 40, or 48 hours; this is followed by incubation at a temperature at which normal growth occurs (average room temperature, e. g., 25-26 degrees Celsius). A typical treatment includes incubation for 30 to 120 minutes at 37 degrees Celsius, followed by a longer incubation (e.g., 24-120 hours) at 25-26 degrees Celsius. The efficiency of genome editing is assessed by any suitable method such as heteroduplex cleavage assay or by sequencing, as described elsewhere in this disclosure. A similar protocol is used for delivery of RNPs made with other CRISPR nucleases.

The above protocols for delivery of gRNAs as RNPs to plant protoplasts are adapted for delivery of guide RNAs alone to monocot or dicot protoplasts that express a Cas9 or other CRISPR nuclease by transient or stable transformation; in this case, the guide RNA complex is prepared as before and added to the protoplasts, but no nuclease and no salmon sperm DNA is added. The remainder of the procedures are identical.

Example 6

This example illustrates genome editing in plants and further illustrates a method of delivering gene-editing effector molecules into a plant cell. This example describes introducing at least one double-strand break (DSB) in a genome in a plant cell or plant protoplast, by delivering at least one effector molecules to the plant cell or plant protoplast using at least one physical agent, such as a particulate, microparticulate, or nanoparticulate. More specifically, this non-limiting example illustrates introducing at least one double-strand break (DSB) in a genome in a plant cell or plant protoplast by contacting the plant cell or plant protoplast with a composition including at least one sequence-specific nuclease and at least one physical agent, such as at least one nanocarrier. Embodiments include those wherein the nanocarrier comprises metals (e.g., gold, silver, tungsten, iron, cerium), magnetic or (super)paramagnetic materials (e.g., iron oxide), ceramics (e.g., aluminum oxide, silicon carbide, silicon nitride, tungsten carbide), polymers (e.g., polystyrene, polydiacetylene, and poly(3,4-ethylenedioxythiophene) hydrate), semiconductors (e.g., quantum dots), silicon (e.g., silicon carbide), carbon (e.g., graphite, graphene, graphene oxide, or carbon nanosheets, nanocomplexes, or nanotubes), composites (e.g., polyvinylcarbazole/graphene, polystyrene/graphene, platinum/graphene, palladium/graphene nanocomposites), a polynucleotide, a poly (AT), a polysaccharide (e.g., dextran, chitosan, pectin, hyaluronic acid, and hydroxyethylcellulose), a polypeptide, or a combination of these. In embodiments, such particulates and nanoparticulates are further covalently or non-covalently functionalized, or further include modifiers or cross-linked materials such as polymers (e.g., linear or branched polyethylenimine, poly-lysine), polynucleotides (e.g., DNA or RNA), polysaccharides, lipids, polyglycols (e.g., polyethylene glycol, thiolated polyethylene glycol), polypeptides or proteins, and detectable labels (e.g., a fluorophore, an antigen, an antibody, or a quantum dot). Embodiments include those wherein the nanocarrier is a nanotube, a carbon nanotube, a multi-walled carbon nanotube, or a single-walled carbon nanotube. Specific nanocarrier embodiments contemplated herein include the single-walled carbon nanotubes, cerium oxide nanoparticles ("nanoceria"), and modifications thereof (e.g., with cationic, anionic, or lipid coatings) described in Giraldo et al. (2014) Nature Materials, 13:400-409; the single-walled carbon nanotubes and heteropolymer complexes thereof described in Zhang et al. (2013) Nature Nanotechnol., 8:959-968 (doi:10.1038/NNANO.2013.236); the single-walled carbon nanotubes and heteropolymer complexes thereof described in Wong et al. (2016) Nano Lett., 16:1161-1172; and the various carbon nanotube preparations described in US Patent Application Publication US 2015/0047074 and International Patent Application PCT/US2015/050885 (published as WO 2016/044698 and claiming priority to U.S. Provisional Patent Application 62/052,767), all of which patent applications are incorporated in their entirety by reference herein. See also, for example, the various types of particles and nanoparticles, their preparation, and methods for their use, e.g., in delivering polynucleotides and polypeptides to cells, disclosed in US Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety.

In these examples, single-walled carbon nanotubes (SWCNT) and modifications thereof are prepared as described in Giraldo et al. (2014) Nature Materials, 13:400-409; Zhang et al. (2013) Nature Nanotechnol., 8:959-968; Wong et al. (2016) Nano Lett., 16:1161-1172; US Patent Application Publication US 2015/0047074; and International Patent Application PCT/US2015/050885 (published as WO 2016/044698). In an initial experiment, a DNA plasmid encoding green fluorescent protein (GFP) as a reporter is non-covalently complexed with a SWCNT preparation and tested on various plant cell preparations including plant cells in suspension culture, plant callus, plant embryos, intact or half seeds, and shoot apical meristem. Delivery to the plant callus, embryos, seeds, and meristem is by treatment with pressure, centrifugation, bombardment, microinjection, infiltration (e.g., with a syringe), or by direct application to the surface of the plant tissue. Efficiency of the SWCNT delivery of GFP across the plant cell wall and the cellular localization of the GFP signal is evaluated by microscopy.

In another experiment, plasmids encoding Cas9 and at least one guide RNA (gRNA), such as those described in Example 10, are non-covalently complexed with a SWCNT preparation and tested on various plant cell preparations including plant cells in suspension culture, plant callus, plant embryos, intact or half seeds, and shoot apical meristem. Delivery to the plant callus, embryos, seeds, and meristem is by treatment with pressure, centrifugation, bombardment, microinjection, infiltration (e.g., with a syringe), or by direct application to the surface of the plant tissue. The gRNA is designed to target the endogenous plant gene phytoene desaturase (PDS) for silencing, where PDS silencing produces a visible phenotype (bleaching, or low/no chlorophyll). Similar experiments are carried out using plasmids encoding Cpf1 nuclease and at least one gRNA.

In another experiment, RNA encoding Cas9 and at least one guide RNA (gRNA), such as those described in Examples 11-15 and 20-28, are non-covalently complexed with a SWCNT preparation and tested on various plant cell preparations including plant cells in suspension culture, plant callus, plant embryos, intact or half seeds, and shoot apical meristem. Delivery to the plant callus, embryos, seeds, and meristem is by treatment with pressure, centrifugation, bombardment, microinjection, infiltration (e.g., with a syringe), or by direct application to the surface of the plant tissue. The gRNA is designed to target the endogenous plant gene phytoene desaturase (PDS) for silencing, where PDS silencing produces a visible phenotype (bleaching, or low/no chlorophyll). Similar experiments are carried out using RNA encoding Cpf1 nuclease and at least one gRNA.

In another experiment, a ribonucleoprotein (RNP), prepared by complexation of Cas9 nuclease and at least one guide RNA (gRNA), is non-covalently complexed with a SWCNT preparation and tested on various plant cell preparations including plant cells in suspension culture, plant callus, plant embryos, intact or half seeds, and shoot apical meristem. Delivery to the plant callus, embryos, seeds, and meristem is by treatment with pressure, centrifugation, bombardment, microinjection, infiltration (e.g., with a syringe), or by direct application to the surface of the plant tissue. The gRNA is designed to target the endogenous plant gene phytoene desaturase (PDS) for silencing, where PDS silencing produces a visible phenotype (bleaching, or low/no chlorophyll). Similar experiments are carried out using RNPs made of Cpf1 nuclease and at least one gRNA.

One of skill in the art would recognize that the above general compositions and procedures can be modified or combined with other reagents and treatments, such as those described in detail in the paragraphs following the heading "Delivery Methods and Delivery Agents". In addition, the single-walled carbon nanotubes (SWCNT) and modifications thereof prepared as described in Giraldo et al. (2014) Nature Materials, 13:400-409; Zhang et al. (2013) Nature Nanotechnol., 8:959-968; Wong et al. (2016) Nano Lett., 16:1161-1172; US Patent Application Publication US 2015/0047074; and International Patent Application PCT/US2015/050885 (published as WO 2016/044698) can be used to prepare complexes with other polypeptides or polynucleotides or a combination of polypeptides and polynucleotides (e.g., with one or more polypeptides or ribonucleoproteins including at least one functional domain selected from the group consisting of: transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes, inhibitor of histone modifying enzymes, histone methyltransferases, histone demethylases, histone kinases, histone phosphatases, histone ribosylases, histone deribosylases, histone ubiquitinases, histone deubiquitinases, histone biotinases, and histone tail proteases).

Example 7

This example illustrates genome editing in plants and further illustrates a method of delivering gene-editing effector molecules into a plant cell. More specifically, this non-limiting example describes introducing at least one double-strand break (DSB) in a genome in a plant cell or plant protoplast, by contacting the plant cell or plant protoplast with a composition including a sequence-specific nuclease complexed with a gold nanoparticle.

In embodiments, at least one DSB is introduced in a genome in a plant cell or plant protoplast, by contacting the plant cell or plant protoplast with a composition that includes a charge-modified sequence-specific nuclease complexed to a charge-modified gold nanoparticle, wherein the complexation is non-covalent, e.g., through ionic or electrostatic interactions. In an embodiment, a sequence-specific nuclease having at least one region bearing a positive charge forms a complex with a negatively-charged gold particle; in another embodiment, a sequence-specific nuclease having at least one region bearing a negative charge forms a complex with a positively-charged gold particle. Any suitable method can be used for modifying the charge of the nuclease or the nanoparticle, for instance, through covalent modification to add functional groups, or non-covalent modification (e.g., by coating a nanoparticle with a cationic, anionic, or lipid coating). In embodiments, the sequence-specific nuclease is a type II Cas nuclease having at least one modification selected from the group consisting of: (a) modification at the N-terminus with at least one negatively charged moiety; (b) modification at the N-terminus with at least one moiety carrying a carboxylate functional group; (c) modification at the N-terminus with at least one glutamate residue, at least one aspartate residue, or a combination of glutamate and aspartate residues; (d) modification at the C-terminus with a localization signal, transit, or targeting peptide; (e) modification at the C-terminus with a nuclear localization signal (NLS), a chloroplast transit peptide (CTP), or a mitochondrial targeting peptide (MTP). In embodiments, the type II Cas nuclease is a Cas9 from *Streptococcus pyogenes* wherein the Cas9 is modified at the N-terminus with at least one negatively charged moiety and modified at the C-terminus with a nuclear localization signal (NLS), a chloroplast transit peptide (CTP), or a mitochondrial targeting peptide (MTP). In embodiments, the type II Cas nuclease is a Cas9 from *Streptococcus pyogenes* wherein the Cas9 is modified at the N-terminus with a polyglutamate peptide and modified at the C-terminus with a nuclear localization signal (NLS). In embodiments, the gold nanoparticle has at least one modification selected from the group consisting of: (a) modification with positively charged moieties; (b) modification with at least one moiety carrying a positively charged amine; (c) modification with at least one polyamine; (d) modification with at least one lysine residue, at least one histidine residue, at least one arginine residue, at least one guanidine, or a combination thereof. Specific embodiments include those wherein: (a) the sequence-specific nuclease is a type II Cas nuclease modified at the N-terminus with at least one negatively charged moiety and modified at the C-terminus with a nuclear localization signal (NLS), a chloroplast transit peptide (CTP), or a mitochondrial targeting peptide (MTP); and the gold nanoparticle is modified with at least one positively charged moiety; (b) the type II Cas nuclease is a Cas9 from *Streptococcus pyogenes* modified at the N-terminus with a polyglutamate peptide and modified at the C-terminus with a nuclear localization signal (NLS); and the gold nanoparticle is modified with at least one at least one lysine residue, at least one histidine residue, at least one arginine residue, at least one guanidine, or a combination thereof; (c) the type II Cas nuclease is a Cas9 from *Streptococcus pyogenes* modified at the N-terminus with a polyglutamate peptide that includes at least 15 glutamate residues and modified at the C-terminus with a nuclear localization signal (NLS); and wherein the gold nanoparticle is modified with at least one at least one lysine residue, at least one histidine residue, at least one arginine residue, at least one guanidine, or a combination thereof. In a specific embodiment, at least one DSB is introduced in a genome in a plant cell or plant protoplast, by contacting the plant cell or plant protoplast with a composition including a sequence-specific nuclease complexed with a gold nanoparticle, wherein the sequence-specific nuclease is a Cas9 from *Streptococcus pyogenes* modified at the N-terminus with a polyglutamate peptide that includes at least 15 glutamate residues and modified at the C-terminus with a nuclear localization signal (NLS); and wherein the gold nanoparticle is in the form of cationic arginine gold nanoparticles (ArgNPs), and wherein when the modified Cas9 and the ArgNPs are mixed, self-assembled nanoassemblies are formed as described in Mout et al. (2017) *ACS Nano*, doi:10.1021/acsnano.6b07600. Similar embodiments employ Cpf1 instead of Cas9 as the sequence-specific nuclease. Other embodiments contemplated herein include the various nanoparticle-protein complexes (e.g., amine-bearing nanoparticles complexed with carboxylate-bearing proteins) described in International Patent Application PCT/US2016/015711, published as International Patent Application Publication WO2016/123514, which claims priority to U.S. Provisional Patent Applications 62/109,389, 62/132,798, and 62/169,805, all of which patent applications are incorporated in their entirety by reference herein.

In embodiments, the sequence-specific nuclease is an RNA-guided DNA endonuclease, such as a type II Cas nuclease, Cas9, or Cpf1, and the composition further includes at least one guide RNA (gRNA) for an RNA-guided nuclease, or a DNA encoding a gRNA for an RNA-guided nuclease. The method effects the introduction of at least one DSB in a genome in a plant cell or plant protoplast; in embodiments, the genome is that of the plant cell or plant protoplast; in embodiments, the genome is that of a nucleus, mitochondrion, plastid, or endosymbiont in the plant cell or plant protoplast. In embodiments, the at least one DSB is introduced into coding sequence, non-coding sequence, or a combination of coding and non-coding sequence. In embodiments, the plant cell or plant protoplast is a plant cell in an intact plant or seedling or plantlet, a plant tissue, seed, embryo, meristem, germline cells, callus, or a suspension of plant cells or plant protoplasts.

In embodiments, at least one dsDNA molecule is also provided to the plant cell or plant protoplast, and is integrated at the site of at least one DSB or at the location where genomic sequence is deleted between two DSBs. Embodiments include those wherein: (a) the at least one DSB is two blunt-ended DSBs, resulting in deletion of genomic sequence between the two blunt-ended DSBs, and wherein the dsDNA molecule is blunt-ended and is integrated into the genome between the two blunt-ended DSBs; (b) the at least one DSB is two DSBs, wherein the first DSB is blunt-ended and the second DSB has an overhang, resulting in deletion of genomic sequence between the two DSBs, and wherein the dsDNA molecule is blunt-ended at one terminus and has an overhang on the other terminus, and is integrated into the genome between the two DSBs; (c) the at least one DSB is two DSBs, each having an overhang, resulting in deletion of genomic sequence between the two DSBs, and wherein the dsDNA molecule has an overhang at each terminus and is integrated into the genome between the two DSBs.

In a non-limiting example, self-assembled green fluorescent protein (GFP)/cationic arginine gold nanoparticles (ArgNPs), nanoassemblies are prepared as described in International Patent Application Publication WO2016/123514. The GFP/ArgNP nanoassemblies are delivered to maize protoplasts, common wheat (*Triticum aestivum*) protoplasts, and kale protoplasts prepared as described in Example 1, and to protoplasts prepared from the Black Mexican Sweet (BMS) maize cell line. Efficiency of transfection or delivery is assessed by fluorescence microscopy at time points after transfection (30 minutes, 1 hour, 3 hours, 6 hours, and overnight). Similar embodiments employ sequence-specific nuclease/ArgNP nanoassemblies where the sequence-specific nuclease is, e.g., Cas9 or Cpf1.

In a non-limiting example, self-assembled GFP/cationic arginine gold nanoparticles (ArgNPs), nanoassemblies are prepared as described in International Patent Application Publication WO2016/123514. The GFP/ArgNP nanoassemblies are co-incubated with common wheat (*Triticum aestivum*) cells in suspension culture. Efficiency of transfection or delivery across the cell wall is assessed by fluorescence microscopy at time points after transfection (30 minutes, 1 hour, 3 hours, 6 hours, and overnight). Similar embodiments employ sequence-specific nuclease/ArgNP nanoassemblies where the sequence-specific nuclease is, e.g., Cas9 or Cpf1.

In a non-limiting example, self-assembled GFP/cationic arginine gold nanoparticles (ArgNPs), nanoassemblies are prepared as described in International Patent Application Publication WO2016/123514. The GFP/ArgNP nanoassemblies are further prepared for Biolistics or particle bombardment and thus delivered to cells from common wheat (*Triticum aestivum*) suspension cultures transferred to semi-solid or solid media, as well as to wheat embryogenic callus. Efficiency of transfection or delivery across the plant cell wall is assessed by fluorescence microscopy at time points after transfection (30 minutes, 1 hour, 3 hours, 6 hours, and overnight). Similar embodiments employ sequence-specific nuclease/ArgNP nanoassemblies where the sequence-specific nuclease is, e.g., Cas9 or Cpf1.

In a non-limiting example, self-assembled GFP/cationic arginine gold nanoparticles (ArgNPs), nanoassemblies are prepared as described in International Patent Application Publication WO2016/123514. The GFP/ArgNP nanoassemblies are delivered by infiltration (e.g., using mild positive pressure or negative pressure) into leaves of *Arabidopsis thaliana* and common wheat (*Triticum aestivum*) plants. Efficiency of transfection or delivery across the plant cell wall is assessed by fluorescence microscopy at time points after transfection (30 minutes, 1 hour, 3 hours, 6 hours, and overnight). Similar embodiments employ sequence-specific nuclease/ArgNP nanoassemblies where the sequence-specific nuclease is, e.g., Cas9 or Cpf1.

In a non-limiting example, self-assembled Cas9/ArgNP nanoassemblies are prepared as described in Mout et al. (2017) *ACS Nano*, doi:10.1021/acsnano.6b07600 or alternatively as described in International Patent Application Publication WO2016/123514, by mixing a Cas9 from *Streptococcus pyogenes* modified at the N-terminus with a polyglutamate peptide that includes at least 15 glutamate residues and modified at the C-terminus with a nuclear localization signal (NLS) with cationic arginine gold nanoparticles (ArgNPs). The Cas9/ArgNP nanoassemblies are delivered to maize protoplasts, common wheat (*Triticum aestivum*) protoplasts, and kale protoplasts prepared as described in Example 1, and to protoplasts prepared from the Black Mexican Sweet (BMS) maize cell line. In one variation of the procedure, the Cas9/ArgNP nanoassemblies are co-delivered with at least one guide RNA (such as those described in Examples 11-15 and 20-28) to the protoplasts. In other variations of the procedure, the self-assembled Cas9/ArgNP nanoassemblies are prepared with at least one guide RNA to allow the modified Cas9 to form a ribonucleoprotein (RNP) either prior to or after formation of the nanoassemblies; the self-assembled RNP/ArgNP nanoassemblies are then delivered to the protoplasts. Efficiency of editing is assessed by any suitable method such as a heteroduplex cleavage assay or by sequencing, as described elsewhere in this disclosure. Similar embodiments employ Cpf1 instead of Cas9 as the sequence-specific nuclease.

In a non-limiting example, self-assembled Cas9/ArgNP nanoassemblies are prepared as described in Mout et al. (2017) *ACS Nano*, doi:10.1021/acsnano.6b07600 or alternatively as described in International Patent Application Publication WO2016/123514, by mixing a Cas9 from *Streptococcus pyogenes* modified at the N-terminus with a polyglutamate peptide that includes at least 15 glutamate residues and modified at the C-terminus with a nuclear localization signal (NLS) with cationic arginine gold nanoparticles (ArgNPs). The Cas9/ArgNP nanoassemblies are co-incubated with plant cells in suspension culture. In one variation of the procedure, the Cas9/ArgNP nanoassemblies are co-delivered with at least one guide RNA (such as those described in Examples 11-15 and 20-28) to common wheat (*Triticum aestivum*) cells in suspension culture. In other variations of the procedure, the self-assembled Cas9/ArgNP nanoassemblies are prepared with at least one guide RNA to allow the modified Cas9 to form a ribonucleoprotein (RNP) either prior to or after formation of the nanoassemblies; the self-assembled RNP/ArgNP nanoassemblies are then delivered to the plant cells in suspension culture. Efficiency of editing is assessed by any suitable method such as a heteroduplex cleavage assay or by sequencing, as described elsewhere in this disclosure. Similar embodiments employ Cpf1 instead of Cas9 as the sequence-specific nuclease.

In a non-limiting example, self-assembled Cas9/ArgNP nanoassemblies are prepared as described in Mout et al. (2017) *ACS Nano*, doi:10.1021/acsnano.6b07600 or alternatively as described in International Patent Application Publication WO2016/123514, by mixing a Cas9 from *Streptococcus pyogenes* modified at the N-terminus with a polyglutamate peptide that includes at least 15 glutamate residues and modified at the C-terminus with a nuclear localization signal (NLS) with cationic arginine gold nanoparticles (ArgNPs). The Cas9/ArgNP nanoassemblies are further prepared for Biolistics or particle bombardment and thus delivered to cells from common wheat (*Triticum aestivum*) suspension cultures transferred to semi-solid or solid media, as well as to wheat embryogenic callus. In one variation of the procedure, the Cas9/ArgNP nanoassemblies are co-delivered with at least one guide RNA (such as those described in Examples 11-15 and 20-28) to the wheat cells or callus. In other variations of the procedure, the self-assembled Cas9/ArgNP nanoassemblies are prepared with at least one guide RNA to allow the modified Cas9 to form a ribonucleoprotein (RNP) either prior to or after formation of the nanoassemblies; the self-assembled RNP/ArgNP nanoassemblies are then delivered to the plant cells or callus. Efficiency of editing is assessed by any suitable method such as a heteroduplex cleavage assay or by sequencing, as described elsewhere in this disclosure. Similar embodiments employ Cpf1 instead of Cas9 as the sequence-specific nuclease.

In a non-limiting example, self-assembled Cas9/ArgNP nanoassemblies are prepared as described in Mout et al. (2017) *ACS Nano*, doi:10.1021/acsnano.6b07600 or alternatively as described in International Patent Application Publication WO2016/123514, by mixing a Cas9 from *Streptococcus pyogenes* modified at the N-terminus with a polyglutamate peptide that includes at least 15 glutamate residues and modified at the C-terminus with a nuclear localization signal (NLS) with cationic arginine gold nanoparticles (ArgNPs). The Cas9/ArgNP nanoassemblies are delivered by infiltration (e.g., using mild positive pressure or negative pressure) into leaves of *Arabidopsis thaliana* and common wheat (*Triticum aestivum*) plants. In one variation of the procedure, the Cas9/ArgNP nanoassemblies are co-delivered with at least one guide RNA (such as those described in Examples 11-15 and 20-28) to the *Arabidopsis* and wheat leaves. In other variations of the procedure, the self-assembled Cas9/ArgNP nanoassemblies are prepared with at least one guide RNA to allow the modified Cas9 to form a ribonucleoprotein (RNP) either prior to or after formation of the nanoassemblies; the self-assembled RNP/ArgNP nanoassemblies are then delivered to the *Arabidopsis* and wheat leaves. Efficiency of editing is assessed by any suitable method such as a heteroduplex cleavage assay or by sequencing, as described elsewhere in this disclosure. Similar embodiments employ Cpf1 instead of Cas9 as the sequence-specific nuclease.

One of skill in the art would recognize that alternatives to the above compositions and procedures can be used to edit plant cells and intact plants, tissues, seeds, and callus. In embodiments, nanoassemblies are made using other sequence-specific nucleases (e.g., zinc-finger nucleases (ZFNs), transcription activator-like effector nucleases (TAL-effector nucleases or TALENs), Argonaute proteins, or a meganuclease or engineered meganuclease) which can be similarly charge-modified. In embodiments, nanoassemblies are made using other nanoparticles (e.g., nanoparticles made of materials such as carbon, silicon, silicon carbide, gold, tungsten, polymers, ceramics, iron oxide, or cobalt ferrite) which can be similarly charge-modified in order to form non-covalent complexes with the charge-modified sequence-specific nuclease. Similar nanoassemblies including other polypeptides (e.g., phosphatases, hydrolases, oxidoreductases, transferases, lyases, recombinases, polymerases, ligases, and isomerases) or polynucleotides or a combination of polypeptides and polynucleotides are made using similar charge modification methods to enable non-covalent complexation with charge-modified nanoparticles. For example, similar nanoassemblies are made by complexing charge-modified nanoparticles with one or more polypeptides or ribonucleoproteins including at least one functional domain selected from the group consisting of: transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes, inhibitor of histone modifying enzymes, histone methyltransferases, histone demethylases, histone kinases, histone phosphatases, histone ribosylases, histone deribosylases, histone ubiquitinases, histone deubiquitinases, histone biotinases, and histone tail proteases.

Example 8

As described herein, microinjection techniques can be used as an alternative to the methods for delivering genome editing or modifying agents to protoplasts as described, e.g., in certain Examples above. Microinjection is typically used to target specific cells in isolated embryo sacs or the shoot apical meristem. See, e.g., U.S. Pat. No. 6,300,543, which is incorporated by reference herein. For example, an injector attached to a Narashige manipulator on a dissecting microscope is adequate for injecting relatively large cells (e.g., the maize egg/synergids/zygote and the central cell) or shoot apical meristem. For smaller cells, such as isolated egg cells and zygotes or microspores, a compound, inverted microscope with an attached Narashige manipulator is preferred. Injection pipette diameter and bevel are also important. A high quality pipette puller and beveler are used to prepare needles with adequate strength, flexibility, and pore diameter. These will vary depending on the cargo being delivered to cells. The volume of fluid to be microinjected is small and should be carefully controlled. An Eppendorf Transjector yields consistent results (Laurie et al., *In Vitro Cell Dev Biol.* 35: 320-325, 1999).

The genetic cargo can be RNA, DNA, protein, or a combination thereof. The cargo can be designed to change one aspect of the target genome or many. The concentration of each cargo component will vary depending on the nature of the manipulation. Typical cargo volumes can vary from 2-20 nanoliters. After microinjection the treated plant parts are maintained on an appropriate media alone (e.g., sterile MS medium with 10% sucrose) or supplemented with a feeder culture. The resulting plantlets are transferred to fresh MS media every two weeks and to larger containers as they grow. Plantlets with a well-developed root system are transferred to soil and maintained in high humidity for 5 days to acclimate. Plants are gradually exposed to the air and cultivated to reproductive maturity.

Preparation of corn embryos for microinjection: Maize cobs and tassels are immediately bagged when they appear to prevent pollination. To obtain zygote-containing maize embryo sacs, hand pollination of silks is performed when the silks are 6-10 cm long, the pollinated ears are bagged and tassels removed, and then ears are harvested 16 hours later. After removing husks and silks, the cobs are cut transversely into 3-cm segments. The segments are surface sterilized in 70% ethanol and then rinsed in sterile distilled, deionized water. Ovaries are then removed and prepared for sectioning. The initial preparation may include mechanical removal of the ovarian wall if needed.

Once the ovaries have been removed, they are attached to a Vibratome sectioning block, using a commercial adhesive such as Locktite cement. Normally 2-3 pairs of ovaries are attached on each sterile sectioning block with the adaxial ovarian surface facing upwards and perpendicular to the longitudinal axis of the rectangular sectioning block (Laurie et al., *In Vitro Cell Dev Biol.*, 35: 320-325, 1999). Ovarian sections (or "nucellar slabs") are obtained at a thickness of 200 to 400 micrometers. An ideal section thickness is 200 micrometers. The embryo sac will remain viable if it is not cut. The sections are collected with fine forceps and evaluated on a dissecting microscope with basal illumination. Sections with an intact embryo sac are placed on semi-solid Murashige-Skoog (MS) culture medium (Campenot et al., 1992) containing 15% sucrose and 0.1 mg/L benzylaminopurine. Sterile Petri dishes containing semi-solid MS medium and nucellar slabs are then placed in an incubator maintained at 26 degrees Celsius. These can be monitored visually by removing plates from the incubator and examining the nucellar slabs with a dissecting microscope in a laminar flow hood.

Preparation of soy embryonic axes for microinjection: Mature soybean seeds are surface sterilized using chlorine gas. The gas is cleared by air flow in a sterile, laminar flow hood. Seeds are wetted with 70% ethanol for 30 seconds and rinsed with sterile distilled, deionized water then incubated in sterile distilled, deionized water for 30 minutes to 12 hours. The embryonic axes are carefully removed from the cotyledons and placed in MS media with the radicle oriented downwards and the apex exposed to air. The embryonic leaves are carefully removed with fine tweezers to expose the shoot apical meristem.

Preparation of rice for microinjection: Rice tissues that are appropriate for genome editing manipulation include embryogenic callus, exposed shoot apical meristems and 1 DAP embryos. There are many approaches to producing embryogenic callus (for example, Tahir 2010 (DOI 10.1007/978-1-61737-988-8_21); Ge et al., 2006 (DOI: 10.1007/s00299-005-0100-7)). Shoot apical meristem explants can be prepared using a variety of methods in the art (see, e.g., Sticklen and Oraby, 2005 (DOI: 10.1079/IVP2004616); Baskaran and Dasgupta, 2012 (DOI 10.1007/s13562-011-0078-x)). This work describes how to prepare and nurture material that is adequate for microinjection.

To prepare 1 DAP embryos for microinjection, Indica or japonica rice are cultivated under ideal conditions in a greenhouse with supplemental lighting with a 13-hour day, day/night temperatures of 30/20 degrees Celsius, relative humidity between 60-80%, and adequate fertigation using Hoagland's solution or an equivalent. The 1 DAP zygotes are identified and prepped essentially as described in Zhang et al., 1999, *Plant Cell Reports* (*DOI* 10.1007/s002990050722). The dissected ovaries with exposed zygotes are placed on the appropriate solid support medium and oriented for easy access using a microinjection needle. Injection and subsequent growth is carried out as described above in this Example.

General preparation of plant meristems for microinjection: In embodiments, microinjection is used to deliver editing reagents to plant meristematic cells. The apical or axillary meristem of a young plant is surgically exposed and genome editing reagents are introduced just below the L1 layer, into the L2 layer, of the meristem, using a microinjection apparatus. The injected tissue is allowed to recover, and the resulting newly formed tissue is examined for the presence of the intended genomic edits. This cycle can be repeated many times; in embodiments this is facilitated by propagating cuttings of the edited plant material from time to time. Modifications to the plant genome can be monitored by one or more molecular assays. Once the intended changes are complete, the plant is permitted to flower, is selfed or crossed, and produces seed. The next generation is examined for the presence and activity of all intended edits.

The genome editing reagents for this work are selected from DNA, RNA, protein, or a combination thereof (such as the ribonucleoproteins described elsewhere in this disclosure). The reagents are delivered using an appropriate microinjection apparatus in a volume of about 2 to about 20 nanoliters per cell. The editing reagents can be delivered alone or as part of a formulation to aid in uptake by the targeted meristematic cells. These reagents can include saponin (e.g., Sigma Cat. No. 47036-50g-F), pectinase, DMSO, Silwet-77, Tween-20, or any other agent that permeabilizes or otherwise makes penetrable the plant cell wall without compromising the cell's activity or interfering with the activity of the editing reagents.

To introduce editing reagents into shoot apical meristem, newly formed leaf tissue at the apex of a young plant is carefully removed to expose the meristem without damaging it. The stem is gently, but firmly supported to counteract the pressure of the microinjection needle. A dissecting or compound microscope with appropriate optics is used to ensure that the microinjection needle accurately contacts the meristematic cells (specifically, the L2 cell layer, which gives rise to the germline). Once the meristem cells are treated, the stem is marked and the plant allowed to recover for several days. One or multiple meristems per plant can be treated, each meristem with identical or distinct editing reagents. The recovery period is long enough for the plant to grow 3-5 new leaves from the treated meristem. When sufficient new leaf tissue has grown, a small piece of a newly formed leaf is excised for molecular analysis. If more genomic edits are required prior to flowering, tissue segments representing edited material can be vegetatively propagated. Excised plantlets are rooted in fresh soil or tissue culture media prior to the next editing step. Care is taken to insure the propagated plant is actively growing (e. g., displays evidence of robust root growth and new leaf formation) before initiating the next microinjection.

Preparation and microinjection of wheat microspores. egg cells and zygotes, and meristems: For microspore preparation, tillers from selected genotypes (Ac Andrews, Fielder and Chris) are collected when the spike reaches the top of the leaf sheath on the stalk. Microspores are isolated following published procedures described by, for example, Sinha and Eudes (2015) *Plant Cell Tissue Org. Cult.*, 122:227-237; doi:10.1007/s11240-015-0763-x; and Sinha et al. (2016) *Frontiers Plant Sci.*, 7:1931; doi:10.3389/fpls.2016.01931. Wheat microspores' diameter is around 50-80 micrometers and they can be micromanipulated and microinjected as described by Jones-Villeneuve et al. (1995) *Plant Cell Tissue Org. Cult.*, 40:97-100; doi:10.1007/BF00041124; and Miki et al. (1989) *Methods Cell Sci.*, 12:139-144; doi:10.1007/BF01404440. Egg cells and zygotes from wheat of preferred genotypes are isolated following published protocols, e.g., Pónya et al. (1999) *Protoplasma*, 208:163-172; doi:10.1007/BF01279087; and Koiso et al. (2017) *Plant Direct*, 2017, 1-10; doi:10.1002/pld3.10. After isolation, microspores, egg cells, and zygotes can each be manipulated using a protocol for single-cell microinjection technique, for example, that described by Zhang (2007) *Protocol Exchange*; doi:10.1038/nprot.2007.487. Shoot apical meristems from preferred cultivars are exposed and explanted using methods such as those described by Hamada et al. (2017) *Scientific Reports*, 7:11443; doi:10.1038/s41598-017-11936-0. Once the meristem is oriented in the appropriate medium it is easily accessible to the microinjection needle. Following microinjection, the explanted meristem is grown directly into a plant without intervening cell culture or callus formation steps, as described by Hamada et al. (2017).

Example 9

This example illustrates a method of directly delivering editing reagents to plant cells or tissues. More specifically, this non-limiting example describes editing reagents or effector molecules (e. g., at least one crRNA or sgRNA or a polynucleotide encoding at least one crRNA or sgRNA or an RNA-guided nuclease or a polynucleotide that encodes the RNA-guided nuclease) by gold microparticle bombardment directly into germline cells of excised soybean (*Glycine max*) embryos.

In a non-limiting protocol, sgRNA and nuclease vectors are delivered by gold microparticle bombardment to non-epidermal cells in soybean embryonic axes. Mature, dry soybean seeds (cv. Williams 82) are surface-sterilized by holding overnight in an enclosed chamber with a beaker containing 100 milliliters 5% sodium hypochlorite solution to which 4 milliliters concentrated (12N) hydrochloric acid were freshly added. The sterilized seeds are imbibed in sterile water for 2-20 hours. Seeds are split by inserting a razor blade into the hilum leaving the embryonic axes intact. The pericarp is removed and the tip of the radicle excised. The leaf primordia and a thin layer of the shoot apical meristems are excised with a scalpel with the aid of a dissecting microscope. Prepared explants are placed on pre-bombardment medium ("Recipe X" with the addition of 2 milligrams/liter 6-benzylaminopurine) for 2-3 days in the dark at 26 (plus or minus 2) degrees Celsius. In an alternative protocol, explants are placed on osmoticum medium ("Recipe X" modified by the addition of 36.8 grams/liter sorbitol and 36.8 grams/liter mannitol) for four hours prior to bombardment. To make a 1-liter quantity of "Recipe X" medium, mix 4.43 g MS salts with B5 vitamins, 10 milliliter 0.2 molar MES hydrate stock solution, 100 milligrams myo-inositol, 30 grams sucrose, 8 grams Oxoid agar (Remel, Inc. Lenexa, KS) and bring volume to 1 liter with water. Adjust pH to 5.8 before adding agar and autoclaving. Add 6-benzylaminopurine (BA) after cooling to about 50 degrees Celsius.

Gold microparticles are prepared as follows. In the following non-limiting embodiment, 1.0 micrometer gold microparticles are used (Bio-Rad, Hercules, CA). (In other protocols, gold microparticles of other sizes (e. g., 0.6 or 1.6 micrometer) are also useful.) Approximately 15-20 milligrams of gold microparticles are transferred to sterile 1.5 milliliter microcentrifuge tubes. Cold absolute ethanol (500 microliters) is added to each tube, and the tubes are placed in the ultrasonicating water bath for 15 seconds. Gold microparticles are allowed to settle ~10-30 minutes followed by pelleting by centrifugation for 1 minute at 3000 rpm. The supernatant is removed and the pellet is carefully rinsed with 1 milliliter ice-cold sterile water. The tubes are tapped gently to disturb the pellets, which are then allowed to settle again. The rinse step is repeated two more times. After the third rinse, the microparticles are pelleted 15 seconds at 5000 rpm, and the final supernatant removed. The pellet is resuspended in 500 microliters sterile water to form a "1×" concentration, placed in the ultrasonicating water bath for 15 seconds, and immediately after is vortexed. Aliquots of 50 microliters are transferred to 1.5-millilter microcentrifuge tubes, with the original preparation continually vortexed during the transfers. The 1× aliquots are stored at −20 degrees Celsius.

Prior to precipitation of DNA on gold microparticles, soy explants are embedded in pre-bombardment medium with the shoot apical meristem arranged parallel with the medium's surface and directly facing the trajectory of the coated microparticles. Approximately, 20-40 explants are placed in the center of the plate, corresponding to the ~3.5-centimeter diameter circle of the tissue platform (Bio-Rad, Hercules, CA). A tube of 1× prepared gold is used for bombardment of three media plates of soy explants. Prepared 1× tubes are thawed on ice, placed in the ultrasonicating water bath for 15 seconds, and then centrifuged at 2000 rpm for 2 minutes. The supernatant is removed and the gold microparticles are resuspended in either 25 microliters DNA (1 microgram/microliter) solution or 25 microliters sterile water as a control. The following is added in order, vortexing between each addition: 220 microliters sterile water, 250 microliters 2.5 molar calcium chloride, and 50 microliters 0.1 molar spermidine. The tubes are placed on ice for 5 minutes, vortexed for ~2 minutes at room temperature, and then centrifuged at 500 rpm for 5 minutes. The supernatant is removed and the pellet is resuspended in 600 microliters absolute ethanol. The tubes are centrifuged for 1 minute at 14000 rpm. The supernatant is removed and the pellet is resuspended in 36 microliters absolute ethanol. (To conserve the amount of gold used, the pellet can be resuspended in about 90 microliters absolute ethanol, and about 10 microliters or about 444 nanograms gold used for each shot for 9 shots.) DNA-coated gold (11 microliters) is placed in the center of autoclaved macrocarriers (Bio-Rad, Hercules, CA) and allowed to dry for approximately 5-10 minutes. The PDS-1000/He Biolistic® particle delivery system (Bio-Rad, Hercules, CA) is assembled. The rupture discs (1,100 psi rupture discs, Bio-Rad, Hercules, CA; 900 or 650 psi rupture discs can also be used) are dipped in 70% ethanol to sterilize, placed in the retaining cap, and tightened with the manufacturer's supplied wrench. The autoclaved stopping screen is placed in the macrocarrier assembly followed by the DNA-coated gold macrocarrier. The system is assembled as directed in the manual. The distance used from stopping screen to soy explants is 6 centimeters. The gun is fired when the vacuum in the chamber reaches 27-28 inches of Hg.

After bombardment, explants are transferred to Recipe X medium containing 0.5 milligrams/liter 6-benzylaminopurine. Plates with bombarded explants are placed in the dark for 2-4 days at 26 (plus or minus 2) degrees Celsius, then moved to a 16-hour light (75 micromoles)/8-hour dark light regime at 26 (plus or minus 2) degrees Celsius for several days to weeks depending on assay performed. For non-destructive assays, soybean shoots are sampled and explants moved to fresh Recipe X medium containing 0.5 milligrams/liter 6-benzylaminopurine. When shoots reach about 2-3 centimeters in length, explants are transferred to shoot elongation media ("Recipe Y"). To make 1 liter of "Recipe Y" medium, mix 4.43 grams MS salts with B5 vitamins, 0.59 grams MES hydrate, and 30 grams sucrose in 1 liter water, adjust pH to 5.7, and add 3 grams Phytagel. Autoclave 35 minutes on liquid cycle and cool to 50 degrees Celsius. In a laminar flow hood, add to 1 liter of cooled medium 0.5 milligrams gibberellic acid (as a premade stock, G362, PhytoTechnologies Laboratories, Shawnee Mission, KS), 500 microliters 50 milligrams/milliliter asparagine stock solution, 5 milligrams glutamine, 400 microliters indole acetic acid (as a 1 milligram/milliliter stock), and 1 milligram trans-zeatin riboside. Pour 100 milliliters per phytatray and allow to cool; store at room temperature. After approximately two weeks of shoot elongation, shoots are of sufficient size to transfer to Jiffy peat pellets, and are later transplanted to soilless mix in pots for maturation, observation of phenotype, and analysis.

In another non-limiting protocol, a ribonucleoprotein (RNP) complex is delivered by gold microparticle bombardment to shoot apical meristem cells. A ribonucleoprotein (RNP) complex is prepared with Cas9 nuclease and crRNA/tracrRNA or sgRNA as described elsewhere in this application. In an example, an RNP preparation is made with 6 microliters of 100 micromolar crRNA annealed with 6 microliters of 100 micromolar tracrRNA, and complexed with 20 micrograms Cas9 nuclease. The RNP preparation was added to a tube of 1× gold microparticles in 50 microliters water, mixed gently, and used at a rate of 14 microliters RNP-coated gold per macrocarrier. Sixty microliters 2.5 molar calcium chloride and 20 microliters 0.1 molar spermidine are optionally added, with vortexing, to this preparation. (To conserve the amount of gold used, one tube of ~1.5 mg gold coated with 5 micrograms Cas9 complexed with 2.5 micrograms crRNA-tracrRNA complex is sufficient for 9 shots.) The samples are dried in Petri dishes with Drierite desiccant (W. A. Hammond DRIERITE Co., LTD, Xenia, OH) for 1-2 hours. The rest of the bombardment procedure is similar to that described above for the DNA-coated gold microparticles. The shoot apical meristems of 48 soybean embryonic axes were sampled 5 days after bombardment and analyzed for the presence of edits of the target gene by any of various molecular assays, including, e. g., T7E1 assay, fragment analyzer assay, Sanger sequencing, and enrichment of edited amplicons by restriction digest and NGS amplicon sequencing.

One of skill in the art would recognize that there are alternative reagents and compositions (e. g., DNA encoding a nuclease or RNPs including a nuclease) including such reagents that are useful for introducing alterations or edits into the genome (e. g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the bombardment technique described herein include use of any of these reagents or compositions. Similarly, the bombardment technique described herein is generally applicable to any plant part, plant tissue, or whole plant, seed, seedling, or embryo (e. g., excised embryos, ovules, pollen, microspores, callus, leaf or other plant part, meristematic tissue), and of any plant species, including common wheat (*Triticum aestivum*), other *Triticum* and *Aegilops* species and hybrids, and related monocots. The preparation of wheat microspores, egg cells and zygotes, and shoot apical meristems is described in Example 8; all of these cell and tissues types are suitable for treatment with biolistics as described here, e. g., for the direct delivery of RNPs including a sequence-specific nuclease and one or more guide RNAs, or alternatively, for delivery of polynucleotides encoding a sequence-specific nuclease and one or more guide RNAs. In particular, shoot apical meristems from wheat cultivars are prepared and edited with RNPs (e.g., Cas9 or Cpf1 or another sequence-specific nuclease together with one or more guide RNAs) with biolistics using methods such as those described by Hamada et al. (2017) *Scientific Reports*, 7:11443; doi:10.1038/s41598-017-11936-0; the meristems are then grown into plants without the need for selection, regeneration, or callus culture.

Example 10

This example illustrates non-limiting compositions and reaction mixtures useful for delivering at least one effector molecule for inducing a genetic alteration in a plant cell or plant protoplast.

Examples of plasmids for delivery of Cas9 (Csn1) endonuclease from the *Streptococcus pyogenes* Type II CRISPR/Cas system (SEQ ID NO:1) and for delivery of a single guide RNA (sgRNA) are provided in Tables 1 and 3. In this non-limiting example, the sgRNA targets the endogenous phytoene desaturase (PDS) in soybean, Glycine mar; one of skill would understand that any other sgRNA sequences for alternative target genes could be substituted in the plasmid.

TABLE 1

SGRNA VECTOR (SEQ ID NO: 1), 3079 BASE PAIRS DNA

| Nucleotide position in SEQ ID NO: 1 | Description | Comment |
|---|---|---|
| 1-3079 | Intact plasmid | SEQ ID NO: 1 |
| 379-395 | M13 forward primer for sequencing | |
| 412-717 | *Glycine max* U6 promoter | |
| 717-736 | *Glycine max* phytoene desaturase targeting sequence (gRNA) | SEQ ID NO: 2 |
| 737-812 | guide RNA scaffold sequence for *S. pyogenes* CRISPR/Cas9 system | SEQ ID NO: 3 |
| 856-874 | M13 reverse primer for sequencing | complement |
| 882-898 | lac repressor encoded by lacI | |
| 906-936 | lac promoter for the *E. coli* lac operon | complement |
| 951-972 | *E. coli* catabolite activator protein (CAP) binding site | |
| 1260-1848 | high-copy-number ColE1/pMB1/pBR322/pUC origin of replication (left direction) | complement |
| 2019-2879 | CDS for bla, beta-lactamase, AmpR | complement; ampicillin selection |
| 2880-2984 | bla promoter | complement |

The sgRNA vector having the sequence of SEQ ID NO:1 contains nucleotides at positions 717-812 encoding a single guide RNA having the sequence of SEQ ID NO:4, which includes both a targeting sequence (gRNA) (SEQ ID NO:2) and a guide RNA scaffold (SEQ ID NO:3); transcription of the sgRNA is driven by a *Glycine max* U6 promoter at nucleotide positions 412-717. The sgRNA vector also includes lac operon and ampicillin resistance sequences for convenient selection of the plasmid in bacterial cultures.

TABLE 2

ENDONUCLEASE VECTOR (SEQ ID NO: 5), 8569 BASE PAIRS DNA

| Nucleotide position in SEQ ID NO: 5 | Description | Comment |
|---|---|---|
| 1-8569 | Intact plasmid | SEQ ID NO: 5 |
| 379-395 | M13 forward primer for sequencing | |
| 419-1908 | *Glycine max* UbiL promoter | |
| 1917-6020 | Cas9 (Csn1) endonuclease from the *Streptococcus pyogenes* type II CRISPR/Cas system | SEQ ID NO: 6 (encodes protein with sequence of SEQ ID NO: 7) |
| 6033-6053 | nuclear localization signal of SV40 large T antigen | SEQ ID NO: 8 (encodes peptide with sequence of SEQ ID NO: 9) |
| 6065-6317 | nopaline synthase (NOS) terminator and poly(A) signal | |
| 6348-6364 | M13 reverse primer for sequencing | complement |
| 6372-6388 | lac repressor encoded by lacI | |
| 6396-6426 | lac promoter for the *E. coli* lac operon | complement |
| 6441-6462 | *E. coli* catabolite activator protein (CAP) binding site | |
| 6750-7338 | high-copy-number ColE1/pMB1/pBR322/pUC origin of replication (left direction) | complement |
| 7509-8369 | CDS for bla, beta-lactamase, AmpR | complement; ampicillin selection |
| 8370-8474 | bla promoter | complement |

The endonuclease vector having the sequence of SEQ ID NO:5 contains nucleotides at positions 1917-6020 having the sequence of SEQ ID NO:6 and encoding the Cas9 nuclease from *Streptococcus pyogenes* that has the amino acid sequence of SEQ ID NO: 7, and nucleotides at positions 6033-6053 having the sequence of SEQ ID NO:8 and encoding the nuclear localization signal (NLS) of simian virus 40 (SV40) large T antigen that has the amino acid sequence of SEQ ID NO:9. Transcription of the Cas9 nuclease and adjacent SV40 nuclear localization signal is driven by a *Glycine max* UbiL promoter at nucleotide positions 419-1908; the resulting transcript including nucleotides at positions 1917-6053 having the sequence of SEQ ID NO:10 encodes a fusion protein having the sequence of SEQ ID NO:11 wherein the Cas9 nuclease is linked through a 4-residue peptide linker to the SV40 nuclear localization signal. The endonuclease vector also includes lac operon and ampicillin resistance sequences for convenient selection of the plasmid in bacterial cultures.

Similar vectors for expression of nucleases and sgRNAs are also described, e. g., in Fauser et al. (2014) *Plant J.*, 79:348-359; and described at www[dot]addgene[dot]org/crispr. It will be apparent to one skilled in the art that analogous plasmids are easily designed to encode other guide polynucleotide or nuclease sequences, optionally including different elements (e. g., different promoters, terminators, selectable or detectable markers, a cell-penetrating peptide, a nuclear localization signal, a chloroplast transit peptide, or a mitochondrial targeting peptide, etc.), and used in a similar manner. Embodiments of nuclease fusion proteins include fusions (with or without an optional peptide linking sequence) between the Cas9 nuclease from *Streptococcus pyogenes* that has the amino acid sequence of SEQ ID NO:7 and at least one of the following peptide sequences: (a) GRKKRRQRRRPPQ ("HIV-1 Tat (48-60)", SEQ ID NO:12), (b) GRKKRRQRRRPQ ("TAT", SEQ ID NO:13), (c) YGRKKRRQRRR ("TAT (47-57)", SEQ ID NO:14), (d) KLALKLALKALKAALKLA ("MAP (KLAL)", SEQ ID NO:15), (e) RQIRIWFQNRRMRWRR ("Penetratin-Arg", SEQ ID NO:16), (f) CSIPPEVKFNKPFVYLI ("antitrypsin (358-374)", SEQ ID NO:17), (g) RRRQRRKKRGGDIMGEWGNEIFGAIAGFLG ("TAT-HA2 Fusion Peptide", SEQ ID NO:18), (h) FVQWFSKFLGRIL-NH2 ("Temporin L, amide", SEQ ID NO:19), (i) LLIILRRRIRKQAHAHSK ("pVEC (Cadherin-5)", SEQ ID NO:20), (j) LGTYTQDFNKFHTFPQTAIGVGAP ("Calcitonin", SEQ ID NO:21), (k) GAAEAAARVYDLGLRRLRQRRRLR-RERVRA ("Neurturin", SEQ ID NO:22), (1) MGLGLHLL-VLAAALQGAWSQPKKKRKV ("Human P1", SEQ ID NO:23), (m) RQIKIWFQNRRMKWKKGG ("Penetratin", SEQ ID NO:24), poly-arginine peptides including (n) RRRRRRRR ("octo-arginine", SEQ ID NO:25) and (o) RRRRRRRRR ("nono-arginine", SEQ ID NO:26), and (p) KKLFKKILKYLKKLFKKILKYLKKKKKKKK ("(BP100x2)-K8", SEQ ID NO:27); these nuclease fusion proteins are specifically claimed herein, as are analogous fusion proteins including a nuclease selected from Cpf1, CasY, CasX, C2c1, or C2c3 and at least one of the peptides having a sequence selected from SEQ ID NOs:12-27. In other embodiments, such vectors are used to produce a guide RNA (such as one or more crRNAs or sgRNAs) or the nuclease protein; guide RNAs and nucleases can be combined to produce a specific ribonucleoprotein complex for delivery to the plant cell; in an example, a ribonucleoprotein including an sgRNA and the Cas9-NLS fusion protein having the sequence of SEQ ID NO: 11 is produced for delivery to a plant cell. The above sgRNA and nuclease vectors are delivered to plant cells or plant protoplasts using compositions and methods described in this disclosure.

A plasmid ("pCas9TPC-GmPDS") having the nucleotide sequence of SEQ ID NO:28 was designed for simultaneous delivery of Cas9 (Csn1) endonuclease from the *Streptococcus pyogenes* Type II CRISPR/Cas system and a single guide RNA (sgRNA) targeting the endogenous phytoene desaturase (PDS) in soybean, *Glycine max*. In this non-limiting example, the sgRNA targets the endogenous phytoene desaturase (PDS) in soybean, Glycine ma; one of skill would understand that any other sgRNA sequences for alternative target genes could be substituted in the plasmid. The sequences of this plasmid and specific elements contained therein are described in Table 3 below.

TABLE 3

PCAS9TPC-GMPDS VECTOR (SEQ ID NO: 163), 14548 BASE PAIRS DNA

| Nucleotide position in SEQ ID NO: 28 | Description | Comment |
|---|---|---|
| 1-14548 | Intact plasmid | SEQ ID NO: 28 |
| 1187-1816 | pVS1 StaA | stability protein from the Pseudomonas plasmid pVS1 |
| 2250-3317 | pVS1 RepA | replication protein from the Pseudomonas plasmid pVS1 |
| 3383-3577 | pVS1 oriV | origin of replication for the Pseudomonas plasmid pVS1 |
| 3921-4061 | basis of mobility region from pBR322 | |
| 4247-4835 | high-copy-number ColE1/pMB1/pBR322/pUC origin of replication (left direction) | complement |
| 5079-5870 | aminoglycoside adenylyltransferase (aadA), confers resistance to spectinomycin and streptomycin | complement |
| 6398-6422 | left border repeat from nopaline C58 T-DNA | |
| 6599-6620 | *E. coli* catabolite activator protein (CAP) binding site | |
| 6635-6665 | lac promoter for the *E. coli* lac operon | |
| 6673-6689 | lac repressor encoded by lacI | |
| 6697-6713 | M13 reverse primer for sequencing | |
| 6728-7699 | PcUbi4-2 promoter | |
| 7714-11817 | Cas9 (Csn1) endonuclease from the *Streptococcus pyogenes* type II CRISPR/Cas system | SEQ ID NO: 6 (encodes protein with sequence of SEQ ID NO: 7) |
| 11830-11850 | nuclear localization signal of SV40 large T antigen | SEQ ID NO: 8 (encodes peptide with sequence of SEQ ID NO: 9) |
| 11868-12336 | Pea3A terminator | |
| 12349-12736 | AtU6-26 promoter | |
| 12737-12756 | *Glycine max* phytoene desaturase targeting sequence (gRNA) | SEQ ID NO: 2 |
| 12757-12832 | guide RNA scaffold sequence for *S. pyogenes* CRISPR/Cas9 system | SEQ ID NO: 3 |
| 12844-12868 | attB2; recombination site for Gateway® BP reaction | complement |
| 13549-14100 | *Streptomyces hygroscopicus* bar or pat, encodes phosphinothricin acetyltransferase, confers resistance to bialophos or phosphinothricin | |
| 14199-14215 | M13 forward primer, for sequencing | complement |
| 14411-14435 | right border repeat from nopaline C58 T-DNA | |

The pCas9TPC-GmPDS vector having the sequence of SEQ ID NO:28 contains nucleotides at positions 12737-12832 encoding a single guide RNA having the sequence of SEQ ID NO:4, which includes both a targeting sequence (gRNA) (SEQ ID NO:2) and a guide RNA scaffold (SEQ ID NO:3); transcription of the single guide RNA is driven by a AtU6-26 promoter at nucleotide positions 12349-12736. This vector further contains nucleotides at positions 7714-11817 having the sequence of SEQ ID NO:6 and encoding the Cas9 nuclease from *Streptococcus pyogenes* that has the amino acid sequence of SEQ ID NO:7, and nucleotides at positions 11830-11850 having the sequence of SEQ ID NO:8 and encoding the nuclear localization signal (NLS) of simian virus 40 (SV40) large T antigen that has the amino acid sequence of SEQ ID NO:9. Transcription of the Cas9 nuclease and adjacent SV40 nuclear localization signal is driven by a PcUbi4-2 promoter at nucleotide positions 6728-7699; the resulting transcript including nucleotides at positions 7714-11850 having the sequence of SEQ ID NO:10 encodes a fusion protein having the sequence of SEQ ID NO:11 wherein the Cas9 nuclease is linked through a 4-residue peptide linker to the SV40 nuclear localization signal. The pCas9TPC-GmPDS vector also includes lac operon, aminoglycoside adenylyltransferase, and phosphinothricin acetyltransferase sequences for convenient selection of the plasmid in bacterial or plant cultures.

A plasmid ("pCas9TPC-NbPDS") having the nucleotide sequence of SEQ ID NO:29 was designed for simultaneous delivery of Cas9 (Csn1) endonuclease from the *Streptococcus pyogenes* Type II CRISPR/Cas system and a single guide RNA (sgRNA) targeting the endogenous phytoene desaturase (PDS) in *Nicotiana benthamiana*; see Nekrasov et al. (2013) *Nature Biotechnol.*, 31:691-693. In this non-limiting example, the sgRNA targets the endogenous phytoene desaturase (PDS) in *Nicotiana benthamiana*; one of skill would understand that other sgRNA sequences for alternative target genes could be substituted in the plasmid. The sequences of this plasmid and specific elements contained therein are described in Table 4 below.

TABLE 4

PCAS9TPC-NBPDS VECTOR (SEQ ID NO: 29), 14548 BASE PAIRS DNA

| Nucleotide position in SEQ ID NO: 29 | Description | Comment |
|---|---|---|
| 1-14548 | Intact plasmid | SEQ ID NO: 29 |
| 1187-1816 | pVS1 StaA | stability protein from the Pseudomonas plasmid pVS1 |
| 2250-3317 | pVS1 RepA | replication protein from the Pseudomonas plasmid pVS1 |
| 3383-3577 | pVS1 oriV | origin of replication for the Pseudomonas plasmid pVS1 |
| 3921-4061 | basis of mobility region from pBR322 | |
| 4247-4835 | high-copy-number ColE1/pMB1/pBR322/pUC origin of replication (left direction) | Complement |
| 5079-5870 | aminoglycoside adenylyltransferase (aadA), confers resistance to spectinomycin and streptomycin | Complement |
| 6398-6422 | left border repeat from nopaline C58 T-DNA | |
| 6599-6620 | *E. coli* catabolite activator protein (CAP) binding site | |
| 6635-6665 | lac promoter for the *E. coli* lac operon | |
| 6673-6689 | lac repressor encoded by lacI | |
| 6697-6713 | M13 reverse primer for sequencing | |
| 6728-7699 | PcUbi4-2 promoter | |
| 7714-11817 | Cas9 (Csn1) endonuclease from the *Streptococcus pyogenes* type II CRISPR/Cas system | SEQ ID NO: 6 (encodes protein with sequence of SEQ ID NO: 7) |
| 11830-11850 | nuclear localization signal of SV40 large T antigen | SEQ ID NO: 8 (encodes peptide with sequence of SEQ ID NO: 9 |
| 11868-12336 | Pea3A terminator | |
| 12349-12736 | AtU6-26 promoter | |
| 12737-12756 | *Nicotiana benthamiana* phytoene desaturase targeting sequence | SEQ ID NO: 30 |
| 12757-12832 | guide RNA scaffold sequence for *S. pyogenes* CRISPR/Cas9 system | SEQ ID NO: 3 |
| 12844-12868 | attB2; recombination site for Gateway ® BP reaction | Complement |
| 13549-14100 | *Streptomyces hygroscopicus* bar or pat, encodes phosphinothricin acetyltransferase, confers resistance to bialophos or phosphinothricin | |
| 14199-14215 | M13 forward primer, for sequencing | Complement |
| 14411-14435 | right border repeat from nopaline C58 T-DNA | |

The pCas9TPC-NbPDS vector having the sequence of SEQ ID NO:29 contains nucleotides at positions 12737-12832 encoding a single guide RNA having the sequence of SEQ ID NO:31, which includes both a targeting sequence (gRNA) (SEQ ID NO:30) and a guide RNA scaffold (SEQ ID NO:3); transcription of the single guide RNA is driven by a AtU6-26 promoter at nucleotide positions 12349-12736. This vector further contains nucleotides at positions 7714-11817 having the sequence of SEQ ID NO:6 and encoding the Cas9 nuclease from *Streptococcus pyogenes* that has the amino acid sequence of SEQ ID NO:7, and nucleotides at positions 11830-11850 having the sequence of SEQ ID NO:8 and encoding the nuclear localization signal (NLS) of simian virus 40 (SV40) large T antigen that has the amino acid sequence of SEQ ID NO:9. Transcription of the Cas9 nuclease and adjacent SV40 nuclear localization signal is driven by a PcUbi4-2 promoter at nucleotide positions 6728-7699; the resulting transcript including nucleotides at positions 7714-11850 having the sequence of SEQ ID NO:10 encodes a fusion protein having the sequence of SEQ ID NO:11 wherein the Cas9 nuclease is linked through a 4-residue peptide linker to the SV40 nuclear localization signal. The pCas9TPC-NbPDS vector also includes lac operon, aminoglycoside adenylyltransferase, and phosphinothricin acetyltransferase sequences for convenient selection of the plasmid in bacterial or plant cultures.

The above examples of plasmids are merely for illustration and are not meant to be limiting. One of ordinary skill in the art would know, for instance, that different promoters, nucleases, guide RNAs and single-guide RNAs can be encoded by and expressed from similar plasmids. For use in monocots such as wheat (*Triticum* spp. including *Triticum aestivum*), many monocot promoters are available, such as promoters identified from wheat and its relations, rice, maize, sorghum, barley, and other species.

Example 11

This example illustrates genome editing in monocot plants and further illustrates a method of identifying a nucleotide sequence associated with a phenotype of interest. More specifically, this non-limiting example describes delivering a guide RNA (gRNA) in the form of a ribonucleoprotein (RNP) to isolated plant protoplasts, followed by screening to identify the protoplasts in which the target nucleotide sequence has been altered by introduction of a double-stranded break (DSB).

The target gene selected for editing was the maize (*Zea mays*) alcohol dehydrogenase ADH1 (see www[dot]maizegdb[dot]org/gene_center/gene/GRMZM2G442658) with the partial genomic sequence:

```
                                        (SEQ ID NO: 32)
GAACAGTGCCGCAGTGGCGCTGATCTTGTATGCTATCCTGCAATCGTGGT

GAACTTATTTCTTTTATATCCTTTACTCCCATGAAAAGGCTAGTAATCTT

TCTCGATGTAACATCGTCCAGCACTGCTATTACCGTGTGGTCCATCCGAC

AGTCTGGCTGAACACATCATACGATCTATGGAGCAAAAATCTATCTTCCC

TGTTCTTTAATGAAGGACGTCATTTTCATTAGTATGATCTAGGAATGTTG

CAACTTGCAAGGAGGCGTTTCTTTCTTTGAATTTAACTAACTCGTTGAGT

GGCCCTGTTTCTCGGACGTAAGGCCTTTGCTGCTCCACACATGTCCATTC

GAATTTTACCGTGTTTAGCAAGGGCGAAAAGTTTGCATCTTGATGATTTA

GCTTGACTATGCGATTGCTTTCCTGGACCCGTGCAGCTGCGGTGGCATGG

GAGGCCGGCAAGCCACTGTCGATCGAGGAGGTGGAGGTAGCGCCTCCGCA

GGCCATGGAGGTGCGCGTCAAGATCCTCTTCACCTCGCTCTGCCACACCG

ACGTCTACTTCTGGGAGGCCAAGGTATCTAATCAGCCATCCCATTTGTGA
```

```
-continued
TCTTTGTCAGTAGATATGATACAACAACTCGCGGTTGACTTGCGCCTTCT

TGGCGGCTTATCTGTCTTAGGGGCAGACTCCCGTGTTCCCTCGGATCTTT

GGCCACGAGGCTGGAGGGTA;
``` the first exon (SEQ ID NO:33), located at nucleotide positions 409-571 of SEQ ID NO:32 is indicated by bold, underlined text and guide RNA (crRNA) sequences were designed to edit this exon.

Maize protoplasts were prepared as described in Example 1. A ribonucleoprotein (RNP) was prepared with Cas9 nuclease (Aldevron, Fargo, ND) and a guide RNA complex of a crRNA (ZmADH1-B) having the sequence GGCCUCCCAGAAGUAGACGUGUUUUAGAGCUAUGCU (SEQ ID NO:34) and a tracrRNA (both purchased from Integrated DNA Technologies, Coralville, IA). This was used for editing the target gene ADH1 in the maize protoplasts following the procedures described in Example 5. A T7 endonuclease (T7E1, New England Biolabs, Ipswich, MA) was used in a heteroduplex cleavage assay to detect on-target editing. In brief, genomic DNA from the protoplasts was amplified by PCR; the amplified products were denatured and re-annealed to allow heteroduplex formation between wild-type or unedited DNA and the edited DNA. T7E1, which recognizes and cleaves mismatched DNA, was used to digest the heteroduplexes, and the resulting cleaved and full-length PCR products are analyzed by gel electrophoresis. The primers used for the T7E1 assay had the sequences GAACAGTGCCGCAGTGGCG (forward primer, SEQ ID NO:35) and TACCCTCCAGCCTCGTGGC (reverse primer, SEQ ID NO:36) for an expected amplicon size of 720 base-pairs (i.e., SEQ ID NO:32). Gel electrophoretic analysis demonstrated the presence of the expected cleaved products.

For quantitation of editing efficiency, next-generation sequencing (NGS) analysis was used. A second set of primers were used for CRISPR sequencing; these had the sequences ACTATGCGATTGCITTCCTGGAC (forward primer, SEQ ID NO:37) and ACCGCGAGTTGTTGTATCATATCT (reverse primer, SEQ ID NO:38) for an expected amplicon size of 230 base-pairs which includes the ADH1 first exon (i.e.,

```
ACTATGCGATTGCTTTCCTGGACCCGTGCAGCTGCGGTGGCATGGGAGGC

CGGCAAGCCACTGTCGATCGAGGAGGTGGAGGTAGCGCCTCCGCAGGCCA

TGGAGGTGCGCGTCAAGATCCTCTTCACCTCGCTCTGCCACACCGACGTC

TACTTCTGGGAGGCCAAGGTATCTAATCAGCCATCCCATTTGTGATCTTT

GTCAGTAGATATGATACAACAACTCGCGGT, SEQ ID NO: 39);
``` the ADH1 first exon (SEQ ID NO:33) is indicated by bold, underlined text. NGS sequencing was used to measure editing efficiency, which was estimated to be 38%.

Another gene selected for editing was the maize (*Zea mays*) Babyboom gene BBM2 (see www[dot]maizegdb[dot]org/gene_center/gene/GRMZM2G141638) with the partial genomic sequence:

```
                                       (SEQ ID NO: 40)
AACCGGTGTAATACATACTAAGGGCTAGTTTGGGAACCCTGGTTTTCTAA

GGAATTTTATTTTTCCAAAAAAAATAGTTTATTTTTCCTTCGGAAATTAG
```

```
-continued
GAATCTCTTATAAAATTCGAGTTCCCAAACTATTCCTAATATATATATCA

TACTCTCCATCAGTCTATATATAGATTACATATAGTAAGTATAGAGTATC

TCGCTATCACATAGTGCCACTAATCTTCTGGAGTGTACCAGTTGTATAAA

TATCTATCAGTATCAGCACTACTGTTTGCTGAATACCCCAAAACTCTCTG

CTTGACTTCTCTTCCCTAACCTTTGCACTGTCCAAAATGGCTTCCTGATC

CCCTCACTTCCTCGAATCATTCTAAGAAGAAACTCAAGCCGCTACCATTA

GGGGCAGATTAATTGCTGCACTTTCAGATAATCTACCATGGCCACTGTGA

ACAACTGGCTCGCTTTCTCCCTCTCCCCGCAGGAGCTGCCGCCCTCCCAG

ACGACGGACTCCACGCTCATCTCGGCCGCCACCGCCGACCATGTCTCCGG

CGATGTCTGCTTCAACATCCCCCAAGGTAGCATCTATCTATCTGGCGACA

TACGTG;
``` promoter sequence (SEQ ID NO:41), located at nucleotide positions 1-254 of SEQ ID NO:40 is indica by bold, underlined text and guide RNA (crRNA) sequences were designed to edit this non-coding DNA.

Maize protoplasts were prepared as described in Example 1. A ribonucleoprotein (RNP) was prepared with Cas9 nuclease (Aldevron, Fargo, ND) and a guide RNA complex of a crRNA (ZmBBM2-2) having the sequence AAGAGAUUCCUAAUUUCCGAGUUUUAGAGCUAUGCU (SEQ ID NO:42) and a tracrRNA (both purchased from Integrated DNA Technologies, Coralville, IA). This was used for editing the target gene BBM2 in the maize protoplasts following the procedures described in Example 5.

For quantitation of editing efficiency, next-generation sequencing (NGS) analysis was used. The primers used for CRISPR sequencing had the sequences GGGAACCCTGGTTTTCTAAG (forward primer, SEQ ID NO:43) and GCAAACAGTAGTGCTGATACTG (reverse primer, SEQ ID NO:44) for an expected amplicon size of 248 base-pairs which includes the BBM2 promoter sequence (i.e.,

```
GGGAACCCTGGTTTTCTAAGGAATTTTATTTTTCCAAAAAAAATAGTTTA

TTTTTCCTTCGGAAATTAGGAATCTCTTATAAAATTCGAGTTCCCAAACT

ATTCCTAATATATATATCATACTCTCCATCAGTCTATATATAGATTACAT

ATAGTAAGTATAGAGTATCTCGCTATCACATAGTGCCACTAATCTTCTGG

AGTGTACCAGTTGTATAAATATCTATCAGTATCAGCACTACTGTTTGC,
SEQ ID NO: 45);
``` the BBM2 promoter sequence (SEQ ID NO:41) is indicated by bold, underlined text.

Similar genomic modifications are carried out in maize or wheat whole plants or in maize or wheat plant tissues using, e.g., delivery techniques as described in Examples 5-9. One of skill in the art would recognize that there are alternative methods for introducing a double-strand break at a precise locus in the genome (e.g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease).

Arrayed screens are conveniently carried out with protoplasts in multi-well (e.g., 24- or 96-well) plates. In embodiments where editing of a target nucleotide sequence is expected to provide an observable phenotype, the phenotype can be used to identify and optionally to select the plant cells or protoplasts having the edited sequence. Optionally, the plant cells or plant protoplasts are grown or cultured under conditions that permit expression of the phenotype, allowing identification and selection of the plant cells or plant protoplasts that exhibit the phenotype.

Pooled screens are carried out in a similar fashion, except that editing is carried out with multiple guide RNAs (e.g., in the form of multiple RNPs) provided to a complement of plant protoplasts. For example, maize (Zea mays, variety B73) protoplasts are treated with a mixture of RNPs for delivering different gRNAs targeting a selection of 2630 transcription factors in 5 families identified in maize (sequences publicly available at grassius[dot]org/tf_browsefamily.html?species=Maize). Similar experiments are carried out in common wheat (Triticum aestivum) protoplasts. Those guides that are over-represented at the readout stage are those that target genes that are identified as candidates for controlling cell division.

Example 12

This example illustrates a method of integrating a heterologous sequence encoded by at least one donor polynucleotide molecule (such as a double-stranded DNA, a single-stranded DNA, a single-stranded DNA/RNA hybrid, or a double-stranded DNA/RNA hybrid) at the site of at least one double-strand break (DSB) in a genome. More specifically, this non-limiting example illustrates using a ribonucleoprotein (RNP) including a guide RNA (gRNA) and a nuclease to effect a DSB in the genome of a monocot plant, and heterologous integration of a nucleic acid sequence that includes a regulatory element (an endonuclease recognition site sequence) and that is encoded by at least one donor polynucleotide molecule at the site of the DSB.

Experimental details were similar to those described in Example 11. As in Example 11, the target gene selected for editing was the maize (Zea mays) alcohol dehydrogenase ADH1 (see www[dot]maizegdb[dot]org/gene_center/gene/GRMZM2G442658) with the partial genomic sequence of SEQ ID NO:32; the first exon (SEQ ID NO:33) is located at nucleotide positions 409-571 of SEQ ID NO:32 and guide RNA (crRNA) sequences were designed to edit this exon.

Maize protoplasts were prepared as described in Examples 1 and 11. A ribonucleoprotein (RNP) was prepared with Cas9 nuclease (Aldevron, Fargo, ND) and a guide RNA complex of a crRNA (ZmADH1-B) having the sequence GGCCUCCCAGAAGUAGACGUGUUUUA-GAGCUAUGCU (SEQ ID NO:34) and a tracrRNA (both purchased from Integrated DNA Technologies, Coralville, IA). A chemically modified double-stranded DNA (dsDNA) donor polynucleotide molecule of 34 base pairs was produced by annealing one strand having the sequence 5'-GTT-TAATTGAGTTGTCATATGTTAATAACGGTAT-3' (SEQ ID NO:46, which contains an NdeI recognition site at nucleotide positions 16-21 shown as underlined font) and a second strand having the sequence 5'-ATACCGTTATTAA-CATATGACAACTCAATTAAAC-3' (SEQ ID NO:47) (both purchased from Integrated DNA Technologies, Coralville, IA); each strand was phosphorylated on the 5' end and contained two phosphorothioate linkages at each terminus (i.e., the two linkages between the most distal three bases on either end of the strand). Transfection procedures for editing the target gene ADH1 in the maize protoplasts were identical to those described in Examples 5 and 11, except the dsDNA was added at a concentration of 1 nanomolar together with the RNP. (In an alternative procedure, the RNP can be added first, followed by the dsDNA.)

A T7 endonuclease (T7E1, New England Biolabs, Ipswich, MA) was used in a heteroduplex cleavage assay to detect on-target editing. In brief, genomic DNA from the protoplasts was amplified by PCR; the amplified products were denatured and re-annealed to allow heteroduplex formation between wild-type or unedited DNA and the edited DNA. T7E1, which recognizes and cleaves mismatched DNA, was used to digest the heteroduplexes, and the resulting cleaved and full-length PCR products are analyzed by gel electrophoresis. The primers used for the T7E1 assay had the sequences GAACAGTGCCGCAGTGGCG (forward primer, SEQ ID NO:35) and TACCCTCCAGCCTCGTGGC (reverse primer, SEQ ID NO:36) for an expected amplicon size of 720 base-pairs (i.e., SEQ ID NO:32). In a separate endonuclease assay, NdeI restriction enzyme was used. In both the T7E1 and NdeI assays, gel electrophoretic analysis demonstrated the presence of the expected cleavage products.

For quantitation of editing efficiency, next-generation sequencing (NGS) analysis used a second set of primers with the sequences ACTATGCGATTGCTTTCCTGGAC (forward primer, SEQ ID NO:37) and ACCGCGAGTTGTTGTATCATATCT (reverse primer, SEQ ID NO:38) for an expected amplicon size of 230 base-pairs (SEQ ID NO:39) which includes the ADH1 first exon (SEQ ID NO:33). The results of NGS sequencing provided an estimated editing efficiency (percentage of the total population of cells in which DSB is correctly induced in the genome) of 23%; alignment of the cloned sequences (not shown) provided an estimated insertion efficiency (percentage of the total population of cells in which the heterologous regulatory element sequence encoded by the donor polynucleotide molecule is successfully introduced at the DSB correctly located in the genome) of 17%.

Additional experiments were carried out using the same procedure for editing the ADH1 maize gene, using variations of the 34-base-pair chemically modified dsDNA molecule (all purchased from Integrated DNA Technologies, Coralville, IA) provided at 1 nanomolar together with the RNP to maize protoplasts. In one set of experiments, the dsDNA molecule was provided by annealing one DNA strand having the sequence of SEQ ID NO:46 and a second DNA strand having the sequence (SEQ ID NO:47); each strand was phosphorylated on the 5' end but contained no phosphorothioate linkages. In a second set of experiments, the dsDNA molecule was provided by annealing one DNA strand having the sequence of SEQ ID NO:46 and a second DNA strand having the sequence (SEQ ID NO:47); each strand was phosphorylated on the 5' end and contained four phosphorothioate linkages at each terminus (i.e., the four linkages between the most distal five bases on either end of the strand). In a second set of experiments, the dsDNA molecule was provided by annealing one DNA strand having the sequence of SEQ ID NO:46 and that was phosphorylated on the 5' end and contained two phosphorothioate linkages at each terminus (i.e., the two linkages between the most distal three bases on either end of the strand), and a second DNA strand having the sequence (SEQ ID NO:47) and that contained two phosphorothioate linkages at each terminus (i.e., the two linkages between the most distal three bases on either end of the strand) but was not phosphorylated on the 5' end.

Similar genomic modifications are carried out in maize or wheat whole plants or in maize or wheat plant tissues using, e.g., delivery techniques as described in Examples 5-9. One of skill in the art would recognize that there are alternative methods for introducing a double-strand break at a precise locus in the genome (e.g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease). One of ordinary skill in the art would further recognize that such techniques are useful for heterologous integration of other regulatory sequences (e.g., transcription factor binding sites, small RNA recognition sites, transcript stabilizing or destabilizing sequences, etc.) at a double-strand break thus introduced at a precise locus in a genome.

Example 13

This example illustrates a method of changing expression of a sequence of interest in a genome, comprising integrating heterologous sequence encoded by a donor polynucleotide molecule (such as a double-stranded DNA, a single-stranded DNA, a single-stranded DNA/RNA hybrid, or a double-stranded DNA/RNA hybrid) at the site of at least one double-strand break (DSB) in a genome. More specifically, this non-limiting example illustrates using a ribonucleoprotein (RNP) including a guide RNA (gRNA) and a nuclease to effect a DSB in the genome of a monocot plant, and heterologous integration of a regulatory sequence encoded by a double-stranded DNA (dsDNA) at the site of the DSB, wherein the regulatory sequence encoded by the dsDNA molecule includes a sequence recognizable by a specific binding agent, and wherein contacting the heterologously integrated regulatory sequence with the specific binding agent results in a change of expression of a sequence of interest. In this particular example, sequence encoded by the dsDNA molecule is integrated at a DSB located in non-coding genomic sequence (i.e., in a promoter region of a gene of interest), the sequence recognizable by a specific binding agent includes an auxin response element (AuxRE) sequence, the specific binding agent is an auxin (e.g., an exogenously applied auxin), and the change of expression is upregulation of the gene of interest.

Experimental details were similar to those described in the preceding Examples. The target gene selected for editing was non-coding sequence, in this case the partial promoter sequence (sequence upstream of the transcription start site) of the maize (*Zea mays*) Lc gene (see www[dot]maizegdb[dot]org/gene_center/gene/GRMZM5G822829) with the sequence of (SEQ ID NO: 48)
GGGTTGTTGTGGGTTGAACCCGTCCCAACCATCATCAACTCGCTAGCCAA

ACACACGCTTAGGGGCCAAAGCAGTGCTATAATATGAGTGGTGGCGCTAT

TATATATAGCGTCAGAGAACTTAGATCTGATATTCTGATGAAGAAAAAAT

GACTTTACTGACTACGAAAGAAGAAGAAAGGAGCTATAGAGAGAGAGAAA

AAGAGGGGTCGTGTAGTGCTTAAACTGTACATGAACAGCAGTAGTGTTAC

AGAAGCTAAACTCAACCAGAGCTCCACCAAAGACAAAGAGGGTCTACTTC

CATCACCGTCTTGCTCGGTCACTTGGAGCTCTGTCCATAAATTAAACCCA

TCTTGGATCCCAAGGTTCGTGGCATATCTGTAGGCATCTACCCCGTCTTC

GTCGTCCGCTCCTCACTAGCTACCAAGAGGTCGCCATTATTGCCAACATA

GAGTGTACGTGGATGTCTATATATATGCCTACTTGCACCCATATGGC;

and guide RNA (crRNA) sequences were designed to edit this non-coding sequence.

Maize protoplasts were prepared as described in the preceding Examples. A ribonucleoprotein (RNP) was prepared with Cas9 nuclease (Aldevron, Fargo, ND) and a guide RNA complex of a crRNA (ZmLc Pro-1) having the sequence GCUCCUCACUAGCUACCAAGGUUUUA-GAGCUAUGCU (SEQ ID NO:49) and a tracrRNA (both purchased from Integrated DNA Technologies, Coralville, IA). Three different lengths of chemically modified double-stranded DNA (dsDNA) molecules were used in this experiment, with each dsDNA added at a concentration of 1 nanomolar together with the RNP. The transfection procedures for editing the target gene Lc in the maize protoplasts were otherwise identical to those described in the preceding Example.

All dsDNA molecules were purchased from Integrated DNA Technologies, Coralville, IA. One dsDNA ("3xDR5") molecule of 34 base pairs was produced by annealing a first strand having the sequence 5'-ccgacaaaaggccgacaaaaggccgacaaaaggt-3' (SEQ ID NO:49) and a second strand having the sequence 5'-accttttgtcggccttttgtcggccttttgtcgg-3' (SEQ ID NO:50, which includes three concatenated copies of an auxin response element having the sequence cctttttgtcgg (SEQ ID NO:51)). A second dsDNA ("6xDR5") molecule of 68 base pairs was produced by annealing a first strand having the sequence 5'-

(SEQ ID NO: 52)
5'-GCCGACAAAAGGCCGACAAAAGGCCGACAAAAGGCCGACAAAAGGCC

GACAAAAGGCCGACAAAAGGT-3' and a second strand having the sequence 5'-

5'-ACCTTTTGTCGGCCTTTTGTCGGCCTTTTGTCGGCCTTTTGTCGGCC

TTTTGTCGGCCTTTTGTCGGC-3', which includes six concatenated copies of the auxin response element having the sequence SEQ ID NO:51). A third dsDNA ("9xDR5") molecule of 100 base pairs was produced by annealing a first strand having the sequence 5'-

(SEQ ID NO: 54)
5'-CCGACAAAAGGCCGACAAAAGGCCGACAAAAGGCCGACAAAAGGCCG

ACAAAAGGCCGACAAAAGGCCGACAAAAGGCCGACAAAAGGCCGACAAAA

GGT-3' and a second strand having the sequence

5'-ACCTTTTGTCGGCCTTTTGTCGGCCTTTTGTCGGCCTTTTGTCGGCC

TTTTGTCGGCCTTTTGTCGGCCTTTTGTCGGCCTTTTGTCGGCCTTTTGT

CGG-3' which includes nine concatenated copies of the auxin response element having the sequence SEQ ID NO:51). In all cases, each strand was phosphorylated on the 5' end and contained two phosphorothioate linkages at each terminus (i.e., the two linkages between the most distal three bases on either end of the strand).

For quantitation of editing efficiency, next-generation sequencing (NGS) analysis was used. A second set of primers were used for CRISPR sequencing; these had the sequences CTCCACCAAAGACAAAGAGGG (forward primer, SEQ ID NO:56) and GCCATATGGGTGCAAGTAGGC (reverse primer, SEQ ID NO:57) for an expected amplicon size of 226 base-pairs (SEQ ID NO:58). Based on the NGS sequencing results, the editing efficiency (percentage of the total population of cells in which DSB is correctly induced in the genome) for the 3xDR5 insertion was estimated to be 34% and the insertion efficiency (percentage of the total population of cells in which the dsDNA molecule is successfully introduced at the DSB correctly located in the genome) was estimated to be 21%; for the 6xDR5 insertion, the editing efficiency was estimated to be 25% and the insertion efficiency was estimated to be 3%; and for the 9xDR5 insertion, the editing efficiency was estimated to be 11% and the insertion efficiency was estimated to be less than 1%.

All of the dsDNA molecules were designed to contain at least one sequence recognizable by a specific binding agent, in this case multiple copies of an auxin response element (SEQ ID NO:51). As the dsDNA molecules were integrated at the site of a DSB in promoter sequence operably linked to the gene of interest (the endogenous maize Lc gene), and the culture medium contained an herbicide (2, 4-dichlorophenoxyacetic acid) with auxin-like properties, expression of the gene of interest (the Lc gene) was expected to increase in cells that had the dsDNA molecule integrated into their genome, relative to that in cells that did not have the dsDNA molecule integrated into their genome. Quantitative RT-PCR was employed on three technical replicates per treatment to measure the relative expression of the Lc gene. Controls were cells that had been subjected to the transfection procedure without an RNP. Results are provided in Table 5 with Lc gene expression levels normalized to tubulin. These data demonstrate that, in each case, integration of the dsDNA molecules containing the auxin response factor sequences into the Lc promoter region resulted in very strong upregulation of Lc expression in the presence of auxin.

TABLE 5

| Treatment | Lc relative expression | standard deviation | Increase in relative expression |
| --- | --- | --- | --- |
| dsDNA = 3xDR5 | 3863.48 | 174.46 | 304-fold |
| dsDNA = 6xDR5 | 1479.15 | 74.99 | 116-fold |
| dsDNA = 9xDR5 | 1030.89 | 28.01 | 81-fold |
| RNP alone (no dsDNA) | 12.72 | 2.63 | 1 |
| no RNP | 1.02 | 0.25 | n.a. |

Similar genomic modifications are carried out in maize or wheat whole plants or in maize or wheat plant tissues using, e.g., delivery techniques as described in Examples 5-9. One of skill in the art would recognize that there are alternative methods for introducing a double-strand break at a precise locus in the genome (e.g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease). One of ordinary skill in the art would further recognize that such techniques are useful for heterologous integration of other regulatory sequences (e.g., transcription factor binding sites, small RNA recognition sites, transcript stabilizing or destabilizing sequences, etc.) at a double-strand break thus introduced at a precise locus in a genome.

Additional experiments carried out in monocots (data not shown) demonstrated that one or more sequence-specific nucleases (e.g., Cas9, Cpf1) were successfully used to introduce at least two DSBs into a genome in such a way that genomic sequence was deleted between the DSBs (leaving a deletion with blunt ends, overhangs, or a combination of a blunt end and an overhang), followed by heterologous integration of a nucleotide sequence (e.g., a sequence encoding a regulatory element, or a sequence encoding replacement nucleotides) encoded by at least one donor polynucleotide molecule between the DSBs (i.e., sequence encoded by at least one individual polynucleotide molecule is integrated at the location of the deleted genomic sequence). In embodiments, this technique is useful, e.g., for replacing regions of genomic sequence such as one or more exons ("exon exchange") or one or more protein domains. In an example, DSBs are introduced into intronic sequence on each side of an exon, resulting in deletion of the exon, and—when heterologous sequence encoded by at least one dsDNA molecule is integrated at the location of the deleted exon—incorporation of a "replacement" exon. In another example, the nuclease Cpf1 is used to effect a DSB containing overhangs at two loci in a genome, for example, in each of the two introns flanking an exon. In cases where one or both of the DSBs is asymmetric (e. g., has at least a one-nucleotide overhang), the sequence encoded by the donor polynucleotide can be integrated at the asymmetric DSB in a specific orientation. For example, this approach is useful for integrating a specifically oriented recombinase recognition site sequence (see, e.g., Table 8) at each of two DSBs effected in a genome, allowing use of a sequence-specific recombinase to mediate deletion, exchange, inversion, or translocation of genomic sequence flanked by the recombinase recognition sites thus integrated. In an embodiment, a first recombinase recognition site sequence is integrated into one DSB and a second recombinase recognition site sequence is integrated into the other DSB; the two recombinase recognition site sequences are heterospecific relative to each other, i. e., each will not recombine together but each will recombine only with another recombination site of its own type. Subsequent to the genomic integration of the heterospecific recombinase recognition site sequences, a donor polynucleotide molecule is provided for recombinase-mediated genomic sequence replacement, for example, replacement of an exon. This donor polynucleotide molecule includes a replacement genomic sequence (for example, a replacement exon sequence) and further includes on each terminus a recombinase recognition site sequence that is homospecific to (i. e., will recombine with) one of the genomically integrated recombinase recognition site sequences. The appropriate recombinase is also provided, resulting in the exchange of the endogenous exon sequence for the replacement exon sequence. Such exon-replacement techniques avoid editing inaccuracies such as unintentional nucleotide changes, deletions, or additions at the nuclease cleavage sites in the resulting exon sequence or the messenger RNA encoded by the exon. In embodiments, these techniques are used to replace a "wild-type" exon (an exon having unmodified, native sequence) of a gene of interest with a modified exon sequence.

One of skill in the art would recognize that there are alternative methods for introducing DSBs into the genome (e.g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the approach described herein include use of any of these methods for introducing a single DSB (or, alternatively, two or more DSBs into a genome in such a way that genomic sequence is deleted between the DSBs); following the introduction of the DSB(s), nucleotide sequence encoded by at least one donor polynucleotide (such as a double-stranded DNA, a single-stranded DNA, a single-stranded DNA/RNA hybrid, or a double-stranded DNA/RNA hybrid) molecule can be heterologously integrated at the location of the DSB (or, alternatively, of genomic sequence that is deleted between two or more DSBs).

Example 14

This example illustrates a method of providing a plant cell having a genome and a modified phenotype, the method including effecting a double-strand break (DSB) at a predetermined genomic locus. More specifically, this non-limiting example illustrates effecting a double-strand break (DSB) at one or at multiple predetermined loci within a first gene (FEA3), thereby reducing that gene's expression; this further results in increasing expression of a second gene (WUS), which is normally repressed by the first gene.

The transcription factor WUSCHL (WUS) is expressed in the organizing center cells below the stem cells in a plant's shoot meristem; WUS expression prevents differentiation of stem cells. WUS activates expression of CLAVATA (CLV) and the CLV signalling pathway, which then controls stem cell proliferation and differentiation. The balance between WUS and CLV is maintained by feedback signalling between the organizing center cells and stem cells. The CLV3 peptide is secreted from stem cells at the tip of the shoot apical meristem, and is bound by CLV1, is a leucine-rich-repeat (LRR) receptor kinase; this results in negative regulation of shoot and floral meristem. Another LRR receptor reported to respond to the CLV3 peptide is FASCIATED EAR3 (FEA3); weak alleles of fea3 have been reported to enhance yield in hybrid maize; see: Je et al. (2016) *Nature Genetics*, 48:785-791; DOI: 10.1038/ng.3567. Reducing expression of FEA3 is predicted to increase expression of WUS.

These experiments were carried out to observe the effects of down-regulating or knocking-out expression of FEA3 in maize cells. Two different crRNAs and a tracrRNA were purchased from Integrated DNA Technologies, Coralville, IA. The first crRNA (ZmFea3-1) had the sequence GCGCUCCUUCUCCUCCAUGGGUUUUAGAGCUAUGCU (SEQ ID NO:59), and the second crRNA (ZmFea3-2) had the sequence CCUCGGCGUGGCGCUCUCGGGUUUUAGAGCUAUGCU (SEQ ID NO:60). Guide RNA complexes were made by mixing 60 microliters of 100 micromolar tracrRNA and 60 microliters of 100 micromolar crRNA, heating the mixture to 95 degrees Celsius for 5 minutes, removing from the heating block, and allowing the tubes to cool to room temperature on the benchtop.

Maize B73 protoplasts were harvested from leaves of B73 maize plants. One milliliter of protoplasts ($2 \times 10^5$ cells per milliliter) was added to each of four reaction tubes. Ribonucleoproteins (RNPs) were prepared by mixing 24 microliters (240 micrograms) Cas9 nuclease (Aldevron, Fargo, ND) and 120 microliters of one of the two guide RNA complexes (AMT3Pro-1 crRNA/tracrRNA or AMT3Pro-2 crRNA/tracrRNA), incubating the mixtures for 5 minutes at room temperature. Editing experiments were carried out in the four reaction tubes with either 72 microliters of one of the two RNP solutions or 72 microliters of both RNP solutions, with sufficient buffer added if necessary to make up a total volume of 144 microliters; 2 microliters (20 micrograms) of salmon sperm DNA (VWR Cat. No.: 95037-160) was added to each tube except for the null control. Maize protoplasts treated with no nuclease, no guide RNA complex, no salmon sperm DNA, and no donor polynucleotide molecule served as a null control. To each tube was added 1.2 milliliters of 40% PEG; the reaction mixtures were mixed gently by tapping and incubated 5 minutes at room temperature. The reactions were stopped by adding 5 milliliters of washing buffer (0.6 molar mannitol, 4 millimolar MES pH 5.7, and 20 millimolar KCl) to each tube and mixed gently by inverting the tube. The tubes were centrifuged 2 minutes at 1200 rpm and the supernatant was then removed. The protoplasts were resuspended in 4 milliliters incubation solution (see Example 5) including the herbicide 2, 4-dichlorophenoxyacetic acid ("2,4-D") plus 50 millimolar $CaCl_2$ added. One milliliter of cells from each tube was transferred to a well in a 6-well plate; the remaining 3 milliliters of cells from each tube were plated in four $10 \times 10$ cm dishes (all pre-coated with 5% calf serum), with another 3 milliliters of incubation buffer added per dish (for an optimal cell density for incubation). The plate and dishes were sealed with Parafilm M® film (Bemis, Oshkosh, WI), incubated 1 hour at 37 degrees Celsius, and then incubated an additional 47 hours at 26 degrees Celsius in the dark. Forty-eight hours after transfection, cells were harvested for analysis.

Quantitative RT-PCR was employed on three technical replicates per treatment to measure the relative expression of the FEA3 and WUS1 genes. Results (mean of triplicates, standard deviation) are provided in Table 6, with relative gene expression levels normalized to tubulin. The data show that use of a single RNP (i.e., providing a DSB at a single precise locus in the FEA3 gene), either Fea3-1 or Fea3-2, was sufficient to knock down FEA3 expression by about two-thirds; this further resulted in about a 2-fold increase in WUS expression. Use of both RNPs (i.e., providing a DSB at two precise loci in the FEA3 gene) knocked down FEA3 expression by about four-fifths, and further resulted in strong (about 15-fold) upregulation of WUS expression.

TABLE 6

|  | FEA3 | | WUS | |
| --- | --- | --- | --- | --- |
| Treatment | Relative expression | SD | Relative expression | SD |
| Null control | 1.00 | 0.04 | 1.00 | 0.09 |
| Fea3-1 | 0.27 | 0.03 | 2.81 | 0.24 |
| Fea3-2 | 0.31 | 0.02 | 2.10 | 0.20 |
| Fea3 1 + 2 | 0.19 | 0.01 | 15.15 | 2.01 |

Similar genomic modifications are carried out in maize or wheat whole plants or in maize or wheat plant tissues using, e.g., delivery techniques as described in Examples 5-9. One of skill in the art would recognize that there are alternative methods for introducing a double-strand break at a precise locus in the genome (e.g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease).

Example 15

This example illustrates a method of providing a plant cell having a modified genome and a modified phenotype, the method including introducing double-strand breaks (DSBs) into multiple loci or into multiple genes, and integrating at the DSBs at least two different heterologous nucleotide sequences encoded by a donor polynucleotide (such as a double-stranded DNA, a single-stranded DNA, a single-stranded DNA/RNA hybrid, or a double-stranded DNA/RNA hybrid) molecule. In this non-limiting example, multiple genomic modifications ("multiplexed edits") were effected in a monocot (maize) cell by using DNA-free direct delivery of multiple ribonucleoproteins (RNPs), each including a nuclease and a guide RNA (gRNA), to introduce a DSB at a predetermined locus in the promoter region of each of two different maize genes involved in nitrogen uptake and utilization; a nitrate-responsive element sequence is then integrated at the locus of the DSB in the first gene (AMT3), and a palindromic 12-nucleotide endogenous maize sequence having homology to the bacterial OCS enhancer is integrated at the locus of the DSB in the second gene (Lc). In this example, a first round of editing to effect a first DSB and heterologous integration of a regulatory sequence encoded by a first donor polynucleotide molecule was carried out, followed by a second round of editing to effect a second DSB and heterologous integration of a regulatory sequence encoded by a second donor polynucleotide molecule; no selection or screening was performed between the editing rounds, and no intervening step involving culture as callus or regenerated plants was performed between the editing rounds. The time between editing rounds was 3 hours or 18 hours.

Two crRNAs, a tracrRNA, and the donor polynucleotide molecules were purchased from Integrated DNA Technologies, Coralville, IA. The first crRNA (AMT3-Prol) had the sequence of SEQ ID NO:61 and the second crRNA (ZmLc-Pro3) had the sequence of SEQ ID NO:62. The first donor polynucleotide molecule was a nitrogen responsive element (AtNRE) encoded by a 43 base-pair chemically modified dsDNA having a first strand with the sequence of SEQ ID NO:63 annealed to a second strand with the sequence of SEQ ID NO:64, and the second donor polynucleotide molecule was a maize OCS homologue encoded by a chemically modified single-stranded DNA with the sequence of SEQ ID NO:65. For both donor polynucleotide molecules, whether dsDNA or ssDNA, each strand was phosphorylated on the 5' end and contained two phosphorothioate linkages at each terminus (i.e., the two linkages between the most distal three bases on either end of the strand). Individual guide RNA complexes were made by mixing 60 microliters of 100 micromolar tracrRNA and 60 microliters of the 100 micromolar crRNA (AMT3-Prol or ZmLc-Pro3), heating the mixture to 95 degrees Celsius for 5 minutes, removing from the heating block, and allowing the tubes to cool to room temperature on the benchtop. To prepare the donor polynucleotide molecules, 150 microliters (100 micromolar) of the first AtNRE strand (SEQ ID NO:63) and 150 microliters (100 micromolar) of the second AtNRE strand (SEQ ID NO:64) were mixed together in a tube; to another tube was added 150 microliters (100 micromolar) of the palindromic OCS homologue ssDNA (SEQ ID NO:65). The tubes were heated to 95 degrees Celsius for 5 minutes, then the heat was turned off and the solution allowed to slowly cool to room temperature in the block.

Maize B73 protoplasts were harvested from leaves of B73 maize plants that had been grown in nitrate-free medium for 13 days. The protoplasts underwent a first editing reaction to integrate a nitrogen-responsive element sequence in the promoter region of the AMT3 gene, and then underwent a second editing reaction to integrate an auxin-responsive element in the promoter region of the Lc gene. Maize protoplasts treated with no nuclease, no guide RNA complex, no salmon sperm DNA, and no donor polynucleotide molecule served as a null control. One milliliter of protoplasts ($2 \times 10^5$ cells per milliliter) was added to each of six reaction tubes. Then, to each of four tubes were added 5 microliters (50 micrograms) Cas9 nuclease (Aldevron, Fargo, ND) and 30 microliters of the AMT3-Prol guide RNA complex (AMT3-Prol crRNA/tracrRNA), and to the remaining two tubes (null controls) were added 90 microliters buffer. All tubes were incubated 5 minutes at room temperature. To each of the first four tubes (treated with the Cas9/AMT3-Prol guide RNA) were added 50 microliters of the AtNRE donor polynucleotide solution and 2 microliters (20 micrograms) salmon sperm DNA (VWR Cat. No.: 95037-160). To each tube was added 1.1 milliliters of 40% PEG; the reaction mixtures were mixed gently by tapping and incubated 5 minutes at room temperature. The reactions were stopped by adding 5 milliliters of washing buffer (0.6 molar mannitol, 4 millimolar MES pH 5.7, and 20 millimolar KCl) to each tube and mixed gently by inverting the tube. The tubes were centrifuged 2 minutes at 1200 rpm and the supernatant was then removed. The protoplasts were resuspended in 5 milliliters incubation solution (see Example 5, but without any nitrate and with 50 millimolar $CaCl_2$ added) and transferred to 10×10 cm dishes pre-coated with 5% calf serum; the dishes were sealed with Parafilm M® film (Bemis, Oshkosh, WI), incubated 30 minutes at 37 degrees Celsius, and then incubated at 26 degrees Celsius in the dark.

After 3 hours incubation at 26 degrees Celsius, two of the plates containing protoplasts treated with the Cas9/AMT3-Prol guide RNA and AtNRE donor polynucleotide molecule were subjected to the second editing reaction as follows. Ten microliters (100 micrograms) Cas9 and 60 microliters of the ZmLc-Pro3 guide RNA were mixed gently in a tube and incubated 5 minutes at room temperature; 50 microliters of the palindromic OCS homologue ssDNA (SEQ ID NO:65) solution and 2 microliters (20 micrograms) salmon sperm DNA (VWR Cat. No.: 95037-160) were then added and mixed gently in the tube. Two of the plates containing protoplasts treated with the Cas9/AMT3-Prol guide RNA and AtNRE donor polynucleotide molecule were harvested by centrifugation 2 minutes at 1200 rpm and the supernatant removed. The protoplasts from an individual plate were resuspended in two tubes each containing 1 milliliter washing buffer. Each tube received half of the prepared RNP (Cas9/ZmLc-Pro3)/OCS ssDNA/salmon sperm DNA mixture, and tapped gently to mix. To each tube was added 1.1 milliliters of 40% PEG; the reaction mixtures were mixed gently by tapping and incubated 5 minutes at room temperature. The reactions were stopped by adding 5 milliliters of washing buffer to each tube and mixed gently by inverting the tube. The tubes were centrifuged 2 minutes at 1200 rpm and the supernatant was then removed. The protoplasts were resuspended in 5 milliliters incubation solution (see Example 5, but without any nitrate and with 50 millimolar $CaCl_2$ added) and transferred to 10×10 cm dishes pre-coated with 5% calf serum; the dishes were sealed with Parafilm M® film (Bemis, Oshkosh, WI), incubated 30 minutes at 37 degrees Celsius, and then incubated at 26 degrees Celsius in the dark.

After 18 hours incubation at 26 degrees Celsius, the remaining two of the plates containing protoplasts treated with the Cas9/AMT3-Prol guide RNA and AtNRE donor polynucleotide molecule were subjected in a similar manner to the second editing reaction. All treatment steps were identical to those carried out at the 3-hour timepoint as described in the immediately preceding paragraph.

Twenty-four additional hours after the 18-hour transfection (editing reaction), half of the plates were treated with 0.5 millimolar $KNO_3$ and half with 0.5 millimolar KCl; cells were incubated 1 hour, and then harvested for analysis.

Quantitative RT-PCR was employed on three technical replicates per treatment to measure the relative expression of the AMT3 and Lc genes. Results (mean of triplicates, standard deviation) are provided in Table 7 and illustrated in FIG. 1, with relative gene expression levels normalized to tubulin. The data show that the endogenous (non-edited) AMT3 and Lc genes both show a moderate (about 4- to 5-fold, relative to KCl controls), nitrate-induced increase in expression. In the cells that underwent a second (ZmLc-Pro3/OCS homologue) transfection or editing reaction 3 hours after the first (AMT3-Pro1/AtNRE) transfection, there is a nitrate-induced increase in Lc expression that may be due to excess AtNRE donor polynucleotide, resulting in the AtNRE sequence being incorporated into the DSB effected by the later-provided Lc-Pro3 guide. In the cells that underwent a second (ZmLc-Pro3/OCS homologue) transfection or editing reaction 18 hours after the first (AMT3-Pro1/AtNRE) transfection, nitrate-induced increase is not observed in Lc expression, indicating that excess AtNRE polynucleotide has degraded and that it is the sequence encoded by the OCS homologue that is incorporated into the DSB effected by the Lc-Pro3 guide. There is increased relative expression of AMT3 even in the absence of nitrate induction, which suggests the possibility of some Cas9 remaining bound to the AMT3-Pro1 site at the time of the second (ZmLc-Pro3/OCS homologue) editing reaction, which might have resulted in unintentional incorporation of some OCS homologue sequence into the AMT3-Pro1 site; this effect is more evident at 3 hours than at 18 hours, indicating that there is less Cas9 remaining bound to the AMT3-Pro1 at 18 hours than at 3 hours. NGS sequencing is performed to verify and quantify correct integration of the donor polynucleotide molecules at the intended loci in the genome.

TABLE 7

| Genome editing treatment | Nutrient treatment | AMT3 Relative Expression | SD | Lc Relative Expression | SD |
| --- | --- | --- | --- | --- | --- |
| Null | KCl | 1.02 | 0.25 | 1.00 | 0.10 |
|  | $KNO_3$ | 3.76 | 0.17 | 5.10 | 1.06 |
| AMT3-Pro1 + AtRNE; at | KCl | 5.74 | 0.30 | 17.66 | 1.00 |
| 3 hours Lc-Pro3 + OCS | $KNO_3$ | 14.45 | 1.18 | 23.67 | 0.98 |
| AMT3-Pro1 + AtRNE; at | KCl | 3.37 | 0.06 | 20.34 | 1.51 |
| 18 hours Lc-Pro3 + OCS | $KNO_3$ | 15.22 | 1.97 | 20.04 | 0.51 |

Similar genomic modifications are carried out in maize or wheat whole plants or in maize or wheat plant tissues using, e.g., delivery techniques as described in Examples 5-9. One of ordinary skill in the art would further recognize that such techniques are useful for heterologous integration of other regulatory sequences (e.g., transcription factor binding sites, small RNA recognition sites, transcript stabilizing or destabilizing sequences, etc.) at a double-strand break thus introduced at a precise locus in a genome. One of skill in the art would further recognize that effecting multiple DSBs in a genome (e.g., effecting multiple DSBs in a sequence of interest or effecting at least one DSB in each of two or more sequences of interest) can be achieved by successive rounds of editing reactions in the same plant cell (or whole plant, plant part or tissue, embryo, or seed) in a manner such as that illustrated by this example. Any of these DSBs can be effected through alternative methods (e.g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the approach described herein include use of any of these methods and effector molecules for simultaneously effecting multiple DSBs in a genome, and, optionally, integrating at least one polynucleotide molecule at one or more DSBs.

Example 16

This example illustrates a method of providing a wheat plant cell having a modified genome and a modified phenotype, in comparison to an unmodified wheat plant having an reference genome, wherein the modified genome differs from the reference genome by (a) heterologous integration of a nucleic acid sequence that is encoded by at least one donor polynucleotide molecule and that includes a regulatory element, at a predetermined locus of a gene of interest or (b) deletion, addition, or substitution of at least one nucleotide in a regulatory element that regulates expression of a gene of interest in the reference genome. In this example, the regulatory element is a miRNA target or recognition site.

U.S. Pat. No. 9,040,774, which is incorporated herein in its entirety, discloses in Table 3 of that patent document multiple examples of nucleotide sequences identified from common wheat (*Triticum aestivum*) that include a microRNA target or recognition site (i.e., the conserved sequence that is recognized and cleaved by mature miRNAs of a given miRNA family). These include miR156 targets (SEQ ID NOs:1243-1247 of U.S. Pat. No. 9,040,774), miR164 targets (SEQ ID NOs:1298-1304 of U.S. Pat. No. 9,040,774), miR166 targets (SEQ ID NOs:1344-1346 of U.S. Pat. No. 9,040,774), miR169 targets (SEQ ID NOs: 1448-1457 of U.S. Pat. No. 9,040,774), miR172 targets (SEQ ID NOs:1550-1560 of U.S. Pat. No. 9,040,774), miR396 targets (SEQ ID NOs:1635-1648 of U.S. Pat. No. 9,040,774), miR393 targets (SEQ ID NOs:1703-1706 of U.S. Pat. No. 9,040,774), miR395 targets (SEQ ID NOs: 1739-1744 of U.S. Pat. No. 9,040,774), miR398 targets (SEQ ID NOs:1763-1780 of U.S. Pat. No. 9,040,774), a miR399 targets (SEQ ID NO:1817 of U.S. Pat. No. 9,040,774), miR408 targets (SEQ ID NOs:1872-1890 of U.S. Pat. No. 9,040,774), miR444 targets (SEQ ID NOs:1951-1953 of U.S. Pat. No. 9,040,774), and miR528 targets (SEQ ID NOs:1984-1990 of U.S. Pat. No. 9,040,774), These wheat miRNA target (recognition site) sequences and their annotation are specifically incorporated by reference herein. Other publicly available disclosures of wheat and related monocot miRNAs and their recognition site sequences, as well as genes that contain such recognition site sequences, include the reference database "miRbase" (available at www[dot]miRbase[dot]org); Yao et al. (2007) *Genome Biol.*, 8:R96; Han et al. (2014) *BMC Genomics*, 15:289; and Dryanova et al. (2008) *Genome.* 51:433-443. Additional disclosures of miRNAs and their recognition site sequences, as well are genes that contain such recognition site sequences are found in US Patent Application Publications No. 2005/0144669 and No. 2009/0172838, which are incorporated herein by reference.

The techniques and protocols described in the preceding examples (e.g., Examples 12 and 14) are used to heterologously integrate at least one copy of a miRNA recognition site at a predetermined locus of a gene of interest in a wheat plant, typically in the 3' untranslated region of the gene of interest (e.g., within about 30 to about 100 nucleotides, or within about 10 to about 200 nucleotides, or within about 10 to about 300 nucleotides, of the stop codon of a gene's coding sequence). This places expression of the gene of interest under control of the mature miRNA that corresponds to the miRNA recognition site thus heterologously integrated in the wheat plant's genome. For example, heterologous integration of one or more copies of a mir172 recognition site sequence in a gene's 3' untranslated region results in that gene's transcript being cleaved by a mature miR172 when that mature microRNA is present in the same cell. In embodiments, heterologously integrating at least one copy of a miRNA recognition site at a predetermined locus of a gene of interest in a wheat plant, wherein the corresponding miRNA is characterized as having a spatially, temporally, or inducibly specific expression pattern (e.g., cell- or tissue-specific expression, or expression at a specific time in the plant's growth cycle, or expression that is inducible by a specific signal), places expression of the gene of interest under control of the mature miRNA that corresponds to the miRNA recognition site in a manner that is correspondingly spatially, temporally, or inducibly specific. For example, heterologous integration of one or more copies of a miRNA recognition site sequence in a gene's 3' untranslated region, wherein the gene is generally constitutively expressed, and wherein the corresponding mature miRNA is specifically expressed only in root tissue, results in that gene's transcript being cleaved (and the gene's expression effectively decreased) by the mature miRNA specifically in root tissue. In another example, heterologous integration of one or more copies of a miRNA recognition site sequence in a gene's 3' untranslated region, wherein the gene is generally expressed in leaf tissue, and wherein the corresponding mature miRNA is also expressed in leaf tissue but specifically only during exposure to light, results in that gene's transcript being cleaved (and the gene's expression effectively decreased) by the mature miRNA in leaf tissue during daylight hours (or during exposure to light).

In an alternative approach, an existing miRNA recognition site in a gene of interest is deleted or mutated so as to be non-functional, using techniques and protocols described in the preceding examples (e.g., by introducing a double-strand break in the gene of interest as illustrated in Examples 11 and 13). This decouples expression of that gene from control by the endogenous mature microRNA.

Example 17

Various embodiments of the invention are related to the heterologous insertion of a non-coding, regulatory sequence at a predetermined locus of a gene of interest. This example illustrates non-limiting embodiments of such nucleotide sequences that, when integrated at a predetermined locus of a gene of interest, can modify the expression of that gene. Embodiments are related to a wheat plant having a modified genome in comparison to an unmodified wheat plant having an reference genome, wherein the modified genome differs from the reference genome by having one or more copies of a regulatory sequence integrated at a predetermined locus between 1-1000 nucleotides upstream of the start codon of the coding sequence of a gene of interest in the reference genome, by having one or more copies of a regulatory sequence integrated at a predetermined locus 1-1000 nucleotides upstream of the start codon of the coding sequence of a gene of interest in the reference genome, or by having one or more copies of a regulatory sequence integrated at a predetermined locus within 1000 nucleotides downstream of the stop codon. Other embodiments are related to a wheat plant having a modified genome in comparison to an unmodified wheat plant having an reference genome, wherein the modified genome differs from the reference genome by a deletion, addition, or substitution of at least one nucleotide in a regulatory element that regulates expression of a gene of interest in the reference genome. In many embodiments the modified genome results in the wheat plant exhibiting a phenotype or trait, in comparison to a wheat plant having the unmodified reference genome.

Table 8 provides non-limiting examples of non-coding, regulatory sequences that, when encoded by at least one donor polynucleotide molecule, can be integrated in a gene of interest (for example, in the 5' untranslated region or in the 3' untranslated region, or in other non-coding or coding regions of the gene). In some embodiments, the heterologously integrated non-coding, regulatory sequences enables further processing of the DNA (or RNA transcript) containing the integrated regulatory sequence; for example, integration of an endonuclease restriction site (e.g., SEQ ID NOs:166 and 167) permits the DNA to be cut by the corresponding endonuclease, and integration of a pair of homospecific recombinase recognition sites at two DSBs permits recombination at the loci of the two DSBS in the presence of the corresponding recombinase.

TABLE 8

| Type of regulation | Name of element | Sequence | SEQ ID NO: |
|---|---|---|---|
| regulatory control by TF | ABFs binding site motif | CACGTGGC | 66 |
| regulatory control by TF | ABRE binding site motif | (C/T)ACGTGGC | 67 |
| regulatory control by TF | ABRE-like binding site motif | (C/G/T)ACGTG(G/T)(A/C) | 68 |
| regulatory control by TF | ACE promoter motif | GACACGTAGA | 69 |
| regulatory control by TF | AG binding site motif | TT(A/G/T)CC(A/T)(A/T)(A/T)(A/T)(A/T)(A/T)GG(A/C/T) | 70 |

TABLE 8-continued

| Type of regulation | Name of element | Sequence | SEQ ID NO: |
|---|---|---|---|
| regulatory control by TF | AG binding site in AP3 | CCATTTTTAGT | 71 |
| regulatory control by TF | AG binding site in SUP | CCATTTTTGG | 72 |
| regulatory control by TF | AGL1 binding site motif | NTT(A/G/T)CC(A/T)(A/T)(A/T)(A/T)NNGG(A/T)AAN | 73 |
| regulatory control by TF | AGL2 binding site motif | NN(A/T)NCCA(A/T)(A/T)(A/T)(A/T)T(A/G)G(A/T)(A/T)AN | 74 |
| regulatory control by TF | AGL3 binding site motif | TT(A/T)C(C/T)A(A/T)(A/T)(A/T)(A/T)T(A/G)G(A/T)AA | 75 |
| regulatory control by TF | AP1 binding site in AP3 | CCATTTTTAG | 76 |
| regulatory control by TF | AP1 binding site in SUP | CCATTTTTGG | 77 |
| regulatory control by TF | ARF binding site motif | TGTCTC | 78 |
| regulatory control by TF | ARF1 binding site motif | TGTCTC | 79 |
| regulatory control by TF | ATHB1 binding site motif | CAAT(A/T)ATTG | 80 |
| regulatory control by TF | ATHB2 binding site motif | CAAT(C/G)ATTG | 81 |
| regulatory control by TF | ATHB5 binding site motif | CAATNATTG | 82 |
| regulatory control by TF | ATHB6 binding site motif | CAATTATTA | 83 |
| regulatory control by TF | AtMYB2 binding site in RD22 | CTAACCA | 84 |
| regulatory control by TF | AtMYC2 binding site in RD22 | CACATG | 85 |
| regulatory control by TF | Box II promoter motif | GGTTAA | 86 |
| regulatory control by TF | CArG promoter motif | CC(A/T)(A/T)(A/T)(A/T)(A/T)(A/T)GG | 87 |
| regulatory control by TF | CArG1 motif in AP3 | GTTTACATAAATGGAAAA | 88 |
| regulatory control by TF | CArG2 motif in AP3 | CTTACCTTTCATGGATTA | 89 |
| regulatory control by TF | CArG3 motif in AP3 | CTTTCCATTTTTAGTAAC | 90 |
| regulatory control by TF | CBF1 binding site in cor15a | TGGCCGAC | 91 |
| regulatory control by TF | CBF2 binding site motif | CCACGTGG | 92 |
| regulatory control by TF | CCA1 binding site motif | AA(A/C)AATCT | 93 |
| regulatory control by TF | CCA1 motif1 binding site in CAB1 | AAACAATCTA | 94 |
| regulatory control by TF | CCA1 motif2 binding site in CAB1 | AAAAAAAATCTATGA | 95 |

TABLE 8-continued

| Type of regulation | Name of element | Sequence | SEQ ID NO: |
|---|---|---|---|
| regulatory control by TF | DPBF1&2 binding site motif | ACACNNG | 96 |
| regulatory control by TF | DRE promoter motif | TACCGACAT | 97 |
| regulatory control by TF | DREB1&2 binding site in rd29a | TACCGACAT | 98 |
| regulatory control by TF | DRE-like promoter motif | (A/G/T)(A/G)CCGACN(A/T) | 99 |
| regulatory control by TF | E2F binding site motif | TTTCCCGC | 100 |
| regulatory control by TF | E2F/DP binding site in AtCDC6 | TTTCCCGC | 101 |
| regulatory control by TF | E2F-varient binding site motif | TCTCCCGCC | 102 |
| regulatory control by TF | EIL1 binding site in ERF1 | TTCAAGGGGCATGTATCTTGAA | 103 |
| regulatory control by TF | EIL2 binding site in ERF1 | TTCAAGGGGCATGTATCTTGAA | 104 |
| regulatory control by TF | EIL3 binding site in ERF1 | TTCAAGGGGCATGTATCTTGAA | 105 |
| regulatory control by TF | EIN3 binding site in ERF1 | GGATTCAAGGGGCATGTATCTTGAATCC | 106 |
| regulatory control by TF | ERE promoter motif | TAAGAGCCGCC | 107 |
| regulatory control by TF | ERF1 binding site in AtCHI-B | GCCGCC | 108 |
| regulatory control by TF | EveningElement promoter motif | AAAATATCT | 109 |
| regulatory control by TF | GATA promoter motif | (A/T)GATA(G/A) | 110 |
| regulatory control by TF | GBF1/2/3 binding site in ADH1 | CCACGTGG | 111 |
| regulatory control by TF | G-box promoter motif | CACGTG | 112 |
| regulatory control by TF | GCC-box promoter motif | GCCGCC | 113 |
| regulatory control by TF | GT promoter motif | TGTGTGGTTAATATG | 114 |
| regulatory control by TF | Hexamer promoter motif | CCGTCG | 115 |
| regulatory control by TF | HSEs binding site motif | AGAANNTTCT | 116 |
| regulatory control by TF | Ibox promoter motif | GATAAG | 117 |
| regulatory control by TF | JASE1 motif in OPR1 | CGTCAATGAA | 118 |
| regulatory control by TF | JASE2 motif in OPR2 | CATACGTCGTCAA | 119 |
| regulatory control by TF | L1-box promoter motif | TAAATG(C/T)A | 120 |

TABLE 8-continued

| Type of regulation | Name of element | Sequence | SEQ ID NO: |
|---|---|---|---|
| regulatory control by TF | LS5 promoter motif | ACGTCATAGA | 121 |
| regulatory control by TF | LS7 promoter motif | TCTACGTCAC | 122 |
| regulatory control by TF | LTRE promoter motif | ACCGACA | 123 |
| regulatory control by TF | MRE motif in CHS | TCTAACCTACCA | 124 |
| regulatory control by TF | MYB binding site promoter | (A/C)ACC(A/T)A(A/C)C | 125 |
| regulatory control by TF | MYB1 binding site motif | (A/C)TCC(A/T)ACC | 126 |
| regulatory control by TF | MYB2 binding site motif | TAACT(G/C)GTT | 127 |
| regulatory control by TF | MYB3 binding site motif | TAACTAAC | 128 |
| regulatory control by TF | MYB4 binding site motif | A(A/C)C(A/T)A(A/C)C | 129 |
| regulatory control by TF | Nonamer promoter motif | AGATCGACG | 130 |
| regulatory control by TF | OBF4,5 binding site in GST6 | ATCTTATGTCATTGATGACGACCTCC | 131 |
| regulatory control by TF | OBP-1,4,5 binding site in GST6 | TACACTTTTGG | 132 |
| regulatory control by TF | OCS promoter motif | TGACG(C/T)AAG(C/G)(A/G)(A/C)T(G/T)ACG(C/T)(A/C)(A/C) | 133 |
| regulatory control by TF | octamer promoter motif | CGCGGATC | 134 |
| regulatory control by TF | PI promoter motif | GTGATCAC | 135 |
| regulatory control by TF | PII promoter motif | TTGGTTTTGATCAAAACCAA | 136 |
| regulatory control by TF | PRHA binding site in PAL1 | TAATTGACTCAATTA | 137 |
| regulatory control by TF | RAV1-A binding site motif | CAACA | 138 |
| regulatory control by TF | RAV1-B binding site motif | CACCTG | 139 |
| regulatory control by TF | RY-repeat promoter motif | CATGCATG | 140 |
| regulatory control by TF | SBP-box promoter motif | TNCGTACAA | 141 |
| regulatory control by TF | T-box promoter motif | ACTTTG | 142 |
| regulatory control by TF | TEF-box promoter motif | AGGGGCATAATGGTAA | 143 |
| regulatory control by TF | TELO-box promoter motif | AAACCCTAA | 144 |
| regulatory control by TF | TGA1 binding site motif | TGACGTGG | 145 |

TABLE 8-continued

| Type of regulation | Name of element | Sequence | SEQ ID NO: |
|---|---|---|---|
| regulatory control by TF | W-box promoter motif | TTGAC | 146 |
| regulatory control by TF | Z-box promoter motif | ATACGTGT | 147 |
| regulatory control by TF | AG binding site in SPL/NOZ | AAAACAGAATAGGAAA | 148 |
| regulatory control by TF | Bellringer/replumless/ pennywise binding site IN AG | AAATTAAA | 149 |
| regulatory control by TF | Bellringer/replumless/ pennywise binding site 2 in AG | AAATTAGT | 150 |
| regulatory control by TF | Bellringer/replumless/ pennywise binding site 3 in AG | ACTAATTT | 151 |
| regulatory control by TF | AGL15 binding site in AtGA2ox6 | CCAATTTAATGG | 152 |
| regulatory control by TF | ATB2/AtbZIP53/ AtbZIP44/GBF5 binding site in ProDH | ACTCAT | 153 |
| regulatory control by TF | LFY binding site in AP3 | CTTAAACCCTAGGGGTAAT | 154 |
| regulatory control by TF | SORLREP1 | TT(A/T)TACTAGT | 155 |
| regulatory control by TF | SORLREP2 | ATAAAACGT | 156 |
| regulatory control by TF | SORLREP3 | TGTATATAT | 157 |
| regulatory control by TF | SORLREP4 | CTCCTAATT | 158 |
| regulatory control by TF | SORLREP5 | TTGCATGACT | 159 |
| regulatory control by TF | SORLIP1 | AGCCAC | 160 |
| regulatory control by TF | SORLIP2 | GGGCC | 161 |
| regulatory control by TF | SORLIP3 | CTCAAGTGA | 162 |
| regulatory control by TF | SORLIP4 | GTATGATGG | 163 |
| regulatory control by TF | SORLIP5 | GAGTGAG | 164 |
| regulatory control by TF | ABFs binding site motif | CACGTGGC | 165 |
| down | NdeI restriction site | GTTTAATTGAGTTGTCATATGTTAATAACGGTAT | 166 |
| down | NdeI restriction site | ATACCGTTATTAACATATGACAACTCAATTAAAC | 167 |
| up (auxin responsive) | 3xDR5 auxin-response element | CCGACAAAAGGCCGACAAAAGGCCGACAAAAGGT | 168 |
| up (auxin responsive) | 3xDR5 auxin-response element | ACCTTTTGTCGGCCTTTTGTCGGCCTTTTGTCGG | 169 |

TABLE 8-continued

| Type of regulation | Name of element | Sequence | SEQ ID NO: |
|---|---|---|---|
| up (auxin responsive) | 6xDR5 auxin-responsive element | GCCGACAAAAGGCCGACAAAAGGCCGACA AAAGGCCGACAAAAGGCCGACAAAAGGCC GACAAAAGGT | 170 |
| up (auxin responsive) | 6xDR5 auxin-responsive element | ACCTTTTGTCGGCCTTTTGTCGGCCTTTTGT CGGCCTTTTGTCGGCCTTTTGTCGGCCTTTT GTCGGC | 171 |
| up (auxin responsive) | 9xDR5 auxin-responsive element | CCGACAAAAGGCCGACAAAAGGCCGACAA AAGGCCGACAAAAGGCCGACAAAAGGCCG ACAAAAGGCCGACAAAAGGCCGACAAAAG GCCGACAAAAGGT | 172 |
| up (auxin responsive) | 9xDR5 auxin-responsive element | ACCTTTTGTCGGCCTTTTGTCGGCCTTTTGT CGGCCTTTTGTCGGCCTTTTGTCGGCCTTTT GTCGGCCTTTTGTCGGCCTTTTGTCGGCCTT TTGTCGG | 173 |
| Cre recombinase recognition site | LoxP (wild-type 1) | ATAACTTCGTATAGCATACATTATACGAAG TTAT | 174 |
| Cre recombinase recognition site | LoxP (wild-type 2) | ATAACTTCGTATAATGTATGCTATACGAAG TTAT | 175 |
| Cre recombinase recognition site | Canonical LoxP | ATAACTTCGTATANNNTANNNTATACGAAG TTAT | 176 |
| Cre recombinase recognition site | Lox 511 | ATAACTTCGTATAATGTATaCTATACGAAGT TAT | 177 |
| Cre recombinase recognition site | Lox 5171 | ATAACTTCGTATAATGTgTaCTATACGAAGT TAT | 178 |
| Cre recombinase recognition site | Lox 2272 | ATAACTTCGTATAAaGTATcCTATACGAAGT TAT | 179 |
| Cre recombinase recognition site | M2 | ATAACTTCGTATAAgaaAccaTATACGAAGTT AT | 180 |
| Cre recombinase recognition site | M3 | ATAACTTCGTATAtaaTACCATATACGAAGTT AT | 181 |
| Cre recombinase recognition site | M7 | ATAACTTCGTATAAgaTAGAATATACGAAGT TAT | 182 |
| Cre recombinase recognition site | M11 | ATAACTTCGTATAaGATAgaaTATACGAAGTT AT | 183 |
| Cre recombinase recognition site | Lox 71 | taccgTTCGTATANNNTANNNTATACGAAGTT AT | 184 |
| Cre recombinase recognition site | Lox 66 | ATAACTTCGTATANNNTANNNTATACGAAcg gta | 185 |
| maize ovule/early kernel transcript down-regulation | miR156j recognition site | GTGCTCTCTCTCTTCTGTCA | 186 |
| maize ovule/early kernel transcript down-regulation | miR156j recognition site | CTGCTCTCTCTCTTCTGTCA | 187 |
| maize ovule/early kernel transcript down-regulation | miR156j recognition site | TTGCTTACTCTCTTCTGTCA | 188 |
| maize ovule/early kernel transcript down-regulation | miR156j recognition site | CCGCTCTCTCTCTTCTGTCA | 189 |

TABLE 8-continued

| Type of regulation | Name of element | Sequence | SEQ ID NO: |
|---|---|---|---|
| maize ovule/early kernel transcript down-regulation | miR159c recognition site | TGGAGCTCCCTTCATTCCAAT | 190 |
| maize ovule/early kernel transcript down-regulation | miR159c recognition site | TCGAGTTCCCTTCATTCCAAT | 191 |
| maize ovule/early kernel transcript down-regulation | miR159c recognition site | ATGAGCTCTCTTCAAACCAAA | 192 |
| maize ovule/early kernel transcript down-regulation | miR159c recognition site | TGGAGCTCCCTTCATTCCAAG | 193 |
| maize ovule/early kernel transcript down-regulation | miR159c recognition site | TAGAGCTTCCTTCAAACCAAA | 194 |
| maize ovule/early kernel transcript down-regulation | miR159c recognition site | TGGAGCTCCATTCGATCCAAA | 195 |
| maize ovule/early kernel transcript down-regulation | miR159c recognition site | AGCAGCTCCCTTCAAACCAAA | 196 |
| maize ovule/early kernel transcript down-regulation | miR159c recognition site | CAGAGCTCCCTTCACTCCAAT | 197 |
| maize ovule/early kernel transcript down-regulation | miR159c recognition site | TGGAGCTCCCTTCACTCCAAT | 198 |
| maize ovule/early kernel transcript down-regulation | miR159c recognition site | TGGAGCTCCCTTCACTCCAAG | 199 |
| maize ovule/early kernel transcript down-regulation | miR159c recognition site | TGGAGCTCCCTTTAATCCAAT | 200 |
| maize embryo transcript down-regulation | miR166b recognition site | TTGGGATGAAGCCTGGTCCGG | 201 |
| maize embryo transcript down-regulation | miR166b recognition site | CTGGGATGAAGCCTGGTCCGG | 202 |
| maize embryo transcript down-regulation | miR166b recognition site | CTGGAATGAAGCCTGGTCCGG | 203 |
| maize embryo transcript down-regulation | miR166b recognition site | CGGGATGAAGCCTGGTCCGG | 204 |
| maize endosperm transcript down-regulation | miR167g recognition site | GAGATCAGGCTGGCAGCTTGT | 205 |

TABLE 8-continued

| Type of regulation | Name of element | Sequence | SEQ ID NO: |
|---|---|---|---|
| maize endosperm transcript down-regulation | miR167g recognition site | TAGATCAGGCTGGCAGCTTGT | 206 |
| maize endosperm transcript down-regulation | miR167g recognition site | AAGATCAGGCTGGCAGCTTGT | 207 |
| maize pollen transcript down-regulation | miR156i recognition site | GTGCTCTCTCTCTTCTGTCA | 208 |
| maize pollen transcript down-regulation | miR156i recognition site | CTGCTCTCTCTCTTCTGTCA | 209 |
| maize pollen transcript down-regulation | miR156i recognition site | TTGCTTACTCTCTTCTGTCA | 210 |
| maize pollen transcript down-regulation | miR156i recognition site | CCGCTCTCTCTCTTCTGTCA | 211 |
| maize pollen transcript down-regulation | mir160b-like recognition site | TGGCATGCAGGGAGCCAGGCA | 212 |
| maize pollen transcript down-regulation | mir160b-like recognition site | AGGAATACAGGGAGCCAGGCA | 213 |
| maize pollen transcript down-regulation | mir160b-like recognition site | GGGTTTACAGGGAGCCAGGCA | 214 |
| maize pollen transcript down-regulation | mir160b-like recognition site | AGGCATACAGGGAGCCAGGCA | 215 |
| maize pollen transcript down-regulation | miR393a recognition site | AAACAATGCGATCCCTTTGGA | 216 |
| maize pollen transcript down-regulation | miR393a recognition site | AGACCATGCGATCCCTTTGGA | 217 |
| maize pollen transcript down-regulation | miR393a recognition site | GGTCAGAGCGATCCCTTTGGC | 218 |
| maize pollen transcript down-regulation | miR393a recognition site | AGACAATGCGATCCCTTTGGA | 219 |
| maize pollen transcript down-regulation | miR396a recognition site | TCGTTCAAGAAAGCCTGTGGAA | 220 |
| maize pollen transcript down-regulation | miR396a recognition site | CGTTCAAGAAAGCCTGTGGAA | 221 |
| maize pollen transcript down-regulation | miR396a recognition site | TCGTTCAAGAAAGCATGTGGAA | 222 |
| maize pollen transcript down-regulation | miR396a recognition site | ACGTTCAAGAAAGCTTGTGGAA | 223 |

TABLE 8-continued

| Type of regulation | Name of element | Sequence | SEQ ID NO: |
|---|---|---|---|
| maize pollen transcript down-regulation | miR396a recognition site | CGTTCAAGAAAGCCTGTGGAA | 224 |
| maize male tissue transcript down-regulation | male tissue-specific siRNA element | GGACAACAAGCACCTTCTTGCCTTGCAAGG CCTCCCTTCCCTATGGTAGCCACTTGAGTGG ATGACTTCACCTTAAAGCTATTGATTCCCTA AGTGCCAGACATAATAGGCTATACATTCTC TCTGGTGGCAACAATGAGCCATTTTGGTTG GTGTGGTAGTCTATTATTGAGTTTTTTTTGG CACCGTACTCCCATGGAGAGTAGAAGACAA ACTCTTCACCGTTGTAGTCGTTGATGGTATT GGTGGTGACGACATCCTTGGTGTGCATGCA CTGGTGAGTCACTGTTGTACTCGGCG | 225 |
| maize male tissue transcript down-regulation | male tissue-specific siRNA element | GGACAACAAGCACCTTCTTGCCTTGCAAGG CCTCCCTTCCCTATGGTAGCCACTTGAGTGG ATGACTTCACCTTAAAGCTATCGATTCCCTA AGTGCCAGACAT | 226 |
| maize male tissue transcript down-regulation | male tissue-specific siRNA element | CTCTTCACCGTTGTAGTCGTTGATGGTATTG GTGGTGACGACATCCTTGGTGTGCATGCAC TGGTGAGTCACTGTTGTAC | 227 |
| maize male tissue transcript down-regulation | male tissue-specific siRNA element | GGACAACAAGCACCTTCTTGCCTTGCAAGG CCTCCCTTCCCTATGGTAGCCACTTGAGTGG ATGACTTCACCTTAAAGCTATCGATTCCCTA AGTGCCAGACATCTCTTCACCGTTGTAGTC GTTGATGGTATTGGTGGTGACGACATCCTT GGTGTGCATGCACTGGTGAGTCACTGTTGT AC | 228 |
| maize male tissue transcript down-regulation | male tissue-specific siRNA element | CTCTTCACCGTTGTAGTCGTTGATGGTATTG GTGGTGACGACATCCTTGGTGTGCATGCAC TGGTGAGTCACTGTTGTACGGACAACAAGC ACCTTCTTGCCTTGCAAGGCCTCCCTTCCCT ATGGTAGCCACTTGAGTGGATGACTTCACC TTAAAGCTATCGATTCCCTAAGTGCCAGAC AT | 229 |
| up (auxin reponsive; constitutive) | ocs enhancer (*Agrobacterium* sp.) | ACGTAAGCGCTTACGT | 230 |
| up (auxin reponsive; constitutive) | 12-nt ocs orthologue (*Zea mays*) | GTAAGCGCTTAC | 231 |
| up (nitrogen responsive) | AtNRE | AAGAGATGAGCTCTTGAGCAATGTAAAGGG TCAAGTTGTTTCT | 232 |
| up (nitrogen responsive) | AtNRE | AGAAACAACTTGACCCTTTACATTGCTCAA GAGCTCATCTCTT | 233 |
| up (auxin responsive) | 3xDR5 auxin-response element; RNA strand of RNA/DNA hybid | ACCUUUUGUCGGCCUUUUGUCGGCCUUUU GUCGG | 234 |
| up (auxin responsive) | 3xDR5 auxin-response element; sticky-ended | TCGGTCCGACAAAAGGCCGACAAAAGGCG GACAAAAGG | 235 |
| up (auxin responsive) | 3xDR5 auxin-response element; sticky-ended | ACCGACCTTTTGTCGGCCTTTTGTCGGCCTT TTGTCGG | 236 |
| down or up (MAMP-responsive) | OsTBF1 uORF2 | ATGGGAGTAGAGGCGGGCGGCGGCTGCGG TGGAGGGCGGTAGTCACCGGATTCTACGT CTGGGGCTGGGAGTTCCTCACCGCCCTCCT GCTCTTCTCGGCCACCACCTCCTACTAG | 237 |
| down or up (MAMP-responsive) | synthetic R-motif | AAAAAAAAAAAAAA | 238 |

TABLE 8-continued

| Type of regulation | Name of element | Sequence | SEQ ID NO: |
|---|---|---|---|
| down or up (MAMP-responsive) | AtTBF1 R-motif | CACATACACACAAAAATAAAAAGA | 239 |
| decreases upregulation | insulator | GAATATATATATATTC | 240 |
| sequence modification | ZmEPSPS exon 1 with two point mutations and heterospecific lox sites | GTGAACAACCTTATGAAATTTGGGCGCATAACTTCGTATAGCATACATTATACGAAGTTATAAAGAACTCGCCCTCAAGGGTTGATCTTATGCCATCGTCATGATAAACAGTGGAGCACGGACGATCCTTTACGTTGTTTTTAACAAACTTTGTCAGAAAACTAGCATCATTAACTTCTTAATGACGATTTCACAACAAAAAAAGGTAACCTCGCTACTAACATAACAAAATACTTGTTGCTTATTAATTATATGTTTTTTAATCTTTGATCAGGGGACAACAGTGGTTGATAACCTGTTGAACAGTGAGGATGTCCACTACATGCTCGGGGCCTTGAGGACTCTTGGTCTCTCTGTCGAAGCGGACAAAGCTGCCAAAAGAGCTGTAGTTGTTGGCTGTGGTGGAAAGTTCCCAGTTGAGGATTCTAAAGAGGAAGTGCAGCTCTTCTTGGGGAATGCTGGAATTGCAATGCGGGCATTGACAGCAGCTGTTACTGCTGCTGGTGGAAATGCAACGTATGTTTCCTCTCTTTCTCTCTACAATACTTGCATAACTTCGTATAAAGTATCCTATACGAAGTTATTGGAGTTAGTATGAAACCCATGGGTATGTCTAGT | 241 |
| decreases upregulation | miniature inverted-repeat transposable element ("MITE") | TACTCCCTCCGTTTCTTTTTATTAGTCGCTGGATAGTGCAATTTTGCACTATCCAGCGACTAATAAAAAGAAACGGAGGGAGTA | 242 |
| decreases upregulation | miniature inverted-repeat transposable element ("MITE") | TACTCCCTCCGTTTCTTTTTATTAGTCGCTGGATAGTGCAAAATTGCACTATCCAGCGACTAATAAAAAGAAACGGAGGGAGTA | 243 |
| up (constitutive) | G-box | ACACGTGACACGTGACACGTGACACGTG | 244 |
| decreased transcript stability | mRNA destabilizing element (mammalian) | TTATTTATTTTATTTATTTTATTTATTTTATTTATT | 245 |
| decreased transcript stability | mRNA destabilizing element (Arabidopsis thaliana) | AATTTTAATTTTAATTTTAATTTTAATTTTAATTTT | 246 |
| increased transcript stability | mRNA stabilizing element | TCTCTTTCTCTTTCTCTTTCTCTTTCTCTTTCTCTT | 247 |
| down | SHAT1-repressor | ATTAAAAAATAAATAAGATATTATTAAAAAAATAAATAAGATATTATTAAAAAAATAATAAGATATTATTAAAAAAATAAATAAGATATT | 248 |
| decreased transcript stability | SAUR mRNA destabilizing element | AGATCTAGGAGACTGACATAGATTGGAGGAGACATTTTGTATAATAAGATCTAGGAGACTGACATAGATTGGAGGAGACATTTTGTATAATA | 249 |
| down by recruiting transcription factors interacting with PRC2 | CTCC | CTCC(T/A/G)CC(G/T/A) | 250 |

TABLE 8-continued

| Type of regulation | Name of element | Sequence | SEQ ID NO: |
|---|---|---|---|
| down by recruiting transcription factors interacting with PRC2 | CCG | (C/T/A)(G/T)C(C/A)(G/A)(C/A)C(G/T)(C/A) | 251 |
| down by recruiting transcription factors interacting with PRC2 | G-box | (C/G)ACGTGGNN(G/A/C)(T/A) | 252 |
| down by recruiting transcription factors interacting with PRC2 | GA repeat | A(G/A)A(G/A)AGA(G/A)(A/G) | 253 |
| down by recruiting transcription factors interacting with PRC2 | AC-rich | CA(A/T/C)CA(C/A)CA(A/C/T) | 254 |
| down by recruiting transcription factors interacting with PRC2 | Telobox (Myb-related telomeric DNA binding motif) | (A/G)AACCC(T/A)A(A/G) | 255 |
| up (Pi starvation response) | P1BS | GNATATNC | 256 |

*abbreviations:
(C/T) = Y; (C/G/T) = B; (G/T) = K; (A/C) = M; (A/G/T) = D; (A/T) = W; (A/C/T) = H; (A/G) = R; (C/G) = S; (A/C/G) = V; (A/C/G/T) = N The regulatory elements disclosed in Table 8 are useful in various approaches to modifying wheat plants and wheat plant cells. In embodiments, at least one of the regulatory sequences is encoded by at least one donor polynucleotide molecule and is heterologously integrated at a predetermined locus in a wheat plant's genome, e.g., by either HDR- or NHEJ-mediated integration, as illustrated in Examples 11-14. In embodiments, a regulatory element is encoded by at least one donor polynucleotide molecule and is heterologously integrated at a predetermined locus between 1-1000 nucleotides upstream of the start codon of the coding sequence of agene of interest in a wheat plant's genome or 1-1000 nucleotides upstream of the start codon of the coding sequence of agene of interest in a wheat plant's genome. In other embodiments, a regulatory element is encoded by at least one donor polynucleotide molecule and is heterologously integrated at a predetermined locus in the 3' untranslated region or within 1000 nucleotides downstream of the stop codon of agene of interest. In other embodiments, a regulatory element is encoded by at least one donor polynucleotide molecule and is heterologously integrated at a predetermined locus in an intron of a gene of interest. In other embodiments, a regulatory element is encoded by at least one donor polynucleotide molecule and is heterologously integrated at a predetermined locus in an exon of a gene of interest. For example, heterologously integrating a regulatory element that is specifically recognized by a transcription factor, e.g., at a predetermined locus between 1-1000 nucleotides upstream of the start codon of the coding sequence of a gene of interest, is expected to place the gene of interest under regulatory control of the corresponding transcription factor, resulting in either increased expression of the gene of interest (e.g., when the regulatory element is selected from SEQ ID NOs:66-165), or in decreased expression of the gene of interest (e.g., when the regulatory element is selected from SEQ ID NOs:250-255). In embodiments, heterologously integrating a regulatory element that specifically responds to a small molecule such as a hormone like auxin or signals related to nutrient availability, e.g., at a predetermined locus between 1-1000 nucleotides upstream of the start codon of the coding sequence of a gene of interest, is expected to place the gene of interest under regulatory control of the corresponding small molecule or signal. For example, heterologously integrating a regulatory element selected from SEQ ID NOs:168-173, 230, 231, 235, and 236), e.g., at a predetermined locus between 1-1000 nucleotides upstream of the start codon of the coding sequence of a gene of interest, is expected to make the gene of interest responsive to auxin; heterologously integrating a regulatory element selected from SEQ ID NOs:232-233), e.g., at a predetermined locus between 1-1000 nucleotides upstream of the start codon of the coding sequence of a gene of interest, is expected to make the gene of interest responsive to nitrogen; see also Examples 13 and 15. In another example, heterologously integrating a G-box regulatory element (e.g., SEQ ID NO:244), e.g., at a predetermined locus between 1-1000 nucleotides upstream of the start codon of the coding sequence of a gene of interest, is expected to upregulate expression of the gene of interest in a constitutive fashion. In another example, heterologously integrating a MAMP-responsive regulatory element (e.g., SEQ ID NOs:237-239), e.g., at a predetermined locus between 1-1000 nucleotides upstream of the start codon of the coding sequence of a gene of interest, is expected to increase or decrease the expression of the gene of interest, depending on the presence or absence of a MAMP signal. Integration of a heterologous cleavage site, such as a endonuclease restriction site (e.g., SEQ ID NOs:166 and 167), or a small RNA recognition site (e.g., SEQ ID NOs:186-229, or the miRNA recognition sites disclosed in Example 16), in various non-coding and coding regions of a gene of interest (including at a predetermined locus between 1-1000 nucleotides upstream of the start codon of the coding sequence of a gene of interest, or at a predetermined locus in the 3' untranslated region or within 1000 nucleotides downstream of the stop codon of a gene of interest, or within introns or exons of the gene of interest), is expected to decrease expression of the gene of interest, or to reduce the stability of the gene of interest's transcript (mRNA). Integration of certain sequences, e.g., at a predetermined locus in the 3' untranslated region or within 1000 nucleotides downstream of the stop codon of a gene of interest, are expected to either stabilize (e.g., SEQ ID NO:247) or destabilize (e.g., SEQ ID NOs:245, 246, and 249) the mRNA transcript of the gene of interest, and thus respectively increase or decrease the apparent expression of the gene of interest. Non-limiting examples of recombinase recognition sites are provided by SEQ ID NOs:174-185; integration of a homospecific pair of recombinase recognition sites allows use of the corresponding sequence-specific recombinase to mediate deletion, exchange, inversion, or translocation of genomic sequence flanked by the recombinase recognition sites thus integrated in the genome (see also Example 13); this approach is useful for replacement of one or more codons in genomic sequence encoding a protein, in order to provide a modified protein with one or more amino acid changes, up to and including replacement of exons or other larger regions of the genome.

In embodiments, a non-coding regulatory element encoded by at least one donor polynucleotide molecule is heterologously integrated at a double-strand break (DSB) at a specific locus in the wheat genome. This DSB locus can be identified by amplification using primers specific for DNA sequence encoded by the donor polynucleotide molecule alone; in other embodiments, the DSB locus is identified by amplification using primers specific for a combination of DNA sequence encoded by the donor polynucleotide molecule and genomic DNA sequence flanking the DSB. Such identification using a heterologously integrated DNA sequence (i. e., that encoded by the polynucleotide molecule) is useful, e. g., to distinguish a cell (such as a wheat plant cell or protoplast) containing sequence encoded by the polynucleotide molecule integrated at the DSB from a cell that does not. Identification of an edited wheat genome from a non-edited g wheat enome is important for various purposes, e. g., for commercial or regulatory tracking of cells or biological material such as wheat plants or seeds containing an edited wheat genome, or a processed product made therefrom.

Example 18

Various embodiments of this invention are related to modifications of genes of interest in a wheat plant, wherein the genes of interest are identified by gene name or by a sequence identifier (SEQ ID NO:) in Table 9. Embodiments of this invention are related to a wheat plant having a modified genome in comparison to an unmodified wheat plant having an reference genome, wherein the modified genome differs from the reference genome by including predetermined modifications of one or more genes of interest, selected from the genes identified by gene name in Table 9, or encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:257-474; embodiments include those wherein the modified genome differs from the reference genome by including multiple predetermined modifications of one or more genes of interest or multiple predetermined modifications of more than one homeoallele of a given gene of interest. In many embodiments the modified genome results in the wheat plant exhibiting a phenotype or trait, in comparison to a wheat plant having the unmodified reference genome.

Other embodiments of this invention are related to a wheat plant having a modified genome that results in the wheat plant exhibiting a phenotype or a trait in comparison to an unmodified wheat plant having an reference genome, wherein the modified genome differs from the reference genome by including predetermined modifications of at least two genes of interest, wherein the at least two genes of interest are selected from the genes identified by gene name in Table 9, or encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:257-474. In many embodiments the modified genome results in the wheat plant exhibiting a phenotype or trait, in comparison to a wheat plant having the unmodified reference genome.

Percent sequence identity is a measurement of the similarity (i.e., conserved nucleotide bases or conserved amino acid residues) between two or more sequences. Two examples of algorithms that are suitable for determining percent sequence identity and sequence similarity are the BLAST and BLAST 2.0 algorithms, which are described in Altschul et al. (1977) *Nuc. Acids Res.*, 25:3389-3402; and Altschul et al. (1990) *J. Mol. Biol.*, 215:403-410, respectively. Software for performing BLAST analyses is publicly available, e.g., through the National Center for Biotechnology Information. Optimal alignment of sequences for comparison can also be conducted using various algorithms (e.g., GAP, BESTFIT, FASTA, and TFASTA in the Wisconsin Genetics Software Package, Genetics Computer Group, 575 Science Dr., Madison, WI), or by manual alignment and visual inspection.

Table 9 provides a selection of wheat genes identified by gene name and sequence identifier (SEQ ID NO:), grouped according to a phenotype or trait expected in a wheat plant in which one or more of these genes is modified in comparison to an unmodified wheat plant having a reference genome, or in a wheat plant having predetermined modifications of at least two of these genes in comparison to an unmodified wheat plant having a reference genome.

TABLE 9

| Trait | Gene Name | Expression Change | Gene ID* | Protein SEQ ID NO: | Genomic DNA SEQ ID NO: |
|---|---|---|---|---|---|
| Architecture | pinBv1 | increase | TraesCS7D01G504800.1 | 257 | 475 |
| Architecture | pinBv1 | increase | TraesCS7A01G514400.1 | 258 | 476 |
| Architecture | pinBv1 | increase | TraesCS7B01G431200.1 | 259 | 477 |
| Architecture | pinBv2 | increase | TraesCS7B01G431200.1 | 260 | 478 |
| Architecture | pinBv2 | increase | TraesCS7D01G504800.1 | 261 | 479 |
| Architecture | pinBv2 | increase | TraesCS7A01G514400.1 | 262 | 480 |
| Architecture | LOC543302 | increase | TraesCS5D01G004100.1 | 263 | 481 |
| Architecture | LOC101290594 | increase | TraesCS7D01G166100.1 | 264 | 482 |
| Architecture | LOC101290594 | increase | TraesCS7A01G164000.1 | 265 | 483 |
| Architecture | LOC101290594 | increase | TraesCS7B01G069800.2 | 266 | 484 |
| Architecture | TaMOR-D | increase | TraesCS4D01G312800.1 | 267 | 485 |
| Architecture | TaMOR-D | increase | TraesCS4B01G316200.1 | 268 | 486 |
| Architecture | TaMOR-D | increase | TraesCS4A01G415400.1 | 269 | 487 |
| Architecture | TaTFL1-2D | increase | TraesCS2D01G292000.1 | 270 | 488 |
| Architecture | TaTFL1-2D | increase | TraesCSU01G202000.1 | 271 | 489 |
| Architecture | TaTFL1-2D | increase | TraesCS2B01G310700.1 | 272 | 490 |
| Architecture | TB-A1 | increase | TraesCS4A01G271300.1 | 273 | 491 |
| Architecture | TB-B1 | increase | TraesCS4B01G042700.1 | 274 | 492 |
| Architecture | TB-D1 | increase | TraesCS4D01G040100.1 | 275 | 493 |
| Architecture | DEP1 | increase/decrease[1] | TraesCS5D01G216900.1 | 276 | 494 |
| Architecture | DEP1 | increase/decrease[1] | TraesCS5B01G208700.1 | 277 | 495 |
| Architecture | Gasr7 | decrease | TraesCS7A01G208100.1 | 278 | 496 |
| Architecture | Gasr7 | decrease | TraesCS7B01G115300.1 | 279 | 497 |
| Architecture | PIN1 | increase/decrease[1] | TraesCS7B01G095500.1 | 280 | 498 |
| Architecture | PIN1 | increase/decrease[1] | TraesCS7D01G191600.1 | 281 | 499 |
| Architecture | PIN1 | increase/decrease[1] | TraesCS7A01G190600.1 | 282 | 500 |
| Architecture | TaMOC1 | decrease | TraesCS7B01G285500.1 | 283 | 501 |
| Architecture | TaMOC1 | decrease | TraesCS7A01G382800.1 | 284 | 502 |
| Architecture | TaMOC1 | decrease | TraesCS7D01G379200.1 | 285 | 503 |
| Architecture | TaPAP2-5A | decrease | TraesCS5A01G391800.1 | 286 | 504 |
| Architecture | TaPAP2-5A | decrease | TraesCS5B01G396700.1 | 287 | 505 |
| Architecture | TaPAP2-5A | decrease | TraesCS5D01G401700.1 | 288 | 506 |
| Architecture | TaVRS1-2B | decrease | TraesCS2B01G218800.1 | 289 | 507 |
| Architecture | TaVRS1-2B | decrease | TraesCS2D01G199200.1 | 290 | 508 |
| Architecture | TaVRS1-2B | decrease | TraesCS2A01G188500.1 | 291 | 509 |
| Architecture | WFZP-A | decrease | TraesCS2A01G116900.1 | 292 | 510 |
| Architecture | WFZP-B | decrease | TraesCS2B01G136100.1 | 293 | 511 |
| Architecture | WFZP-D | decrease | TraesCS2D01G118200.1 | 294 | 512 |
| Architecture | TaFT-B1 | decrease | TraesCS7B01G013100.1 | 295 | 513 |
| Architecture | TaFT-B1 | decrease | TraesCS7D01G111600.1 | 296 | 514 |
| Architecture | TaFT-B1 | decrease | TraesCS7A01G115400.1 | 297 | 515 |
| Architecture | LOC542960 | AA change | TraesCS7D01G158500.1 | 298 | 516 |
| Architecture | LOC542960 | AA change | TraesCS7B01G062200.1 | 299 | 517 |
| Architecture | LOC542960 | AA change | TraesCS7A01G158000.1 | 300 | 518 |
| Architecture | TaSnrk2.10-4A | SNP change | TraesCS4D01G078100.2 | 301 | 519 |
| Architecture | TaSnrk2.10-4A | SNP change | TraesCS4A01G235600.2 | 302 | 520 |
| Architecture | TaSnrk2.10-4A | SNP change | TraesCS4B01G079300.1 | 303 | 521 |
| Abiotic stress | TaSK5 | increase | TraesCS3D01G177600.2 | 304 | 522 |
| Abiotic stress | TaSK5 | increase | TraesCS3B01G201800.2 | 305 | 523 |
| Abiotic stress | TaSK5 | increase | TraesCS3A01G164200.1 | 306 | 524 |
| Abiotic stress | TaOBF1a | increase | TraesCS5A01G088300.1 | 307 | 525 |
| Abiotic stress | TaOBF1a | increase | TraesCS5D01G100700.1 | 308 | 526 |
| Abiotic stress | TaOBF1a | increase | TraesCS5B01G094300.1 | 309 | 527 |
| Abiotic stress | TaPIMP1 | increase | TraesCS1D01G078600.1 | 310 | 528 |
| Abiotic stress | TaPIMP1 | increase | TraesCS1A01G076200.1 | 311 | 529 |
| Abiotic stress | TaPIMP1 | increase | TraesCS1B01G094500.1 | 312 | 530 |
| Abiotic stress | TaWRKY2 | increase | TraesCS1D01G072900.1 | 313 | 531 |
| Abiotic stress | TaWRKY2 | increase | TraesCS1B01G088900.2 | 314 | 532 |
| Abiotic stress | TaWRKY19 | increase | TraesCS2B01G209200.1 | 315 | 533 |
| Abiotic stress | TaWRKY19 | increase | TraesCS2A01G182700.1 | 316 | 534 |
| Abiotic stress | TaWRKY19 | increase | TraesCS2D01G190500.1 | 317 | 535 |
| Abiotic stress | LOC100415880 | increase | TraesCS3A01G289200.1 | 318 | 536 |
| Abiotic stress | LOC100415880 | increase | TraesCS3B01G323800.1 | 319 | 537 |
| Abiotic stress | TaNAC2a | increase | TraesCS5B01G480900.2 | 320 | 538 |
| Abiotic stress | TaNAC2a | increase | TraesCS5D01G481200.1 | 321 | 539 |
| Abiotic stress | TaNAC2a | increase | TraesCS5A01G468300.1 | 322 | 540 |
| Abiotic stress | LEA3 | increase | TraesCS1B01G381200.1 | 323 | 541 |
| Abiotic stress | TaUb2 | increase | TraesCS7D01G454100.1 | 324 | 542 |
| Abiotic stress | TaUb2 | increase | TraesCS5A01G073800.1 | 325 | 543 |
| Abiotic stress | NAC69-1 | increase | TraesCS5B01G142100.1 | 326 | 544 |
| Abiotic stress | NAC69-1 | increase | TraesCS5D01G148800.1 | 327 | 545 |
| Abiotic stress | NAC69-1 | increase | TraesCS5A01G143200.1 | 328 | 546 |
| Abiotic stress | NAC2 | increase | TraesCS5A01G468300.1 | 329 | 547 |
| Abiotic stress | NAC2 | increase | TraesCS5B01G480900.2 | 330 | 548 |
| Abiotic stress | NAC2 | increase | TraesCS5D01G481200.1 | 331 | 549 |

TABLE 9-continued

| Trait | Gene Name | Expression Change | Gene ID* | Protein SEQ ID NO: | Genomic DNA SEQ ID NO: |
|---|---|---|---|---|---|
| Abiotic stress | TaMDC1 | increase | TraesCS3A01G185800.1 | 332 | 550 |
| Abiotic stress | TaMDC1 | increase | TraesCS3D01G189800.1 | 333 | 551 |
| Abiotic stress | TaMDC1 | increase | TraesCS3B01G215400.1 | 334 | 552 |
| Abiotic stress | TaSC | increase | TraesCS5D01G242500.1 | 335 | 553 |
| Abiotic stress | TaSC | increase | TraesCS5B01G233800.1 | 336 | 554 |
| Abiotic stress | Waox1a | increase | TraesCS2D01G436700.1 | 337 | 555 |
| Abiotic stress | ALMT1 | increase | TraesCS4D01G283600.1 | 338 | 556 |
| Abiotic stress | SOD | increase | TraesCS3A01G023200.2 | 339 | 557 |
| Abiotic stress | SOD | increase | TraesCS3D01G022900.1 | 340 | 558 |
| Abiotic stress | SOD | increase | TraesCS3B01G021600.2 | 341 | 559 |
| Abiotic stress | CHP | increase | TraesCS7D01G545700.1 | 342 | 560 |
| Abiotic stress | TaAQP7 | increase | TraesCS6D01G212900.1 | 343 | 561 |
| Abiotic stress | TaAQP7 | increase | TraesCS6A01G222100.1 | 344 | 562 |
| Abiotic stress | TaAQP7 | increase | TraesCS6B01G259000.1 | 345 | 563 |
| Abiotic stress | TaAQP8 | increase | TraesCS2B01G425600.1 | 346 | 564 |
| Abiotic stress | TaAQP8 | increase | TraesCS2B01G605900.1 | 347 | 565 |
| Abiotic stress | TaAQP8 | increase | TraesCS6D01G227500.1 | 348 | 566 |
| Abiotic stress | TaWRKY10 | increase | TraesCS3D01G113200.1 | 349 | 567 |
| Abiotic stress | TaWRKY10 | increase | TraesCS3B01G129900.1 | 350 | 568 |
| Abiotic stress | CIPK 14 | increase | TraesCS4B01G120400.1 | 351 | 569 |
| Abiotic stress | CIPK14 | increase | TraesCS4A01G194800.1 | 352 | 570 |
| Abiotic stress | CIPK14 | increase | TraesCS4D01G118500.2 | 353 | 571 |
| Abiotic stress | TaWRKY1 | increase | TraesCS1D01G300700.1 | 354 | 572 |
| Abiotic stress | TaWRKY1 | increase | TraesCS1A01G301100.1 | 355 | 573 |
| Abiotic stress | TaWRKY33 | increase | TraesCS6B01G175100.2 | 356 | 574 |
| Abiotic stress | TaWRKY33 | increase | TraesCS6A01G146900.1 | 357 | 575 |
| Abiotic stress | TaGAPC1 | increase | TraesCS7D01G309500.1 | 358 | 576 |
| Abiotic stress | TaGAPC1 | increase | TraesCS7B01G213300.1 | 359 | 577 |
| Abiotic stress | TaGAPC1 | increase | TraesCS7A01G313100.1 | 360 | 578 |
| Abiotic stress | UBA | decrease | TraesCS6A01G208300.2 | 361 | 579 |
| Abiotic stress | UBA | decrease | TraesCS6B01G236800.1 | 362 | 580 |
| Disease | Fhb1 | increase | TraesCS2A01G589100.1 | 363 | 581 |
| Disease | Fhb1 | increase | TraesCSU01G137400.1 | 364 | 582 |
| Disease | Fhb1 | increase | TraesCS5A01G516500.1 | 365 | 583 |
| Disease | Lr34 | increase; AA change | TraesCS7D01G080300.1 | 366 | 584 |
| Disease | Lr34 | increase; AA change | TraesCS4A01G384800.1 | 367 | 585 |
| Disease | Lr34 | increase; AA change | TraesCS5D01G163700.1 | 368 | 586 |
| Disease | Lr67 | increase | TraesCS4D01G243100.1 | 369 | 587 |
| Disease | Lr67 | increase | TraesCS4B01G243500.1 | 370 | 588 |
| Disease | Lr67 | increase | TraesCS4A01G066200.1 | 371 | 589 |
| Disease | Sr22 | increase | TraesCS1D01G040400.1 | 372 | 590 |
| Disease | Sr22 | increase | TraesCSU01G135200.1 | 373 | 591 |
| Disease | Sr22 | increase | TraesCS1B01G049900.1 | 374 | 592 |
| Disease | Sr33 | increase | TraesCS1D01G029100.2 | 375 | 593 |
| Disease | Sr33 | increase | TraesCS1A01G029100.1 | 376 | 594 |
| Disease | Sr33 | increase | TraesCS1A01G026400.2 | 377 | 595 |
| Disease | Sr35 | increase | TraesCS3D01G474300.1 | 378 | 596 |
| Disease | Sr35 | increase | TraesCS3D01G474000.2 | 379 | 597 |
| Disease | Sr35 | increase | TraesCS3A01G479400.2 | 380 | 598 |
| Disease | Sr45 | increase | TraesCS7D01G486400.1 | 381 | 599 |
| Disease | Sr45 | increase | TraesCS7B01G406700.1 | 382 | 600 |
| Disease | Sr45 | increase | TraesCS7A01G499600.1 | 383 | 601 |
| Disease | Sr50 | increase | TraesCS1D01G028200.1 | 384 | 602 |
| Disease | Sr50 | increase | TraesCS1D01G029200.3 | 385 | 603 |
| Disease | Sr50 | increase | TraesCS1B01G034500.1 | 386 | 604 |
| Disease | Tsn1 | increase | TraesCS5B01G059000.1 | 387 | 605 |
| Disease | Tsn1 | increase | TraesCS5D01G005400.1 | 388 | 606 |
| Disease | Tsn1 | increase | TraesCS4A01G026300.1 | 389 | 607 |
| Disease | Yr36 (WKS1) | increase | TraesCS7B01G458700.1 | 390 | 608 |
| Disease | Yr36 (WKS1) | increase | TraesCS7D01G523200.2 | 391 | 609 |
| Disease | Yr36 (WKS1) | increase | TraesCS7A01G538600.2 | 392 | 610 |
| Disease | Snn1 | decrease/KO[2] | TraesCS1B01G004100.1 | 393 | 611 |
| Disease | Snn1 | decrease/KO[2] | TraesCS6B01G055400.1 | 394 | 612 |
| Disease | Snn1 | decrease/KO[2] | TraesCS2B01G563900.2 | 395 | 613 |
| Disease | TaMLO-A1 | decrease/KO[2] | TraesCS5A01G494800.1 | 396 | 614 |
| Disease | TaMLO-B1 | decrease/KO[2] | TraesCS4B01G322700.1 | 397 | 615 |
| Disease | TaMLO-D1 | decrease/KO[2] | TraesCS4D01G319100.1 | 398 | 616 |
| Flowering Time | FT | increase/decrease[1] | TraesCS7B01G013100.1 | 399 | 617 |
| Flowering Time | FT | increase/decrease[1] | TraesCS7D01G111600.1 | 400 | 618 |
| Flowering Time | FT | increase/decrease[1] | TraesCS7A01G115400.1 | 401 | 619 |
| Flowering Time | FKF1 | increase/decrease[1] | TraesCS4A01G164000.1 | 402 | 620 |
| Flowering Time | FKF1 | increase/decrease[1] | TraesCS4B01G157500.1 | 403 | 621 |

TABLE 9-continued

| Trait | Gene Name | Expression Change | Gene ID* | Protein SEQ ID NO: | Genomic DNA SEQ ID NO: |
|---|---|---|---|---|---|
| Flowering Time | PhyB | increase/decrease[1] | TraesCS4A01G122500.2 | 404 | 622 |
| Flowering Time | PhyB | increase/decrease[1] | TraesCS4B01G182400.1 | 405 | 623 |
| Flowering Time | PhyB | increase/decrease[1] | TraesCS4D01G183400.1 | 406 | 624 |
| Flowering Time | WCO1 | increase/decrease[1] | TraesCS7D01G213000.2 | 407 | 625 |
| Flowering Time | WCO1 | increase/decrease[1] | TraesCS7A01G211300.1 | 408 | 626 |
| Flowering Time | WCO1 | increase/decrease[1] | TraesCS7B01G118300.1 | 409 | 627 |
| Flowering Time | ZenMFT-3D | increase/decrease[1] | TraesCS3D01G004100.1 | 410 | 628 |
| Flowering Time | ZenMFT-3D | increase/decrease[1] | TraesCS3B01G010100.1 | 411 | 629 |
| Flowering Time | ZenMFT-3D | increase/decrease[1] | TraesCS3A01G006600.1 | 412 | 630 |
| Flowering Time | MADS | increase/decrease[1] | TraesCS5D01G294500.1 | 413 | 631 |
| Flowering Time | MADS | increase/decrease[1] | TraesCS5A01G286800.1 | 414 | 632 |
| Flowering Time | MADS | increase/decrease[1] | TraesCS5B01G286100.2 | 415 | 633 |
| Flowering Time | TaGI1 | increase/decrease[1] | TraesCS3A01G116300.1 | 416 | 634 |
| Flowering Time | TaGI1 | increase/decrease[1] | TraesCS3B01G135400.1 | 417 | 635 |
| Flowering Time | TaGI1 | increase/decrease[1] | TraesCS3D01G118200.2 | 418 | 636 |
| Flowering Time | WAP1 | increase/decrease[1] | TraesCS1B01G434000.1 | 419 | 637 |
| Flowering Time | WAP1 | increase/decrease[1] | TraesCS1A01G404500.1 | 420 | 638 |
| Flowering Time | WAP1 | increase/decrease[1] | TraesCS1D01G412200.1 | 421 | 639 |
| Flowering Time | NFYB-A | increase/decrease[1] | TraesCS2A01G359400.1 | 422 | 640 |
| Flowering Time | NFYB-B | increase/decrease[1] | TraesCS2B01G378700.1 | 423 | 641 |
| Flowering Time | NFYB-D | increase/decrease[1] | TraesCS2D01G358300.1 | 424 | 642 |
| Photosynthesis | NAC1 | increase | TraesCS3D01G078900.1 | 425 | 643 |
| Photosynthesis | NAC1 | increase | TraesCS3B01G093300.1 | 426 | 644 |
| Photosynthesis | NAC1 | increase | TraesCS3A01G078400.1 | 427 | 645 |
| Photosynthesis | Skp1 | increase | TraesCS6D01G001600.1 | 428 | 646 |
| Photosynthesis | Skp1 | increase | TraesCS6B01G004300.1 | 429 | 647 |
| Photosynthesis | Skp1 | increase | TraesCS6A01G000300.1 | 430 | 648 |
| Photosynthesis | TIF | increase | TraesCS2D01G224400.1 | 431 | 649 |
| Photosynthesis | TIF | increase | TraesCS2B01G244400.1 | 432 | 650 |
| Photosynthesis | TIF | increase | TraesCS2A01G219000.1 | 433 | 651 |
| Photosynthesis | WCBP1 | AA change[3] | TraesCS5B01G095800.2 | 434 | 652 |
| Senescence | WRKY | increase | TraesCS5D01G190800.1 | 435 | 653 |
| Senescence | WRKY | increase | TraesCS5A01G185700.1 | 436 | 654 |
| Senescence | WRKY | increase | TraesCS5B01G183800.1 | 437 | 655 |
| Senescence | TaSAG6 | increase | TraesCS3D01G116400.1 | 438 | 656 |
| Senescence | TaSAG6 | increase | TraesCS3A01G113900.2 | 439 | 657 |
| Senescence | TaSAG6 | increase | TraesCS3B01G133400.1 | 440 | 658 |
| Senescence | TaSAG3 | increase | TraesCS5D01G126700.1 | 441 | 659 |
| Senescence | TaSAG3 | increase | TraesCS5A01G120000.3 | 442 | 660 |
| Senescence | TaSAG3 | increase | TraesCS5B01G121400.3 | 443 | 661 |
| Senescence | TaSAG1 | increase | TraesCS2B01G440400.1 | 444 | 662 |
| Senescence | TaSAG1 | increase | TraesCS2A01G421400.1 | 445 | 663 |
| Senescence | TaSAG1 | increase | TraesCS2D01G418400.2 | 446 | 664 |
| Senescence | FeSOD | increase | TraesCS7D01G086400.1 | 447 | 665 |
| Senescence | FeSOD | increase | TraesCS7A01G090400.1 | 448 | 666 |
| Senescence | FeSOD | increase | TraesCS4A01G390300.1 | 449 | 667 |
| Senescence | CWINV2SM | increase | TraesCS4B01G356800.1 | 450 | 668 |
| Senescence | CWINV2SM | increase | TraesCS4D01G350500.1 | 451 | 669 |
| Senescence | CWINV2SM | increase | TraesCS5A01G526200.1 | 452 | 670 |
| Senescence | CWINV1SM | increase | TraesCS2D01G293200.1 | 453 | 671 |
| Senescence | CWINV1SM | increase | TraesCS2B01G311900.1 | 454 | 672 |
| Senescence | SOD | increase | TraesCS2B01G567600.1 | 455 | 673 |
| Senescence | SOD | increase | TraesCS2D01G538300.1 | 456 | 674 |
| Senescence | SOD | increase | TraesCS2A01G537100.1 | 457 | 675 |
| Senescence | APX | increase/decrease[1] | TraesCS7A01G272200.1 | 458 | 676 |
| Senescence | APX | increase/decrease[1] | TraesCS7B01G169800.1 | 459 | 677 |
| Senescence | APX | increase/decrease[1] | TraesCS7D01G272500.1 | 460 | 678 |
| Senescence | GS2 | increase/decrease[1] | TraesCS2D01G500600.1 | 461 | 679 |
| Senescence | GS2 | increase/decrease[1] | TraesCS2A01G500400.1 | 462 | 680 |
| Senescence | GS2 | increase/decrease[1] | TraesCS2B01G528300.1 | 463 | 681 |
| Senescence | NAM | decrease | TraesCS7A01G194700.1 | 464 | 682 |
| Senescence | NAM | decrease | TraesCS7B01G100300.1 | 465 | 683 |
| Senescence | NAM | decrease | TraesCS7D01G196300.1 | 466 | 684 |
| Senescence | rbcL | decrease | TraesCS5D01G425100.1 | 467 | 685 |
| Senescence | rbcL | decrease | TraesCS3B01G186100.1 | 468 | 686 |
| Senescence | rbcL | decrease | TraesCS5D01G010200.1 | 469 | 687 |
| Senescence | IVR1 | decrease | TraesCS5B01G556600.1 | 470 | 688 |
| Senescence | IVR1 | decrease | TraesCS5D01G552900.1 | 471 | 689 |

TABLE 9-continued

| Trait | Gene Name | Expression Change | Gene ID* | Protein SEQ ID NO: | Genomic DNA SEQ ID NO: |
|---|---|---|---|---|---|
| Senescence | IVR1 | decrease | TraesCS4A01G321700.1 | 472 | 690 |
| Senescence | a1 | decrease | TraesCS3D01G501900.1 | 473 | 691 |
| Senescence | a1 | decrease | TraesCS3A01G494800.1 | 474 | 692 |

*Gene ID based on the genome and annotation provided as the first version of the reference sequence (RefSeqv1.0) of the bread wheat *Triticum aestivum* variety Chinese Spring, produced by the International Wheat Genome Sequencing Consortium (IWGSC), publicly accessible at: wheat-urgi[dot] Versailles[dot]inra[dot]fr/Seq-Repository/Assemblies
[1]increase/decrease indicates that different desirable phenotypes or traits are expected with either an increase or a decrease in expression
[2]decrease/KO indicates a decrease in expression, up to and including a degree considered a "knock out" ("KO")), i.e., where expression is decreased to none, or not detectable, or essentially a "loss of function" of the gene of interest
[3]Stripe-rust-resistant WCBP1 modified allele includes a SNP in exon 1 and a 36 bp deletion in exon 4, in comparison to susceptible (unmodified) sequence; see Li et al. (2015) BMC Plant Biology, 15:239; doi:10.1186/s12870-015-0612-4.

Embodiments of the invention are related to wheat plants exhibiting modified architecture, i.e., a modified wheat plant structure, such as changes in vegetative tissue structure or reproductive tissue structure, including changes in root structure, stem structure, leaf structure, inflorescence structure, seed structure, plant height, tillering, improved tolerance of high density plantings, or improved resistance to lodging. Embodiments include a wheat plant having a modified genome that results in the wheat plant exhibiting modified architecture in comparison to an unmodified wheat plant having an reference genome, wherein the modified genome differs from the reference genome by including predetermined modifications of at least two genes of interest (e.g., modification of regulatory sequence that affects expression of the gene of interest), wherein each of the predetermined modifications is selected from the group consisting of: (a) heterologous integration of a nucleic acid sequence that is encoded by at least one donor polynucleotide molecule and that includes a regulatory element having a nucleotide sequence selected from the group consisting of SEQ ID NOs:66-256 at a predetermined locus between 1-1000 nucleotides upstream of the start codon of the coding sequence of a gene of interest in the reference genome, wherein the gene of interest is selected from the group consisting of pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, and TaSnrk2.10-4A, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:257-303; (b) heterologous integration of a nucleic acid sequence that is encoded by at least one donor polynucleotide molecule and that includes a regulatory element having a nucleotide sequence selected from the group consisting of SEQ ID NOs:66-256 at a predetermined locus in the 3' untranslated region or within 1000 nucleotides downstream of the stop codon of a gene of interest in the reference genome, wherein the gene of interest is selected from the group consisting of pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, and TaSnrk2.10-4A, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:257-303; (c) deletion, addition, or substitution of at least one nucleotide in a regulatory element that regulates expression of a gene of interest in the reference genome, wherein the gene of interest is selected from the group consisting of pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, and TaSnrk2.10-4A, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:257-303; (d) deletion, addition, or substitution of at least one nucleotide in coding sequence of a gene of interest in the reference genome, wherein the gene of interest is selected from the group consisting of pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, and TaSnrk2.10-4A, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:257-303; and (e) a combination of any of (a), (b), (c), and (d). In embodiments, the gene encoding a protein having at least 90% identity to a sequence selected from the group consisting of the sequences identified by SEQ ID NOs:257-303 is selected from the group consisting of the genomic sequences identified by SEQ ID NOs:475-521. In embodiments, the at least two genes of interest include at least one homeoallele each of two or more genes selected from the group consisting of pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, and TaSnrk2.10-4A. In embodiments, the modified genome further differs from the reference genome by including (a) a predetermined modification in at least one homeoallele of a gene selected from TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, Lr34, Lr67, Sr22, Sr33, Sr35, Sr45, Sr50, Tsn1, Yr36 (WKS1), Snn1, TaMLO-A 1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV1SM, SOD, APX, GS2, NAM, rbcL, IVR1, and a1, or (b) a predetermined modification in a gene encoding a protein having at least 90% identity to a sequence selected from the group consisting of the sequences identified by SEQ ID NOs:304-474 in Table 9, or (c) a predetermined modification in a genomic sequence selected from the group consisting of the sequences identified by SEQ ID NOs:522-692 in Table 9; wherein the predetermined modification is selected from the group consisting of (a) heterologous integration of a non-coding regulatory element sequence that is encoded by at least one donor polynucleotide molecule at a predetermined locus between 1-1000 nucleotides upstream of the start codon of the coding sequence of the gene; (b) heterologous integration of a non-coding regulatory element sequence that is encoded by at least one donor polynucleotide molecule at a predetermined locus in the 3' untranslated region or within 1000 nucleotides downstream of the stop codon of the gene; (c) deletion, addition, or substitution of at least one nucleotide in a regulatory element or non-coding sequence that regulates expression of the gene; (d) deletion, addition, or substitution of at least one nucleotide in coding sequence of the gene; and (e) a combination of any of (a), (b), (c), and (d).

Embodiments of the invention are related to wheat plants exhibiting improved abiotic stress tolerance or improved resistance to abiotic stress, such as, but not limited to, wheat plants exhibiting improved tolerance to heat, cold, drought, salt, or nutrient (e. g., nitrogen, phosphorus, potassium) deficiencies. Embodiments include a wheat plant having a modified genome that results in the wheat plant exhibiting improved abiotic stress tolerance in comparison to an unmodified wheat plant having an reference genome, wherein the modified genome differs from the reference genome by including predetermined modifications of at least two genes of interest (e.g., modification of regulatory sequence that affects expression of the gene of interest), wherein each of the predetermined modifications is selected from the group consisting of: (a) heterologous integration of a nucleic acid sequence that is encoded by at least one donor polynucleotide molecule and that includes a regulatory element having a nucleotide sequence selected from the group consisting of SEQ ID NOs:66-256 at a predetermined locus between 1-1000 nucleotides upstream of the start codon of the coding sequence of a gene of interest in the reference genome, wherein the gene of interest is selected from the group consisting of TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, and UBA, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:304-362 in Table 9; (b) heterologous integration of a nucleic acid sequence that is encoded by at least one donor polynucleotide molecule and that includes a regulatory element that has a nucleotide sequence selected from SEQ ID NOs:66-256 at a predetermined locus in the 3' untranslated region or within 1000 nucleotides downstream of the stop codon of a gene of interest in the reference genome, wherein the gene of interest is selected from the group consisting of TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, and UBA, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:304-362 in Table 9; (c) deletion, addition, or substitution of at least one nucleotide in a regulatory element that regulates expression of a gene of interest in the reference genome, wherein the gene of interest is selected from the group consisting of TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, and UBA, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:304-362 in Table 9; (d) deletion, addition, or substitution of at least one nucleotide in coding sequence of a gene of interest in the reference genome, wherein the gene of interest is selected from the group consisting of TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, and UBA, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:304-362 in Table 9; and (e) a combination of any of (a), (b), (c), and (d). In embodiments, the gene encoding a protein having at least 90% identity to a sequence selected from the group consisting of the sequences identified by SEQ ID NOs:304-362 is selected from the group consisting of the genomic sequences identified by SEQ ID NOs:522-580. In embodiments, the at least two genes of interest include at least one homeoallele each of two or more genes selected from the group consisting of TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, and UBA. In embodiments, the modified genome further differs from the reference genome by including (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, Fhb1, Lr34, Lr67, Sr22, Sr33, Sr35, Sr45, Sr50, Tsn1, Yr36 (WKS1), Snn1, TaMLO-A1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV1SM, SOD, APX, GS2, NAM, rbcL, IVR1, and a1, or (b) a predetermined modification in a gene encoding a protein having at least 90% identity to a sequence selected from the group consisting of the sequences identified by SEQ ID NOs:257-303 and 363-474 in Table 9, or (c) a predetermined modification in a genomic sequence selected from the group consisting of the sequences identified by SEQ ID NOs:475-521 and 581-692 in Table 9; wherein the predetermined modification is selected from the group consisting of (a) heterologous integration of a non-coding regulatory element sequence that is encoded by at least one donor polynucleotide molecule at a predetermined locus between 1-1000 nucleotides upstream of the start codon of the coding sequence of the gene; (b) heterologous integration of a non-coding regulatory element sequence that is encoded by at least one donor polynucleotide molecule at a predetermined locus in the 3' untranslated region or within 1000 nucleotides downstream of the stop codon of the gene; (c) deletion, addition, or substitution of at least one nucleotide in a regulatory element or non-coding sequence that regulates expression of the gene; (d) deletion, addition, or substitution of at least one nucleotide in coding sequence of the gene; and (e) a combination of any of (a), (b), (c), and (d).

Embodiments of the invention are related to wheat plants exhibiting improved disease resistance, e.g., improved resistance to or tolerance of infection by plant pathogens, and improved resistance to pests transmitting such pathogens. Embodiments include a wheat plant having a modified genome that results in the wheat plant exhibiting improved disease resistance in comparison to an unmodified wheat plant having an reference genome, wherein the modified genome differs from the reference genome by including predetermined modifications of at least two genes of interest (e.g., modification of regulatory sequence that affects expression of the gene of interest), wherein each of the predetermined modifications is selected from the group consisting of: (a) heterologous integration of a nucleic acid sequence that is encoded by at least one donor polynucleotide molecule and that includes a regulatory element having a nucleotide sequence selected from the group consisting of SEQ ID NOs:66-256 at a predetermined locus between 1-1000 nucleotides upstream of the start codon of the coding sequence of a gene of interest in the reference genome, wherein the gene of interest is selected from the group consisting of Fhb1, Lr34, Lr67, Sr22, Sr33, Sr35, Sr45, Sr50, Tsn1, Yr36 (WKS1), Snn1, TaMLO-A1, TaMLO-B1, and TaMLO-D1, or is a gene encoding a protein having at least 90% (e.g., at least 90/a, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:363-398 in Table 9; (b) heterologous integration of a nucleic acid sequence that is encoded by at least one donor polynucleotide molecule and that includes a regulatory element that has a nucleotide sequence selected from SEQ ID NOs:66-256 at a predetermined locus in the 3' untranslated region or within 1000 nucleotides downstream of the stop codon of a gene of interest in the reference genome, wherein the gene of interest is selected from the group consisting of Fhb1, Lr34, Lr67, Sr22, Sr33, Sr35, Sr45, Sr50, Tsn1, Yr36 (WKS1), Snn1, TaMLO-A1, TaMLO-B1, and TaMLO-D1, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:363-398 in Table 9; (c) deletion, addition, or substitution of at least one nucleotide in a regulatory element that regulates expression of a gene of interest in the reference genome, wherein the gene of interest is selected from the group consisting of Fhb1, Lr34, Lr67, Sr22, Sr33, Sr35, Sr45, Sr50, Tsn1, Yr36 (WKS1), Snn1, TaMLO-A1, TaMLO-B1, and TaMLO-D1, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:363-398 in Table 9; (d) deletion, addition, or substitution of at least one nucleotide in coding sequence of a gene of interest in the reference genome, wherein the gene of interest is selected from the group consisting of Fhb1, Lr34, Lr67, Sr22, Sr33, Sr35, Sr45, Sr50, Tsn1, Yr36 (WKS1), Snn1, TaMLO-A1, TaMLO-B1, and TaMLO-D1, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:363-398 in Table 9; and (e) a combination of any of (a), (b), (c), and (d). In embodiments, the gene encoding a protein having at least 90% identity to a sequence selected from the group consisting of the sequences identified by SEQ ID NOs:363-398 is selected from the group consisting of the genomic sequences identified by SEQ ID NOs:581-616. In embodiments, the at least two genes of interest include at least one homeoallele each of two or more genes selected from the group consisting of Fhb1, Lr34, Lr67, Sr22, Sr33, Sr35, Sr45, Sr50, Tsn1, Yr36 (WKS1), Snn1, TaMLO-A1, TaMLO-B1, and TaMLO-D1. In embodiments, the modified genome further differs from the reference genome by including (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV ISM, SOD, APX, GS2, NAM, rbcL, IVR1, and a1, or (b) a predetermined modification in a gene encoding a protein having at least 90% identity to a sequence selected from the group consisting of the sequences identified by SEQ ID NOs:257-362 and 399-474 in Table 9, or (c) a predetermined modification in a genomic sequence selected from the group consisting of the sequences identified by SEQ ID NOs:475-580 and 617-692 in Table 9; wherein the predetermined modification is selected from the group consisting of (a) heterologous integration of a non-coding regulatory element sequence that is encoded by at least one donor polynucleotide molecule at a predetermined locus between 1-1000 nucleotides upstream of the start codon of the coding sequence of the gene; (b) heterologous integration of a non-coding regulatory element sequence that is encoded by at least one donor polynucleotide molecule at a predetermined locus in the 3' untranslated region or within 1000 nucleotides downstream of the stop codon of the gene; (c) deletion, addition, or substitution of at least one nucleotide in a regulatory element or non-coding sequence that regulates expression of the gene; (d) deletion, addition, or substitution of at least one nucleotide in coding sequence of the gene; and (e) a combination of any of (a), (b), (c), and (d).

Embodiments of the invention are related to wheat plants exhibiting modified flowering time, e.g., flowering time that begins earlier in the growing season, begins later in the growing season, or occurs over a longer period of time during the growing season, in comparison to that exhibited by a control wheat plant. Embodiments include a wheat plant having a modified genome that results in the wheat plant exhibiting modified flowering time in comparison to an unmodified wheat plant having an reference genome, wherein the modified genome differs from the reference genome by including predetermined modifications of at least two genes of interest (e.g., modification of regulatory sequence that affects expression of the gene of interest), wherein each of the predetermined modifications is selected from the group consisting of: (a) heterologous integration of a nucleic acid sequence that is encoded by at least one donor polynucleotide molecule and that includes a regulatory element having a nucleotide sequence selected from the group consisting of SEQ ID NOs:66-256 at a predetermined locus between 1-1000 nucleotides upstream of the start codon of the coding sequence of a gene of interest in the reference genome, wherein the gene of interest is selected from the group consisting of FT, FKF1, PhyB, WCO1, ZenMFT-3D, MADS, TaGI1, WAP1, NFYB-A, NFYB-B, and NFYB-D, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:399-424 in Table 9; (b) heterologous integration of a nucleic acid sequence that is encoded by at least one donor polynucleotide molecule and that includes a regulatory element that has a nucleotide sequence selected from SEQ ID NOs:66-256 at a predetermined locus in the 3' untranslated region or within 1000 nucleotides downstream of the stop codon of a gene of interest in the reference genome, wherein the gene of interest is selected from the group consisting of FT, FKF1, PhyB, WCO1, ZenMFT-3D, MADS, TaGI1, WAP1, NFYB-A, NFYB-B, and NFYB-D, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:399-424 in Table 9; (c) deletion, addition, or substitution of at least one nucleotide in a regulatory element that regulates expression of a gene of interest in the reference genome, wherein the gene of interest is selected from the group consisting of FT, FKF1, PhyB, WCO1, ZenMFT-3D, MADS, TaGI1, WAP1, NFYB-A, NFYB-B, and NFYB-D, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:399-424 in Table 9; (d) deletion, addition, or substitution of at least one nucleotide in coding sequence of a gene of interest in the reference genome, wherein the gene of interest is selected from the group consisting of FT, FKF1, PhyB, WCO1, ZenMFT-3D, MADS, TaGI1, WAP1, NFYB-A, NFYB-B, and NFYB-D, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:399-424 in Table 9; and (e) a combination of any of (a), (b), (c), and (d). In embodiments, the gene encoding a protein having at least 90% identity to a sequence selected from the group consisting of the sequences identified by SEQ ID NOs: 399-424 is selected from the group consisting of the genomic sequences identified by SEQ ID NOs:617-642. In embodiments, the at least two genes of interest include at least one homeoallele each of two or more genes selected from the group consisting of FT, FKF1, PhyB, WCO1, ZenMFT-3D, MADS, TaGI1, WAP1, NFYB-A, NFYB-B, and NFYB-D. In embodiments, the modified genome further differs from the reference genome by including (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, Lr34, Lr67, Sr22, Sr33, Sr35, Sr45, Sr50, Tsn1, Yr36 (WKS1), Snn1, TaMLO-A1, TaMLO-B1, TaMLO-D1, NAC1, Skp1, TIF, WCBP1, WRKY, TaSAG6, TaSAG3, TaSAG1, FeSOD, CWINV2SM, CWINV1SM, SOD, APX, GS2, NAM, rbcL, IVR1, and al, or (b) a predetermined modification in a gene encoding a protein having at least 90% identity to a sequence selected from the group consisting of the sequences identified by SEQ ID NOs:257-398 and 425-474 in Table 9, or (c) a predetermined modification in a genomic sequence selected from the group consisting of the sequences identified by SEQ ID NOs:475-616 and 643-692 in Table 9; wherein the predetermined modification is selected from the group consisting of (a) heterologous integration of a non-coding regulatory element sequence that is encoded by at least one donor polynucleotide molecule at a predetermined locus between 1-1000 nucleotides upstream of the start codon of the coding sequence of the gene; (b) heterologous integration of a non-coding regulatory element sequence that is encoded by at least one donor polynucleotide molecule at a predetermined locus in the 3' untranslated region or within 1000 nucleotides downstream of the stop codon of the gene; (c) deletion, addition, or substitution of at least one nucleotide in a regulatory element or non-coding sequence that regulates expression of the gene; (d) deletion, addition, or substitution of at least one nucleotide in coding sequence of the gene; and (e) a combination of any of (a), (b), (c), and (d).

Embodiments of the invention are related to wheat plants exhibiting improved photosynthesis, e.g., photosynthesis that is more efficient under given conditions of light (intensity, quality, timing, and duration), temperature, or other conditions, in comparison to photosynthesis in a control wheat plant. Embodiments include a wheat plant having a modified genome that results in the wheat plant exhibiting modified architecture in comparison to an unmodified wheat plant having an reference genome, wherein the modified genome differs from the reference genome by including predetermined modifications of at least two genes of interest (e.g., modification of regulatory sequence that affects expression of the gene of interest), wherein each of the predetermined modifications is selected from the group consisting of: (a) heterologous integration of a nucleic acid sequence that is encoded by at least one donor polynucleotide molecule and that includes a regulatory element having a nucleotide sequence selected from the group consisting of SEQ ID NOs:66-256 at a predetermined locus between 1-1000 nucleotides upstream of the start codon of the coding sequence of a gene of interest in the reference genome, wherein the gene of interest is selected from the group consisting of NAC1, Skp1, TIF, and WCBP1, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:425-434 in Table 9; (b) heterologous integration of a nucleic acid sequence that is encoded by at least one donor polynucleotide molecule and that includes a regulatory element that has a nucleotide sequence selected from SEQ ID NOs:66-256 at a predetermined locus in the 3' untranslated region or within 1000 nucleotides downstream of the stop codon of a gene of interest in the reference genome, wherein the gene of interest is selected from the group consisting of NAC1, Skp1, TIF, and WCBP1, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:425-434 in Table 9; (c) deletion, addition, or substitution of at least one nucleotide in a regulatory element that regulates expression of a gene of interest in the reference genome, wherein the gene of interest is selected from the group consisting of NAC1, Skp1, TIF, and WCBP1, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:425-434 in Table 9; (d) deletion, addition, or substitution of at least one nucleotide in coding sequence of a gene of interest in the reference genome, wherein the gene of interest is selected from the group consisting of NAC1, Skp1, TIF, and WCBP1, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:425-434 in Table 9; and (e) a combination of any of (a), (b), (c), and (d). In embodiments, the gene encoding a protein having at least 90% identity to a sequence selected from the group consisting of the sequences identified by SEQ ID NOs:425-434 is selected from the group consisting of the genomic sequences identified by SEQ ID NOs:643-652. In embodiments, the at least two genes of interest include at least one homeoallele each of two or more genes selected from the group consisting of NAC1, Skp1, TIF, and WCBP1. In embodiments, the modified genome further differs from the reference genome by including (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, Lr34, Lr67, Sr22, Sr33, Sr35, Sr45, Sr50, Tsn1, Yr36 (WKS1), Snn1, TaMLO-A1, TaMLO-B1, TaMLO-D1, FT, FKF1, PhyB, WCO1, ZenMFT-3D, MADS, TaGI1, WAP1, NFYB-A, NFYB-B, NFYB-D, WRKY, TaSAG6, TaSAG3, TaSAG1, FeSOD, CWINV2SM, CWINV1SM, SOD, APX, GS2, NAM, rbcL, IVR1, al, or (b) a predetermined modification in a gene encoding a protein having at least 90% identity to a sequence selected from the group consisting of the sequences identified by SEQ ID NOs:257-424 and 435-474 in Table 9, or (c) a predetermined modification in a genomic sequence selected from the group consisting of the sequences identified by SEQ ID NOs:475-642 and 653-692 in Table 9; wherein the predetermined modification is selected from the group consisting of (a) heterologous integration of a non-coding regulatory element sequence that is encoded by at least one donor polynucleotide molecule at a predetermined locus between 1-1000 nucleotides upstream of the start codon of the coding sequence of the gene; (b) heterologous integration of a non-coding regulatory element sequence that is encoded by at least one donor polynucleotide molecule at a predetermined locus in the 3' untranslated region or within 1000 nucleotides downstream of the stop codon of the gene; (c) deletion, addition, or substitution of at least one nucleotide in a regulatory element or non-coding sequence that regulates expression of the gene; (d) deletion, addition, or substitution of at least one nucleotide in coding sequence of the gene; and (e) a combination of any of (a), (b), (c), and (d).

Embodiments of the invention are related to wheat plants exhibiting modified senescence, e.g., senescence that begins earlier in the growing season, begins later in the growing season, or occurs over a longer period of time during the growing season, in comparison to that exhibited by a control wheat plant. Embodiments include a wheat plant having a modified genome that results in the wheat plant exhibiting modified senescence in comparison to an unmodified wheat plant having an reference genome, wherein the modified genome differs from the reference genome by including predetermined modifications of at least two genes of interest (e.g., modification of regulatory sequence that affects expression of the gene of interest), wherein each of the predetermined modifications is selected from the group consisting of: (a) heterologous integration of a nucleic acid sequence that is encoded by at least one donor polynucleotide molecule and that includes a regulatory element having a nucleotide sequence selected from the group consisting of SEQ ID NOs:66-256 at a predetermined locus between 1-1000 nucleotides upstream of the start codon of the coding sequence of a gene of interest in the reference genome, wherein the gene of interest is selected from the group consisting of WRKY, TaSAG6, TaSAG3, TaSAG1, FeSOD, CWINV2SM, CWINV 1SM, SOD, APX, GS2, NAM, rbcL, IVR1, and a1, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:435-474 in Table 9; (b) heterologous integration of a nucleic acid sequence that is encoded by at least one donor polynucleotide molecule and that includes a regulatory element that has a nucleotide sequence selected from SEQ ID NOs:66-256 at a predetermined locus in the 3' untranslated region or within 1000 nucleotides downstream of the stop codon of a gene of interest in the reference genome, wherein the gene of interest is selected from the group consisting of WRKY, TaSAG6, TaSAG3, TaSAG1, FeSOD, CWINV2SM, CWINV1SM, SOD, APX, GS2, NAM, rbcL, IVR1, and a1, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:435-474 in Table 9; (c) deletion, addition, or substitution of at least one nucleotide in a regulatory element that regulates expression of a gene of interest in the reference genome, wherein the gene of interest is selected from the group consisting of WRKY, TaSAG6, TaSAG3, TaSAG1, FeSOD, CWINV2SM, CWINV1SM, SOD, APX, GS2, NAM, rbcL, IVR1, and a1, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:435-474 in Table 9; (d) deletion, addition, or substitution of at least one nucleotide in coding sequence of a gene of interest in the reference genome, wherein the gene of interest is selected from the group consisting of WRKY, TaSAG6, TaSAG3, TaSAG1, FeSOD, CWINV2SM, CWINV 1SM, SOD, APX, GS2, NAM, rbcL, IVR1, and a1, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:435-474 in Table 9; and (e) a combination of any of (a), (b), (c), and (d). In embodiments, the gene encoding a protein having at least 90% identity to a sequence selected from the group consisting of the sequences identified by SEQ ID NOs:435-474 is selected from the group consisting of the genomic sequences identified by SEQ ID NOs:653-692. In embodiments, the at least two genes of interest include at least one homeoallele each of two or more genes selected from the group consisting of WRKY, TaSAG6, TaSAG3, TaSAG1, FeSOD, CWINV2SM, CWINV ISM, SOD, APX, GS2, NAM, rbcL, IVR1, and al. In embodiments, the modified genome further differs from the reference genome by including (a) a predetermined modification in at least one homeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, Lr34, Lr67, Sr22, Sr33, Sr35, Sr45, Sr50, Tsn1, Yr36 (WKS1), Snn1, TaMLO-A1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, and WCBP1, or (b) a predetermined modification in a gene encoding a protein having at least 90% identity to a sequence selected from the group consisting of the sequences identified by SEQ ID NOs:257-434 in Table 9, or (c) a predetermined modification in a genomic sequence selected from the group consisting of the sequences identified by SEQ ID NOs:475-652 in Table 9; wherein the predetermined modification is selected from the group consisting of (a) heterologous integration of a non-coding regulatory element sequence that is encoded by at least one donor polynucleotide molecule at a predetermined locus between 1-1000 nucleotides upstream of the start codon of the coding sequence of the gene; (b) heterologous integration of a non-coding regulatory element sequence that is encoded by at least one donor polynucleotide molecule at a predetermined locus in the 3' untranslated region or within 1000 nucleotides downstream of the stop codon of the gene; (c) deletion, addition, or substitution of at least one nucleotide in a regulatory element or non-coding sequence that regulates expression of the gene; (d) deletion, addition, or substitution of at least one nucleotide in coding sequence of the gene; and (e) a combination of any of (a), (b), (c), and (d).

The wheat genes identified by name or sequence identifier (SEQ ID NO:) in Table 9 are associated with various phenotypes or traits including plant architecture, abiotic stress resistance, disease resistance, modified flowering time, photosynthesis, and modified senescence. Modification of two or more genes as disclosed in Table 9 is carried out to provide an improved wheat plant having one or more of these desirable traits. In embodiments, these phenotypes and traits include sub-categories of traits, and may overlap. For example, embodiments of wheat plants exhibiting modified architecture also exhibit other phenotypes or traits such as modified flowering time or improved resistance to abiotic stress. In an example, a wheat plant exhibiting modified root architecture may further exhibit improved resistance to drought conditions, improved resistance to insect pests, and improved resistance to lodging. In embodiments, a wheat plant having one or more of the modifications disclosed herein exhibits improved yield, in comparison to a control wheat plant lacking the modifications.

Each of the genes listed in Table 9 can be modified from the sequence as found in a reference wheat genome, using any of the gene modification methods disclosed herein. In particular, each of the genes can be modified using the precise modification methods described herein which introduce predetermined changes at specific locations in a gene of interest in the reference genome, in the absence of off-target effects. In embodiments, each of the genes in Table 9 may be modified, either singly or in multiplexed fashion, using techniques employing sequence-specific nucleases as disclosed herein (see, e.g., Examples 1-17). Embodiments include those wherein at least one non-coding regulatory element is heterologously integrated, e.g., at a predetermined locus between 1-1000 nucleotides upstream of the start codon of the coding sequence of a gene of interest in a reference wheat genome, or at a predetermined locus in the 3' untranslated region or within 1000 nucleotides downstream of the stop codon of a gene of interest in a reference wheat genome, or within an intron or within an exon of a gene of interest in a reference wheat genome, thereby providing a modified gene of interest and thus a modified wheat genome. Embodiments include wheat plants having a modified genome in comparison to a control wheat plant having an unmodified, reference genome, wherein the modified genome includes predetermined modifications of at least two genes disclosed in Table 9, wherein the predetermined modifications are selected from (a) heterologous integration of at least one non-coding regulatory element at a predetermined locus between 1-1000 nucleotides upstream of the start codon of the coding sequence of a gene of interest in the reference wheat genome, (b) heterologous integration of at least one non-coding regulatory element at a predetermined locus in the 3' untranslated region or within 1000 nucleotides downstream of the stop codon of a gene of interest in the reference wheat genome, and (c) heterologous integration of at least one non-coding regulatory element within an intron or within an exon of a gene of interest in the reference wheat genome.

Embodiments of the invention are related to a wheat plant having a modified genome in comparison to an unmodified wheat plant having an reference genome, wherein the modified genome differs from the reference genome by including predetermined modifications of one or more genes of interest, selected from the genes identified by gene name in Table 9, or encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:257-474, or selected from the genomic sequences identified as SEQ ID NOs:475-692. In embodiments, the predetermined modifications of at least two genes of interest include modifications of only non-coding sequences of the reference genome, or of only coding sequences of the reference genome, or of a combination of coding and non-coding sequences of the reference genome. In embodiments, at least one of the predetermined modifications of at least two genes of interest results in increased expression of the gene of interest, relative to expression of the gene of interest in the reference genome. In embodiments, increased expression of the gene of interest is achieved by increasing endogenous promoter activity of the gene of interest (e.g., heterologous integration of a regulatory element between 0 and 1000 nucleotides of the start codon of the gene of interest), or by stabilizing the mRNA transcript of the gene of interest. In embodiments, at least one of the predetermined modifications of at least two genes of interest results in decreased expression of the gene of interest, relative to expression of the gene of interest in the reference genome. In embodiments, decreased expression of the gene of interest is achieved by reducing endogenous promoter activity of the gene of interest (e.g., by deletion of one or more nucleotides in the promoter or 5' UTR of the gene of interest, or by heterologous integration of a regulatory element between 0 and 1000 nucleotides of the start codon of the gene of interest), or by heterologous integration of a regulatory element between 0 and 1000 nucleotides of the start codon of the gene of interest), or by destabilizing the mRNA transcript of the gene of interest. In embodiments, at least one of the predetermined modifications of at least two genes of interest includes multiple predetermined modifications of a single gene of interest in the reference genome. In embodiments, the predetermined modifications of at least two genes of interest includes a predetermined modification of multiple homeoalleles of a gene of interest. In embodiments, the wheat plant is a *Triticum* sp. or an *Aegilops* sp. (e.g., *Aegilops tauschii*). In specific embodiments, the wheat plant is common or bread wheat (*Triticum aestivum*), spelt (*Triticum spelta*), emmer (*Triticum dicoccum*), einkorn (*Triticum monococcum*), durum wheat (*Triticum durum*), or a synthetic hexaploid wheat ("SHW", see, e.g., Ogbonnaya et al. "Synthetic Hexaploids: Harnessing Species of the Primary Gene Pool for Wheat Improvement" In: Plant Breeding Reviews, Volume 37, 1st edition; edited by Jules Janick, published 2013 by John Wiley & Sons, Inc.). In embodiments, the wheat plant is an allotetraploid, wherein the reference genome consists of an A genome and a B genome, and wherein at least one of the predetermined modifications of at least two genes of interest includes: (a) a predetermined modification of both homeoalleles of the gene of interest in the A genome, (b) a predetermined modification of both homeoalleles of the gene of interest in the B genome, or (c) a predetermined modification of at least two (e.g., 2, 3, or all 4) homeoalleles of the gene of interest in the A genome and the B genome. In embodiments, the wheat plant is an allohexaploid, wherein the reference genome consists of an A genome, a B genome, and a D genome, and wherein at least one of the predetermined modifications of at least two genes of interest includes: a) a predetermined modification of both homeoalleles of the gene of interest in the A genome, (b) a predetermined modification of both homeoalleles of the gene of interest in the B genome, (c) a predetermined modification of both homeoalleles of the gene of interest in the D genome, or (d) a predetermined modification of at least two (e.g., 2, 3, 4, 5, or all 6) homeoalleles of the gene of interest in any combination of the A genome, the B genome, and the D genome. In embodiments, the wheat plant is an allotetraploid, wherein the reference genome consists of an A genome and a B genome, and wherein the A genome only, the B genome only, or both the A and B genomes is heterozygous for at least one of the predetermined modifications of at least two genes of interest. In embodiments, the wheat plant is an allotetraploid, wherein the reference genome consists of an A genome and a B genome, and wherein the A genome only, the B genome only, or both the A and B genomes is homozygous for at least one of the predetermined modifications of at least two genes of interest. In embodiments, the wheat plant is an allohexaploid, wherein the reference genome consists of an A genome, a B genome, and a D genome, and wherein the A genome only, the B genome only, the D genome only, or any combination of the A, B, and D genomes is heterozygous for at least one of the predetermined modifications of at least two genes of interest. In embodiments, the wheat plant is an allohexaploid, wherein the reference genome consists of an A genome, a B genome, and a D genome, and wherein the A genome only, the B genome only, the D genome only, or any combination of the A, B, and D genomes is homozygous for at least one of the predetermined modifications of at least two genes of interest. In embodiments, the modified genome is more than 99.9% identical to the reference genome. In embodiments, the modified genome is devoid of mitotically or meiotically generated genetic or epigenetic changes relative to the reference genome. In embodiments, the modified genome includes a difference of epigenetic changes in less than 0.01% of the genome relative to the reference genome. In embodiments, the modified genome includes: (a) a difference of DNA methylation in less than 0.01% of the genome, relative to the reference genome; or (b) a difference of DNA methylation in less than 0.005% of the genome, relative to the reference genome; or (c) a difference of DNA methylation in less than 0.001% of the genome, relative to the reference genome; see, for example, Stelpflug et al. (2014) *Genetics*, 198:209-218; doi: 10.1534/genetics.114.165480. In embodiments, the gene of interest is located on a chromosome in the wheat plant cell, and the modified genome includes: (a) a difference of DNA methylation in less than 0.01% of the portion of the genome that is contained within the chromosome containing the gene of interest, relative to the reference genome; or (b) a difference of DNA methylation in less than 0.005% of the portion of the genome that is contained within the chromosome containing the gene of interest, relative to the reference genome; or (c) a difference of DNA methylation in less than 0.001% of the portion of the genome that is contained within the chromosome containing the gene of interest, relative to the reference genome. In embodiments, the modified genome has not more unintended changes in comparison to the reference genome than $1 \times 10^{-8}$ mutations per bp per replication.

Embodiments of the invention are related to a wheat plant having a modified genome in comparison to an unmodified wheat plant having an reference genome, wherein the modified genome differs from the reference genome by including predetermined modifications of one or more genes of interest, selected from the genes identified by gene name in Table 9, or encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:257-474, or selected from the genomic sequences identified as SEQ ID NOs:475-692, wherein the predetermined modifications are selected from (a) heterologous integration of a nucleic acid sequence that is encoded by at least one donor polynucleotide molecule and that includes a regulatory element, at a predetermined locus between 1-1000 nucleotides upstream of the start codon of the coding sequence of a gene of interest in the reference wheat genome, (b) heterologous integration of a nucleic acid sequence that is encoded by at least one donor polynucleotide molecule and that includes a regulatory element, at a predetermined locus in the 3' untranslated region or within 1000 nucleotides downstream of the stop codon of a gene of interest in the reference wheat genome, and (c) heterologous integration of a nucleic acid sequence that is encoded by at least one donor polynucleotide molecule and that includes a regulatory element, within an intron or within an exon of a gene of interest in the reference wheat genome. In embodiments, the heterologous integration of a nucleic acid sequence is by an HDR mechanism. In embodiments, the heterologous integration of a nucleic acid sequence is by an NHEJ mechanism; in such embodiments the donor polynucleotide molecule lacks homology to the genome sequences adjacent to the integration site, i.e., lacks homology to the predetermined locus in the reference genome. In embodiments, the donor polynucleotide molecule includes ribonucleotides, deoxyribonucleotides, dideoxyribonucleotides, non-canonical nucleotides, and chemically modified nucleotides. In embodiments, the donor polynucleotide molecule is selected from the group consisting of a blunt-ended double-stranded DNA, a double-stranded DNA with at least one unpaired nucleotide at one terminus or at both termini, a single-stranded DNA, a blunt-ended double-stranded DNA/RNA hybrid, and a double-stranded DNA/RNA hybrid with at least one unpaired nucleotide at one terminus or at both termini.

Embodiments of the invention are related to a wheat plant having a modified genome in comparison to an unmodified wheat plant having an reference genome, wherein the modified genome differs from the reference genome by including predetermined modifications of one or more genes of interest, selected from the genes identified by gene name in Table 9, or encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:257-474, or selected from the genomic sequences identified as SEQ ID NOs:475-692, wherein the predetermined modifications include deletion, addition, or substitution of at least one nucleotide in a regulatory element that regulates expression of a gene of interest in the reference genome or deletion, addition, or substitution of at least one nucleotide in coding sequence of a gene of interest in the reference genome. In embodiments, deletion, addition, or substitution of at least one nucleotide occurs at a double-strand break in the reference genome or between multiple double-strand breaks in the reference genome.

Modifications to the wheat genes listed in Table 9 may be combined with modifications to other sequences in the wheat genome, such as the genes disclosed in Table 10, for the purpose of improving one or more wheat traits. In such embodiments, the modified wheat genome further differs from the reference wheat genome by including (a) a predetermined modification in at least one homoeoallele of a gene disclosed in Table 10 and selected from TsVP, ZmSEC14p, ACC synthase, D-myo-inositol-3-phosphate synthase (IPS), ZmbZIP72, ZmPLC1, ZmGOLS2, ZmPIS, ZmNF-YB, ZmPsbA, HB2, ZmPP2C2, ZmCIPK16, ZmSAPK8, OsABA8ox3, OsORAP1, OsDIS1, OsVPE3, OsRZFP34, ZFP185, DCA1, OsSRFP1, SQS, OsTPP1, SAPK6, JIOsPR10, OsClpD1, MSD1, OsWR1, OsTPS1, OsGS, OgTT1, OsFKBP20, OsANN1, OsSIK1, OsNHX1, OsMGD, OsDHODH1, Oshsp16.9, OsGME-2, OsChl1, OsCYP18-2, OsCNX, OsCBL8, OsCDPK13, OsRAN2, OsGGP, OVP1, ZFP177, RGG1, OsEm1, CTB4a, GS2, COLD1, OsACA6, OsRab7, OsTOP6A 1, osHsp101, OsAMTR1, Rubisco activase, OsSPX1, OsGME-1, OsMPG1, SNAC3, OsSDIR1, OsPgk2a-P, glyoxalase II, OsPUB15, OsIMP, OsHBP1b, OsCYP2, OsPEXI1 (Os03g0302000), OsCPK4, EG1, OsCBSX4, OsSIDP366, OsSUV3, GA2ox6, SAPK9, OsRbohA, OsCAS, OsRacB, OsECS, OsVTE1, SAPK4, OsCDPK7, NUS1, OsGL1-2, OsSce1, OsPsbR1, OsCYP21-4, OsPIP1;3, OsCIPK03, OsGRX8, OsMIOX, SLG, CKX3, HAP3A, CDPK9, JAR1, MFO1, LFY, ZMM4, HD3A, MADS24, BRD2, SK2(T)(SCL, FGR), SLR1, ILI5, GW2, ZmPTR1, GA2OX3, ETR2, EXPA4, D2, D61, PDR6, ACO4, Rab6a, OsSERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, ZmPP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, Zm NPR1, Zm LOX3, ALD1, RLCK185, LCB2A1, PhyB1, COP1, WRKY51, Os PLDbeta1, RAC5, OsCPK12, GF14e, Os SBP, OsHIR1, BWMKY1, AOS1, Os LOL2, GH3, GH3-8, XB3, GLP1, Os MAPK6, ACS2, OsLRR1, OsMPK3, Os SGT1, GAP1, Os RAC1, Os TPC1, GH3-2, OsBIANK1, CIPK14, OS BIDK1, OsMPK6, Os MKK4, Gns1, Os CCR1, Os MAPKY5, RACK1A, OsG1, OsphyB, Hd16, RCN1, SPL11, Spin1, PAL, PAL1, OsAGPS1, NRAMP3, OsMTP1, ATM3, OsYSL2, DMAS1, OsMRP5, OsSULTR3;3, AMT1;2, OsAMT3;1, OsNRT2.3b, GS1;2, OsARG, OsNRT2.1, AMT1;1, AlaAT, ABC1, NADH-GOGAT, RBCS, NLA1, PHF1, OsMYB2P-1, CASTOR, INO1, sedoheptulose-1,7-bisphosphatase (SBPase), Fbpase; fructose-1,6-bisphosphatase, OsDET1, Os02g0465900, OsHox32, OsBZR1, OsNAL1, AlaAT, ZmNRT2.2, esp1, ZmGW2-CHR5, Asn synthetase, AspAT, NAD(H)-dependent GOGAT 1, Gln1-3, obap1, ZmAAP4 (amino acid permease 4), crtRB1, ZmMRP1, ZmDA1, ZmDAR1, APS1, 6-phospho-fructokinase, wx1, shrunken 1, sus1, brittle endosperm bt2, sugary 1, sbe1, MADS22, RT, GAMYB, HSP90, AOS2, SPS1, NYC1, D35, PIMT1, PIMT2, TYDC, TEM, CYP703A3, D1|D2|Os07g0558500, ABA8OX1, OsABA2, NCED1, ZEP1, ALDH7, CHS1, APX2, DOS, HOX33, NYC3, and APX1 as disclosed in Table 10, or (b) a predetermined modification in a gene encoding a protein having at least 90% identity to a sequence selected from SEQ ID NOs:693-976 as disclosed in Table 10, or (c) a predetermined modification in a genomic sequence selected from SEQ ID NO:977-1260 as disclosed in Table 10. In embodiments, the predetermined modification in the gene disclosed in Table 10 is at least one selected from: (a)

heterologous integration of a nucleic acid sequence that is encoded by at least one donor polynucleotide molecule and that includes a regulatory element (e.g., a regulatory element having a nucleotide sequence selected from SEQ ID NOs: 66-256) at a predetermined locus between 0-1000 nucleotides upstream of the start codon of the coding sequence of the gene disclosed in Table 10 or 0-1000 nucleotides upstream of the start codon of the coding sequence of the gene disclosed in Table 10; (b) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus in the 3' untranslated region (e.g., within 1000 nucleotides downstream of the stop codon) of the gene disclosed in Table 10; (c) deletion, addition, or substitution of at least one nucleotide in a regulatory element that regulates expression of the gene disclosed in Table 10; (d) deletion, addition, or substitution of at least one nucleotide in coding sequence of the gene disclosed in Table 10; and (e) a combination of any of (a), (b), (c), and (d); wherein the gene disclosed in Table 10 is selected from TsVP, ZmSEC14p, ACC synthase, D-myo-inositol-3-phosphate synthase (IPS), ZmbZIP72, ZmPLC1, ZmGOLS2, ZmPIS, ZmNF-YB, ZmPsbA, HB2, ZmPP2C2, ZmCIPK16, ZmSAPK8, OsABA8ox3, OsORAP1, OsDIS1, OsVPE3, OsRZFP34, ZFP185, DCA1, OsSRFP1, SQS, OsTPP1, SAPK6, JIOsPR10, OsClpD1, MSD1, OsWR1, OsTPS1, OsGS, OgTT1, OsFKBP20, OsANN1, OsSIK1, OsNHX1, OsMGD, OsDHODH1, Oshsp16.9, OsGME-2, OsChI1, OsCYP18-2, OsCNX, OsCBL8, OsCDPK13, OsRAN2, OsGGP, OVP1, ZFP177, RGG1, OsEm1, CTB4a, GS2, COLD1, OsACA6, OsRab7, OsTOP6A1, osHsp101, OsAMTR1, Rubisco activase, OsSPX1, OsGME-1, OsMPG1, SNAC3, OsSDIR1, OsPgk2a-P, glyoxalase II, OsPUB15, OsIMP, OsHBP1b, OsCYP2, OsPEX11 (Os03g0302000), OsCPK4, EG1, OsCBSX4, OsSIDP366, OsSUV3, GA2ox6, SAPK9, OsRbohA, OsCAS, OsRacB, OsECS, OsVTE1, SAPK4, OsCDPK7, NUS1, OsGL1-2, OsSce1, OsPsbR1, OsCYP21-4, OsPIP1;3, OsCIPK03, OsGRX8, OsMIOX, SLG, CKX3, HAP3A, CDPK9, JAR1, MFO1, LFY, ZMM4, HD3A, MADS24, BRD2, SK2(T) (SCL, FGR), SLR1, ILI5, GW2, ZmPTR1, GA2OX3, ETR2, EXPA4, D2, D61, PDR6, ACO4, Rab6a, OsSERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, ZmPP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, Zm NPR1, Zm LOX3, ALD1, RLCK185, LCB2A 1, PhyB1, COP1, WRKY51, Os PLD-beta1, RAC5, OsCPK12, GF14e, Os SBP, OsHIR1, BWMKY1, AOS1, Os LOL2, GH3, GH3-8, XB3, GLP1, Os MAPK6, ACS2, OsLRR1, OsMPK3, Os SGT1, GAP1, Os RAC1, Os TPC1, GH3-2, OsBIANK1, CIPK14, OS BIDK1, OsMPK6, Os MKK4, Gns1, Os CCR1, Os MAPKY5, RACK1A, OsG1, OsphyB, Hd16, RCN1, SPL11, Spin1, PAL, PAL1, OsAGPS1, NRAMP3, OsMTP1, ATM3, OsYSL2, DMAS1, OsMRP5, OsSULTR3;3, AMT1;2, OsAMT3;1, OsNRT2.3b, GS1;2, OsARG, OsNRT2.1, AMT1;1, AlaAT, ABC1, NADH-GOGAT, RBCS, NLA1, PHF1, OsMYB2P-1, CASTOR, INO1, sedoheptulose-1,7-bisphosphatase (SBPase), Fbpase; fructose-1,6-bisphosphatase, OsDET1, Os02g0465900, OsHox32, OsBZR1, OsNAL1, AlaAT, ZmNRT2.2, esp1, ZmGW2-CHR5, Asn synthetase, AspAT, NAD(H)-dependent GOGAT 1, Gln1-3, obap1, ZmAAP4 (amino acid permease 4), crtRB1, ZmMRP1, ZmDA1, ZmDAR1, APS1, 6-phospho-fructokinase, wx1, MADS22, RT, GAMYB, HSP90, AOS2, SPS1, NYC1, D35, PIMT1, PIMT2, TYDC, TEM, CYP703A3, D1|D2|Os07g0558500, ABA8OX1, OsABA2, NCED1, ZEP1, ALDH7, CHS1, APX2, DOS, HOX33, NYC3, and APX1 as disclosed in Table 10, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs: 693-976. The results of these combined modifications of the wheat genes identified by gene name or by sequence identifier in Table 9 and Table 10 on a trait or traits may be additive or synergistic. Any of the wheat sequences of Table 9 and Table 10 may also be modified for the purpose of tracking the expression or localizing the expression or activity of the listed genes and gene products, for example, by modifying the expression pattern to a desired specificity (e.g., cell- or tissue-specific, developmentally specific, temporally specific, or inducibly specific) by methods disclosed in this specification, such as by the addition or deletion of a regulatory element (e.g., a small RNA recognition site or a regulatory element that is recognized by a transcription factor, hormone, or other signal) to the gene or to regulatory sequence that affects the gene's expression.

Further embodiments of the invention are related to progeny seed and plants of the wheat plant having a modified genome as has been specifically described in detail in this Example. Embodiments include seed of the wheat plant having a modified genome and progeny wheat plants of the wheat plant having a modified genome. In embodiments of the wheat plant having a modified genome, or of its progeny wheat plant or seed, the modified genome is associated with a trait selected from the group consisting of modified architecture, improved abiotic stress tolerance, improved disease resistance or tolerance, modified flowering time, improved photosynthesis efficiency, and modified senescence; in embodiments, related sub-categories of traits include, but are not limited to, e.g., changes in abscisic acid (ABA) signaling or response, biomass, cold tolerance, drought tolerance, tolerance to high temperatures, tolerance to low temperatures, salt tolerance, fertilization, fertility, flowering time, flower architecture, inflorescence architecture, lodging resistance, root architecture, shoot architecture, leaf architecture, yield; disease resistance, insect resistance, population density stress, shading stress, photosynthesis and respiration traits, seed weight, drydown rate, grain size, nitrogen utilization, oil production, oil metabolism, protein production, protein metabolism, provitamin A or carotenoid production, provitamin A or carotenoid metabolism, seed composition, seed filling (including sugar and nitrogen transport), starch production, and starch metabolism. Embodiments also include a processed product made from the seed of the wheat plant having a modified genome, a processed product made from the wheat plant having a modified genome, and a processed product made from progeny wheat plants of the wheat plant having a modified genome. Thus, a related embodiment is a method of manufacturing a processed wheat product, including the steps of: (a) growing a wheat plant having a modified genome as has been described in detail in this Example; and (b) processing the wheat plant into a processed wheat product, thereby manufacturing a processed wheat product. In embodiments, the processed wheat product is selected from the group consisting of intact wheat grains, wheat berries, cracked wheat, parched wheat, malt, grits, groats, semolina, middlings, flakes, flour, meal, bran, germ, endosperm, starch, gluten, protein, oil, chaff, fibre, and straw.

Additional embodiments are related to detection methods for identifying a wheat plant that has been subjected to genomic modification according to the methods described herein, where that modification method yields a low frequency of off-target mutations. A given off-target mutation that is found to result in a unique sequence in the genome and that does not result in an undesirable phenotype or trait, preferably one that results in no change in any coding sequence, can be used as an identifiable marker in the modified wheat plant which may be then unambiguously identified by suitable detection methods. Such detection methods include a step of identifying the off-target mutations (e.g., an insertion of a non-specific sequence, a deletion, or an indel resulting from the use of the genome editing agents, or non-specific insertions of part or all of a sequence encoded by one or more donor polynucleotide molecules at one or more coding or non-coding loci in a genome). Such "track and trace" detection methods can be used to track the movement of a wheat plant cell or wheat plant or product thereof through a supply chain. The presence of such an identified mutation in a processed product or commodity product is prima facie evidence that the product contains, or is derived from, a wheat plant cell, wheat plant, or wheat seed of this invention. In related embodiments, the presence of the off-target mutations is detected using PCR, a chip-based assay, probes specific for the mutation, or any other technique known in the art to be useful for detecting the presence of particular nucleic acid sequences.

Example 19

Various embodiments of this invention are related to modifications of genes of interest in a wheat plant, wherein the genes of interest are identified by gene name or by a sequence identifier (SEQ ID NO:) in Table 10. Embodiments of this invention are related to a wheat plant having a modified genome in comparison to an unmodified wheat plant having an reference genome, wherein the modified genome differs from the reference genome by including predetermined modifications of one or more genes of interest, selected from the genes identified by gene name in Table 10, or encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:693-976, or selected from the genomic sequences identified by SEQ ID NOs:977-1260; embodiments include those wherein the modified genome differs from the reference genome by including multiple predetermined modifications of one or more genes of interest or multiple predetermined modifications of more than one homeoallele of a given gene of interest. In many embodiments the modified genome results in the wheat plant exhibiting a desirable phenotype or trait, in comparison to a wheat plant having the unmodified reference genome.

Table 10 provides a selection of common wheat (*Triticum aestivum*) genes identified by gene name (taken from a monocot orthologue), gene ID, and sequence identifier (SEQ ID NO:), grouped according to a phenotype or trait expected in a wheat plant in which one or more of these genes is modified in comparison to an unmodified wheat plant having a reference genome.

TABLE 10

| Trait | Trait subcategory | Orthologue Gene Name | Expression change | Gene ID* | Protein SEQ ID NO: | Genomic DNA SEQ ID NO: |
|---|---|---|---|---|---|---|
| Abiotic stress | Biomass | TsVP | + | TraesCS7B01G433800.1 | 693 | 977 |
| Abiotic stress | Cold tolerance | SEC14p | + | TraesCS6D01G149100.1 | 694 | 978 |
| Abiotic stress | Drought tolerance | ACC synthase | − | TraesCS4D01G058200.1 | 695 | 979 |
| Abiotic stress | Drought tolerance | D-myo-inositol-3-phosphate synthase (IPS) | + | TraesCS4A01G038500.1 | 696 | 980 |
| Abiotic stress | Drought tolerance | bZIP72 | + | TraesCS3B01G220400.2 | 697 | 981 |
| Abiotic stress | Drought tolerance | PLC1 | + | TraesCS5A01G155300.1 | 698 | 982 |
| Abiotic stress | Drought tolerance | GOLS2 | + | TraesCS4D01G180800.1 | 699 | 983 |
| Abiotic stress | Drought tolerance | PIS | + | TraesCS2A01G469200.1 | 700 | 984 |
| Abiotic stress | Drought tolerance | NF-YB | + | TraesCS3D01G347000.1 | 701 | 985 |
| Abiotic stress | Drought tolerance | PsbA | + | TraesCS1D01G179900.1 | 702 | 986 |
| Abiotic stress | flooding tolerance | HB2 | + | TraesCS1A01G338400.1 | 703 | 987 |
| Abiotic stress | Low temperature tolerance | PP2C2 | + | TraesCS3B01G240000.1 | 704 | 988 |
| Abiotic stress | Salt tolerance | CIPK16 | + | TraesCS5A01G225300.1 | 705 | 989 |
| Abiotic stress | Salt tolerance | SAPK8 | + | TraesCS5D01G411900.1 | 706 | 990 |
| Abiotic stress | | ABA8ox3 | − | TraesCS5B01G236500.1 | 707 | 991 |

TABLE 10-continued

| Trait | Trait subcategory | Orthologue Gene Name | Expression change | Gene ID* | Protein SEQ ID NO: | Genomic DNA SEQ ID NO: |
|---|---|---|---|---|---|---|
| Abiotic stress | | RAP1 | − | TraesCS5D01G199900.1 | 708 | 992 |
| Abiotic stress | | DIS1 | − | TraesCS4A01G148400.2 | 709 | 993 |
| Abiotic stress | | VPE3 | − | TraesCS6B01G285900.1 | 710 | 994 |
| Abiotic stress | | RZFP34 | − | TraesCS3B01G323600.3 | 711 | 995 |
| Abiotic stress | | ZFP185 | − | TraesCS6D01G154100.1 | 712 | 996 |
| Abiotic stress | | DCA1 | − | TraesCS1B01G159900.2 | 713 | 997 |
| Abiotic stress | | SRFP1 | − | TraesCS4D01G064500.2 | 714 | 998 |
| Abiotic stress | | SQS | − | TraesCS5A01G454500.1 | 715 | 999 |
| Abiotic stress | | TPP1 | + | TraesCS6D01G230500.1 | 716 | 1000 |
| Abiotic stress | | SAPK6 | + | TraesCS2D01G302500.1 | 717 | 1001 |
| Abiotic stress | | JIOsPR10 | + | TraesCS1B01G115600.1 | 718 | 1002 |
| Abiotic stress | | ClpD1 | + | TraesCS5A01G321300.1 | 719 | 1003 |
| Abiotic stress | | MSD1 | + | TraesCS2A01G537100.1 | 720 | 1004 |
| Abiotic stress | | WR1 | + | TraesCS6A01G181400.2 | 721 | 1005 |
| Abiotic stress | | TPS1 | + | TraesCS1B01G351600.1 | 722 | 1006 |
| Abiotic stress | | GS | + | TraesCS6B01G327500.1 | 723 | 1007 |
| Abiotic stress | | TT1 | + | TraesCS3B01G319500.2 | 724 | 1008 |
| Abiotic stress | | FKBP20 | + | TraesCS1D01G282500.1 | 725 | 1009 |
| Abiotic stress | | ANN1 | + | TraesCS6A01G300400.1 | 726 | 1010 |
| Abiotic stress | | SIK1 | + | TraesCS4A01G422700.1 | 727 | 1011 |
| Abiotic stress | | NHX1 | + | TraesCS2B01G141900.2 | 728 | 1012 |
| Abiotic stress | | MGD | + | TraesCS6D01G352200.1 | 729 | 1013 |
| Abiotic stress | | DHODH1 | + | TraesCS6D01G278900.1 | 730 | 1014 |
| Abiotic stress | | hsp16.9 | + | TraesCSU01G164000.1 | 731 | 1015 |
| Abiotic stress | | GME-2 | + | TraesCS5B01G302500.1 | 732 | 1016 |
| Abiotic stress | | ChI1 | + | TraesCS3B01G379900.1 | 733 | 1017 |
| Abiotic stress | | CYP18-2 | + | TraesCS7A01G279300.1 | 734 | 1018 |
| Abiotic stress | | CNX | + | TraesCS6B01G129800.1 | 735 | 1019 |
| Abiotic stress | | CBL8 | + | TraesCS1B01G272000.2 | 736 | 1020 |
| Abiotic stress | | CDPK13 | + | TraesCS4D01G318400.2 | 737 | 1021 |
| Abiotic stress | | RAN2 | + | TraesCS1D01G420600.2 | 738 | 1022 |
| Abiotic stress | | GGP | + | TraesCS5D01G122900.1 | 739 | 1023 |
| Abiotic stress | | OVP1 | + | TraesCS7B01G433800.1 | 740 | 1024 |
| Abiotic stress | | ZFP177 | + | TraesCS2D01G246800.3 | 741 | 1025 |
| Abiotic stress | | RGG1 | + | TraesCS5B01G381300.1 | 742 | 1026 |
| Abiotic stress | | Em1 | + | TraesCS1D01G226000.1 | 743 | 1027 |
| Abiotic stress | | CTB4a | + | TraesCS2A01G012900.1 | 744 | 1028 |

TABLE 10-continued

| Trait | Trait subcategory | Orthologue Gene Name | Expression change | Gene ID* | Protein SEQ ID NO: | Genomic DNA SEQ ID NO: |
|---|---|---|---|---|---|---|
| Abiotic stress | | GS2 | + | TraesCS2D01G500600.1 | 745 | 1029 |
| Abiotic stress | | COLD1 | + | TraesCS2B01G458500.1 | 746 | 1030 |
| Abiotic stress | | ACA6 | + | TraesCS2B01G454000.2 | 747 | 1031 |
| Abiotic stress | | Rab7 | + | TraesCS3D01G290000.1 | 748 | 1032 |
| Abiotic stress | | TOP6A1 | + | TraesCS5D01G401100.1 | 749 | 1033 |
| Abiotic stress | | Hsp101 | + | TraesCS1B01G352400.1 | 750 | 1034 |
| Abiotic stress | | AMTR1 | + | TraesCS1B01G308900.1 | 751 | 1035 |
| Abiotic stress | | Rubisco activase | + | TraesCS4B01G140300.1 | 752 | 1036 |
| Abiotic stress | | SPX1 | + | TraesCS7A01G376200.1 | 753 | 1037 |
| Abiotic stress | | GME-1 | + | TraesCS1D01G410200.1 | 754 | 1038 |
| Abiotic stress | | MPG1 | + | TraesCS3B01G395400.1 | 755 | 1039 |
| Abiotic stress | | SNAC3 | + | TraesCS3B01G126200.3 | 756 | 1040 |
| Abiotic stress | | SDIR1 | + | TraesCS4D01G209300.2 | 757 | 1041 |
| Abiotic stress | | Pgk2a-P | + | TraesCS6A01G158300.1 | 758 | 1042 |
| Abiotic stress | | glyoxalase II | + | TraesCS5B01G303100.1 | 759 | 1043 |
| Abiotic stress | | PUB15 | + | TraesCS3D01G527900.1 | 760 | 1044 |
| Abiotic stress | | IMP | + | TraesCS4D01G151200.1 | 761 | 1045 |
| Abiotic stress | | HBP1b | + | TraesCS3B01G220400.2 | 762 | 1046 |
| Abiotic stress | | CYP2 | + | TraesCS6D01G066700.1 | 763 | 1047 |
| Abiotic stress | | PEX11 (Os03g0302000) | + | TraesCS4B01G186600.1 | 764 | 1048 |
| Abiotic stress | | CPK4 | + | TraesCS6B01G111800.1 | 765 | 1049 |
| Abiotic stress | | EG1 | + | TraesCS3B01G427100.1 | 766 | 1050 |
| Abiotic stress | | CBSX4 | + | TraesCS4A01G247300.1 | 767 | 1051 |
| Abiotic stress | | SIDP366 | + | TraesCS7B01G332200.1 | 768 | 1052 |
| Abiotic stress | | SUV3 | + | TraesCS5B01G389300.1 | 769 | 1053 |
| Abiotic stress | | GA2ox6 | + | TraesCS2A01G379000.1 | 770 | 1054 |
| Abiotic stress | | SAPK9 | + | TraesCS4D01G078100.2 | 771 | 1055 |
| Abiotic stress | | RbohA | + | TraesCS3D01G279900.1 | 772 | 1056 |
| Abiotic stress | | CAS | + | TraesCS6A01G290600.1 | 773 | 1057 |
| Abiotic stress | | RacB | + | TraesCS6D01G068500.2 | 774 | 1058 |
| Abiotic stress | | ECS | + | TraesCS1B01G090500.1 | 775 | 1059 |
| Abiotic stress | | VTE1 | + | TraesCS1A01G223300.2 | 776 | 1060 |
| Abiotic stress | | SAPK4 | + | TraesCS3B01G413800.1 | 777 | 1061 |
| Abiotic stress | | CDPK7 | + | TraesCS2A01G456100.1 | 778 | 1062 |
| Abiotic stress | | NUS1 | + | TraesCS4D01G013900.1 | 779 | 1063 |
| Abiotic stress | | GL1-2 | + | TraesCS6B01G178000.1 | 780 | 1064 |
| Abiotic stress | | Sce1 | + | TraesCS1D01G203200.1 | 781 | 1065 |

TABLE 10-continued

| Trait | Trait subcategory | Orthologue Gene Name | Expression change | Gene ID* | Protein SEQ ID NO: | Genomic DNA SEQ ID NO: |
|---|---|---|---|---|---|---|
| Abiotic stress | | PsbR1 | + | TraesCS6A01G374400.2 | 782 | 1066 |
| Abiotic stress | | CYP21-4 | + | TraesCS2B01G255000.1 | 783 | 1067 |
| Abiotic stress | | PIP1;3 | + | TraesCS6B01G450200.1 | 784 | 1068 |
| Abiotic stress | | CIPK03 | + | TraesCS4D01G179700.2 | 785 | 1069 |
| Abiotic stress | | GRX8 | + | TraesCS2B01G302700.1 | 786 | 1070 |
| Abiotic stress | | MIOX | + | TraesCS7A01G357800.1 | 787 | 1071 |
| Architecture | BR homeostasis-grain size and leaf angle | SLG | +/− | TraesCS5A01G077700.1 | 788 | 1072 |
| Architecture | Branching/Tillering | CKX3 | − | TraesCS1D01G157000.1 | 789 | 1073 |
| Architecture | chloroplast development | HAP3A | − | TraesCS3D01G347000.1 | 790 | 1074 |
| Architecture | fertility | CDPK9 | + | TraesCS4D01G027600.1 | 791 | 1075 |
| Architecture | fertilization/flower opening/dehiecnse | JAR1 | +/− | TraesCS1B01G459500.1 | 792 | 1076 |
| Architecture | flower development | MFO1 | +/− | TraesCS6A01G259000.1 | 793 | 1077 |
| Architecture | flower structure | LFY | | TraesCS2D01G442200.1 | 794 | 1078 |
| Architecture | Flowering time/architecture | ZMM4 | +/− | TraesCS5A01G391700.1 | 795 | 1079 |
| Architecture | flowering time/SAM | HD3A | +/− | TraesCS7B01G013100.1 | 796 | 1080 |
| Architecture | flowering tme/structure | MADS24 | +/− | TraesCS5D01G294500.1 | 797 | 1081 |
| Architecture | flowers and seeds | BRD2 | + | TraesCS7B01G484200.1 | 798 | 1082 |
| Architecture | fragrance | SK2(T)(SCL, FGR) | +/− | TraesCS6A01G371100.1 | 799 | 1083 |
| Architecture | GA response, plant growth | SLR1 | +/− | TraesCS4A01G271000.1 | 800 | 1084 |
| Architecture | grain length | ILI5 | + | TraesCS6A01G306200.1 | 801 | 1085 |
| Architecture | grain weight | GW2 | +/− | TraesCS6D01G176900.2 | 802 | 1086 |
| Architecture | Growth | PTR1 | + | TraesCS4A01G262700.1 | 803 | 1087 |
| Architecture | height | GA2OX3 | +/− | TraesCS3A01G294000.1 | 804 | 1088 |
| Architecture | Height | ETR2 | +/− | TraesCS2D01G000500.1 | 805 | 1089 |
| Architecture | Height | EXPA4 | +/− | TraesCS1B01G310300.1 | 806 | 1090 |
| Architecture | height & leaf angle | D2 | +/− | TraesCS3B01G121200.2 | 807 | 1091 |
| Architecture | height & leaf angle | D61 | +/− | TraesCS3D01G246500.1 | 808 | 1092 |
| Architecture | improved cuticle, pathogenres | PDR6 | + | TraesCS3A01G122500.2 | 809 | 1093 |
| Architecture | Internode length | ACO4 | +/− | TraesCS4A01G221300.1 | 810 | 1094 |
| Architecture | iron acquisition | Rab6a | + | TraesCS4A01G407500.1 | 811 | 1095 |
| Architecture | leaf angle | SERK1 | − | TraesCS7A01G293300.3 | 812 | 1096 |
| Architecture | leaf angle & seed size | D11 | + | TraesCS2D01G331100.1 | 813 | 1097 |
| Architecture | leaf size | FTL1 | +/− | TraesCS3B01G162000.2 | 814 | 1098 |
| Architecture | lodging | BC1 | + | TraesCS5B01G101400.1 | 815 | 1099 |
| Architecture | Lodging resitance | Strongculm2a | + | TraesCS7A01G481600.1 | 816 | 1100 |
| Architecture | Lodging resitance | BrittleStalk2 | + | TraesCS5B01G101400.1 | 817 | 1101 |
| Architecture | melatonin synthesis, stress resistance, yield | SNAT1 | + | TraesCS1B01G312700.3 | 818 | 1102 |
| Architecture | Meristem | AGO1A | +/− | TraesCS6A01G254600.2 | 819 | 1103 |
| Architecture | Meristem | AGO1B | +/− | TraesCS2A01G403100.2 | 820 | 1104 |
| Architecture | Meristem | AGO1C | +/− | TraesCSU01G081900.1 | 821 | 1105 |
| Architecture | Midrib | DL | +/− | TraesCS4A01G058800.3 | 822 | 1106 |
| Architecture | Panicle architecture | DEP3 | +/− | TraesCS7D01G452000.1 | 823 | 1107 |
| Architecture | Plant architecture | CYP734A2 | +/− | TraesCS6B01G207300.1 | 824 | 1108 |

TABLE 10-continued

| Trait | Trait subcategory | Orthologue Gene Name | Expression change | Gene ID* | Protein SEQ ID NO: | Genomic DNA SEQ ID NO: |
|---|---|---|---|---|---|---|
| Architecture | Plant architecture | CYP734A4 | +/− | TraesCS7B01G254100.2 | 825 | 1109 |
| Architecture | Plant architecture | CYP734A6 | +/− | TraesCS3D01G128700.1 | 826 | 1110 |
| Architecture | Plant height | CEL9D | +/− | TraesCS4A01G131400.1 | 827 | 1111 |
| Architecture | Root architecture | PP2AA1 | + | TraesCS5D01G172700.3 | 828 | 1112 |
| Architecture | Root Architecture | rth 1 (root hair) | + | TraesCS4A01G243100.3 | 829 | 1113 |
| Architecture | Root Architecture | CKX4 | +/− | TraesCS3A01G481000.1 | 830 | 1114 |
| Architecture | Root hairs | LSI1 | + | TraesCS6D01G286400.1 | 831 | 1115 |
| Architecture | Root hairs | CSLD1 | + | TraesCS1A01G196100.1 | 832 | 1116 |
| Architecture | Root hairs | CSLD3 | + | TraesCS2D01G126100.1 | 833 | 1117 |
| Architecture | root hairs | EXPA7 | +/− | TraesCS5D01G494800.1 | 834 | 1118 |
| Architecture | root hairs | EXPA10 | +/− | TraesCS2A01G393700.1 | 835 | 1119 |
| Architecture | Root System Architecture | EXPA8 | + | TraesCS3D01G175800.1 | 836 | 1120 |
| Architecture | SAM | PNH1 | + | TraesCS7D01G351700.1 | 837 | 1121 |
| Architecture | SAM | OSH15 | +/− | TraesCS2B01G268200.1 | 838 | 1122 |
| Architecture | SAM/RAM maintenance | QHB | + | TraesCS3B01G399800.1 | 839 | 1123 |
| Architecture | senescence and yield | LOG1 | − | TraesCS3B01G241600.1 | 840 | 1124 |
| Architecture | shoot Architecture | compact plant2 (ct2) | − | TraesCS7A01G000200.1 | 841 | 1125 |
| Architecture | shoot regeneration | SERK1 | + | TraesCS3D01G091000.1 | 842 | 1126 |
| Architecture | shoot/root ratio | PIN | +/− | TraesCS6A01G308600.1 | 843 | 1127 |
| Architecture | tiller angle and architecture | LPA1 | +/− | TraesCS6B01G434400.1 | 844 | 1128 |
| Architecture | Tillering | MADS57 | +/− | TraesCS6B01G322700.2 | 845 | 1129 |
| Architecture | Tillering & size | D14 | +/− | TraesCS4B01G258200.1 | 846 | 1130 |
| Architecture | Tillers | AGR1 | +/− | TraesCS7A01G492400.1 | 847 | 1131 |
| Architecture | vesicular trafficking | ric2 | + | TraesCS7D01G368300.1 | 848 | 1132 |
| Biotic stress | blast resistance | VAMP714 | + | TraesCS7B01G228700.1 | 849 | 1133 |
| Biotic stress | blight resistance\|bacterial leaf streak resistance | XA5 | +/− | TraesCS1D01G024600.1 | 850 | 1134 |
| Biotic Stress | Disease Resistance | GST23 | AA change | TraesCS5D01G254000.1 | 851 | 1135 |
| Biotic Stress | Disease Resistance | NPR1 | + | TraesCS3D01G302900.1 | 852 | 1136 |
| Biotic Stress | Disease Resistance | LOX3 | + | TraesCS4B01G037900.1 | 853 | 1137 |
| Biotic stress | fungal resistance | ALD1 | + | TraesCS4B01G264500.1 | 854 | 1138 |
| Biotic stress | fungal resistance | RLCK185 | + | TraesCS1D01G235800.1 | 855 | 1139 |
| Biotic stress | herbivore resistance | LCB2A1 | + | TraesCS3A01G443500.2 | 856 | 1140 |
| Biotic Stress | Population density/stress/shading | PhyB1 | − | TraesCS4D01G183400.1 | 857 | 1141 |
| Biotic Stress | Population density/stress/shading | COP1 | + | TraesCS6D01G305800.1 | 858 | 1142 |
| Biotic stress | Xanthomonas resistance | WRKY51 | + | TraesCS2A01G270200.2 | 859 | 1143 |
| Biotic stress | | PLDbeta1 | − | TraesCS1A01G187400.1 | 860 | 1144 |
| Biotic stress | | RAC5 | − | TraesCS1D01G325200.1 | 861 | 1145 |
| Biotic stress | | CPK12 | − | TraesCS2A01G407200.1 | 862 | 1146 |
| Biotic stress | | GF14e | − | TraesCS3A01G055600.1 | 863 | 1147 |
| Biotic stress | | SBP | + | TraesCS3A01G422100.1 | 864 | 1148 |
| Biotic stress | | HIR1 | + | TraesCS5A01G497400.1 | 865 | 1149 |
| Biotic stress | | BWMKY1 | + | TraesCS7D01G403700.2 | 866 | 1150 |
| Biotic stress | | AOS1 | + | TraesCS5D01G413200.1 | 867 | 1151 |
| Biotic stress | | LOL2 | + | TraesCS5D01G059500.1 | 868 | 1152 |
| Biotic stress | | GH3 | + | TraesCS3A01G324100.1 | 869 | 1153 |
| Biotic stress | | GH3-8 | + | TraesCS2B01G210600.1 | 870 | 1154 |
| Biotic stress | | XB3 | + | TraesCS1D01G035300.1 | 871 | 1155 |
| Biotic stress | | GLP1 | + | TraesCS7B01G084000.1 | 872 | 1156 |
| Biotic stress | | MAPK6 | + | TraesCS7A01G111300.1 | 873 | 1157 |
| Biotic stress | | ACS2 | + | TraesCS2A01G396400.1 | 874 | 1158 |
| Biotic stress | | LRR1 | + | TraesCS3D01G327800.1 | 875 | 1159 |

TABLE 10-continued

| Trait | Trait subcategory | Orthologue Gene Name | Expression change | Gene ID* | Protein SEQ ID NO: | Genomic DNA SEQ ID NO: |
|---|---|---|---|---|---|---|
| Biotic stress | | MPK3 | + | TraesCS6B01G146300.1 | 876 | 1160 |
| Biotic stress | | SGT1 | + | TraesCS3D01G227500.1 | 877 | 1161 |
| Biotic stress | | GAP1 | + | TraesCS2B01G529400.1 | 878 | 1162 |
| Biotic stress | | RAC1 | + | TraesCS3D01G161900.1 | 879 | 1163 |
| Biotic stress | | TPC1 | + | TraesCS3B01G303100.1 | 880 | 1164 |
| Biotic stress | | GH3-2 | + | TraesCS3B01G335300.1 | 881 | 1165 |
| Biotic stress | | BIANK1 | + | TraesCS5A01G296900.1 | 882 | 1166 |
| Biotic stress | | CIPK14 | + | TraesCS4A01G194800.1 | 883 | 1167 |
| Biotic stress | | BIDK1 | + | TraesCS2D01G534600.1 | 884 | 1168 |
| Biotic stress | | MPK6 | + | TraesCS1D01G192200.1 | 885 | 1169 |
| Biotic stress | | MKK4 | + | TraesCS6D01G328800.1 | 886 | 1170 |
| Biotic stress | | Gns1 | + | TraesCS7D01G552500.1 | 887 | 1171 |
| Biotic stress | | CCR1 | + | TraesCS6D01G365700.1 | 888 | 1172 |
| Biotic stress | | MAPKY5 | + | TraesCS4B01G197800.1 | 889 | 1173 |
| Biotic stress | | RACK1A | + | TraesCS3D01G264000.1 | 890 | 1174 |
| Flowering Time | Flowering time | GI | +/− | TraesCS3B01G135400.1 | 891 | 1175 |
| Flowering Time | Flowering time | phyB | +/− | TraesCS4D01G183400.1 | 892 | 1176 |
| Flowering Time | Flowering time | Hd16 | +/− | TraesCS5A01G431600.1 | 893 | 1177 |
| Flowering Time | Flowering time | RCN1 | +/− | TraesCS5B01G127600.1 | 894 | 1178 |
| Flowering Time | Flowering time | SPL11 | +/− | TraesCS5A01G078400.1 | 895 | 1179 |
| Flowering Time | Flowering time | Spin1 | +/− | TraesCS5D01G481600.1 | 896 | 1180 |
| Nutrient use efficiency | allelopathy and rhizosphere | PAL | + | TraesCS6A01G222700.1 | 897 | 1181 |
| Nutrient use efficiency | Biotic Stress\|Cold and salt stress\|broad-spectrum disease resistance\|disease | PAL1 | + | TraesCS6A01G222900.1 | 898 | 1182 |
| Nutrient use efficiency | eating quality in rice | AGPS1 | allele | TraesCS5D01G182600.1 | 899 | 1183 |
| Nutrient use efficiency | High Iron Stress | NRAMP3 | + | TraesCS7D01G451900.1 | 900 | 1184 |
| Nutrient use efficiency | iron | MTP1 | + | TraesCS1B01G090400.1 | 901 | 1185 |
| Nutrient use efficiency | iron | ATM3 | + | TraesCS4B01G172000.1 | 902 | 1186 |
| Nutrient use efficiency | iron | YSL2 | + | TraesCS6B01G283900.1 | 903 | 1187 |
| Nutrient use efficiency | Iron transport | DMAS1 | + | TraesCS4A01G074800.1 | 904 | 1188 |
| Nutrient use efficiency | low phytic acid | MRP5 | AA change | TraesCS5A01G512500.2 | 905 | 1189 |
| Nutrient use efficiency | low phytic acid | SULTR3;3 | − | TraesCS2D01G508800.1 | 906 | 1190 |
| Nutrient use efficiency | NUE | AMT1;2 | + | TraesCS6A01G226800.1 | 907 | 1191 |
| Nutrient use efficiency | NUE | AMT3;1 | + | TraesCS3A01G381700.1 | 908 | 1192 |
| Nutrient use efficiency | NUE | NRT2.3b | + | TraesCS3B01G285900.1 | 909 | 1193 |
| Nutrient use efficiency | NUE | GS1;2 | + | TraesCS4B01G240900.1 | 910 | 1194 |
| Nutrient use efficiency | NUE | ARG | + | TraesCS2D01G034900.1 | 911 | 1195 |
| Nutrient use efficiency | NUE | NRT2.1 | + | TraesCS6B01G044400.1 | 912 | 1196 |
| Nutrient use efficiency | NUE | AMT1;1 | + | TraesCS2B01G383600.1 | 913 | 1197 |
| Nutrient use efficiency | NUE | AlaAT | + | TraesCS1A01G085600.1 | 914 | 1198 |
| Nutrient use efficiency | NUE | ABC1 | + | TraesCS2D01G132900.1 | 915 | 1199 |
| Nutrient use efficiency | NUE | NADH-GOGAT | + | TraesCS3A01G266300.2 | 916 | 1200 |
| Nutrient use efficiency | Photosynthesis | RBCS | − | TraesCS2B01G079500.1 | 917 | 1201 |
| Nutrient use efficiency | PUE | NLA1 | − | TraesCS2D01G113300.1 | 918 | 1202 |

TABLE 10-continued

| Trait | Trait subcategory | Orthologue Gene Name | Expression change | Gene ID* | Protein SEQ ID NO: | Genomic DNA SEQ ID NO: |
|---|---|---|---|---|---|---|
| Nutrient use efficiency | PUE | PHF1 | + | TraesCS7A01G454100.1 | 919 | 1203 |
| Nutrient use efficiency | PUE | MYB2P-1 | + | TraesCS1D01G084400.1 | 920 | 1204 |
| Nutrient use efficiency | Salt Stress | CASTOR | + | TraesCS5D01G530700.1 | 921 | 1205 |
| Nutrient use efficiency | Salt tolerance | INO1 | +/AA change | TraesCS4A01G038500.1 | 922 | 1206 |
| Photosynthesis | photosynthesis | sedoheptulose 1,7-bisphosphatase (SBPase) | + | TraesCS3D01G359900.2 | 923 | 1207 |
| Photosynthesis | photosynthesis | Fbpase; fructose-1,6-bisphosphatase | + | TraesCS1B01G283600.1 | 924 | 1208 |
| Photosynthesis | | DET1 | AA change | TraesCS3B01G231100.1 | 925 | 1209 |
| Photosynthesis | | Os02g0465900 | + | TraesCS6D01G065900.1 | 926 | 1210 |
| Photosynthesis | | Hox32 | + | TraesCS5D01G385300.1 | 927 | 1211 |
| Photosynthesis | | BZR1 | + | TraesCS2A01G187800.1 | 928 | 1212 |
| Photosynthesis | | NAL1 | + | TraesCS2A01G420900.2 | 929 | 1213 |
| Resource Partitioning | Biomass (seed weight) | AlaAT | + | TraesCS1A01G085600.1 | 930 | 1214 |
| Resource Partitioning | Biomass (stress response) | NRT2.2 | + | TraesCS6B01G044400.1 | 931 | 1215 |
| Resource Partitioning | Drydown rate | esp1 | − | TraesCS1D01G225900.1 | 932 | 1216 |
| Resource Partitioning | GrainSize | GW2-CHR5 | +/− | TraesCS6D01G176900.1 | 933 | 1217 |
| Resource Partitioning | Nitrogen | Asn synthetase | + | TraesCS1D01G390500.1 | 934 | 1218 |
| Resource Partitioning | Nitrogen | AspAT | + | TraesCS3B01G331100.1 | 935 | 1219 |
| Resource Partitioning | Nitrogen | NAD(H)-dependent GOGAT 1 | + | TraesCS3A01G266300.2 | 936 | 1220 |
| Resource Partitioning | Nitrogen | Gln1-3 | + | TraesCS6A01G298100.2 | 937 | 1221 |
| Resource Partitioning | Oil body accumulation | obap1 | + | TraesCS5D01G250600.1 | 938 | 1222 |
| Resource Partitioning | Protein | AAP4 (amino acid permease 4) | + | TraesCS3B01G441300.1 | 939 | 1223 |
| Resource Partitioning | provitamin A | crtRB1 | − | TraesCS2B01G414500.1 | 940 | 1224 |
| Resource Partitioning | Seed composition | MRP1 | + | TraesCS7D01G364700.1 | 941 | 1225 |
| Resource Partitioning | seed filling - sugar nitrogen transport | DA1 | − or AA change | TraesCS2B01G007700.1 | 942 | 1226 |
| Resource Partitioning | seed filling - sugar nitrogen transport | DAR1 | − or AA change | TraesCS4D01G009200.1 | 943 | 1227 |
| Resource Partitioning | Starch | APS1 | + | TraesCS5A01G382900.1 | 944 | 1228 |
| Resource Partitioning | starch | 6-phospho-fructokinase | + | TraesCS5D01G085500.2 | 945 | 1229 |
| Resource Partitioning | Starch | wx1 | + | TraesCS4A01G418200.1 | 946 | 1230 |
| Resource Partitioning | starch | shrunken 1 | + | TraesCS7B01G063400.2 | 947 | 1231 |
| Resource Partitioning | Starch | sus 1 | + | TraesCS7D01G036600.2 | 948 | 1232 |
| Resource Partitioning | starch | brittle endosperm bt2 | + | TraesCS7D01G284900.2 | 949 | 1233 |
| Resource Partitioning | Starch | sugary 1 | +/− | TraesCS7A01G251400.1 | 950 | 1234 |
| Resource Partitioning | Starch | sbe1 | +/− | TraesCS7A01G549100.3 | 951 | 1235 |
| Senescence | Brassinosteroid (BR) regulation | MADS22 | − | TraesCS6B01G343900.1 | 952 | 1236 |
| Senescence | Fe-deficiency; induced programmed cell death; Leaf development; | RT | +/− | TraesCS2D01G351300.2 | 953 | 1237 |

TABLE 10-continued

| Trait | Trait subcategory | Orthologue Gene Name | Expression change | Gene ID* | Protein SEQ ID NO: | Genomic DNA SEQ ID NO: |
|---|---|---|---|---|---|---|
| | Male sterility; Micronutrient mobilization-iron and Zinc; Oxidative stress; Programmed cell death; Developmental regulation; Cytokinin oxidase/dehydrogenase | | | | | |
| Senescence | GA - regulation, Male sterility | GAMYB | + | TraesCS3A01G336500.1 | 954 | 1238 |
| Senescence | Immune response; Programmed cell death | HSP90 | +/− | TraesCS7B01G446900.3 | 955 | 1239 |
| Senescence | Leaf senescence | AOS2 | − | TraesCS4B01G237600.1 | 956 | 1240 |
| Senescence | Photosynthesis | SPS1 | + | TraesCS3B01G461800.1 | 957 | 1241 |
| Senescence | Premature senescence; salt stress; stay green; stress response/ early leaf senescence | NYC1 | +/− | TraesCS3D01G159800.1 | 958 | 1242 |
| Senescence | seed germination | D35 | − | TraesCS7A01G362300.2 | 959 | 1243 |
| Senescence | Aging/protein repair | PIMT1 | + | TraesCS7D01G278200.1 | 960 | 1244 |
| Senescence | Aging/protein repair | PIMT2 | + | TraesCS2A01G324200.1 | 961 | 1245 |
| Senescence | Disease resistance | TYDC | +/− | TraesCS3A01G296900.1 | 962 | 1246 |
| Senescence | Flag leaf senescence | TET9 | +/− | TraesCS7D01G359600.1 | 963 | 1247 |
| Senescence | GA - regulation | CYP703A3 | − | TraesCS7A01G309300.1 | 964 | 1248 |
| Senescence | height & leaf angle | D1|D2|Os07g0558500 | +/− | TraesCS2B01G233300.1 | 965 | 1249 |
| Senescence | leaf senescence | ABA8OX1 | + | TraesCS6D01G243800.1 | 966 | 1250 |
| Senescence | leaf senescence | OsABA2 | +/− | TraesCS2B01G335400.2 | 967 | 1251 |
| Senescence | leaf senescence | NCED1 | +/− | TraesCS5D01G383500.1 | 968 | 1252 |
| Senescence | leaf senescence | ZEP1 | +/− | TraesCS2A01G340400.2 | 969 | 1253 |
| Senescence | Oxidative and abiotic stresses | ALDH7 | + | TraesCS5B01G210100.1 | 970 | 1254 |
| Senescence | Oxidative stress response | CHS1 | +/− | TraesCS2B01G558400.1 | 971 | 1255 |
| Senescence | Root hairs; leaf senescence; Stress response/early leaf senescence | APX2 | + | TraesCS2D01G080000.1 | 972 | 1256 |
| Senescence | Senescence; Leaf senescence | DOS | + | TraesCS3D01G109300.1 | 973 | 1257 |
| Senescence | Senescence; Leaf development | HOX33 | + | TraesCS5D01G052300.1 | 974 | 1258 |
| Senescence | Staygreen; leaf senescence | NYC3 | +/− | TraesCS7D01G346100.1 | 975 | 1259 |
| Senescence | Stress response/ early leaf senescence | APX1 | + | TraesCS4B01G197900.1 | 976 | 1260 |

*Gene ID based on the genome and annotation provided as the first version of the reference sequence (RefSeqv1.0) of the bread wheat *Triticum aestivum* variety Chinese Spring, produced by the International Wheat Genome Sequencing Consortium (IWGSC), publicly accessible at: wheat-urgi[dot]Versailles[dot]inra[dot]fr/Seq-Repository/Assemblies
"+" means increased gene expression; "−" means decreased gene expression; "+/−" means increase/decrease, indicating that different desirable phenotypes or traits are expected with either an increase or a decrease in expression Table 10 provides a selection of wheat genes identified by gene name and sequence identifier (SEQ ID NO:), grouped according to a phenotype or trait expected in a wheat plant in which one or more of these genes is modified in comparison to an unmodified wheat plant having a reference genome, or in a wheat plant having predetermined modifications of at least two of these genes in comparison to an unmodified wheat plant having a reference genome. An embodiment of the invention is related to a wheat plant cell having a modified genome in comparison to an unmodified wheat plant cell having an reference genome, wherein the modified genome differs from the reference genome by including at least one predetermined modification of a gene disclosed in Table 10, wherein the at least one predetermined modification is selected from the group consisting of: (a) a predetermined modification in at least one homeoallele of a gene disclosed in Table 10 and selected from TsVP, SEC14p, ACC synthase, D-myo-inositol-3-phosphate synthase (IPS), bZIP72, PLC1, GOLS2, PIS, NF-YB, PsbA, HB2, PP2C2, CIPK16, SAPK8, ABA8ox3, ORAP1, DIS1, VPE3, RZFP34, ZFP185, DCA1, SRFP1, SQS, TPP1, SAPK6, JIOsPR10, ClpD1, MSD1, WR1, TPS1, GS, OgTT1, FKBP20, ANN1, SIK1, NHX1, MGD, DHODH1, hsp16.9, GME-2, ChI1, CYP18-2, CNX, CBL8, CDPK13, RAN2, GGP, OVP1, ZFP177, RGG1, Em1, CTB4a, GS2, COLD1, ACA6, Rab7, TOP6A1, Hsp101, AMTR1, Rubisco activase, SPX1, GME-1, MPG1, SNAC3, SDIR1, Pgk2a-P, glyoxalase II, PUB15, IMP, HBP1b, CYP2, PEX11 (Os03g0302000), CPK4, EG1, CBSX4, SIDP366, SUV3, GA2ox6, SAPK9, RbohA, CAS, RacB, ECS, VTE1, SAPK4, CDPK7, NUS1, GL1-2, Sce1, PsbR1, CYP21-4, PIP1;3, CIPK03, GRX8, MIOX, SLG, CKX3, HAP3A, CDPK9, JAR1, MFO1, LFY, ZMM4, HD3A, MADS24, BRD2, SK2(T)(SCL, FGR), SLR1, ILI5, GW2, PTR1, GA2OX3, ETR2, EXPA4, D2, D61, PDR6, ACO4, Rab6a, SERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, PP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, NPR1, LOX3, ALD1, RLCK185, LCB2A1, PhyB1, COP1, WRKY51, PLDbeta1, RAC5, CPK12, GF14e, SBP, HIR1, BWMKY1, AOS1, LOL2, GH3, GH3-8, XB3, GLP1, MAPK6, ACS2, LRR1, MPK3, SGT1, GAP1, RAC1, TPC1, GH3-2, BIANK1, CIPK14, BIDK1, MPK6, MKK4, Gns1, CCR1, MAPKY5, RACK1A, GI, phyB, Hd16, RCN1, SPL11, Spin1, PAL, PAL1, AGPS1, NRAMP3, MTP1, ATM3, YSL2, DMAS1, MRP5, SULTR3;3, AMT1;2, AMT3;1, NRT2.3b, GS1;2, ARG, NRT2.1, AMT1;1, AlaAT, ABC1, NADH-GOGAT, RBCS, NLA1, PHF1, MYB2P-1, CASTOR, INO1, sedo-heptulose-1,7-bisphosphatase (SBPase), Fbpase; fructose-1,6-bisphosphatase, DET1, Os02g0465900, Hox32, BZR1, NAL1, AlaAT, NRT2.2, esp1, GW2-CHR5, Asn synthetase, AspAT, NAD(H)-dependent GOGAT 1, Gln1-3, obap1, AAP4 (amino acid permease 4), crtRB1, MRP1, DA1, DAR1, APS1, 6-phospho-fructokinase, wx1, shrunken 1, sus1, brittle endosperm bt2, sugary 1, sbe1, MADS22, RT, GAMYB, HSP90, AOS2, SPS1, NYC1, D35, PIMT1, PIMT2, TYDC, TEM, CYP703A3, D1|D2|Os07g0558500, ABA8OX1, ABA2, NCED1, ZEP1, ALDH7, CHS1, APX2, DOS, HOX33, NYC3, and APX1 as disclosed in Table 10, or (b) a predetermined modification in a gene encoding a protein having at least 90% identity to a sequence selected from SEQ ID NOs:693-976 as disclosed in Table 10, or (c) a predetermined modification in a genomic sequence selected from SEQ ID NO:977-1260 as disclosed in Table 10. In embodiments, the predetermined modification in the gene disclosed in Table 10 is at least one selected from: (a) heterologous integration of a nucleic acid sequence that is encoded by at least one donor polynucleotide molecule and that includes a regulatory element (e.g., a regulatory element having a nucleotide sequence selected from SEQ ID NOs: 66-256) at a predetermined locus between 0-1000 nucleotides upstream of the start codon of the coding sequence of the gene disclosed in Table 10 or 0-1000 nucleotides upstream of the start codon of the coding sequence of the gene disclosed in Table 10; (b) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus in the 3' untranslated region (e.g., within 1000 nucleotides downstream of the stop codon) of the gene disclosed in Table 10; (c) deletion, addition, or substitution of at least one nucleotide in a regulatory element that regulates expression of the gene disclosed in Table 10; (d) deletion, addition, or substitution of at least one nucleotide in coding sequence of the gene disclosed in Table 10; and (e) a combination of any of (a), (b), (c), and (d); wherein the gene disclosed in Table 10 is selected from TsVP, SEC14p, ACC synthase, D-myo-inositol-3-phosphate synthase (IPS), bZIP72, PLC1, GOLS2, PIS, NF-YB, PsbA, HB2, PP2C2, CIPK16, SAPK8, ABA8ox3, ORAP1, DIS1, VPE3, RZFP34, ZFP185, DCA1, SRFP1, SQS, TPP1, SAPK6, JIOsPR10, ClpD1, MSD1, WR1, TPS1, GS, OgTT1, FKBP20, ANN1, SIK1, NHX1, MGD, DHODH1, hsp16.9, GME-2, ChI1, CYP18-2, CNX, CBL8, CDPK13, RAN2, GGP, OVP1, ZFP177, RGG1, Em1, CTB4a, GS2, COLD1, ACA6, Rab7, TOP6A1, Hsp101, AMTR1, Rubisco activase, SPX1, GME-1, MPG1, SNAC3, SDIR1, Pgk2a-P, glyoxalase II, PUB15, IMP, HBP1b, CYP2, PEX11 (Os03g0302000), CPK4, EG1, CBSX4, SIDP366, SUV3, GA2ox6, SAPK9, RbohA, CAS, RacB, ECS, VTE1, SAPK4, CDPK7, NUS1, GL1-2, Sce1, PsbR1, CYP21-4, PIP1;3, CIPK03, GRX8, MIOX, SLG, CKX3, HAP3A, CDPK9, JAR1, MFO1, LFY, ZMM4, HD3A, MADS24, BRD2, SK2(T)(SCL, FGR), SLR1, ILI5, GW2, PTR1, GA2OX3, ETR2, EXPA4, D2, D61, PDR6, ACO4, Rab6a, SERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, PP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, NPR1, LOX3, ALD1, RLCK185, LCB2A1, PhyB1, COP1, WRKY51, PLDbeta1, RAC5, CPK12, GF14e, SBP, HIR1, BWMKY1, AOS1, LOL2, GH3, GH3-8, XB3, GLP1, MAPK6, ACS2, LRR1, MPK3, SGT1, GAP1, RAC1, TPC1, GH3-2, BIANK1, CIPK14, BIDK1, MPK6, MKK4, Gns1, CCR1, MAPKY5, RACK1A, GI, phyB, Hd16, RCN1, SPL11, Spin1, PAL, PAL1, AGPS1, NRAMP3, MTP1, ATM3, YSL2, DMAS1, MRP5, SULTR3;3, AMT1;2, AMT3;1, NRT2.3b, GS1;2, ARG, NRT2.1, AMT1;1, AlaAT, ABC1, NADH-GOGAT, RBCS, NLA1, PHF1, MYB2P-1, CASTOR, INO1, sedo-heptulose-1,7-bisphosphatase (SBPase), Fbpase; fructose-1,6-bisphosphatase, DET1, Os02g0465900, Hox32, BZR1, NAL1, AlaAT, NRT2.2, esp1, GW2-CHR5, Asn synthetase, AspAT, NAD(H)-dependent GOGAT 1, Gln1-3, obap1, AAP4 (amino acid permease 4), crtRB1, MRP1, DA1, DAR1, APS1, 6-phospho-fructokinase, wx1, shrunken 1, sus1, brittle endosperm bt2, sugary 1, sbe1, MADS22, RT, GAMYB, HSP90, AOS2, SPS1, NYC1, D35, PIMT1, PIMT2, TYDC, TET9, CYP703A3, D1|D2|Os07g0558500, ABA8OX1, ABA2, NCED1, ZEP1, ALDH7, CHS1, APX2, DOS, HOX33, NYC3, and APX1 as disclosed in Table 10, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:693-976, or is a genomic sequence selected from SEQ ID NO:977-1260 as disclosed in Table 10.

An embodiment of the invention is related to a wheat plant cell having a modified genome and exhibiting improved abiotic stress tolerance in comparison to an unmodified wheat plant cell having an reference genome, wherein the modified genome differs from the reference genome by including at least one predetermined modification of a gene disclosed in Table 10, wherein the at least one predetermined modification is selected from the group consisting of: (a) a predetermined modification in at least one homeoallele of a gene disclosed in Table 10 and selected from TsVP, SEC14p, ACC synthase, D-myo-inositol-3-phosphate synthase (IPS), bZIP72, PLC1, GOLS2, PIS, NF-YB, PsbA, HB2, PP2C2, CIPK16, SAPK8, ABA8ox3, ORAP1, DIS1, VPE3, RZFP34, ZFP185, DCA1, SRFP1, SQS, TPP1, SAPK6, JIOsPR10, ClpD1, MSD1, WR1, TPS1, GS, OgTT1, FKBP20, ANN1, SIK1, NHX1, MGD, DHODH1, hsp16.9, GME-2, ChI1, CYP18-2, CNX, CBL8, CDPK13, RAN2, GGP, OVP1, ZFP177, RGG1, Em1, CTB4a, GS2, COLD1, ACA6, Rab7, TOP6A1, Hsp101, AMTR1, Rubisco activase, SPX1, GME-1, MPG1, SNAC3, SDIR1, Pgk2a-P, glyoxalase II, PUB15, IMP, HBP1b, CYP2, PEX11 (Os03g0302000), CPK4, EG1, CBSX4, SIDP366, SUV3, GA2ox6, SAPK9, RbohA, CAS, RacB, ECS, VTE1, SAPK4, CDPK7, NUS1, GL1-2, Sce1, PsbR1, CYP21-4, PIP1;3, CIPK03, GRX8, and MIOX as disclosed in Table 10, or (b) a predetermined modification in a gene encoding a protein having at least 90% identity to a sequence selected from SEQ ID NOs:693-787 as disclosed in Table 10, or (c) a predetermined modification in a genomic sequence selected from SEQ ID NO:977-1071 as disclosed in Table 10. In embodiments, the predetermined modification in the gene disclosed in Table 10 is at least one selected from: (a) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus between 0-1000 nucleotides upstream of the start codon of the coding sequence of the gene disclosed in Table 10 or 0-1000 nucleotides upstream of the start codon of the coding sequence of the gene disclosed in Table 10; (b) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus in the 3' untranslated region (e.g., within 1000 nucleotides downstream of the stop codon) of the gene disclosed in Table 10; (c) deletion, addition, or substitution of at least one nucleotide in a regulatory element that regulates expression of the gene disclosed in Table 10; (d) deletion, addition, or substitution of at least one nucleotide in coding sequence of the gene disclosed in Table 10; and (e) a combination of any of (a), (b), (c), and (d); wherein the gene disclosed in Table 10 is selected from TsVP, SEC14p, ACC synthase, D-myo-inositol-3-phosphate synthase (IPS), bZIP72, PLC1, GOLS2, PIS, NF-YB, PsbA, HB2, PP2C2, CIPK16, SAPK8, ABA8ox3, ORAP1, DIS1, VPE3, RZFP34, ZFP185, DCA1, SRFP1, SQS, TPP1, SAPK6, JIOsPR10, ClpD1, MSD1, WR1, TPS1, GS, OgTT1, FKBP20, ANN1, SIK1, NHX1, MGD, DHODH1, hsp16.9, GME-2, ChI1, CYP18-2, CNX, CBL8, CDPK13, RAN2, GGP, OVP1, ZFP177, RGG1, Em1, CTB4a, GS2, COLD1, ACA6, Rab7, TOP6A1, Hsp101, AMTR1, Rubisco activase, SPX1, GME-1, MPG1, SNAC3, SDIR1, Pgk2a-P, glyoxalase II, PUB15, IMP, HBP1b, CYP2, PEX11 (Os03g0302000), CPK4, EG1, CBSX4, SIDP366, SUV3, GA2ox6, SAPK9, RbohA, CAS, RacB, ECS, VTE1, SAPK4, CDPK7, NUS1, GL1-2, Sce1, PsbR1, CYP21-4, PIP1;3, CIPK03, GRX8, and MIOX as disclosed in Table 10, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:693-787, or is a genomic sequence selected from SEQ ID NO:977-1071 as disclosed in Table 10.

An embodiment of the invention is related to a wheat plant cell having a modified genome and exhibiting modified architecture in comparison to an unmodified wheat plant cell having an reference genome, wherein the modified genome differs from the reference genome by including at least one predetermined modification of a gene disclosed in Table 10, wherein the at least one predetermined modification is selected from the group consisting of: (a) a predetermined modification in at least one homeoallele of a gene disclosed in Table 10 and selected from SLG, CKX3, HAP3A, CDPK9, JAR1, MFO1, LFY, ZMM4, HD3A, MADS24, BRD2, SK2(T)(SCL, FGR), SLR1, ILI5, GW2, PTR1, GA2OX3, ETR2, EXPA4, D2, D61, PDR6, ACO4, Rab6a, SERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, PP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, and ric2 as disclosed in Table 10, or (b) a predetermined modification in a gene encoding a protein having at least 90% identity to a sequence selected from SEQ ID NOs:788-848 as disclosed in Table 10, or (c) a predetermined modification in a genomic sequence selected from SEQ ID NO:1072-1132 as disclosed in Table 10. In embodiments, the predetermined modification in the gene disclosed in Table 10 is at least one selected from: (a) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus between 0-1000 nucleotides upstream of the start codon of the coding sequence of the gene disclosed in Table 10 or 0-1000 nucleotides upstream of the start codon of the coding sequence of the gene disclosed in Table 10; (b) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus in the 3' untranslated region (e.g., within 1000 nucleotides downstream of the stop codon) of the gene disclosed in Table 10; (c) deletion, addition, or substitution of at least one nucleotide in a regulatory element that regulates expression of the gene disclosed in Table 10; (d) deletion, addition, or substitution of at least one nucleotide in coding sequence of the gene disclosed in Table 10; and (e) a combination of any of (a), (b), (c), and (d); wherein the gene disclosed in Table 10 is selected from SLG, CKX3, HAP3A, CDPK9, JAR1, MFO1, LFY, ZMM4, HD3A, MADS24, BRD2, SK2(T) (SCL, FGR), SLR1, ILI5, GW2, PTR1, GA2OX3, ETR2, EXPA4, D2, D61, PDR6, ACO4, Rab6a, SERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, PP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, and ric2 as disclosed in Table 10, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:788-848, or is a genomic sequence selected from SEQ ID NO:1072-1132 as disclosed in Table 10.

An embodiment of the invention is related to a wheat plant cell having a modified genome and exhibiting improved biotic stress tolerance in comparison to an unmodified wheat plant cell having an reference genome, wherein the modified genome differs from the reference genome by including at least one predetermined modification of a gene disclosed in Table 10, wherein the at least one predetermined modification is selected from the group consisting of: (a) a predetermined modification in at least one homeoallele of a gene disclosed in Table 10 and selected from VAMP714, XA5, GST23, NPR1, LOX3, ALD1, RLCK185, LCB2A1, PhyB1, COP1, WRKY51, PLDbeta1, RAC5, CPK12, GF14e, SBP, HIR1, BWMKY1, AOS1, LOL2, GH3, GH3-8, XB3, GLP1, MAPK6, ACS2, LRR1, MPK3, SGT1, GAP1, RAC1, TPC1, GH3-2, BIANK1, CIPK14, BIDK1, MPK6, MKK4, Gns1, CCR1, MAPKY5, and RACK1A as disclosed in Table 10, or (b) a predetermined modification in a gene encoding a protein having at least 90% identity to a sequence selected from SEQ ID NOs:849-890 as disclosed in Table 10, or (c) a predetermined modification in a genomic sequence selected from SEQ ID NO:1133-1174 as disclosed in Table 10. In embodiments, the predetermined modification in the gene disclosed in Table 10 is at least one selected from: (a) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus between 0-1000 nucleotides upstream of the start codon of the coding sequence of the gene disclosed in Table 10 or 0-1000 nucleotides upstream of the start codon of the coding sequence of the gene disclosed in Table 10; (b) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus in the 3' untranslated region (e.g., within 1000 nucleotides downstream of the stop codon) of the gene disclosed in Table 10; (c) deletion, addition, or substitution of at least one nucleotide in a regulatory element that regulates expression of the gene disclosed in Table 10; (d) deletion, addition, or substitution of at least one nucleotide in coding sequence of the gene disclosed in Table 10; and (e) a combination of any of (a), (b), (c), and (d); wherein the gene disclosed in Table 10 is selected from VAMP714, XA5, GST23, NPR1, LOX3, ALD1, RLCK185, LCB2A1, PhyB1, COP1, WRKY51, PLDbeta1, RAC5, CPK12, GF14e, SBP, HIR1, BWMKY1, AOS1, LOL2, GH3, GH3-8, XB3, GLP1, MAPK6, ACS2, LRR1, MPK3, SGT1, GAP1, RAC1, TPC1, GH3-2, BIANK1, CIPK14, BIDK1, MPK6, MKK4, Gns1, CCR1, MAPKY5, and RACK1A as disclosed in Table 10, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:849-890, or is a genomic sequence selected from SEQ ID NO:1133-1174 as disclosed in Table 10.

An embodiment of the invention is related to a wheat plant cell having a modified genome and exhibiting modified flowering time in comparison to an unmodified wheat plant cell having an reference genome, wherein the modified genome differs from the reference genome by including at least one predetermined modification of a gene disclosed in Table 10, wherein the at least one predetermined modification is selected from the group consisting of: (a) a predetermined modification in at least one homeoallele of a gene disclosed in Table 10 and selected from GI, phyB, Hd16, RCN1, SPL11, and Spin1 as disclosed in Table 10, or (b) a predetermined modification in a gene encoding a protein having at least 90% identity to a sequence selected from SEQ ID NOs:891-896 as disclosed in Table 10, or (c) a predetermined modification in a genomic sequence selected from SEQ ID NO:1175-1180 as disclosed in Table 10. In embodiments, the predetermined modification in the gene disclosed in Table 10 is at least one selected from: (a) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus between 0-1000 nucleotides upstream of the start codon of the coding sequence of the gene disclosed in Table 10 or 0-1000 nucleotides upstream of the start codon of the coding sequence of the gene disclosed in Table 10; (b) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus in the 3' untranslated region (e.g., within 1000 nucleotides downstream of the stop codon) of the gene disclosed in Table 10; (c) deletion, addition, or substitution of at least one nucleotide in a regulatory element that regulates expression of the gene disclosed in Table 10; (d) deletion, addition, or substitution of at least one nucleotide in coding sequence of the gene disclosed in Table 10; and (e) a combination of any of (a), (b), (c), and (d); wherein the gene disclosed in Table 10 is selected from GI, phyB, Hd16, RCN1, SPL11, and Spin1 as disclosed in Table 10, or is a gene encoding a protein having at least 90% (e.g., at least 90%, at least 910/a, at least 92%, at least 93%, at least 94%, at least 95%, at least 96%, at least 97%, at least 98%, at least 99%, or at least 99.5%) identity to a sequence selected from SEQ ID NOs:891-896, or is a genomic sequence selected from SEQ ID NO:1175-1180 as disclosed in Table 10.

An embodiment of the invention is related to a wheat plant cell having a modified genome and exhibiting modified or improved nutrient utilization efficiency in comparison to an unmodified wheat plant cell having an reference genome, wherein the modified genome differs from the reference genome by including at least one predetermined modification of a gene disclosed in Table 10, wherein the at least one predetermined modification is selected from the group consisting of: (a) a predetermined modification in at least one homeoallele of a gene disclosed in Table 10 and selected from PAL, PAL 1, AGPS1, NRAMP3, MTP1, ATM3, YSL2, DMAS1, MRP5, SULTR3;3, AMT1;2, AMT3;1, NRT2.3b, GS1;2, ARG, NRT2.1, AMT1;1, AlaAT, ABC1, NADH-GOGAT, RBCS, NLA1, PHF1, MYB2P-1, CASTOR, and INO1 as disclosed in Table 10, or (b) a predetermined modification in a gene encoding a protein having at least 90% identity to a sequence selected from SEQ ID NOs:897-922 as disclosed in Table 10, or (c) a predetermined modification in a genomic sequence selected from SEQ ID NO:1181-1206 as disclosed in Table 10. In embodiments, the predetermined modification in the gene disclosed in Table 10 is at least one selected from: (a) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus between 0-1000 nucleotides upstream of the start codon of the coding sequence of the gene disclosed in Table 10 or 0-1000 nucleotides upstream of the start codon of the coding sequence of the gene disclosed in Table 10; (b) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus in the 3' untranslated region (e.g., within 1000 nucleotides downstream of the stop codon) of the gene disclosed in Table 10; (c) deletion, addition, or substitution of at least one nucleotide in a regulatory element that regulates expression of the gene disclosed in Table 10; (d) deletion, addition, or substitution of at least one nucleotide in coding sequence of the gene disclosed in Table 10; and (e) a combination of any of (a), (b), (c), and (d); wherein the gene disclosed in Table 10 is selected from PAL, PAL1, AGPS1, NRAMP3, MTP1, ATM3, YSL2, DMAS1, MRP5, SULTR3;3, AMT1;2, AMT3;1, NRT2.3b, GS1;2, ARG, NRT2.1, AMT1;1, AlaAT, ABC1, NADH-GOGAT, RBCS, NLA1, PHF1, MYB2P-1, CASTOR, and INO1 as disclosed in Table 10, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:897-922, or is a genomic sequence selected from SEQ ID NO:1181-1206 as disclosed in Table 10.

An embodiment of the invention is related to a wheat plant cell having a modified genome and exhibiting improved photosynthesis efficiency in comparison to an unmodified wheat plant cell having an reference genome, wherein the modified genome differs from the reference genome by including at least one predetermined modification of a gene disclosed in Table 10, wherein the at least one predetermined modification is selected from the group consisting of: (a) a predetermined modification in at least one homeoallele of a gene disclosed in Table 10 and selected from sedoheptulose-1,7-bisphosphatase (SBPase), Fbpase; fructose-1,6-bisphosphatase, DET1, Os02g0465900, Hox32, BZR1, and NAL1 as disclosed in Table 10, or (b) a predetermined modification in a gene encoding a protein having at least 90% identity to a sequence selected from SEQ ID NOs:923-929 as disclosed in Table 10, or (c) a predetermined modification in a genomic sequence selected from SEQ ID NO:1207-1213 as disclosed in Table 10. In embodiments, the predetermined modification in the gene disclosed in Table 10 is at least one selected from: (a) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus between 0-1000 nucleotides upstream of the start codon of the coding sequence of the gene disclosed in Table 10 or 0-1000 nucleotides upstream of the start codon of the coding sequence of the gene disclosed in Table 10; (b) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus in the 3' untranslated region (e.g., within 1000 nucleotides downstream of the stop codon) of the gene disclosed in Table 10; (c) deletion, addition, or substitution of at least one nucleotide in a regulatory element that regulates expression of the gene disclosed in Table 10; (d) deletion, addition, or substitution of at least one nucleotide in coding sequence of the gene disclosed in Table 10; and (e) a combination of any of (a), (b), (c), and (d); wherein the gene disclosed in Table 10 is selected from sedoheptulose-1,7-bisphosphatase (SBPase), Fbpase; fructose-1,6-bisphosphatase, DET1, Os02g0465900, Hox32, BZR1, and NAL1 as disclosed in Table 10, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:923-929, or is a genomic sequence selected from SEQ ID NO:1207-1213 as disclosed in Table 10.

An embodiment of the invention is related to a wheat plant cell having a modified genome and exhibiting modified resource partitioning in comparison to an unmodified wheat plant cell having an reference genome, wherein the modified genome differs from the reference genome by including at least one predetermined modification of a gene disclosed in Table 10, wherein the at least one predetermined modification is selected from the group consisting of: (a) a predetermined modification in at least one homeoallele of a gene disclosed in Table 10 and selected from AlaAT, NRT2.2, esp1, GW2-CHR5, Asn synthetase, AspAT, NAD(H)-dependent GOGAT 1, Gln1-3, obap1, AAP4 (amino acid permease 4), crtRB1, MRP1, DA1, DAR1, APS1, 6-phospho-fructokinase, wx1, shrunken 1, sus1, brittle endosperm bt2, sugary 1, and sbe1 as disclosed in Table 10, or (b) a predetermined modification in a gene encoding a protein having at least 90% identity to a sequence selected from SEQ ID NOs:930-951 as disclosed in Table 10, or (c) a predetermined modification in a genomic sequence selected from SEQ ID NO:1214-1235 as disclosed in Table 10. In embodiments, the predetermined modification in the gene disclosed in Table 10 is at least one selected from: (a) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus between 0-1000 nucleotides upstream of the start codon of the coding sequence of the gene disclosed in Table 10 or 0-1000 nucleotides upstream of the start codon of the coding sequence of the gene disclosed in Table 10; (b) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus in the 3' untranslated region (e.g., within 1000 nucleotides downstream of the stop codon) of the gene disclosed in Table 10; (c) deletion, addition, or substitution of at least one nucleotide in a regulatory element that regulates expression of the gene disclosed in Table 10; (d) deletion, addition, or substitution of at least one nucleotide in coding sequence of the gene disclosed in Table 10; and (e) a combination of any of (a), (b), (c), and (d); wherein the gene disclosed in Table 10 is selected from AlaAT, NRT2.2, esp1, GW2-CHR5, Asn synthetase, AspAT, NAD(H)-dependent GOGAT 1, Gln1-3, obap1, AAP4 (amino acid permease 4), crtRB1, MRP1, DA1, DAR1, APS1, 6-phospho-fructokinase, wx1, shrunken 1, sus1, brittle endosperm bt2, sugary 1, and sbe1 as disclosed in Table 10, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:930-951, or is a genomic sequence selected from SEQ ID NO:1214-1235 as disclosed in Table 10.

An embodiment of the invention is related to a wheat plant cell having a modified genome and exhibiting modified senescence in comparison to an unmodified wheat plant cell having an reference genome, wherein the modified genome differs from the reference genome by including at least one predetermined modification of a gene disclosed in Table 10, wherein the at least one predetermined modification is selected from the group consisting of: (a) a predetermined modification in at least one homeoallele of a gene disclosed in Table 10 and selected from MADS22, RT, GAMYB, HSP90, AOS2, SPS1, NYC1, D35, PIMT1, PIMT2, TYDC, TET9, CYP703A3, D1|D2|Os07g0558500, ABA8OX1, ABA2, NCED1, ZEP1, ALDH7, CHS1, APX2, DOS, HOX33, NYC3, and APX1 as disclosed in Table 10, or (b) a predetermined modification in a gene encoding a protein having at least 90% identity to a sequence selected from SEQ ID NOs:952-976 as disclosed in Table 10, or (c) a predetermined modification in a genomic sequence selected from SEQ ID NO:1236-1260 as disclosed in Table 10. In embodiments, the predetermined modification in the gene disclosed in Table 10 is at least one selected from: (a) heterologous integration of a nucleic acid sequence that is encoded by at least one donor polynucleotide molecule and that includes a regulatory element (e.g., a regulatory element having a nucleotide sequence selected from SEQ ID NOs: 66-256) at a predetermined locus between 0-1000 nucleotides upstream of the start codon of the coding sequence of the gene disclosed in Table 10 or 0-1000 nucleotides upstream of the start codon of the coding sequence of the gene disclosed in Table 10; (b) heterologous integration of a nucleic acid sequence that is encoded by at least one donor polynucleotide molecule and that includes a regulatory element (e.g., a regulatory element having a nucleotide sequence selected from SEQ ID NOs:66-256) at a predetermined locus in the 3' untranslated region (e.g., within 1000 nucleotides downstream of the stop codon) of the gene disclosed in Table 10; (c) deletion, addition, or substitution of at least one nucleotide in a regulatory element that regulates expression of the gene disclosed in Table 10; (d) deletion, addition, or substitution of at least one nucleotide in coding sequence of the gene disclosed in Table 10; and (e) a combination of any of (a), (b), (c), and (d); wherein the gene disclosed in Table 10 is selected from MADS22, RT, GAMYB, HSP90, AOS2, SPS1, NYC1, D35, PIMT1, PIMT2, TYDC, TEM, CYP703A3, D1|D2|Os07g0558500, ABA8OX1, ABA2, NCED1, ZEP1, ALDH7, CHS1, APX2, DOS, HOX33, NYC3, and APX1 as disclosed in Table 10, or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:952-976, or is a genomic sequence selected from SEQ ID NO:1236-1260 as disclosed in Table 10.

Each of the genes disclosed in Table 10 can be modified from the sequence as found in a reference wheat genome, using any of the gene modification methods disclosed herein. In particular, each of the genes disclosed in Table 10 can be modified using the precise modification methods described herein which introduce predetermined changes at specific locations in a gene of interest in the reference genome, in the absence of off-target effects. In embodiments, each of the genes disclosed in Table 10 may be modified, either singly or in multiplexed fashion, using techniques employing sequence-specific nucleases as disclosed herein (see, e.g., Examples 1-17). In embodiments of the wheat plant cell having a modified genome, the at least one predetermined modification of the gene disclosed in Table 10 includes a modification of only non-coding sequence of the reference genome, or of only coding sequence of the reference genome, or of a combination of coding and non-coding sequences of the reference genome. In embodiments, the at least one predetermined modification of the gene disclosed in Table 10 results in increased expression of the gene, relative to expression of the gene in the reference genome. In embodiments, the at least one predetermined modification of a gene disclosed in Table 10 includes a modification of only non-coding sequence of the reference genome, or of only coding sequence of the reference genome, or of a combination of coding and non-coding sequences of the reference genome. In embodiments, the at least one predetermined modification of gene disclosed in Table 10 results in increased expression of the gene, relative to expression of the gene in the reference genome. In embodiments, the at least one predetermined modification of a gene disclosed in Table 10 results in decreased expression of the gene, relative to expression of the gene in the reference genome.

In embodiments of the wheat plant cell having a modified genome, the at least one predetermined modification of a gene disclosed in Table 10 includes multiple predetermined modifications of a single gene disclosed in Table 10 in the reference genome. In embodiments, the at least one predetermined modification of a gene disclosed in Table 10 includes predetermined modifications of multiple genes disclosed in Table 10 in the reference genome; in embodiments, the multiple genes disclosed in Table 10 include at least one homeoallele each of two or more genes selected from TsVP, SEC14p, ACC synthase, D-myo-inositol-3-phosphate synthase (IPS), bZIP72, PLC1, GOLS2, PIS, NF-YB, PsbA, HB2, PP2C2, CIPK16, SAPK8, ABA8ox3, ORAP1, DIS1, VPE3, RZFP34, ZFP185, DCA1, SRFP1, SQS, TPP1, SAPK6, JIOsPR10, ClpD1, MSD1, WR1, TPS1, GS, OgTT1, FKBP20, ANN1, SIK1, NHX1, MGD, DHODH1, hsp16.9, GME-2, ChI1, CYP18-2, CNX, CBL8, CDPK13, RAN2, GGP, OVP1, ZFP177, RGG1, Em1, CTB4a, GS2, COLD1, ACA6, Rab7, TOP6A1, Hsp101, AMTR1, Rubisco activase, SPX1, GME-1, MPG1, SNAC3, SDIR1, Pgk2a-P, glyoxalase II, PUB15, IMP, HBP1b, CYP2, PEX11 (Os03g0302000), CPK4, EG1, CBSX4, SIDP366, SUV3, GA2ox6, SAPK9, RbohA, CAS, RacB, ECS, VTE1, SAPK4, CDPK7, NUS1, GL1-2, Sce1, PsbR1, CYP21-4, PIP1;3, CIPK03, GRX8, MIOX, SLG, CKX3, HAP3A, CDPK9, JAR1, MFO1, LFY, ZMM4, HD3A, MADS24, BRD2, SK2(T)(SCL, FGR), SLR1, ILI5, GW2, PTR1, GA2OX3, ETR2, EXPA4, D2, D61, PDR6, ACO4, Rab6a, SERK1, D11, FTL1, BC1, Strongculm2a, BrittleStalk2, SNAT1, AGO1A, AGO1B, AGO1C, DL, DEP3, CYP734A2, CYP734A4, CYP734A6, CEL9D, PP2AA1, rth1 (root hair), CKX4, LSI1, CSLD1, CSLD3, EXPA7, EXPA10, EXPA8, PNH1, OSH15, QHB, LOG1, compact plant2 (ct2), SERK1, PIN, LPA1, MADS57, D14, AGR1, ric2, VAMP714, XA5, GST23, NPR1, LOX3, ALD1, RLCK185, LCB2A1, PhyB1, COP1, WRKY51, PLDbeta1, RAC5, CPK12, GF14e, SBP, HIR1, BWMKY1, AOS1, LOL2, GH3, GH3-8, XB3, GLP1, MAPK6, ACS2, LRR1, MPK3, SGT1, GAP1, RAC1, TPC1, GH3-2, BIANK1, CIPK14, BIDK1, MPK6, MKK4, Gns1, CCR1, MAPKY5, RACK1A, GI, phyB, Hd16, RCN1, SPL11, Spin1, PAL, PAL1, AGPS1, NRAMP3, MTP1, ATM3, YSL2, DMAS1, MRP5, SULTR3;3, AMT1;2, AMT3;1, NRT2.3b, GS1;2, ARG, NRT2.1, AMT1;1, AlaAT, ABC1, NADH-GOGAT, RBCS, NLA1, PHF1, MYB2P-1, CASTOR, INO1, sedo-heptulose-1,7-bisphosphatase (SBPase), Fbpase; fructose-1,6-bisphosphatase, DET1, Os02g0465900, Hox32, BZR1, NAL1, AlaAT, NRT2.2, esp1, GW2-CHR5, Asn synthetase, AspAT, NAD(H)-dependent GOGAT 1, Gln1-3, obap1, AAP4 (amino acid permease 4), crtRB1, MRP1, DA1, DAR1, APS1, 6-phospho-fructokinase, wx1, shrunken 1, sus1, brittle endosperm bt2, sugary 1, sbe1, MADS22, RT, GAMYB, HSP90, AOS2, SPS1, NYC1, D35, PIMT1, PIMT2, TYDC, TET9, CYP703A3, D1|D2|Os07g0558500, ABA8OX1, ABA2, NCED1, ZEP1, ALDH7, CHS1, APX2, DOS, HOX33, NYC3, and APX1 as disclosed in Table 10.

In embodiments of the wheat plant cell having a modified genome, the wheat plant cell is a cell of a *Triticum* sp. or an *Aegilops* sp. (e.g., *Aegilops tauschii*). In embodiments, the wheat plant cell is a cell of common or bread wheat (*Triticum aestivum*), spelt (*Triticum spelta*), emmer (*Triticum dicoccum*), einkorn (*Triticum monococcum*), durum wheat (*Triticum durum*), or a synthetic hexaploid wheat ("SHW", see, e.g., Ogbonnaya et al. "Synthetic Hexaploids: Harnessing Species of the Primary Gene Pool for Wheat Improvement" In: *Plant Breeding Reviews*, Volume 37, 1st edition; edited by Jules Janick, published 2013 by John Wiley & Sons, Inc.). In embodiments, the wheat plant cell with the modified genome is an isolated wheat cell or protoplast, or is a cell in a wheat plant or in a part or tissue of a wheat plant, or is a cell in a wheat meristem, zygotic or somatic embryo, microspore, pollen, ovule, or seed. In embodiments, the wheat plant cell is diploid. In embodiments, the wheat plant cell is haploid. In embodiments, the wheat plant cell is a doubled haploid. In embodiments, the wheat plant cell with the modified genome is (a) a cell of an allotetraploid wheat plant, wherein the reference genome consists of an A genome and a B genome, at least one of which is modified in the wheat plant cell with the modified genome; or (b) is a cell of an allohexaploid wheat plant, wherein the reference genome consists of an A genome, a B genome, and a D genome, at least one of which is modified in the wheat plant cell with the modified genome. In embodiments, the at least one predetermined modification of a gene disclosed in Table 10 includes a predetermined modification of multiple homeoalleles of a gene disclosed in Table 10. In embodiments, the wheat plant cell is a cell of an allotetraploid wheat plant, wherein the reference genome consists of an A genome and a B genome, and wherein the at least one predetermined modification of a gene disclosed in Table 10 includes (a) a predetermined modification of both homeoalleles of the gene in the A genome, (b) a predetermined modification of both homeoalleles of the gene in the B genome, or (c) a predetermined modification of at least two (e.g., 2, 3, or all 4) homeoalleles of the gene in the A genome and the B genome. In embodiments, the wheat plant cell is a cell of an allohexaploid wheat plant, wherein the reference genome consists of an A genome, a B genome, and a D genome, and wherein the at least one predetermined modification of a gene disclosed in Table 10 includes a) a predetermined modification of both homeoalleles of the gene in the A genome, (b) a predetermined modification of both homeoalleles of the gene in the B genome, (c) a predetermined modification of both homeoalleles of the gene in the D genome, or (d) a predetermined modification of at least two (e.g., 2, 3, 4, 5, or all 6) homeoalleles of the gene in any combination of the A genome, the B genome, and the D genome. In embodiments, the wheat plant cell is a cell of an allotetraploid wheat plant, wherein the reference genome consists of an A genome and a B genome, and wherein the A genome only, the B genome only, or both the A and B genomes is heterozygous for the at least one predetermined modification of a gene disclosed in Table 10. In embodiments, the wheat plant cell is a cell of an allotetraploid wheat plant, wherein the reference genome consists of an A genome and a B genome, and wherein the A genome only, the B genome only, or both the A and B genomes is homozygous for the at least one predetermined modification of a gene disclosed in Table 10. In embodiments, the wheat plant cell is a cell of an allohexaploid wheat plant, wherein the reference genome consists of an A genome, a B genome, and a D genome, and wherein the A genome only, the B genome only, the D genome only, or any combination of the A, B, and D genomes is heterozygous for the at least one predetermined modification of a gene disclosed in Table 10. In embodiments, the wheat plant cell is a cell of an allohexaploid wheat plant, wherein the reference genome consists of an A genome, a B genome, and a D genome, and wherein the A genome only, the B genome only, the D genome only, or any combination of the A, B, and D genomes is homozygous for the at least one predetermined modification of a gene disclosed in Table 10. In embodiments, the modified genome is more than 99.9% identical to the reference genome. In embodiments, the modified genome is devoid of mitotically or meiotically generated genetic or epigenetic changes relative to the reference genome. In embodiments, the modified genome includes a difference of epigenetic changes in less than 0.01% of the genome relative to the reference genome. In embodiments, the modified genome includes: (a) a difference of DNA methylation in less than 0.01% of the genome, relative to the reference genome; or (b) a difference of DNA methylation in less than 0.005% of the genome, relative to the reference genome; or (c) a difference of DNA methylation in less than 0.001% of the genome, relative to the reference genome. In embodiments, the gene disclosed in Table 10 is located on a chromosome in the wheat plant cell, and the modified genome includes: (a) a difference of DNA methylation in less than 0.01% of the portion of the genome that is contained within the chromosome containing the gene disclosed in Table 10, relative to the reference genome; or (b) a difference of DNA methylation in less than 0.005% of the portion of the genome that is contained within the chromosome containing the gene disclosed in Table 10, relative to the reference genome; or (c) a difference of DNA methylation in less than 0.001% of the portion of the genome that is contained within the chromosome containing the gene disclosed in Table 10, relative to the reference genome. In embodiments, the modified genome has not more unintended changes in comparison to the reference genome than $1 \times 10^{\wedge}8$ mutations per bp per replication.

Embodiments of the invention are related to a wheat plant cell having a modified genome in comparison to an unmodified wheat plant cell having an reference genome, wherein the modified genome differs from the reference genome by including at least one predetermined modification of a gene disclosed in Table 10 and selected from the genes identified by gene name in Table 10, or encoding a protein having at least 90/a (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:693-976, or selected from the genomic sequences identified as SEQ ID NOs:977-1260, wherein the at least one predetermined modification is selected from (a) heterologous integration of a nucleic acid sequence that is encoded by at least one donor polynucleotide molecule and that includes a regulatory element, at a predetermined locus between 1-1000 nucleotides upstream of the start codon of the coding sequence of a gene disclosed in Table 10 in the reference wheat genome or 1-1000 nucleotides upstream of the start codon of the coding sequence of a gene disclosed in Table 10 in the reference wheat genome, (b) heterologous integration of a nucleic acid sequence that is encoded by at least one donor polynucleotide molecule and that includes a regulatory element, at a predetermined locus in the 3' untranslated region or within 1000 nucleotides downstream of the stop codon of a gene disclosed in Table 10 in the reference wheat genome, and (c) heterologous integration of a nucleic acid sequence that is encoded by at least one donor polynucleotide molecule and that includes a regulatory element, within an intron or within an exon of a gene disclosed in Table 10 in the reference wheat genome. In embodiments, the heterologous integration of a nucleic acid sequence is by an HDR mechanism. In embodiments, the heterologous integration of a nucleic acid sequence is by an NHEJ mechanism. In embodiments, the donor polynucleotide molecule includes ribonucleotides, deoxyribonucleotides, dideoxyribonucleotides, non-canonical nucleotides, and chemically modified nucleotides. In embodiments, the donor polynucleotide molecule is selected from the group consisting of a blunt-ended double-stranded DNA, a double-stranded DNA with at least one unpaired nucleotide at one terminus or at both termini, a single-stranded DNA, a blunt-ended double-stranded DNA/RNA hybrid, and a double-stranded DNA/RNA hybrid with at least one unpaired nucleotide at one terminus or at both termini. In embodiments, the donor polynucleotide molecule lacks homology to the genome sequences adjacent to the integration site or lacks homology to the predetermined locus in the reference genome.

Embodiments of the invention are related to a wheat plant cell having a modified genome in comparison to an unmodified wheat plant cell having an reference genome, wherein the modified genome differs from the reference genome by including at least one predetermined modification of a gene disclosed in Table 10 and selected from the genes identified by gene name in Table 10, or encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from SEQ ID NOs:693-976, or selected from the genomic sequences identified as SEQ ID NOs:977-1260, wherein the at least one predetermined modification includes deletion, addition, or substitution of at least one nucleotide in a regulatory element that regulates expression of a gene disclosed in Table 10 in the reference genome or deletion, addition, or substitution of at least one nucleotide in coding sequence of a gene disclosed in Table 10 in the reference genome. In embodiments, deletion, addition, or substitution of at least one nucleotide occurs at a double-strand break in the reference genome or between multiple double-strand breaks in the reference genome.

Embodiments of the invention are related to a wheat plant cell having a modified genome in comparison to an unmodified wheat plant cell having an reference genome, wherein the modified genome differs from the reference genome by including at least one predetermined modification of a gene disclosed in Table 10 and selected from the genes identified by gene name in Table 10, or encoding a protein having at least 90% identity to a sequence selected from SEQ ID NOs:693-976, or selected from the genomic sequences identified as SEQ ID NOs:977-1260, and wherein the modified genome further differs from the reference genome by including (a) a predetermined modification in at least one homoeoallele of a gene selected from pinBv1, pinBv2, LOC543302, LOC101290594, TaMOR-D, TaTFL1-2D, TB-A1, TB-B1, TB-D1, DEP1, Gasr7, PIN1, TaMOC1, TaPAP2-5A, TaVRS1-2B, WFZP-A, WFZP-B, WFZP-D, TaFT-B1, LOC542960, TaSnrk2.10-4A, TaSK5, TaOBF1a, TaPIMP1, TaWRKY2, TaWRKY19, LOC100415880, TaNAC2a, LEA3, TaUb2, NAC69-1, NAC2, TaMDC1, TaSC, Waox1a, ALMT1, SOD, CHP, TaAQP7, TaAQP8, TaWRKY10, CIPK14, TaWRKY1, TaWRKY33, TaGAPC1, UBA, Fhb1, Lr34, Lr67, Sr22, Sr33, Sr35, Sr45, Sr50, Tsn1, Yr36 (WKS1), Snn1, TaMLO-A1, TaMLO-B1, TaMLO-D1, FT, FKF1, PhyB, WCO1, ZenMFT-3D, MADS, TaGI1, WAP1, NFYB-A, NFYB-B, NFYB-D, NAC1, Skp1, TIF, WCBP1, WRKY, TaSAG6, TaSAG3, TaSAG1, FeSOD, CWINV2SM, CWINV 1SM, SOD, APX, GS2, NAM, rbcL, IVR1, and a1 as disclosed in Table 9, or (b) a predetermined modification in a gene encoding a protein having at least 90% identity (e.g., at least 90%, at least 91%, at least 92%, at least 93%, at least 94%, at least 95%, at least 96%, at least 97%, at least 98%, at least 99%, or at least 99.5%) to a sequence selected from SEQ ID NOs:257-474 as disclosed in Table 9, or (c) a predetermined modification in a gene selected from the genomic sequences identified as SEQ ID NOs:475-692 as disclosed in Table 9.

Further embodiments of the invention are related to progeny seed and plants of the wheat plant having a modified genome as has been specifically described in detail in this Example. Embodiments include seed of the wheat plant having a modified genome and progeny wheat plants of the wheat plant having a modified genome. In embodiments of the wheat plant having a modified genome, or of its progeny wheat plant or seed, the modified genome is associated with a trait selected from the group consisting of abiotic stress, architecture, biotic stress, nutrient use efficiency, photosynthesis, resource partitioning, and senescence; in embodiments, related sub-categories of traits include, but are not limited to, those disclosed in Table 10, e.g., changes in abscisic acid (ABA) signaling or response, biomass, cold tolerance, drought tolerance, tolerance to high temperatures, tolerance to low temperatures, salt tolerance, fertilization, fertility, flowering time, flower architecture, inflorescence architecture, lodging resistance, root architecture, shoot architecture, leaf architecture, yield; disease resistance, insect resistance, population density stress, shading stress, photosynthesis and respiration traits, seed weight, drydown rate, grain size, nitrogen utilization, oil production, oil metabolism, protein production, protein metabolism, provitamin A or carotenoid production, provitamin A or carotenoid metabolism, seed composition, seed filling (including sugar and nitrogen transport), starch production, and starch metabolism. Embodiments also include a processed product made from the seed of the wheat plant having a modified genome, a processed product made from the wheat plant having a modified genome, and a processed product made from progeny wheat plants of the wheat plant having a modified genome. Thus, a related embodiment is a method of manufacturing a processed wheat product, including the steps of: (a) growing a wheat plant having a modified genome as has been described in detail in this Example; and (b) processing the wheat plant into a processed wheat product, thereby manufacturing a processed wheat product. In embodiments, the processed wheat product is selected from the group consisting of intact wheat grains, wheat berries, cracked wheat, parched wheat, malt, grits, groats, semolina, middlings, flakes, flour, meal, bran, germ, endosperm, starch, gluten, protein, oil, chaff, fibre, and straw. Related embodiments include a method of manufacturing a processed wheat product, including the steps of: (a) growing a wheat plant having a modified genome as has been specifically described in detail in this Example, or growing its progeny wheat plants; and (b) processing the wheat plant (or its progeny wheat plants) into a processed wheat product, thereby manufacturing a processed wheat product. In embodiments, the processed wheat product is selected from the group consisting of intact wheat grains, wheat berries, cracked wheat, parched wheat, malt, grits, groats, semolina, middlings, flakes, flour, meal, bran, germ, endosperm, starch, gluten, protein, oil, chaff, fibre, and straw.

Additional embodiments are related to detection methods for identifying a wheat plant that has been subjected to genomic modification according to the methods described herein, where that modification method yields a low frequency of off-target mutations. A given off-target mutation that is found to result in a unique sequence in the genome and that does not result in an undesirable phenotype or trait, preferably one that results in no change in any coding sequence, can be used as an identifiable marker in the modified wheat plant which may be then unambiguously identified by suitable detection methods. Such detection methods include a step of identifying the off-target mutations (e.g., an insertion of a non-specific sequence, a deletion, or an indel resulting from the use of the genome editing agents, or non-specific insertions of part or all of a sequence encoded by one or more donor polynucleotide molecules at one or more coding or non-coding loci in a genome). Such "track and trace" detection methods can be used to track the movement of a wheat plant cell or wheat plant or product thereof through a supply chain. The presence of such an identified mutation in a processed product or commodity product is prima facie evidence that the product contains, or is derived from, a wheat plant cell, wheat plant, or wheat seed of this invention. In related embodiments, the presence of the off-target mutations is detected using PCR, a chip-based assay, probes specific for the mutation, or any other technique known in the art to be useful for detecting the presence of particular nucleic acid sequences.

Example 20

This example illustrates embodiments of the invention related to wheat plants exhibiting modified architecture. This example illustrates a wheat plant having a modified genome that results in the wheat plant exhibiting modified architecture in comparison to an unmodified wheat plant having an reference genome, wherein the modified genome differs from the reference genome by including predetermined modifications of a gene of interest (e.g., modification of regulatory sequence that affects expression of the gene of interest), wherein the predetermined modification is a heterologous integration of a nucleic acid sequence that is encoded by at least one donor polynucleotide molecule and that includes a regulatory element at a predetermined locus between 1-1000 nucleotides upstream of the start codon of the coding sequence of the gene of interest in the reference genome or 1-1000 nucleotides upstream of the start codon of the coding sequence of the gene of interest in the reference genome, wherein the gene of interest is TaMOR-D, or is a gene encoding a protein having at least 90% identity to the sequence identified by SEQ ID NO:267, or is genomic sequence identified by SEQ ID NO:485. In embodiments, the regulatory element is one having a nucleotide sequence selected from the group consisting of SEQ ID NOs:66-256. More specifically, this example illustrates heterologous integration of a nucleic acid sequence that is encoded by at least one donor polynucleotide molecule and that includes regulatory element consisting of the auxin-responsive monocot ocs orthologue with SEQ ID NO:231 at one of three double-strand breaks (DSBs) located at predetermined loci between 1-1000 nucleotides upstream of the start codon of the coding sequence of the TaMOR-D gene in the reference genome or 1-1000 nucleotides upstream of the start codon of the coding sequence of the TaMOR-D gene in the reference genome. In this example, the regulatory element is encoded by a donor polynucleotide molecule that entirely lacks homology to the genome sequences adjacent to the integration site, i.e., that lacks homology to the predetermined locus in the reference genome.

The wheat gene TaMOR (MORE ROOT) encodes a plant-specific transcription factor belonging to the ASYMMETRIC LEAVES2/LATERAL ORGAN BOUNDARIES (AS2/LOB) protein family. TaMOR mainly localizes to root initiation sites. Transgenic expression of the wheat gene TaMOR in rice produced transgenic rice plants exhibiting more lateral roots, more crown roots, a longer main panicle, a higher number of primary branches on the main panicle, a higher grain number per plant, and higher yield per plant than wild type rice plants; however, overexpression of TaMOR-D under the control of the strong 35S promoter caused lethality in some transformants.; see Li et al. (2016) *J. Exp. Botany.*, 67:4155-4167; doi.org/10.1093/jxb/erw193.

This example illustrates modification of the endogenous TaMOR-D gene in wheat plants for root architecture improvement and grain yield enhancement. The amino acid sequences of TaMOR-A, -B and -D are highly conserved and thus this approach is also useful for modification of the endogenous wheat TaMOR-A or TaMOR-B. In this non-limiting example, an "OCS orthologue" regulatory element (a monocot orthologue of the *Arabidopsis thaliana* enhancer OCS, identified in *Zea mays*) is heterologously integrated into non-coding sequence at one of three predetermined loci upstream of the start codon of the coding sequence of the endogenous wheat gene TaMOR-D to provide a modified wheat plant exhibiting increased expression of TaMOR-D and modified plant architecture. (Alternative regulatory elements that similarly up-regulate expression are disclosed in Table 8.)

The protein sequence of the D genome homeoallele of TaMOR is provided in Table 9 as SEQ ID NO:267 with the corresponding D genome genomic sequence of SEQ ID NO:485. Promoter sequence of TaMOR-D was identified as having the nucleotide sequence tgcctgct-gatgtgcacgaatataaatgtacatacacttgtgcttatattttcccttgctaattttat-caaagttgtctctgatcccaagcaaaaagttctaaattaat ttcccatcacatat-tgtctccgagctgaataaaaagacagctccacttctggccaggtgatgtatgaa-atgtttgtatatgt attatccccgggtttat-caactggactgtgctggcgagtcgcgctgcaacgcatcccaactaat-cacaaaataaatcatcacacgggcaagcagtcacgat agcaactaaactaaaaacacgagagaaagttgtgtataattgcgcccg-gatgacctagccccattgtgctttgtccttctcttgggattggcagagtggtgta taaaagggcaggccttagcggaggaggagagcgcgccattggaagct-caaaataatgtaggcggttggccaccg gggagacacgccggaattgtttat-tcccttaggccctaatccccaaccatgcactccgcctcccttcctcttcctctcct-tataagca (SEQ ID NO:1261). Guide RNAs were designed to effect double-strand breaks (DSBs) at one of three predetermined loci upstream of the TaMOR-D gene's transcription start site. For use with a Cpf1 nuclease, the guides had the sequences UAAUUUCUACUCUUGUAGAUUUCCC-UUAGGCCCUAAUCCCC (SEQ ID NO:1262), effecting a DSB at 46 nucleotides upstream of the transcription start site, UAAUUUCUACUCUUGUAGAUUAGGUACAC-UAAUACUAUACA (SEQ ID NO:1263), effecting a DSB at 188 nucleotides upstream of the transcription start site, and UAAUUUCUACUCUUGUAGAUU-CAACUGGACUGUGCUGGCGA (SEQ ID NO:1264), effecting a DSB at 355 nucleotides upstream of the transcription start site. For use with a Cas9 nuclease, the guides had the sequences CUUAUAAGGAGAGGAAGAG-GAGUUUUAGAGCUAUGCU (SEQ ID NO:1265), effecting a DSB at 20 nucleotides upstream of the transcription start site, GUGUACCUACAAAAAAUGGGAGUUUUA-GAGCUAUGCU (SEQ ID NO:1266), effecting a DSB at 160 nucleotides upstream of the transcription start site, and UCACAAAAUAAAUCAUCACACGUUUUAGAGC-UAUGCU (SEQ ID NO:1267), effecting a DSB at 309 nucleotides upstream of the transcription start site. A nucleic acid sequence encoded by a donor polynucleotide molecule and encoding the monocot ocs enhancer GTAAGCGCTTAC (SEQ ID NO:231) is heterologously integrated at each DSB to constitutively increase the expression of TaMOR-D. In certain experiments, the donor polynucleotide is a single-stranded DNA that is phosphorylated on the 5' end and that contains two phosphorothioate linkages at each terminus (i.e., the two linkages between the most distal three bases on either end of the strand); alternative donor polynucleotides are non-chemically modified single-stranded DNA molecules, chemically modified or non-chemically modified double-stranded DNA molecules, and chemically modified or non-chemically modified double-stranded DNA/RNA hybrid molecules.

In one set of experiments, wheat protoplasts are prepared as described in Examples 1-4, and the editing reagents are delivered as RNPs (nuclease and guide RNAs), together with the donor polynucleotide encoding the monocot ocs orthologue, following protocols similar to those described in Examples 5 and 11-15. For experiments carried out in protoplasts, the TaMOR-D transcript level is measured by qPCR. In another set of experiments, wheat meristems are prepared as described in Examples 8 and 9, the editing reagents are prepared as RNPs (nuclease and guide RNAs) as described in Example 5 and delivered together with the donor polynucleotide encoding the monocot ocs orthologue by microinjection following protocols similar to those described in Example 8 or by biolistics following protocols similar to those described in Example 9, and plants grown directly from the treated meristems without selection or use of callus culture. In these experiments, the increase in transcript level of TaMOR-D can also be measured by qPCR. The modified plants grown from the microinjection- or biolistics-treated meristems are analyzed for changes in root morphology, other changes in stem, leaf, or inflorescence architecture, changes in total biomass, and changes in seed number and total seed yield. The modified wheat plants containing a heterologously integrated monocot ocs enhancer within 1 to about 500 nucleotides of the TaMOR-D start codon are expected to exhibit at least one trait selected from improved root architecture (e.g., more lateral roots and/or more crown roots) and increased grain number and higher yield per plant, in comparison to a control wheat plant that lacks the genomic modifications. A similar approach to upregulating expression levels of the conserved homeoalleles TaMOR-A or TaMOR-B by homologous integration of an expression-increasing non-coding regulatory element in the 5' untranslated region of the gene is also expected to provide a similar phenotype in modified wheat plants.

Example 21

This example illustrates embodiments of the invention related to wheat plants exhibiting modified architecture. This example illustrates a wheat plant having a modified genome that results in the wheat plant exhibiting modified architecture in comparison to an unmodified wheat plant having an reference genome, wherein the modified genome differs from the reference genome by including predetermined modifications of a gene of interest (e.g., modification of regulatory sequence that affects expression of the gene of interest), wherein the predetermined modification is a heterologous integration of a nucleic acid sequence that is encoded by at least one donor polynucleotide molecule and that includes a regulatory element at a predetermined locus between 1-1000 nucleotides upstream of the start codon of the coding sequence of a gene of interest in the reference genome or 1-1000 nucleotides upstream of the start codon of the coding sequence of a gene of interest in the reference genome, wherein the gene of interest is TB-D1, or is a gene encoding a protein having at least 90% identity to the sequence identified by SEQ ID NO:275, or is genomic sequence identified by SEQ ID NO:493. In embodiments, the regulatory element is one having a nucleotide sequence selected from the group consisting of SEQ ID NOs:66-256. More specifically, this example illustrates heterologous integration of a nucleic acid sequence that is encoded by at least one donor polynucleotide molecule and that includes regulatory element consisting of the constitutively up-regulating "G-box enhancer" regulatory element (SEQ ID NO:244) at one of three double-strand breaks (DSBs) located at predetermined loci between 1-1000 nucleotides upstream of the start codon of the coding sequence of the TaTB-D1 gene in the reference genome or 1-1000 nucleotides upstream of the start codon of the coding sequence of the TaTB-D1 gene in the reference genome. In this example, the regulatory element is encoded by a donor polynucleotide molecule that entirely lacks homology to the genome sequences adjacent to the integration site, i.e., that lacks homology to the predetermined locus in the reference genome.

An ortholog of the maize domestication gene, TEOSINTE BRANCHED1 (TB1), regulates wheat inflorescence architecture in a dosage-dependent manner. The increased dosage of TB1 promotes paired spikelet production through interacting with FLOWERING LOCUS T1 (FT1). TB-D1 is also the gene responsible for the inflorescence and plant architecture phenotypes observed in highly-branched plants; see Dixon et al. (2018) *Plant Cell*; doi:10.1105/tpc.17.00961.

This example illustrates modification of the endogenous Teosinte Branched (TB1) gene in wheat plants for modified branching or inflorescence architecture and increased grain yield. In this non-limiting example, an "G-box enhancer" regulatory element (SEQ ID NO:244) is heterologously integrated at one of three predetermined loci upstream of the start codon of the coding sequence of the endogenous wheat gene TB-D1 to provide a modified wheat plant exhibiting increased expression of TB-D1 and modified branching or inflorescence architecture. (Alternative regulatory elements that similarly up-regulate expression are disclosed in Table 8.)

The protein sequences of the *Triticum aestivum* wheat D genome homeoallele of TB1 is provided in Table 9 as SEQ ID NO:275, with the corresponding genomic sequence SEQ ID NO:493. Promoter sequence about 350 basepairs upstream of the start codon of TB-D1 was identified as having the nucleotide sequence gccctcctacaaagagcccat-gatgtgtgtgtgtgtgtgtctgtgtgtgaactcaggat-gagctaggtaccagtgccctcctcctcategccctctgcaa ctcccatgg-gagatttatctcttcctagtcctagacctctttaactatctctttcgttetctcttca-cccgcagacacacaagcgtgaagagcggcttatgcat ggccgggcacatct-gatcatagctcctaggccacggccacaccctctct-cacacacagtagaagcgcgcagctagcagttgctcttcttccgagggcc tagagacgggtggtctcagggtcttggagtcccatcactaaagc (SEQ ID NO:1268). Guide RNAs were designed to effect double-strand breaks (DSBs) at one of three predetermined loci upstream of the TB-D1 gene's transcription start site. For use with a Cpf1 nuclease, the guides had the sequences UAAUUUCUACUCUUGUAGAUGUGAUGGGACUC-CAAGACCCU (SEQ ID NO:1269), effecting a DSB at 25 nucleotides upstream of the transcription start site, UAAUUUCUACUCUUGUAGAUGUUCUCUCUUC-CACCCGCAGA (SEQ ID NO:1270), effecting a DSB at 174 nucleotides upstream of the transcription start site, and UAAUUUCUACUCUUGUAGAUUCUCUUCCUAGUC-CUAGACCU (SEQ ID NO:1271), effecting a DSB at 212 nucleotides upstream of the transcription start site. A nucleic acid sequence encoded by a donor polynucleotide molecule and encoding the G-box enhancer ACACGTGACACGTGACACGTGACACGTG (SEQ ID NO:244) is heterologously integrated at each DSB to constitutively increase the expression of TB-D1. In certain experiments, the donor polynucleotide is a single-stranded DNA that is phosphorylated on the 5' end and that gtgcagttt (SEQ ID NO:1274) was used together with the guide RNA to introduce the G1907C SNP (shown in uppercase font) and also to introduce a T to C mutation (shown in underlined upper case font) to destroy the PAM sequence. In certain experiments, the donor polynucleotide is a single-stranded DNA that is phosphorylated on the 5' end and that contains two phosphorothioate linkages at each terminus (i.e., the two linkages between the most distal three bases on either end of the strand); alternative donor polynucleotides are non-chemically modified single-stranded DNA molecules, chemically modified or non-chemically modified double-stranded DNA molecules, and chemically modified or non-chemically modified double-stranded DNA/RNA hybrid molecules.

In one set of experiments, wheat protoplasts are prepared as described in Examples 1-4, and the editing reagents are delivered as RNPs (nuclease and guide RNAs), together with the donor polynucleotide encoding the TaSnRK2.10 replacement sequence including the G1907C SNP and PAM-destroying mutation, following protocols similar to those described in Examples 5 and 11-15. For experiments carried out in protoplasts, CRISPR amplicon sequencing is used to verify the presence of the intended edits in the TaSnRK2.10 gene. In another set of experiments, wheat meristems are prepared as described in Examples 8 and 9, the editing reagents are prepared as RNPs (nuclease and guide RNAs) as described in Example 5 and delivered together with the donor polynucleotide encoding the TaSnRK2.10 replacement sequence including the G1907C SNP and PAM-destroying mutation by microinjection following protocols similar to those described in Example 8 or by biolistics following protocols similar to those described in Example 9, and plants grown directly from the treated meristems without selection or use of callus culture. In these experiments, CRISPR amplicon sequencing is again used to verify the presence of the intended edits in the TaSnRK2.10 gene. The modified plants grown from the microinjection- or biolistics-treated meristems are analyzed for changes in plant architecture, changes in total biomass, and changes in seed number and total seed yield. The modified wheat plants containing the modified TaSnRK2.10 gene are expected to exhibit at least one trait selected from modified architecture and higher yield per plant, in comparison to a control wheat plant that lacks the genomic modifications.

Example 23

This example illustrates embodiments of the invention related to wheat plants exhibiting improved disease resistance, e.g., improved resistance to or tolerance of infection by plant pathogens, and improved resistance to pests transmitting such pathogens. More specifically, this example illustrates a wheat plant having a modified genome that results in the wheat plant exhibiting improved disease resistance in comparison to an unmodified wheat plant having an reference genome, wherein the modified genome differs from the reference genome by including predetermined modifications of a gene of interest (e.g., modification of regulatory sequence that affects expression of the gene of interest), wherein the predetermined modifications include deletion, addition, or substitution of at least one nucleotide in a regulatory element that regulates expression of a gene of interest in the reference genome and deletion, addition, or substitution of at least one nucleotide in coding sequence of a gene of interest in the reference genome, wherein the gene of interest is Lr34, or is a gene encoding a protein having at least 90% identity to a sequence selected from the group consisting of the sequences identified by SEQ ID NO:366 in Table 9, or is genomic sequence selected from the group consisting of the genomic sequences identified by SEQ ID NO:584. More specifically, this example illustrates replacement of coding sequence (exons 11 and 12) of the endogenous wild-type Lr34 gene on chromosome 4A by effecting two separate double-stranded breaks in the reference genome followed by site-specific integration of nucleotide sequence of two donor polynucleotide molecules encoding the desired nucleic acid changes (nucleotide deletions in exon 11 and a single nucleotide replacement in exon 12). In this example, the donor polynucleotide molecule has sequence homology to the genome sequences adjacent to the DSB and the exon replacement is believed to involve homology-directed repair (HDR).

The ABC transporter-like wheat gene Lr34 is associated with wheat resistance to leaf rust (caused by *Puccinia triticina*), stripe rust (*P. striiformis*) and powdery mildew (*Blumeria graminis*). The Lr34 gene is expressed in adult plants during the critical grain-filling stage and is most effective in the flag leaf. See Krattinger et al. (2009) *Science*, 323:1360-1363; doi:10.1126/science.1166453. A known Lr34 resistant haplotype occurs in three breeding lineages in wheat; this includes a deletion of 3 bp in exon 11 and a SNP in exon 12, which is believed to convert a Tyr to His, affecting a transmembrane domain connecting the two nucleotide binding domains. A survey of North American wheat varieties has shown that the resistant Lr34 is not universally present; see Kolmer et al. (2008) *Crop Sci.*, 48:5; doi:10.2135/cropsci2007.08.0474.

This example illustrates modification of the endogenous wild-type Lr34 gene on chromosome 4A in wheat plants for increased grain yield. In this non-limiting example, a donor polynucleotide molecule is used to replace the wild-type sequence with a rust-resistant LR34 sequence identified in Chinese Spring wheat. Editing the resistance allele into commercial wheat germplasm is expected to provide durable resistance, thereby reducing fungicide use, reducing fungal disease epidemics, and providing yield advantages.

The protein sequence of the *Triticum aestivum* wheat D genome homeoallele of Lr34 is provided in Table 9 as SEQ ID NO:366, with the corresponding genomic sequence SEQ ID NO:584. Exon 11 of this Lr34 allele has the sequence (SEQ ID NO: 1275)
CTTGCCATTATTGCACTCGTAACAATGTCTGTATTCCTTCGAACTCGCAT

GACAATAAGTTTCACTCATGCAAATTACTATATGGGAGCATTATTTTTTT

CCATCTTCATGATTATGTTAAATGGCATACCAGAGATGAGCATGCAGATT

GGGAGACTCCCAAGTTTTTACAAGCAAAAGAGCTACTATTTCTATTCATC

ATGGGCATATGCAATACCAGCTTCAGTCCTAAAGGTCCCTATTTCCATAC

TGGATTCGCTTGTATGGATATCTATCACATATTATGGTATTGGTTATACA

CCTACTGTTTCAAG with the 3 b deletion found in the resistant allele shown in underlined font; exon 12 of this Lr34 allele has the sequence (SEQ ID NO: 1276)
GTTCTTCTGCCAGTTTCTGATACTTTGTCTTCTCCATCATTCAGTCACCT

CGCAGTATCGATTTATTGCTTCATACTTCCAAACACCTATTGTGTCTTTC

```
                                                        -continued
TTCTACCTTTTTCTTGCTCTAACAGTATTCCTTACATTCGGAGGCTTCAT

TCTTCCCAAGA
``` with the T→C SNP shown in underlined font. A Cpf1 guide RNA for editing exon 11 with the sequence UAAUUUC-UACUCUUGUAGAUACAUAAUCAUGAAGAUG-GAAA (SEQ ID NO:1277) was designed to introduce a DSB 5244 base pairs base pairs downstream of the transcription start site; this guide RNA is delivered with a donor polynucleotide molecule with the sequence

```
                                              (SEQ ID NO: 1278)
CATTATTGCACTCGTAACAATGTCTGTATTCCTTCGAACTCGCATGACA

ATAAGTTTCACTCATGCAAATTACTATATGGGAGCATTATTTTTTTCCA

TCATGATTATGTTAAATGGCATACCAGAGATGAGCATGCAGATTGGGAG

ACTCCCAAGTTTTTACAAGCAAAAGAGCTACTATTTCTATTCATCATGG

GCAT,
``` which effects the TTC deletion in exon 11. A Cpf1 guide RNA for editing exon 12 with the sequence UAAUUUC-UACUCUUGUAGAUUCUUCUCCAUCAUUCAGUCAC (SEQ ID NO:1279) was designed to introduce a DSB 5590 base pairs downstream of the transcription start site; this is delivered with a donor polynucleotide molecule with the sequence aacattgagaaactctacmtntcat-ttctaggttcttctgccagtgtctCtgtcttctccatcattcagtcacctcgcagCatc-gattta ttgettcatacttccaaacacctattgtgtetttcttc-tacctttttcttgctctaacagtattccttacattcggaggcttcattcttc (SEQ ID NO:1280), which effects the T4C mutation (shown in upper case font) in exon 12 and also introduces a T4C mutation (shown in underlined upper case font) to destroy the PAM sequence. In certain experiments, the donor polynucleotide is a single-stranded DNA that is phosphorylated on the 5' end and that contains two phosphorothioate linkages at each terminus (i.e., the two linkages between the most distal three bases on either end of the strand); alternative donor polynucleotides are non-chemically modified single-stranded DNA molecules, chemically modified or non-chemically modified double-stranded DNA molecules, and chemically modified or non-chemically modified double-stranded DNA/RNA hybrid molecules. In certain experiments, the donor polynucleotide is covalently or non-covalently linked or tethered to the corresponding RNP either to the nuclease or to the guide RNA; RNPs prepared with tethered donors are useful in delivery protocols where multiple RNP/donor compositions are delivered simultaneously to plant cells or tissues.

In one set of experiments, wheat protoplasts are prepared as described in Examples 1-4. The editing reagents are prepared as two RNP/donor compositions; the first included an RNP made with Cpf1 nuclease and the exon 11 guide RNA, together with the donor polynucleotide encoding the corresponding Lr43 exon 11 replacement sequence, and the second included an RNP made with Cpf1 nuclease and the exon 12 guide RNA, together with the donor polynucleotide encoding the corresponding Lr43 exon 12 replacement sequence. The RNP/donor compositions were delivered sequentially to the protoplasts following protocols similar to those described in Examples 5, 11-14, and especially Example 15. For experiments carried out in protoplasts, CRISPR amplicon sequencing is used to verify the presence of the intended edits in the Lr34 gene. In another set of experiments, wheat meristems are prepared as described in Examples 8 and 9, the editing reagents are prepared as two RNP/donor compositions as described above and delivered to the wheat meristems by sequential microinjection delivery following protocols similar to those described in Example 8 or by sequential biolistics delivery following protocols similar to those described in Example 9, and plants grown directly from the treated meristems without selection or use of callus culture. Alternatively, the different RNP/donor compositions are prepared with donor molecules linked or tethered to the RNP nuclease or guide RNA, and are delivered simultaneously. In these experiments, CRISPR amplicon sequencing is again used to verify the presence of the intended edits in the Lr34 gene. The modified plants grown from the microinjection- or biolistics-treated meristems are tested for resistance to rust infection. The modified wheat plants containing the modified Lr34 gene are expected to exhibit at least one trait selected from improved resistance to rust infections and higher yield per plant, in comparison to a control wheat plant that lacks the genomic modifications.

Example 24

This example illustrates embodiments of the invention related to wheat plants exhibiting improved disease resistance, e.g., improved resistance to or tolerance of infection by plant pathogens, and improved resistance to pests transmitting such pathogens. More specifically, this example illustrates a wheat plant having a modified genome that results in the wheat plant exhibiting improved disease resistance in comparison to an unmodified wheat plant having an reference genome, wherein the modified genome differs from the reference genome by including predetermined modifications of all homeoalleles of a gene of interest, wherein the predetermined modifications include deletion, addition, or substitution of at least one nucleotide in coding sequence of a gene of interest in the reference genome, wherein the gene of interest is TaMLO (including TaMLO-A1, TaMLO-B1, and TaMLO-D1), or is a gene encoding a protein having at least 90% (e.g., at least 90%, at least 91%, at least 92%, at least 93%, at least 94%, at least 95%, at least 96%, at least 97%, at least 98%, at least 99%, or at least 99.5%) identity to a sequence selected from the group consisting of the sequences identified by SEQ ID NOs:396-398 in Table 9, or is genomic sequence selected from the group consisting of the genomic sequences identified by SEQ ID NOs:614-616. More specifically, this example illustrates introduction of a double-strand break in coding sequence (a single exon) of all homeoalleles of TaMLO, followed by deletion, addition, or substitution of at least one nucleotide, effectively resulting in knocking-out expression of a functional MLO protein.

In wheat, powdery mildew is caused by Blumeria graminis f. sp. tritici, which can lead to serious losses in epidemics. A recent survey of USA wheat germplasm has shown that many QTLs are required to achieve some measure of resistance and so inevitably there is widespread divergence in the levels of resistance in commercial wheats varieties and selection for sustained resistance is difficult; see Liu et al. (2017) Sci. Reports, 7: 11743; doi:10.1038/s41598-017-11230-z. Deletion of the MLO (MILDEW-RESISTANCE LOCUS) genes produces strong resistance to powdery mildew in Arabidopsis, tomato, barley and wheat.

In this example, a single Cas9 guide RNA was designed to cut at a predetermined locus in the MLO homeoalleles in all three of the genomes in hexaploid common wheat, Triticum aestivum. This gRNA, with the sequence UCACGCAGGACCCAAUCUCCGUUUUAGAGC-
UAUGCU (SEQ ID NO:1281), effects DSBs located 343 base pairs from the MLO transcription start site in TaMLO-A exon 2, 333 base pairs from the MLO transcription start site in TaMLO-B exon 1, and 343 base pairs from the MLO transcription start site in TaMLO-D exon 2. The TaMLO-A exon 2 sequence is provided as (SEQ ID NO: 1282)
TGGTTCCACAAGCGGCACAAGAACGCGCTGGCGGAGGCGCTGGAGAAGAT

GAAGGCGGAGCTGATGCTGGTGGGATTCATCTCGCTGCTGCTCGCCGTCA

CGCAGGACCCAATCTCCGGGATATGCATCTCCCAGAAGGCCGCCAGCATC

ATGCGCCCTGCAAGGTGGAACCCGGTTCCGTCAAGAGCAAGTACAAGGA

CTACTACTGCGCCAAAGAG (genomic sequence recognized by the guide shown in underlined font with the PAM sequence shown in italics). The TaMLO-B exon 1 sequence is provided as (SEQ ID NO: 1283)
ATGGCGGACGACGACGAGTACCCCCCAGCGAGGACGCTGCCGGAGACGCC

GTCCTGGGCGGTGGCCCTCGTCTTCGCCGTCATGATCATCGTGTCCGTCC

TCCTGGAGCACGCGCTCCATAAGCTCGGCCATGTAAGTTCCTTCCCGGAA

AAAGTAAATGAGTGTCTGCCCCAGTCAGACTCAGCTCATGGCTTCCTCCT

TGTTGGCGTGTGTAAGCAGTGGTTCCACAAGCGGCACAAGAACGCGCTGG

CGGAGGCGCTGGAGAAGATCAAGGCGGAGCTCATGCTGGTGGGCTTCATC

TCGCTGCTGCTCGCCGTGACGCAGGACCCCATCTCCGGGATATGCATCTC

CGAGAAGGCCGCCAGCATCATGCGGCCCTGCAAGCTGCCCCCTGGCTCCG

TCAAGAGCAAGTACAAAGACTACTACTGCGCCAAACAG (genomic sequence recognized by the guide shown in underlined font, with 2 mismatches shown in bold font, and the PAM sequence shown in italics). The TaMLO-D exon 2 sequence is provided as (SEQ ID NO: 1284)
TGGTTCCACAAGCGGCACAAGAACGCGCTGGCGGAGGCGCTGGAGAAGAT

CAAAGCGGAGCTGATGCTGGTGGGGTTCATCTCGCTGCTGCTCGCCGTGA

CGCAGGACCCAATCTCCGGGATATGCATCTCCGAGAAGGCCGCCAGCATC

ATGCGGCCCTGCAGCCTGCCCCCTGGTTCCGTCAAGAGCAAGTACAAAGA

CTACTACTGCGCCAAAAAG (genomic sequence recognized by the guide shown in underlined font, with 1 mismatch shown in bold on an % sequence shown in italics).

In one set of experiments, wheat protoplasts are prepared as described in Examples 1-4, and the editing reagents are delivered as an RNP (nuclease and guide RNA), following protocols similar to those described in Examples 5, 12, 14, 15, and especially Examples 11 and 13. For experiments carried out in protoplasts, qPCR is used to measure TaMLO transcript levels and CRISPR amplicon sequencing is used to verify the presence of the intended edits in the TaMLO homeoalleles. In another set of experiments, wheat meristems are prepared as described in Examples 8 and 9, the editing reagents are prepared as an RNP (nuclease and guide RNA) as described in Example 5 and delivered by microinjection following protocols similar to those described in Example 8 or by biolistics following protocols similar to those described in Example 9, and plants grown directly from the treated meristems without selection or use of callus culture. In these experiments, qPCR is used to measure TaMLO transcript levels and CRISPR amplicon sequencing is again used to verify the presence of the intended edits in the TaMLO homeoalleles. The modified plants grown from the microinjection- or biolistics-treated meristems are tested for resistance to powdery mildew infection. The modified wheat plants containing the modified TaMLO gene are expected to exhibit at least one trait selected from improved resistance to powdery mildew infections and higher yield per plant, in comparison to a control wheat plant that lacks the genomic modifications.

Example 25

This example illustrates embodiments of the invention related to wheat plants exhibiting modified flowering time. More specifically, this example illustrates a wheat plant having a modified genome that results in the wheat plant exhibiting modified flowering time in comparison to an unmodified wheat plant having an reference genome, wherein the modified genome differs from the reference genome by including predetermined modifications of a gene of interest (e.g., modification of regulatory sequence that affects expression of the gene of interest), wherein the predetermined modifications include heterologous integration of a nucleic acid sequence that is encoded by at least one donor polynucleotide molecule and that includes a regulatory element having a nucleotide sequence selected from the group consisting of SEQ ID NOs:66-256 at a predetermined locus in the 3' untranslated region or within 1000 nucleotides downstream of the stop codon of a gene of interest in the reference genome, wherein the gene of interest is PHYB, or is a gene encoding a protein having at least 90% identity to a sequence selected from the group consisting of the sequences identified by SEQ ID NOs:404-406, or is genomic sequence identified by SEQ ID NOs:622-624. In this non-limiting specific example, the PHYB gene with the protein sequence of SEQ ID NO:404 and the genomic sequence of SEQ ID NO:622 was modified, but a similar approach can be used to modify the endogenous PHYB on chromosomes in the B genome or the D genome, or to modify two or more homeoalleles on any combination of the A, B, and D genomes of common wheat. More specifically, this example illustrates integration of a heterologous regulatory element in a predetermined locus in non-coding sequence, i.e., the 3' untranslated region of the endogenous wild-type PHYB gene on chromosome 4A, by effecting a DSB in the reference genome followed by integration at the DSB of a non-coding mRNA destabilizing sequence encoded by a donor polynucleotide molecule. In this example, the regulatory element is encoded by a donor polynucleotide molecule that entirely lacks homology to the genome sequences adjacent to the integration site, i.e., that lacks homology to the predetermined locus in the reference genome.

In cereal crops such as wheat, optimal timing of developmental transitions enables maximizing grain yield. Modulation of flowering time allows different wheat varieties to be adapted for different regions and climates. The genes phytochrome B (PHYB) and phytochrome C (PHYC) are both required for the photoperiodic induction of wheat flowering. Under long day photoperiod, phyB null mutant was reported to exhibit a severe delay in flowering; see Pearce et al. (2016) *BMC Plant Biology* (2016) 16:141; doi:10.1186/s12870-016-0831-3. In this example, the expression of PHYB is effectively decreased by destabilizing the gene's mRNA sufficiently to provide a wheat plant having a modified genome and exhibiting a delay in flowering time.

The 350 base pairs located immediately 3' to the PHYB stop codon (i.e., the 3' untranslated region nucleotides at positions 8349-8698 of PHYB genomic sequence SEQ ID NO:622) in chromosome 4A of common wheat (*Triticum aestivum*) is provided by tatggcaagct-gaaagctgacctcgcctaactgttcggtcagccaggtgacttgagattcccgga-taggagggagcctagttcgtgagaagcccgcaaa atcaatatgagcacgccgg-gagctgcaaatgtgattcccggccattcctggcacgccgactgtacgcgaagt-gttattcgattagagtttcatggcggcga gcactgaacat-gaacactgacggtaatgtagctggtagcataggcccatgactacttgga-taaagtaaatacgatgttcttagccgctatgtatatatacatg agaatatctcttgtat-tatggataaggagagctgtacagctcccacg (SEQ ID NO:1285). A first Cpf1 guide RNA with the sequence UAAUUUCUA-CUCUUGUAGAUCGGGCUUCUCACGAACUAGGC (SEQ ID NO:1286) was designed to effect a DSB at 7424 nucleotides downstream of the PHYB transcription start site. A second Cpf1 guide RNA with the sequence UAAUUUC-UACUCUUGUAGAUAUGGCGGCGAGCACUGAA-CAU (SEQ ID NO:1287) was designed to effect a DSB at 7557 nucleotides downstream of the PHYB transcription start site. These gRNAs were delivered (as Cpf1 RNPs) together with a donor polynucleotide encoding a mRNA-destabilizing sequence AATTTTAATTTTAATTTTAATTT-TAATTTTAATTTT (SEQ ID NO:246). Depending on the combination of the donor polynucleotide with one or both of the Cpf1 RNPs, the miRNA destabilizing element is heterologously inserted at either of the DSBs, or at both of the DSBs. In certain experiments, the donor polynucleotide is a single-stranded DNA that is phosphorylated on the 5' end and that contains two phosphorothioate linkages at each terminus (i.e., the two linkages between the most distal three bases on either end of the strand); alternative donor polynucleotides are non-chemically modified single-stranded DNA molecules, chemically modified or non-chemically modified double-stranded DNA molecules, and chemically modified or non-chemically modified double-stranded DNA/RNA hybrid molecules.

In one set of experiments, wheat protoplasts are prepared as described in Examples 1-4, and the editing reagents are delivered as RNPs (nuclease and one or both of the two guide RNAs), together with the donor polynucleotide encoding the mRNA destabilizing element, following protocols similar to those described in Examples 5 and 11-15. For experiments carried out in protoplasts, the PHYB transcript levels, as well as those of the downstream PHYB-regulated genes, PPD1, FT1, and VRN1, are measured by qPCR. In another set of experiments, wheat meristems are prepared as described in Examples 8 and 9, the editing reagents are prepared as RNPs (nuclease and one or both of the guide RNAs) as described in Example 5 and delivered together with the donor polynucleotide encoding the mRNA destabilizing element by microinjection following protocols similar to those described in Example 8 or by biolistics following protocols similar to those described in Example 9, and plants grown directly from the treated meristems without selection or use of callus culture. In these experiments, the increase in transcript level of PHYB, as well as those of the downstream PHYB-regulated genes, PPD1, FT1, and VRN1, can also be measured by qPCR. The modified plants grown from the microinjection- or biolistics-treated meristems are analyzed for changes in flowering time. The modified wheat plants containing at least one heterologously integrated mRNA destabilizing sequence within 1 to about 350 nucleotides downstream of the PHYB stop codon are expected to exhibit delayed flowering time, in comparison to a control wheat plant that lacks the genomic modifications.

Example 26

This example illustrates embodiments of the invention related to wheat plants exhibiting modified architecture. More specifically, this example illustrates a wheat plant having a modified genome that results in the wheat plant exhibiting modified architecture in comparison to an unmodified wheat plant having an reference genome, wherein the modified genome differs from the reference genome by including predetermined modifications of a gene of interest (e.g., modification of regulatory sequence that affects expression of the gene of interest), wherein the predetermined modifications include deletion, addition, or substitution of at least one nucleotide in a regulatory element that regulates expression of a gene of interest in the reference genome, wherein the gene of interest is TaMOC1, or is a gene encoding a protein having at least 90% identity to the sequence identified by SEQ ID NO:284, or is genomic sequence identified by SEQ ID NO:502. More specifically, this example illustrates replacement of non-coding sequence in both the 5' untranslated region and the 3' untranslated region of the endogenous wild-type TaMOC1 gene on chromosome 7A by effecting four separate double-stranded breaks in the reference genome followed by site-specific integration at each DSB of nucleotide sequence encoded by donor polynucleotide molecules to effect the desired nucleic acid changes (two single-nucleotide polymorphisms and an InDel in the 5' flanking region and one single-nucleotide polymorphism in the 3' flanking region). In this example, the donor polynucleotide molecules have sequence homology to the genome sequences adjacent to the DSB and the replacement of the non-coding sequences is believed to involve homology-directed repair (HDR).

Tomato Ls, *Arabidopsis* LAS, and rice MOC1 are orthologous genes that regulate axillary meristem initiation and outgrowth, which is involved in determining final plant architecture and floral structures. Sequence polymorphism assays and genetic mapping with 262 accessions suggested that the haplotype TaMOC1-7A HapH was significantly associated with higher spikelet number per spike; see Zhang et al. (2015) *Sci. Reports.* 5:12211; doi:10.1038/srep12211. This haplotype includes sequence polymorphisms only in the 5' and 3' UTRs, indicating that it is the expression level of TaMOC1 that is involved in controlling spikelet number. The TaMOC1-7A HapH haplotype can be recreated through editing a wheat genome by introducing two SNPs and one InDel in the 5' flanking region and one SNP in the 3' flanking region.

The TaMOC1 gene of the *Triticum aestivum* A genome has the protein sequence of SEQ ID NO:284 and the genomic sequence of SEQ ID NO:502. RNPs including a Cpf1 nuclease and guide RNA were prepared for delivery with specific donor polynucleotides encoding sequences to be integrated at predetermined loci in the TaMOC1 genomic sequence. A first guide RNA with the sequence UAAUUUC-UACUCUUGUAGAUUAGAUGCAGUAACUAGU-CGUA (SEQ ID NO:1288) is designed to effect a DSB at a predetermined locus 587 nucleotides upstream from the TaMOC1 transcription start site; this is delivered with a donor polynucleotide molecule having the sequence taccacaaaatccaattegccctaagctagcaatagcccctactacacgcaggtgtccattcatctatctatccgatctaaagctgccactgattaatGgt aAttctagatgcagtaactagtcgtagaagctaagctctggcgtatgaacctcgtccatgagccaccattccttggaatgtttcagattcccctcg (SEQ ID NO:1289), which is designed to effect a first nucleotide change of A to G (shown in upper case font) at 613 nucleotides upstream of the TSS (shown in upper case font) and a second nucleotide change of T to A (shown in underlined upper case font) to destroy the PAM sequence. A second guide RNA with the sequence UAAUUUCUACUCUUGUAGAUCCCUUCCCCCUCUACAUAGUU (SEQ ID NO:1290) is designed to effect a DSB at a predetermined locus 420 nucleotides upstream from the TaMOC1 transcription start site; this is delivered with a donor polynucleotide molecule having the sequence cacccaaatcatcctcgtcacagtccaggagataaaagacaacgccaccctcgccaccaccAttcccttccccctctacatagttagagagagagaga ggggttgtgaggagagagaaagcagtactactggtgccgagcaaaatacctactctccctccctctctcatctgtgagtttgcacagtgcatctagtaggc (SEQ ID NO:1291), which is designed to effect a two-nucleotide deletion of AG at 404 nucleotides upstream of the TSS and a nucleotide change of T to A (shown in underlined upper case font) to destroy the PAM sequence. A third guide RNA with the sequence UAAUUUCUACUCUUGUAGAUCACAGUGCAUCUAGUAGGCUA (SEQ ID NO:1292) is designed to effect a DSB at a predetermined locus 302 nucleotides upstream from the TaMOC1 transcription start site; this is delivered with a donor polynucleotide molecule having the sequence tgtgaggagagagaaagcagtactactggtgccgagcaaaatacctactctccctccctctctcatctgtgagAttgcacagtgcatctagtaggctatg Gctgacattatttgtagtagcgtagtggttgctggtgatggtgctcctgggttctcccctctcactcactcgcacaagctagctagcagcagcagcata (SEQ ID NO:1293), which is designed to effect a first nucleotide change of A to G (shown in upper case font) at 298 nucleotides upstream of the TSS (shown in upper case font) and a second nucleotide change of T to A (shown in underlined upper case font) to destroy the PAM sequence. A fourth guide RNA with the sequence UAAUUUCUACUCUUGUAGAUACACCUCUAAUCCAAUGCGAU (SEQ ID NO:1294) is designed to effect a DSB at a predetermined locus 1621 nucleotides downstream from the TaMOC1 transcription start site; this is delivered with a donor polynucleotide molecule having the sequence aaccctagctagctatcagcatgatgttaattttcattggctgcccgganctggaaagcttagaaatgcacgGggat cgcattggattagaggtgtcaaCacttgtgaggtgtacaacgtaaaagtaccaatttcatctattttcctctttctaggttgttcatttctt (SEQ ID NO:1295), which is designed to effect a first nucleotide change of A to G (shown in upper case font) at 1671 nucleotides downstream of the TSS (shown in upper case font) and a second nucleotide change of A to C (shown in underlined upper case font) to destroy the PAM sequence. In certain experiments, the donor polynucleotide is a single-stranded DNA that is phosphorylated on the 5' end and that contains two phosphorothioate linkages at each terminus (i.e., the two linkages between the two most distal three bases on either end of the strand); alternative donor polynucleotides are non-chemically modified single-stranded DNA molecules, chemically modified or non-chemically modified double-stranded DNA molecules, and chemically modified or non-chemically modified double-stranded DNA/RNA hybrid molecules. In certain experiments, the donor polynucleotide is covalently or non-covalently linked or tethered to the corresponding RNP either to the nuclease or to the guide RNA; RNPs prepared with tethered donors are useful in delivery protocols where multiple RNP/donor compositions are delivered simultaneously to plant cells or tissues.

In one set of experiments, wheat protoplasts are prepared as described in Examples 1-4. The editing reagents are prepared as four separate RNP/donor compositions as described above, and were delivered sequentially to the protoplasts following protocols similar to those described in Examples 5, 11-14, and especially Example 15. For experiments carried out in protoplasts, CRISPR amplicon sequencing is used to verify the presence of the intended edits in the TaMOC1-7A gene. In another set of experiments, wheat meristems are prepared as described in Examples 8 and 9, the editing reagents are prepared as four separate RNP/donor compositions as described above and delivered to the wheat meristems by sequential microinjection delivery following protocols similar to those described in Example 8 or by sequential biolistics delivery following protocols similar to those described in Example 9, and plants grown directly from the treated meristems without selection or use of callus culture. Alternatively, the different RNP/donor compositions are prepared with donor molecules linked or tethered to the RNP nuclease or guide RNA, and are delivered simultaneously or in groups. In these experiments, CRISPR amplicon sequencing is again used to verify the presence of the intended edits in the TaMOC1-7A gene. The modified plants grown from the microinjection- or biolistics-treated meristems are analyzed for phenotypic changes and grain yield. The modified wheat plants containing the modified TaMOC1-7A gene are expected to exhibit at least one trait selected from higher spikelet number per spike and increased yield, in comparison to a control wheat plant that lacks the genomic modifications. In another embodiment, both TaMOC1 and TaSnRK2.10 (see Example 22) are modified according to the procedures disclosed herein. The modified plants are analyzed for changes in plant architecture, changes in total biomass, and changes in seed number and total seed yield. Wheat plants containing both of these modifications are expected to exhibit at least one trait selected from increased biomass, higher spikelet number per spike, and increased yield, in comparison to a control wheat plant that lacks the genomic modifications.

Example 27

This example illustrates embodiments of the invention related to wheat plants exhibiting improved nutrient utilization. More specifically, this example illustrates a wheat plant having a modified genome that results in the wheat plant exhibiting improved nitrogen use efficiency in comparison to an unmodified wheat plant having an reference genome, wherein the modified genome differs from the reference genome by including predetermined modifications of a gene of interest (e.g., modification of regulatory sequence that affects expression of the gene of interest), wherein the predetermined modifications include heterologous integration of a nucleic acid sequence that is encoded by at least one donor polynucleotide molecule and that includes a non-coding regulatory element, at a predetermined locus between 1-1000 nucleotides upstream of the start codon of the coding sequence of a gene of interest in the reference genome or 1-1000 nucleotides upstream of the start codon of the coding sequence of a gene of interest in the reference genome, wherein the gene of interest is at least one gene selected from the genes identified by orthologue gene name, gene ID, and protein and genomic sequence identifiers (SEQ ID NOs) in Table 11 (see also Table 10 for disclosure of these genes), or is a gene encoding a protein having at least 90% identity to a sequence selected from the group identified by SEQ ID NOs: 907-914, 916, 934, 935, and 937. In embodiments, the regulatory element is one having a nucleotide sequence selected from the group consisting of SEQ ID NOs:66-256. In embodiments, the regulatory element is a non-coding sequence that, when heterologously inserted in the 5' untranslated region of the at least one gene of interest, effects an increase in expression of the at least one gene of interest. In embodiments, the regulatory element is a non-coding sequence that, when heterologously inserted in the 5' untranslated region of the at least one gene of interest, effects an increase in expression of the at least one gene of interest as well as a change in expression of one or more genes downstream of the at least one gene of interest. In this non-limiting, specific example, a nitrogen-responsive element, AtNRE, provided as a double-stranded DNA donor polynucleotide consisting of DNA strands with the sequences AAGAGATGAGCTCTT-GAGCAATGTAAAGGGTCAAGTTGTTTTCT (SEQ ID NO:232) and AGAAACAACTTGACCCTTTACATTGCT-CAAGAGCTCATCTCTT (SEQ ID NO:233) is heterologously integrated in the 5' untranslated region, i.e., at a predetermined locus between 1-1000 nucleotides upstream of the start codon of the coding sequence, of a gene of interest in the reference wheat genome or 1-1000 nucleotides upstream of the start codon of the coding sequence, of a gene of interest in the reference wheat genome, wherein the gene of interest is at least one gene selected from the genes identified by orthologue gene name, gene ID, and protein and genomic sequence identifiers (SEQ ID NOs) in Table 11, or is a gene encoding a protein having at least 90% identity to a sequence selected from the group identified by SEQ ID NOs: 907-914, 916, 934, 935, and 937. By modifying multiple genes selected from the genes identified by orthologue gene name, gene ID, and protein and genomic sequence identifiers (SEQ ID NOs) in Table 11, or is a gene encoding a protein having at least 90% identity to a sequence selected from the group identified by SEQ ID NOs: 907-914, 916, 934, 935, and 937, nitrogen use efficiency is expected to be enhanced.

TABLE 11

| Orthologue gene name | Gene ID* | Protein SEQ ID NO: | Genomic DNA SEQ ID NO: |
|---|---|---|---|
| AMT1;2 | TraesCS6A01G226800.1 | 907 | 1191 |
| AMT3;1 | TraesCS3A01G381700.1 | 908 | 1192 |
| NRT2.3b | TraesCS3B01G285900.1 | 909 | 1193 |
| GS1;2 | TraesCS4B01G240900.1 | 910 | 1194 |
| ARG | TraesCS2D01G034900.1 | 911 | 1195 |
| NRT2.2; NRT2.1 | TraesCS6B01G044400.1 | 912 | 1196 |
| AMT1;1 | TraesCS2B01G383600.1 | 913 | 1197 |
| AlaAT | TraesCS1A01G085600.1 | 914 | 1198 |
| NAD(H)-dependent GOGAT 1 | TraesCS3A01G266300.2 | 916 | 1200 |
| Asn synthetase | TraesCS1D01G390500.1 | 934 | 1218 |
| AspAT | TraesCS3B01G331100.1 | 935 | 1219 |
| Gln1-3 | TraesCS6A01G298100.2 | 937 | 1221 |

*Gene ID based on the genome and annotation provided as the first version of the reference sequence (RefSeqv1.0) of the bread wheat *Triticum aestivum* variety Chinese Spring, produced by the International Wheat Genome Sequencing Consortium (IWGSC), publicly accessible at: wheat-urgi[dot]Versailles[dot]inra[dot]fr/Seq-Repository/Assemblies In one set of experiments, wheat protoplasts are prepared as described in Examples 1-4. The editing reagents are prepared as RNP/donor compositions (i.e., nuclease, guide RNA(s), and AtNRE donor polynucleotide), and were delivered to the protoplasts following protocols similar to those described in Examples 5, and 11-15. Experiments using different combinations of RNPs are carried out to provide initial data on the resulting changes in nitrogen metabolism. For experiments carried out in protoplasts, qPCR or RNA-Seq is used to measure expression level of the genes of interest, and CRISPR amplicon sequencing is used to verify the presence of the intended edits in the genes of interest. In subsequent experiments, wheat meristems are prepared as described in Examples 8 and 9, the editing reagents are prepared as RNP/donor compositions as described above and delivered to the wheat meristems by microinjection delivery following protocols similar to those described in Example 8 or by biolistics delivery following protocols similar to those described in Example 9, and plants grown directly from the treated meristems without selection or use of callus culture. When the same donor polynucleotide is used for modifying multiple genes of interest, the different RNP/donor compositions can be delivered simultaneously or in groups. In these experiments, qPCR or RNA-Seq is used to measure expression level of the genes of interest, and CRISPR amplicon sequencing is again used to verify the presence of the intended edits in the genes of interest. The modified plants grown from the microinjection- or biolistics-treated meristems are grown under conditions of sufficient nitrogen and under conditions of nitrogen insufficiency (nitrogen stress), and analyzed for expression levels of the genes of interest, phenotypic changes, and grain yield. The modified wheat plants containing the modified genes of interest are expected to exhibit at least one trait selected from improved nitrogen use efficiency and increased yield, in comparison to a control wheat plant that lacks the genomic modifications.

Example 28

This example illustrates a non-limiting embodiment of an aspect of the invention that employs genomic sequence modification methods as described in this disclosure to provide a wheat plant having a modified genome that includes at least a change in the genome that results in an amino acid change of glutamic acid to leucine at position 166 in the ABA receptor gene Ta2DS-FL (SEQ ID NO:12%), wherein the modified wheat plant exhibits at least one trait selected from improved drought tolerance and improved cold tolerance, in comparison to a control wheat plant that lacks the genomic modifications.

Abscisic acid (ABA) is the primary plant hormone involved in regulating plant water status and plant response to changes in internal and external water potential. ABA receptors are at the top of the ABA signal transduction cascade that regulates plant water status. The overexpression of the pyrabactin resistance-like (PYL) abscisic acid (ABA) receptor OsPYL3 was reported to substantially improve drought and cold stress tolerance in rice, and changes in conserved abscisic acid (ABA) receptor amino acids have been reported to render the receptor hypersensitive to ABA; see U.S. Patent Application Publication 2016/0194653, incorporated herein by reference.

Several ABA receptor sequences have been reported; see Gordon et al. (2016) PLoS ONE 11(10):e0164996; doi.org/10.1371/journal.pone.0164996. The receptor Ta2DS-FL, which is expressed in leaf and root and exhibits ABA-mediated repression of transcription, has the protein sequence (SEQ ID NO: 1296)
MPTPYSAAALQQHQRLVSSSGGLAATGAHRCGEHDGTVPPEVARHHEHAA

PGGRCCCSAVVQRVAAPAADVWAVVRRFDQPQAYKSFVRSCALLDGDGGV

GTLREVRVVSGLPAASSRERLEILDDERHVLSFSVVGGEHRLRNYRSVTT

VHPAPGESASATLVVE<u>E</u>SYVVDVPPGNTPEDTRVFVDTIVKCNLQSLARTA

EKLAGRGAAYGAL, which has a glutamic acid residue at position 166 (shown in underlined font) that, if changed to leucine, is expect to make the protein hypersensitive to ABA. A partial genomic sequence of Ta2DS-FL is provided by (SEQ ID NO: 1297)
GCCCAAACCAAGCCAAACGAACCAGCGCCGCAGCCCGCAGCGCACCCATC

CCACCAAACAAACAGCTAGCAGGCGAGGCGACCCGCTCCGACCTCGAGCC

<u>GATGCCGACGCCGTACAGCGCGGCGGCGCTGCAGCAGCACCAGCGTCTGG</u>

<u>TCTCCTCCTCCGGCGGCCTGGCGGCGACGGGGCCCACAGGTGCGGCGAG</u>

<u>CACGACGGGACGGTGCCGCCGGAGGTGGCGCGGCACCACGAGCACGCGGC</u>

<u>GCCGGGGGGCGCTGCTGCTGCTCGGCGGTGGTGCAGCGCGTGGCGGCGC</u>

<u>CGGCGGCGGACGTGTGGGCCGTGGTCCGGCGCTTCGACCAGCCGCAGGCG</u>

<u>TACAAGAGCTTCGTGCGCAGCTGCGCGCTGCTGGACGGCGACGGCGGCGT</u>

<u>GGGCACGCTGCGCGAGGTGCGCGTGGTGTCGGGCCTCCCCGCGGCGTCCA</u>

<u>GCCGGGAGCGGCTGGAGATCCTGGACGACGAGCGGCACGTGCTGAGCTTC</u>

<u>AGCGTGGTGGGCGGCGAGCACCGGCTCCGCAACTACCGGTCGGTGACCAC</u>

<u>GGTGCACCCGGCGCCGGGGGAGAGCGCGTCGGCGACGCTGGTGGTGGAGT</u>

<u>CGTACGTGGTGGACGTGCCCCCCGGGAACACGCCCGAGGACACCCGCGTC</u>

<u>TTCGTGGACACCATCGTCAAGTGCAACCTCCAGTCCCTCGCCCGCACCGC</u>

<u>CGAGAAGCTCGCCGGCCGGGGGCGGCCTACGGCGCGCTGCCGTGATCGA</u>

TCGATCCGACCGGAACCCGCAGTCGCCGGCCCGCGCCTCCCTCCGGTGGT

CAACTCGAGCCCGGCCCTCCCGGCTCGGCCGCAGGGGCGTTTCGGTAAAA

TCGCGCACCGATTTTCCGATTAATGAATCCAAATCCATGGTGGTGGTGGT

GCGCGGGTGGTGGCGACCGATTATTTTTCTCTTGTTCTTTCTGGCGTGAA

GGCGAGGGGTCGGTGGGTCGGTTCGGACCGGTCGGTGCGCTTTCGCGGCT

GGCCCCTCGCTGTTTCTCCTTATCGCGAGACACACCCCCCTGTAGTAGTG

GTAGCTCTAGTTTTTGTTCGTTCCCCTTTGTTTGATCTCGGGTAAGATGA

TGATAAGATTTGACAGGAATTGAGGAGTAAAAACTAGCTTCGACCGATGC

AAGGCTCATCGACATCTCTGTATATATACTTTTAGTTTCCCGTTCCATTG

TGTGTGTTGTCATCATCACCATTTTGGTCGTGACATTTCATCAATCAAAT

TTACAAGATGTTCAACGAGGCACAACGGACCAGAGCCGTCACGGTCTTGT

TGGACCAAATCAACAGAGCGATTATCTTCTTTGCACATTATGAGGTCTTT

GTCACACACATTTTCTCCTAGCATATAC, where the open reading frame (a single exon) is shown in underlined font and the location of the codon encoding the glutamic acid residue at position 166 in the protein is shown in bold underlined font. A first DNA expression cassette encoding a Cpf1 guide RNA with the sequence (SEQ ID NO: 1298)
aagggatctttaaacatacgaacagatcacttaaagttcttctgaagcaa cttaaagttatcaggcatgcatggatcttggaggaatcagatgtgcagtc agggaccatagcacaagacaggcgtcttctactggtgctaccagcaaatg ctggaagccgggaacactgggtacgttggaaaccacgtgatgtgaagaag taagataaactgtaggagaaaagcatttcgtagtgggccatgaagcctt caggacatgtattgcagtatgggccggcccattacgcaattggacgacaa caaagactagtattagtaccacctcggctatccacatagatcaaagctga tttaaaagagttgtgcagatgatccgtggcaGTTTCAAAGATTAAATAAT

TTCTACTAAGTGTAGATCCGGGGGGCACGTCCACCACTTTCAAAGATTAA

ATAATTTCTACTAAGTGTAGAT*ttttttttt*agtagtagcatctgac contains a OsU3 promoter (shown as the 5' nucleotides in lower case font), the Ta_2DS target sequence (s own in upper case font with the crRNA repeats underlined), and a terminator (shown in italicized lower case font). The Cpf1 guide RNA encoded by this first expression cassette is designed to be delivered with a donor polynucleotide molecule with the sequence (SEQ ID NO: 1299)
GCGCCGGGGGAGAGCGCGTCGGCGACGCTGGTGGTGC<u>T</u>GTCGTACGTGG TGGACGTGCCCCCCG<u>T</u>GAACACGCCCGAGGACACCCGCGTCTTCGTGGA

CA, which is designed to effect the sequence changes indicated by the underlined nucleotides.

A second DNA expression cassette encoding a Cpf1 guide RNA with the sequence (SEQ ID NO: 1300)
aagggatctttaaacatacgaacagatcacttaaagttcttctgaagcaa cttaaagttatcaggcatgcatggatcttggaggaatcagatgtgcagtc agggaccatagcacaagacaggcgtcttctactggtgctaccagcaaatg ctggaagccgggaacactgggtacgttggaaaccacgtgatgtgaagaag taagataaactgtaggagaaaagcatttcgtagtgggccatgaagcctt caggacatgtattgcagtatgggccggcccattacgcaattggacgacaa caaagactagtattagtaccacctcggctatccacatagatcaaagctga tttaaaagagttgtgcagatgatccgtggcaGTTTCAAAGATTAAATAAT

TTCTACTAAGTGTAGATCCCCGGCGCCGGGTGCACCGTTTCAAAGATTAA

ATAATTTCTACTAAGTGTAGAT*ttttttttt*agtagtagcatctgac contains a OsU3 promoter (shown as the 5' nucleotides in lower case font), the Ta_2DS target sequence (shown in upper case font with the crRNA repeats underlined), and a terminator (shown in italicized lower case font). The Cpf1 guide RNA encoded by this second expression cassette is designed to be delivered with a donor polynucleotide molecule with the sequence (SEQ ID NO: 1301)
TGGTGGGCGGCGAGCACCGGCTCCGCAACTACCGGTCGGTGACCACGGT

GCACCCGGCGCCGGGGGAATCCGCGTCGGCGACGCTGGTGGTGCTGTCG

TA, which is designed to effect the sequence changes indicated by the underlined nucleotides.

In one set of experiments, wheat protoplasts are prepared as described in Examples 1-4. The editing reagents are prepared as separate RNP/donor compositions as described above, and were delivered sequentially to the protoplasts following protocols similar to those described in Examples 5, 11-14, and especially Example 15. For experiments carried out in protoplasts, CRISPR amplicon sequencing is used to verify the presence of the intended edits in the Ta2DS-FL gene. In another set of experiments, wheat meristems are prepared as described in Examples 8 and 9, the editing reagents are prepared as separate RNP/donor compositions as described above and delivered to the wheat meristems by sequential microinjection delivery following protocols similar to those described in Example 8 or by sequential biolistics delivery following protocols similar to those described in Example 9, and plants grown directly from the treated meristems without selection or use of callus culture. Alternatively, the different RNP/donor compositions are prepared with donor molecules linked or tethered to the RNP nuclease or guide RNA, and are delivered simultaneously. In these experiments, CRISPR amplicon sequencing is again used to verify the presence of the intended edits in the Ta2DS-FL gene. The effects of the edits on downstream genes affected by ABA receptors can be measured by qPCR. The modified plants grown from the microinjection- or biolistics-treated meristems are tested for their tolerance to drought (water insufficiency stress) and to cold stress. The modified wheat plants containing the modified Ta2DS-FL gene are expected to exhibit at least one trait selected from improved drought tolerance and improved cold tolerance, in comparison to a control wheat plant that lacks the genomic modifications.

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this invention have been described in terms of embodiments and illustrative examples, it will be apparent to those of skill in the art that substitutions and variations can be applied to the materials and methods described herein without departing from the concept, spirit, and scope of the invention. For instance, while the particular examples provided illustrate the methods and embodiments described herein using a specific plant, the principles in these examples are applicable to any plant of interest; similarly, while the particular examples provided illustrate the methods and embodiments described herein using a particular sequence-specific nuclease such as Cas9, one of skill in the art would recognize that alternative sequence-specific nucleases (e.g., CRISPR nucleases other than Cas9, such as CasX, CasY, and Cpf1, zinc-finger nucleases, transcription activator-like effector nucleases, Argonaute proteins, and meganucleases) are useful in various embodiments. All such similar substitutes and modifications apparent to those skilled in the art are deemed to be within the spirit, scope, and concept of the invention as encompassed by the embodiments of the inventions recited herein and the specification and appended claims.

SEQUENCE LISTING

The patent contains a lengthy sequence listing. A copy of the sequence listing is available in electronic form from the USPTO web site (https://seqdata.uspto.gov/?pageRequest=docDetail&DocID=US11866719B1). An electronic copy of the sequence listing will also be available from the USPTO upon request and payment of the fee set forth in 37 CFR 1.19(b)(3).

We claim:

1. A wheat plant, or a cell thereof, having a modified genome that results in the wheat plant exhibiting modified architecture in comparison to an unmodified wheat plant having a reference genome, wherein the modified genome differs from the reference genome by comprising at least one predetermined modification of a gene, wherein the at least one predetermined modification comprises heterologous integration of a nucleic acid sequence that is encoded by at least one donor polynucleotide molecule and that comprises a regulatory element, at a predetermined locus between 1-1000 nucleotides upstream of the start codon of the coding sequence of the gene in the reference genome, wherein the regulatory element comprises SEQ ID NO: 231, and wherein the predetermined modification of the gene results in increased expression of the gene relative to expression of the gene in the reference genome.

2. The wheat plant of claim 1, wherein the modified genome is more than 99.9% identical to the reference genome.

3. The wheat plant of claim 1, wherein the gene of interest is located on a chromosome in the wheat plant cell, and wherein the modified genome comprises:
   (a) a difference of DNA methylation in less than 0.01% of the portion of the genome that is contained within the chromosome containing the gene of interest, relative to the reference genome; or
   (b) a difference of DNA methylation in less than 0.005% of the portion of the genome that is contained within the chromosome containing the gene of interest, relative to the reference genome; or
   (c) a difference of DNA methylation in less than 0.001% of the portion of the genome that is contained within the chromosome containing the gene of interest, relative to the reference genome.

4. Seed or progeny plants of the wheat plant of claim 1, wherein the seed or progeny plants comprise the at least one predetermined modification.

5. A method of manufacturing a processed wheat product, comprising processing the seed or progeny plants of claim 4 into a processed wheat product, thereby manufacturing a processed wheat product.

6. The wheat plant of claim 1, wherein the predetermined modification of the gene comprises modification of only non-coding sequences of the reference genome.

7. The wheat plant of claim 1, wherein the predetermined modification of the gene comprises multiple predetermined modifications of the gene in the reference genome.

8. The wheat plant of claim 1, wherein the predetermined modification of the gene comprises a predetermined modification of multiple homeoalleles of the gene.

9. The wheat plant of claim 1, wherein the wheat plant is a *Triticum* sp., an *Aegilops* sp., common or bread wheat (*Triticum aestivum*), spelt (*Triticum spelta*), emmer (*Triticum dicoccum*), einkorn (*Triticum monococcum*), durum wheat (*Triticum durum*), or synthetic hexaploid wheat.

10. The wheat plant of claim 1, wherein the wheat plant is an allotetraploid, wherein the reference genome consists of an A genome and a B genome, and wherein the predetermined modification of the gene comprises: (a) a predetermined modification of both homeoalleles of the gene of interest in the A genome, (b) a predetermined modification of both homeoalleles of the gene of interest in the B genome, or (c) a predetermined modification of at least two homeoalleles of the gene of interest in the A genome and the B genome.

11. The wheat plant of claim 1, wherein the wheat plant is an allohexaploid, wherein the reference genome consists of an A genome, a B genome, and a D genome, and wherein the predetermined modification of the gene comprises: a) a predetermined modification of both homeoalleles of the gene of interest in the A genome, (b) a predetermined modification of both homeoalleles of the gene of interest in the B genome, (c) a predetermined modification of both homeoalleles of the gene of interest in the D genome, or (d) a predetermined modification of at least two homeoalleles of the gene of interest in any combination of the A genome, the B genome, and the D genome.

12. The wheat plant of claim 1, wherein the plant comprises the predetermined modification in each of two genes.

13. The wheat plant of claim 12, wherein the two genes are selected from the group consisting of a gene encoding a protein having at least 95% identity to a sequence selected from the group consisting of SEQ ID NOs: 800, 802, and 816.

14. The wheat plant of claim 1, wherein the gene encodes a protein having at least 95% identity to SEQ ID NO: 816, or is the genomic sequence of SEQ ID NO: 1100.

\* \* \* \* \*